(12) United States Patent
Bender et al.

(10) Patent No.: US 8,796,466 B2
(45) Date of Patent: *Aug. 5, 2014

(54) HEPATITIS C VIRUS INHIBITORS

(75) Inventors: John A. Bender, Middletown, CT (US); Piyasena Hewawasam, Middletown, CT (US); John F. Kadow, Wallingford, CT (US); Omar D. Lopez, Wallingford, CT (US); Nicholas A. Meanwell, East Hampton, CT (US); Van N. Nguyen, Meriden, CT (US); Jeffrey Lee Romine, Meriden, CT (US); Lawrence B. Snyder, Killingworth, CT (US); Denis R. St. Laurent, Newington, CT (US); Gan Wang, Wallingford, CT (US); Ningning Xu, Wallingford, CT (US); Makonen Belema, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 232 days.

This patent is subject to a terminal disclaimer.

(21) Appl. No.: 12/729,940

(22) Filed: Mar. 23, 2010

(65) Prior Publication Data

US 2011/0077280 A1 Mar. 31, 2011

Related U.S. Application Data

(60) Provisional application No. 61/164,531, filed on Mar. 30, 2009.

(51) Int. Cl.
| | | |
|---|---|---|
| *A61K 31/4178* | (2006.01) | |
| *A61K 31/4184* | (2006.01) | |
| *A61P 31/14* | (2006.01) | |
| *C07D 403/14* | (2006.01) | |
| *C07D 405/14* | (2006.01) | |

(52) U.S. Cl.
USPC .............. 548/313.1; 548/302.1; 548/312.1; 514/394; 514/397

(58) Field of Classification Search
None
See application file for complete search history.

(56) References Cited

U.S. PATENT DOCUMENTS

| | | | |
|---|---|---|---|
| 5,654,451 A | 8/1997 | Kari | |
| 7,894,996 B2 | 2/2011 | Rice et al. | |
| 2010/0158862 A1 | 6/2010 | Kim et al. | |
| 2010/0226882 A1* | 9/2010 | Or et al. | 424/85.5 |
| 2011/0092415 A1 | 4/2011 | DeGoey et al. | |
| 2012/0115855 A1* | 5/2012 | Li et al. | 514/228.2 |

FOREIGN PATENT DOCUMENTS

| | | |
|---|---|---|
| WO | WO 94/15909 | 7/1994 |
| WO | WO 2004/005264 | 1/2004 |
| WO | WO 2006/022442 | 3/2006 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/076034 | 7/2007 |
| WO | WO 2007/077186 | 7/2007 |
| WO | WO 2007/081517 | 7/2007 |
| WO | WO 2007/138242 | 12/2007 |
| WO | WO 2008/014430 | 1/2008 |
| WO | WO 2008/021927 | 2/2008 |
| WO | WO 2008/021928 | 2/2008 |
| WO | WO 2008/021936 | 2/2008 |
| WO | WO 2008/070447 | 6/2008 |
| WO | WO 2008/133753 | 11/2008 |
| WO | WO2008/144380 A1 | 11/2008 |
| WO | WO 2009/020825 | 2/2009 |
| WO | WO 2009/020828 | 2/2009 |
| WO | WO 2009/102318 | 8/2009 |
| WO | WO 2009/102325 | 8/2009 |
| WO | WO 2009/102568 | 8/2009 |
| WO | WO 2009/102633 | 8/2009 |
| WO | WO 2009/102694 | 8/2009 |
| WO | WO 2010/017401 | 2/2010 |
| WO | WO 2010/039793 | 4/2010 |
| WO | WO 2010/062821 | 6/2010 |

(Continued)

OTHER PUBLICATIONS

U.S. Appl. No. 12/846,152, filed Jul. 29, 2010, Romine.
U.S. Appl. No. 12/889,705, filed Sep. 24, 2010, Belema et al.
U.S. Appl. No. 13/195,317, filed Aug. 1, 2011, Gao et al.
U.S. Appl. No. 13/198,529, filed Aug. 4, 2011, Belema et al.

(Continued)

*Primary Examiner* — Dennis Heyer
(74) *Attorney, Agent, or Firm* — Pamela A. Mingo

(57) ABSTRACT

This disclosure concerns novel compounds of Formula (I) as defined in the specification and compositions comprising such novel compounds. These compounds are useful antiviral agents, especially in inhibiting the function of the NS5A protein encoded by Hepatitis C virus (HCV). Thus, the disclosure also concerns a method of treating HCV related diseases or conditions by use of these novel compounds or a composition comprising such novel compounds.

4 Claims, No Drawings

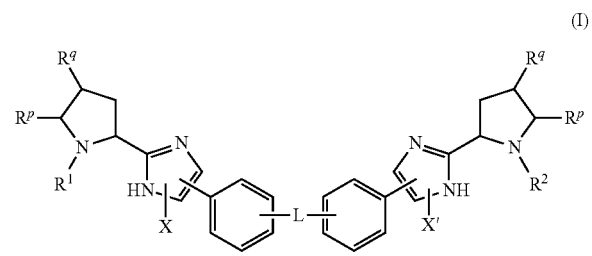

(56) References Cited

FOREIGN PATENT DOCUMENTS

| | | |
|---|---|---|
| WO | WO 2010/065668 | 6/2010 |
| WO | WO 2010/065674 | 6/2010 |
| WO | WO 2010/065681 | 6/2010 |
| WO | WO 2010/075376 | 7/2010 |
| WO | WO 2010/091413 | 8/2010 |
| WO | WO 2010/094977 | 8/2010 |
| WO | WO 2010/096302 | 8/2010 |
| WO | WO 2010/096462 | 8/2010 |
| WO | WO 2010/096777 | 8/2010 |
| WO | WO 2010/099527 | 9/2010 |
| WO | WO 2010/111483 | 9/2010 |
| WO | WO 2010/111534 | 9/2010 |
| WO | WO 2010/111673 | 9/2010 |
| WO | WO 2010/117704 | 10/2010 |
| WO | WO 2010/117977 | 10/2010 |
| WO | WO 2010/120621 | 10/2010 |
| WO | WO 2010/120935 | 10/2010 |
| WO | WO 2010/122162 | 10/2010 |
| WO | WO 2010/132538 | 11/2010 |
| WO | WO 2010/132601 | 11/2010 |
| WO | WO 2010/138368 | 12/2010 |
| WO | WO 2010/138488 | 12/2010 |
| WO | WO 2010/138790 | 12/2010 |
| WO | WO 2010/138791 | 12/2010 |
| WO | WO 2010/144646 | 12/2010 |
| WO | WO 2010/148006 | 12/2010 |
| WO | WO 2011/004276 | 1/2011 |
| WO | WO 2011/009084 | 1/2011 |
| WO | WO 2011/015657 | 2/2011 |
| WO | WO 2011/015658 | 2/2011 |
| WO | WO 2011/026920 | 3/2011 |
| WO | WO 2011/028596 | 3/2011 |
| WO | WO 2011/031904 | 3/2011 |
| WO | WO 2011/031934 | 3/2011 |
| WO | WO 2011/046811 | 4/2011 |
| WO | WO 2011/050146 | 4/2011 |
| WO | WO 2011/054834 | 5/2011 |
| WO | WO 2011/059850 | 5/2011 |
| WO | WO 2011/059887 | 5/2011 |
| WO | WO 2011/060000 | 5/2011 |
| WO | WO 2011/066241 | 6/2011 |
| WO | WO 2011/068941 | 6/2011 |
| WO | WO 2011/075439 | 6/2011 |
| WO | WO 2011/075607 | 6/2011 |
| WO | WO 2011/075615 | 6/2011 |
| WO | WO 2011/079327 | 6/2011 |
| WO | WO 2011/081918 | 7/2011 |
| WO | WO 2011/082077 | 7/2011 |
| WO | WO 2011/087740 | 7/2011 |
| WO | WO 2011/091417 | 7/2011 |
| WO | WO 2011/091446 | 7/2011 |
| WO | WO 2011/091532 | 8/2011 |

OTHER PUBLICATIONS

Fridell, R.A. et al., "Resistance Analysis of the Hepatitis C Virus NS5A Inhibitor BMS-790052 in an In Vitro Replicon System", Antimicrobial Agents and Chemotherapy, vol. 54, No. 9, pp. 3641-3650 (2010).

Gao, M. et al., "Chemical genetics strategy identifies an HCV NS5A inhibitor with a potent clinical effect", Nature, vol. 465, pp. 96-100 (2010).

Lemm, J.A. et al., "Identification of Hepatitis C Virus NS5A Inhibitors", Journal of Virology, vol. 84, No. 1, pp. 482-491 (2010).

Romine, J.L. et al., "Inhibitors of HCV NS5A: From Iminothiazolidinones to Symmetrical Stilbenes", ACS Medicinal Chemistry Letters, vol. 2, pp. 224-229 (2011).

* cited by examiner

HEPATITIS C VIRUS INHIBITORS

CROSS-REFERENCE TO RELATED APPLICATIONS

This application claims the benefit of U.S. Provisional Application Ser. No. 61/164,531 filed Mar. 30, 2009.

FIELD OF THE DISCLOSURE

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

BACKGROUND OF THE DISCLOSURE

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

The current standard of care for HCV, which employs a combination of pegylated-interferon and ribavirin, has a non-optimal success rate in achieving sustained viral response and causes numerous side effects. Thus, there is a clear and long-felt need to develop effective therapies to address this under-met medical need.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); C. Rice, et al., WO2006093867.

The present disclosure provides compounds which selectively inhibit HCV viral replication, as characterized by Formula (I):

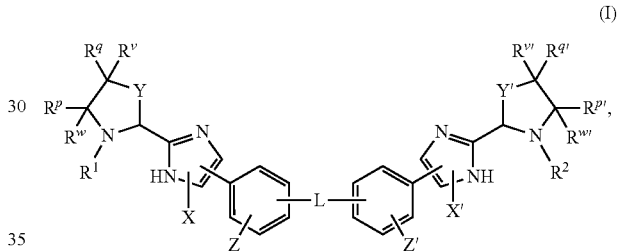

or a pharmaceutically acceptable salt thereof, wherein:

L is selected from —O—, —CH$_2$CH$_2$—, —CH=CH—, —C≡C—, —OCH$_2$—, —CH$_2$O—, —CH$_2$OCH$_2$—,

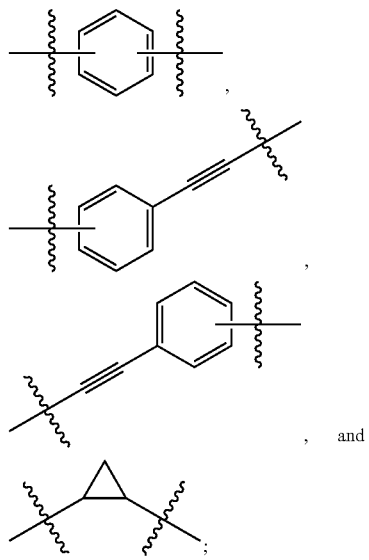

, and

;

X is hydrogen (H) or halogen and Z is hydrogen; or
X and Z, together with the carbon atoms to which they are attached, form a five- to eight-membered aromatic or non-aromatic fused ring optionally containing one or two heteroatoms independently selected from nitrogen, oxygen, and sulfur; wherein the five- to eight-membered ring is optionally substituted with one, two, or three substitutents independently selected from alkoxy, alkoxyalkyl, alkoxycarbonyl, alkyl, alkylsulfonyl, aryl, arylalkyl, arylsulfonyl, carboxy, formyl, halo, haloalkoxy, haloalkyl, hydroxy, hydroxyalkyl, —$NR^aR^b$, ($NR^aR^b$)alkyl, ($NR^aR^b$)carbonyl, oxo, and spirocycle;

X' is hydrogen (H) or halogen and Z' is hydrogen; or

X' and Z', together with the carbon atoms to which they are attached, form a five- to eight-membered aromatic or non-aromatic fused ring optionally containing one or two heteroatoms independently selected from nitrogen, oxygen, and sulfur; wherein the five- to eight-membered ring is optionally substituted with one, two, or three substitutents independently selected from alkoxy, alkoxyalkyl, alkoxycarbonyl, alkyl, alkylsulfonyl, aryl, arylalkyl, arylsulfonyl, carboxy, formyl, halo, haloalkoxy, haloalkyl, hydroxy, hydroxyalkyl, ($NR^aR^b$)alkyl, ($NR^aR^b$)carbonyl, oxo, and spirocycle;

Y and Y' are each independently —$CH_2$—, —$CH_2CH_2$—, or —$CH_2O$—, wherein the —$CH_2O$— is drawn such that the oxygen atom is bound to the carbon atom substituted with $R^v$ and $R^q$ or $R^{v'}$ and $R^{q'}$;

$R^p$ is hydrogen or $C_1$ to $C_4$ alkyl;

$R^q$ is hydrogen, alkyl, or halo; or $R^p$ and $R^q$, together with the carbon atoms to which they are attached, form a cycloalkyl ring;

$R^v$ is selected from hydrogen, alkyl, halo, and hydroxy; or $R^v$ and $R^q$, together with the carbon atom to which they are attached, form an ethylenyl group or a cycloalkyl ring;

$R^{p'}$ is hydrogen or $C_1$ to $C_4$ alkyl;

$R^{q'}$ is hydrogen, alkyl, or halo; or $R^{p'}$ and $R^{q'}$, together with the carbon atoms to which they are attached, form a cycloalkyl ring;

$R^{v'}$ are independently selected from hydrogen, alkyl, halo, and hydroxy; or $R^{v'}$ and $R^{q'}$, together with the carbon atom to which they are attached, form an ethylenyl group or a cycloalkyl ring;

$R^w$ and $R^{w'}$ are independently selected from hydrogen and alkyl;

$R^1$ is hydrogen or —$C(O)R^x$;

$R^2$ is hydrogen or —$C(O)R^y$;

$R^x$ and $R^y$ are independently selected from cycloalkyl, heteroaryl, heterocyclyl, alkoxy, and alkyl, said alkyl being substituted by one or more substituents independently selected from aryl, alkenyl, cycloalkyl, heterocyclyl, heteroaryl, —$OR^3$, —$C(O)OR^4$, —$NR^aR^b$, and —$C(O)NR^cR^d$, wherein any said aryl and heteroaryl may optionally be substituted with one or more substituents independently selected from alkenyl, alkyl, haloalkyl, arylalkyl, heterocyclyl, heterocyclylalkyl, halogen, cyano, nitro, —$C(O)OR^4$, —$OR^5$, —$NR^aR^b$, ($NR^aR^b$)alkyl, and (MeO)(HO)P(O)O—, and wherein any said cycloalkyl and heterocyclyl may optionally be fused onto an aromatic ring and may optionally be substituted with one or more substituents independently selected from alkyl, hydroxyl, halogen, aryl, —$NR^aR^b$, oxo, and —$C(O)OR^4$;

$R^3$ is hydrogen, alkyl, or arylalkyl;

$R^4$ is alkyl or arylalkyl;

$R^5$ is hydrogen, alkyl, or arylalkyl;

$R^a$ and $R^b$ are independently selected from hydrogen, alkyl, cycloalkyl, arylalkyl, heteroaryl, —$C(O)R^6$, —$C(O)OR^7$, —$C(O)NR^cR^d$, and ($NR^cR^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;

$R^6$ is alkyl;

$R^7$ is alkyl, arylalkyl, cycloalkyl, or haloalkyl; and $R^c$ and $R^d$ are independently selected from hydrogen, alkyl, arylalkyl, and cycloalkyl.

In a first embodiment of the first aspect the present disclosure provides a compound of Formula (I) further characterized by Formula (Ia):

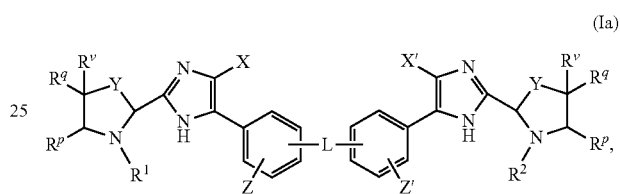

(Ia)

or a pharmaceutically acceptable salt or a tautomer thereof, wherein:

X is hydrogen or chloro (Cl) and Z is hydrogen; or

X and Z, together with the carbon atoms to which they are attached, form a six-membered aromatic or non-aromatic fused ring;

X' is hydrogen or chloro (Cl) and Z' is hydrogen; or

X' and Z', together with the carbon atoms to which they are attached, form a six-membered aromatic or non-aromatic fused ring;

Y is —$CH_2$—, —$CH_2CH_2$—, or —$CH_2O$—, wherein the —$CH_2O$— is drawn such that the oxygen atom is bound to the carbon atom substituted with $R^v$ and $R^q$;

$R^p$ is hydrogen or $C_1$ to $C_4$ alkyl;

$R^q$ is hydrogen, alkyl, or halo; or $R^p$ and $R^q$, together with the carbon atoms to which they are attached, form a cycloalkyl ring; and $R^v$ is selected from hydrogen, alkyl, halo, and hydroxy; or $R^v$ and $R^q$, together with the carbon atom to which they are attached, form an ethylenyl group or a cycloalkyl ring.

In a second embodiment of the first aspect the present disclosure provides a compound of Formula (I) further characterized by Formula (Ib):

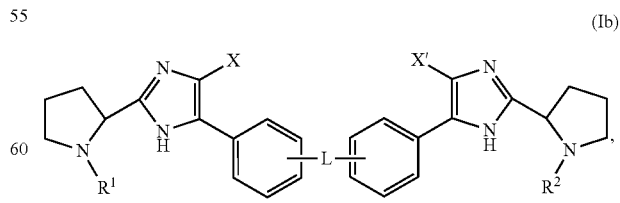

(Ib)

or a pharmaceutically acceptable salt or a tautomer thereof.

In a third embodiment of the first aspect the present disclosure provides a compound of Formula (I) further characterized by Formula (Ic):

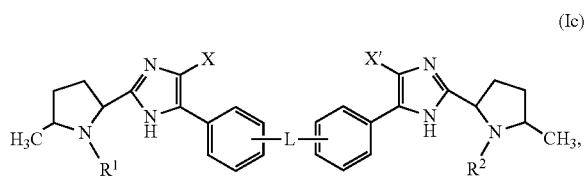

(Ic)

or a pharmaceutically acceptable salt or a tautomer thereof.

In a fourth embodiment of the first aspect the present disclosure provides a compound of Formula (I) further characterized by Formula (Id):

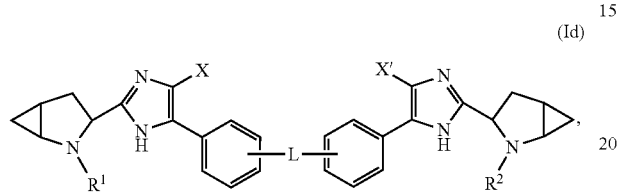

(Id)

or a pharmaceutically acceptable salt or a tautomer thereof.

In a fifth embodiment of the first aspect the present disclosure provides a compound of Formula (Ia), or a pharmaceutically acceptable salt thereof, wherein:

$R^1$ is —C(O)$R^x$;
$R^2$ is —C(O)$R^y$;
$R^x$ and $R^y$ are independently alkyl substituted by at least one —$NR^aR^b$, characterized by Formula (A):

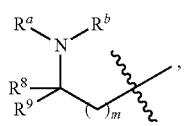

(A)

wherein:
m is 0 or 1;
$R^8$ is hydrogen or alkyl;
$R^9$ is selected from hydrogen, cycloalkyl, aryl, heteroaryl, heterocyclyl, and alkyl optionally substituted with a substituent selected from aryl, alkenyl, cycloalkyl, heterocyclyl, heteroaryl, heterobicyclyl, —$OR^3$, —C(O)$OR^4$, —$NR^aR^b$, and —C(O)$NR^cR^d$,
wherein any said aryl and heteroaryl may optionally be substituted with one or more substituents independently selected from alkyl, haloalkyl, arylalkyl, heterocyclyl, heterocyclylalkyl, halogen, cyano, nitro, —C(O)$OR^4$, —$OR^5$, —$NR^aR^b$, ($NR^aR^b$)alkyl, and (MeO)(HO)P(O)O—, and
wherein any said cycloalkyl and heterocyclyl may optionally be fused onto an aromatic ring and may optionally be substituted with one or more substituents independently selected from alkyl, hydroxyl, halogen, aryl, —$NR^aR^b$, oxo, and —C(O)$OR^4$; and
$R^3$, $R^4$, $R^5$, $R^a$, $R^b$, $R^c$, and $R^d$ are defined as in Formula (I).

In a sixth embodiment of the first aspect the present disclosure provides a compound of Formula (Ia) or a pharmaceutically acceptable salt thereof, wherein
m is 0;
$R^8$ is hydrogen or $C_1$ to $C_4$ alkyl;
$R^9$ is selected from hydrogen, $C_1$ to $C_6$ alkyl optionally substituted with —$OR^{12}$, $C_3$ to $C_6$ cycloalkyl, allyl, —$CH_2$C(O)$NR^cR^d$, ($NR^cR^d$)alkyl,

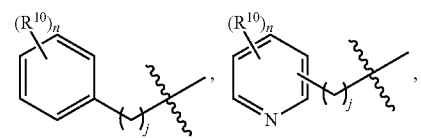

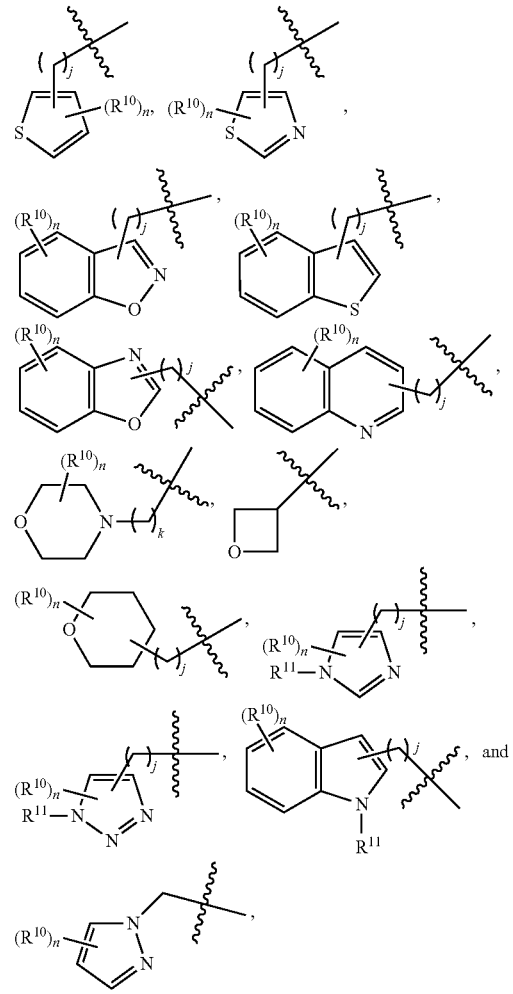

wherein j is 0 or 1;
k is 1, 2, or 3;
n is 0 or an integer selected from 1 through 4;
each $R^{10}$ is independently hydrogen, $C_1$ to $C_4$ alkyl, $C_1$ to $C_4$ haloalkyl, halogen, nitro, —OBn, or (MeO)(OH)P(O)O—;
$R^{11}$ is hydrogen, $C_1$ to $C_4$ alkyl, or benzyl;
$R^{12}$ is hydrogen, $C_1$ to $C_4$ alkyl, or benzyl;
$R^a$ is hydrogen or $C_1$ to $C_4$ alkyl;
$R^b$ is $C_1$ to $C_4$ alkyl, $C_3$ to $C_6$ cycloalkyl, benzyl, 3-pyridyl, pyrimidin-5-yl, acetyl, —C(O)$OR^7$, or —C(O)$NR^cR^d$;
$R^7$ is $C_1$ to $C_4$ alkyl or $C_1$ to $C_4$ haloalkyl;
$R^c$ is hydrogen or $C_1$ to $C_4$ alkyl; and
$R^d$ is hydrogen, $C_1$ to $C_4$ alkyl, or $C_3$ to $C_6$ cycloalkyl.

In a seventh embodiment of the first aspect the present disclosure provides a compound of Formula (Ia) or a pharmaceutically acceptable salt thereof, wherein
m is 0;
$R^8$ is hydrogen;
$R^9$ is phenyl optionally substituted with one up to five substituents independently selected from $C_1$ to $C_6$ alkyl, $C_1$ to $C_4$ haloalkyl, halogen, $C_1$ to $C_6$ alkoxy, hydroxyl, cyano, and nitro; and NR$^a$R$^b$ is a heterocyclyl or heterobicyclyl group selected from:

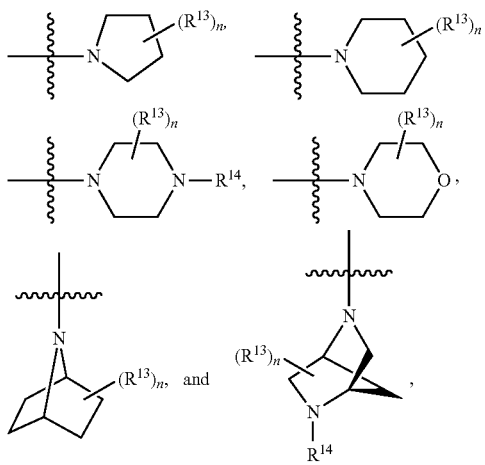

wherein n is 0, 1, or 2;
each R$^{13}$ is independently selected from C$_1$ to C$_6$ alkyl, phenyl, trifluoromethyl, halogen, hydroxyl, methoxy, and oxo; and
R$^{14}$ is C$_1$ to C$_6$ alkyl, phenyl, benzyl, or —C(O)OR$^{15}$ group, wherein R$^{15}$ is C$_1$ to C$_4$ alkyl, phenyl, or benzyl.

In an eighth embodiment of the first aspect the present disclosure provides a compound of Formula (Ia) or a pharmaceutically acceptable salt thereof, wherein
m is 1;
R$^8$ is hydrogen;
R$^9$ is C$_1$ to C$_6$ alkyl, arylalkyl, or heteroarylalkyl;
R$^a$ is hydrogen; and
R$^b$ is —C(O)OR$^7$, wherein R$^7$ is C$_1$ to C$_6$ alkyl.

In a ninth embodiment of the first aspect the present disclosure provides a compound of Formula (Ia) or a pharmaceutically acceptable salt thereof, wherein
R$^1$ is —C(O)R$^x$;
R$^2$ is —C(O)R$^y$;
R$^x$ and R$^y$ are heteroaryl or heterocyclyl independently selected from:

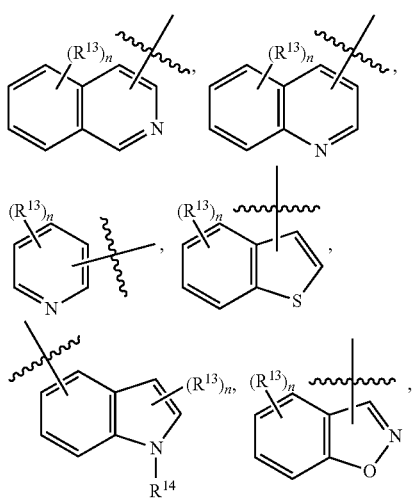

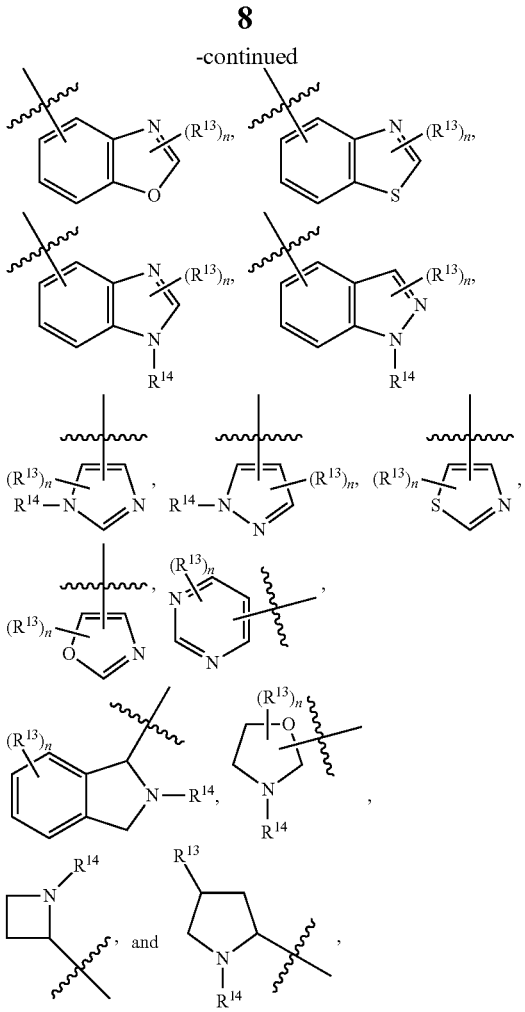

wherein n is 0 or an integer selected from 1 through 4;
each R$^{13}$ is independently selected from hydrogen, C$_1$ to C$_6$ alkyl, C$_1$ to C$_4$ haloalkyl, phenyl, benzyl, C$_1$ to C$_6$ alkoxy, C$_1$ to C$_4$ haloalkoxy, heterocyclyl, halogen, NR$^c$R$^d$, hydroxyl, cyano, and oxo, where R$^c$ and R$^d$ are independently hydrogen or C$_1$ to C$_4$ alkyl; and
R$^{14}$ is hydrogen (H), C$_1$ to C$_6$ alkyl, benzyl, or —C(O)OR$^4$, wherein R$^4$ is C$_1$ to C$_6$ alkyl.

In a tenth embodiment of the first aspect the present disclosure provides a compound of Formula (Ia) or a pharmaceutically acceptable salt thereof, wherein
R$^1$ is —C(O)R$^x$;
R$^2$ is —C(O)R$^y$;
R$^x$ and R$^y$ are cycloalkyl independently selected from:

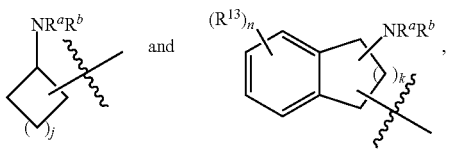

wherein
j is 0, 1, 2, or 3;
k is 0, 1, or 2;
n is 0 or an integer selected from 1 through 4;

each $R^{13}$ is independently selected from hydrogen, $C_1$ to $C_6$ alkyl, $C_1$ to $C_4$ haloalkyl, $C_1$ to $C_6$ alkoxy, halogen, hydroxyl, cyano, and nitro; and $R^a$ and $R^b$ are each independently hydrogen, $C_1$ to $C_6$ alkyl, or —C(O)OR$^7$, wherein $R^7$ is $C_1$ to $C_6$ alkyl.

In an eleventh embodiment of the first aspect the present disclosure provides a compound of Formula (Ia) or a pharmaceutically acceptable salt thereof, wherein $R^1$ is —C(O)R$^x$;

$R^2$ is —C(O)R$^y$;

$R^x$ and $R^y$ are independently arylalkyl, wherein aryl part of said arylalkyl may optionally be substituted with (NR$^a$R$^b$)alkyl; and $R^a$ and $R^b$ are independently hydrogen, $C_1$ to $C_6$ alkyl, or benzyl, or alternatively, $R^a$ and $R^b$, together with the nitrogen atom to which they are attached, form a five- or six-membered ring selected from

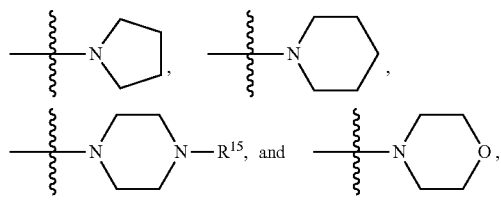

wherein $R^{15}$ is hydrogen, $C_1$ to $C_6$ alkyl, or benzyl.

In a twelfth embodiment of the first aspect the present disclosure provides a compound of Formula (Ia) or a pharmaceutically acceptable salt thereof, wherein $R^1$ and $R^2$ are the same and are selected from the group consisting of

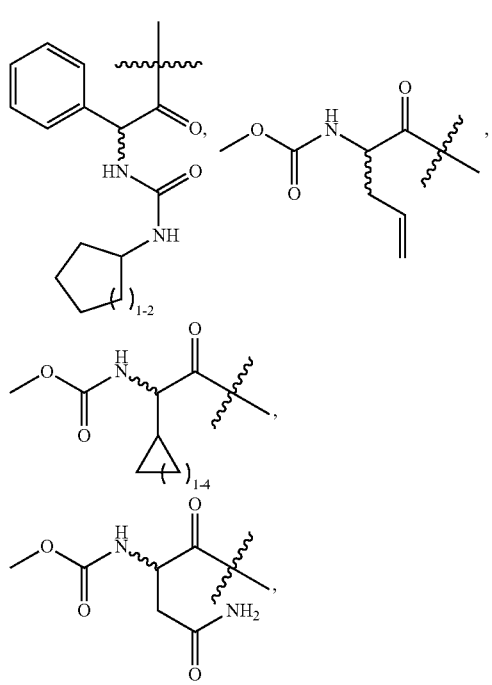

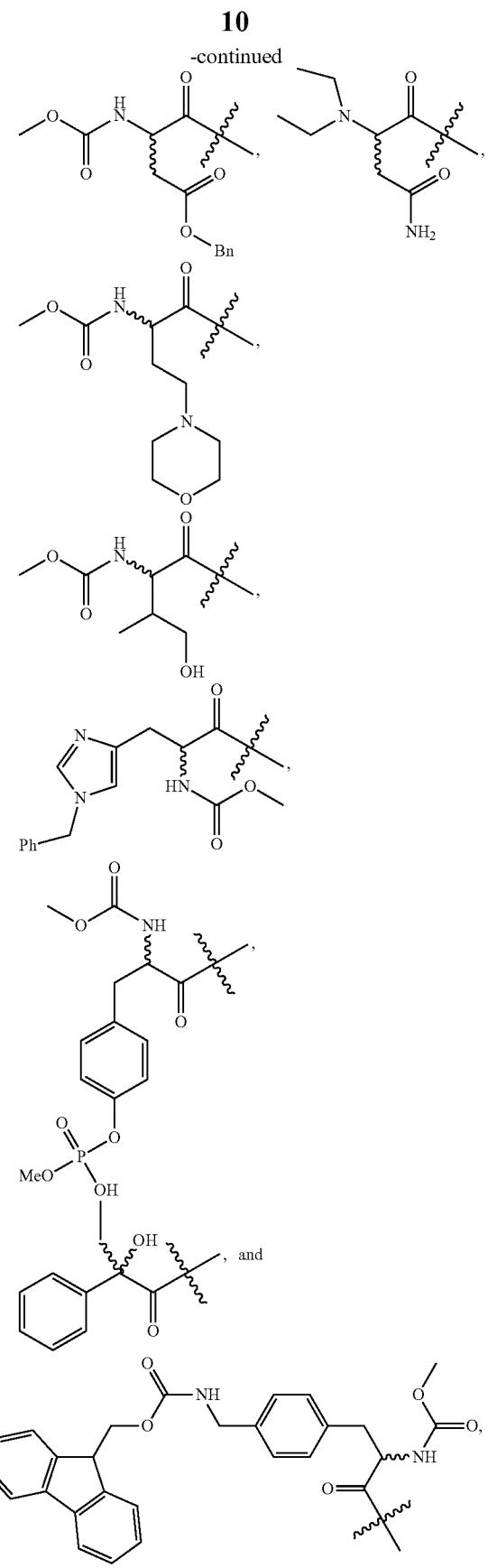

wherein a squiggle bond (〜) in the structure indicates that a stereogenic center to which the bond is attached can take either (R)- or (S)-configuration so long as chemical bonding principles are not violated.

In a thirteenth embodiment of the first aspect the present disclosure provides a compound of Formula (I), or a pharmaceutically acceptable salt thereof, wherein
$R^1$ is —C(O)$R^x$;
$R^2$ is —C(O)$R^y$; and
$R^x$ and $R^y$ are both t-butoxy.

In a fourteenth embodiment of the first aspect the present disclosure provides a compound of Formula (I), or a pharmaceutically acceptable salt thereof, wherein
$R^1$ and $R^2$ are both hydrogen.

In a second aspect the present disclosure provides a compound of Formula (II):

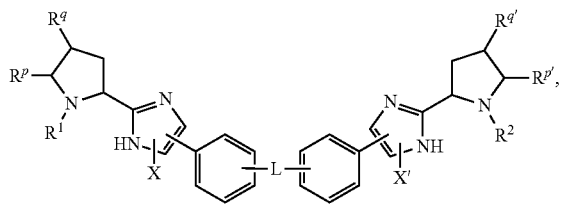

(I)

or a pharmaceutically acceptable salt thereof, wherein:

L is selected from —O—, —CH$_2$CH$_2$—, —CH=CH—, —C≡C—, —OCH$_2$—, —CH$_2$O—, —CH$_2$OCH$_2$—,

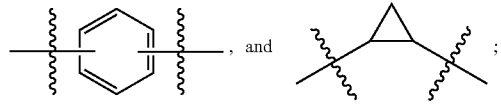

, and

;

X and X' are independently hydrogen (H) or halogen;
$R^p$ is hydrogen or $C_1$ to $C_4$ alkyl, and $R^q$ is hydrogen, or alternatively, $R^p$ and $R^q$, together with the carbon atoms to which they are attached, form a cyclopropyl ring;
$R^{p'}$ is hydrogen or $C_1$ to $C_4$ alkyl, and $R^{q'}$ is hydrogen, or alternatively, $R^{p'}$ and $R^{q'}$, together with the carbon atoms to which they are attached, form a cyclopropyl ring;
$R^1$ is hydrogen or —C(O)$R^x$;
$R^2$ is hydrogen or —C(O)$R^y$;
$R^x$ and $R^y$ are independently selected from cycloalkyl, heteroaryl, heterocyclyl, alkoxy, and alkyl, said alkyl being substituted by one or more substituents independently selected from aryl, alkenyl, cycloalkyl, heterocyclyl, heteroaryl, —OR$^3$, —C(O)OR$^4$, —NR$^a$R$^b$, and —C(O)NR$^c$R$^d$,
wherein any said aryl and heteroaryl may optionally be substituted with one or more substituents independently selected from alkyl, haloalkyl, arylalkyl, heterocyclyl, heterocyclylalkyl, halogen, cyano, nitro, —C(O)OR$^4$, —OR$^5$, —NR$^a$R$^b$, (NR$^a$R$^b$)alkyl, and (MeO)(HO)P(O)O—, and
wherein any said cycloalkyl and heterocyclyl may optionally be fused onto an aromatic ring and may optionally be substituted with one or more substituents independently selected from alkyl, hydroxyl, halogen, aryl, —NR$^a$R$^b$, oxo, and —C(O)OR$^4$;
$R^3$ is hydrogen, alkyl, or arylalkyl;
$R^4$ is alkyl or arylalkyl;
$R^5$ is hydrogen, alkyl, or arylalkyl;
$R^a$ and $R^b$ are independently selected from hydrogen, alkyl, cycloalkyl, arylalkyl, heteroaryl, —C(O)R$^6$, —C(O)OR$^7$, —C(O)NR$^c$R$^d$, and (NR$^c$R$^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;
$R^6$ is alkyl;
$R^7$ is alkyl, arylalkyl, or haloalkyl; and
$R^c$ and $R^d$ are independently selected from hydrogen, alkyl, arylalkyl, and cycloalkyl.

In a third aspect the present disclosure provides a composition comprising a compound of Formula (I), or a pharmaceutically acceptable salt thereof, and a pharmaceutically acceptable carrier, wherein Formula (I) is defined according to any of the embodiments described above in the first aspect of the present disclosure.

In a first embodiment of the third aspect the composition further comprises at least one additional compound having anti-HCV activity.

In a second embodiment of the third aspect at least one of the additional compounds is an interferon or a ribavirin.

In a third embodiment of the third aspect the interferon is selected from interferon alpha 2B, pegylated interferon alpha, consensus interferon, interferon alpha 2A, and lymphoblastoid interferon tau.

In a fourth embodiment of the third aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the third aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of Formula (I), or a pharmaceutically acceptable salt thereof, wherein Formula (I) is defined according to any of the embodiments described above in the first aspect of the present disclosure.

In a first embodiment of the fourth aspect the method further comprises administering at least one additional compound having anti-HCV activity prior to, after or simultaneously with the compound of Formula (I), or a pharmaceutically acceptable salt thereof.

In a second embodiment of the fourth aspect at least one of the additional compounds is an interferon or a ribavirin.

In a third embodiment of the fourth aspect the interferon is selected from interferon alpha 2B, pegylated interferon alpha, consensus interferon, interferon alpha 2A, and lymphoblastoid interferon tau.

In a fourth embodiment of the fourth aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the fourth aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

The compounds of the present disclosure can be effective to inhibit the function of the HCV NS5A protein. In particular, the compounds of the present disclosure can be effective to inhibit the HCV 1b genotype or multiple genotypes of HCV.

Therefore, this disclosure also encompasses: (1) compositions comprising a compound of Formula (I), or a pharmaceutically acceptable salt thereof, and a pharmaceutically acceptable carrier; and (2) a method of treating an HCV infection in a patient, comprising administering to the patient a therapeutically effective amount of a compound of Formula (I), or a pharmaceutically acceptable salt thereof.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

Certain features of the structure of Formula (I) are further illustrated below:

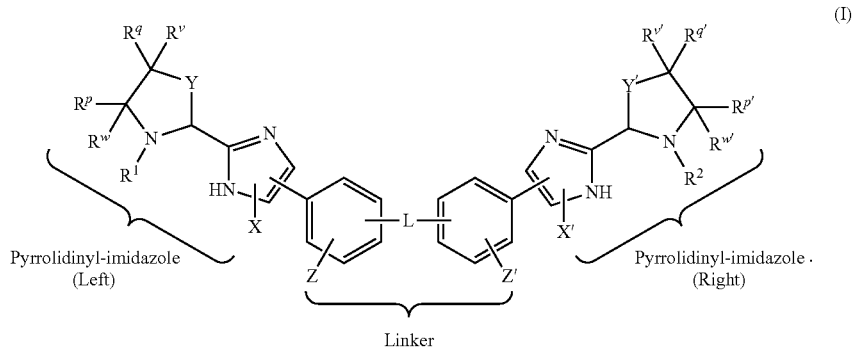

In Formula (I), as depicted above, the "pyrrolidinyl-imidazole" moiety on the left side of the "linker" is independent from the "pyrrolidinyl-imidazole" moiety on the right side of the linker group in respect to, e.g., (1) tautomer form of imidazole ring, (2) absolute configuration of the stereogenic centers on the pyrrolidine ring, and (3) substituents on the pyrrolidine nitrogen, i.e., $R^1$ and $R^2$ are independent from each other, although in some circumstances they are preferably the same.

It should be understood that the depiction of a pyrrolidine moiety on the "left" side or on the "right" side is for illustration purpose only, which does not in any way limit the scope of the disclosure.

In the linker group of Formula (I), the linkage between "L" and the two benzene rings encompasses all the following combinations:

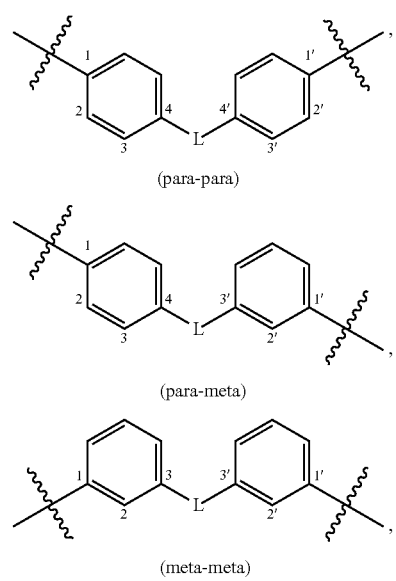

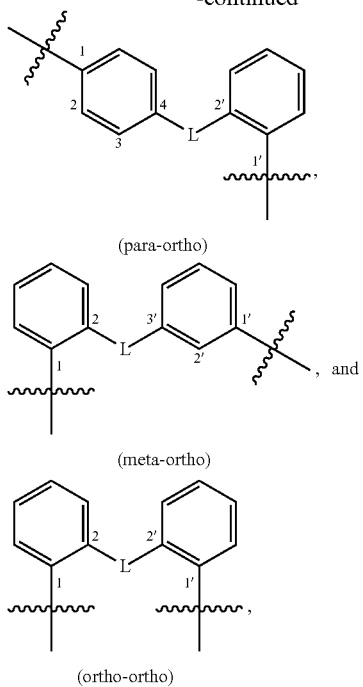

(para-ortho)

(meta-ortho)

(ortho-ortho)

wherein the "para-para," "para-meta," and "meta-meta" linkages are preferred.

Likewise, in Formula (I), when L is a phenylene

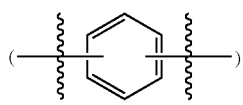

group, it can link to the adjacent two benzene rings by the following manners:

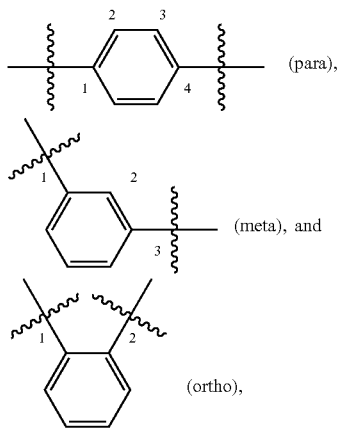

(para), (meta), and (ortho), wherein the "para" and "meta" arrangements are preferred, and the "para" arrangement is the more preferred.

In Formula (I), when L is a vinylene (—CH═CH—) group, it can take either trans- or cis-configuration, as depicted below:

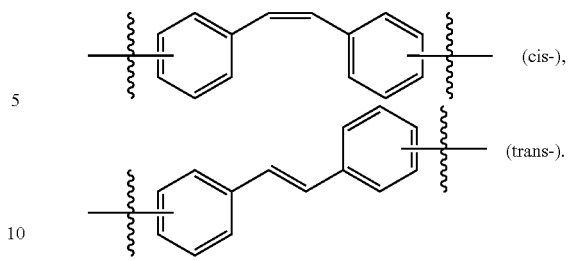

(cis-), (trans-).

In Formula (I), when L is a cyclopropylene

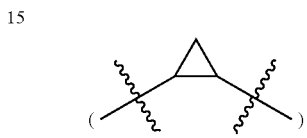

group, the two benzene substituents can be either trans- or cis- to each other, forming one of the following four configurations:

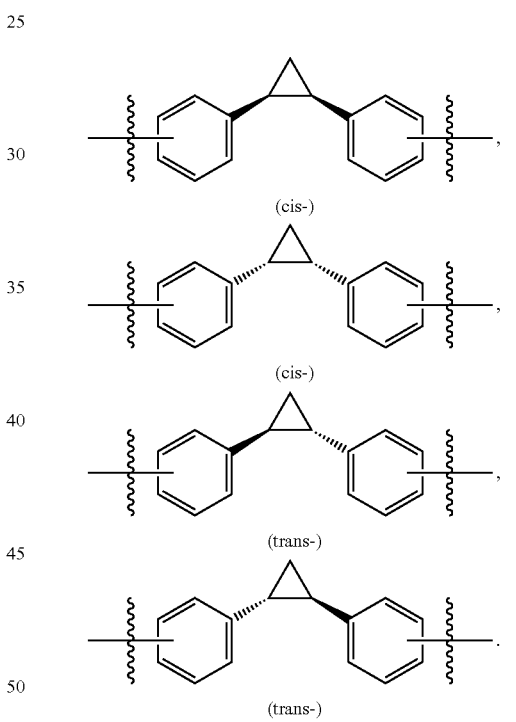

(cis-), (cis-), (trans-)

(trans-)

In a pyrrolidine ring of a pyrrolidinyl-imidazole moiety, the stereogenic carbon center to which the imidazole group is attached can take either (R)- or (S)-configuration as depicted below:

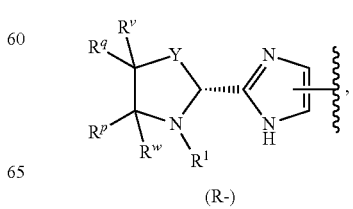

(R-)

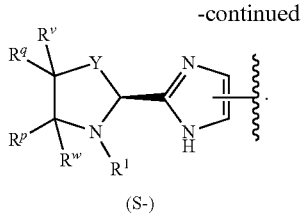

(S-)

When a cyclopropyl ring is fused onto a pyrrolidine ring of a pyrrolidinyl-imidazole moiety, i.e., when ($R^p$, $R^q$) together is —CH$_2$—, the CH$_2$ group of the fused cyclopropyl ring can take either α- or β-position relative to the pyrrolidine ring, as depicted below:

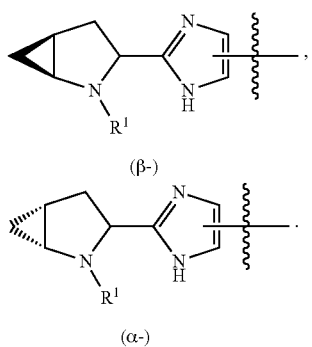

Thus, this disclosure is intended to cover all possible stereoisomers even when a single stereoisomer, or no stereochemistry, is described in a structure.

In Formula (I), the linkage between a benzene ring of the linker group and an imidazole ring of a pyrrolidinyl-imidazole moiety can take place in either the C-4 or the C-5 position (see below) of the imidazole ring. As a person of ordinary skill in the art would understand, due to tautomerization of the imidazole ring, a bonding of a benzene ring to the C-4 position may be equivalent to a bonding of the benzene ring to the C-5 position, as shown in the following equation:

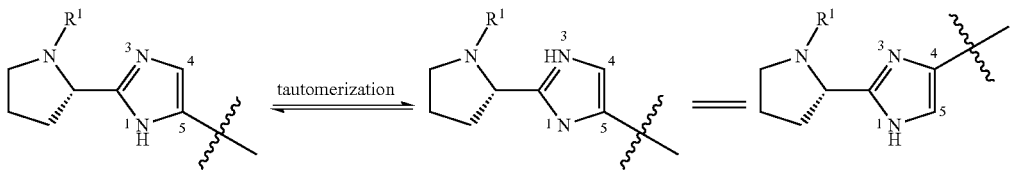

The sample principle also applies to substituent X or X'.

Thus, this disclosure is intended to cover all possible tautomers even when a structure depicts only one of them.

In this disclosure, a floating bond (e.g.,

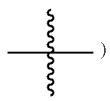)

or a floating substituent (e.g., —$R^{13}$) on a structure indicates that the bond or substituent can attach to any available position of the structure by removal of a hydrogen from the available position. It should be understood that in a bicyclic or polycyclic ring structure, unless specifically defined otherwise, the position of a floating bond or a floating substituent does not limit the position of such bond or substituent to a specific ring. Thus, the following two substituents should be construed to be equivalent:

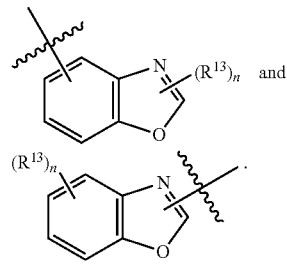

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, for substituent)($R^{10}$)$_n$, when n is 2, each of the two $R^{10}$ groups may be the same or different.

All patents, patent applications, and literature references cited in the specification are herein incorporated by reference in their entirety. In the case of inconsistencies, the present disclosure, including definitions, will prevail.

DEFINITIONS

Definitions have been provided above for each of the groups defined. In addition, the following definitions shall be used.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group may be substituted as described in the definition of the term "aryl."

The term "acetyl," as used herein, refers to —C(O)CH$_3$.

The term "alkenyl," as used herein, refers to a monovalent, straight or branched hydrocarbon chain having one or more, preferably one to two, double bonds therein.

The double bond of an alkenyl group can be unconjugated or conjugated to another unsaturated group. Suitable alkenyl groups include, but are not limited to, C$_2$ to C$_{10}$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkoxy," as used herein, refers to an alkyl group attached to the parent molecular moiety through an oxygen atom. Representative examples of alkoxy group include, but are not limited to, methoxy ($CH_3O$—), ethoxy ($CH_3CH_2O$—), and t-butoxy (($CH_3)_3CO$—).

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon by removal of a hydrogen from one of the saturated carbons. The alkyl group preferably contains from one to ten carbon atoms.

Representative examples of alkyl group include, but are not limited to, methyl, ethyl, isopropyl, and tert-butyl.

The term "alkylcarbonyl," as used herein, refers to an alkyl group attached to the parent molecular moiety through a carbonyl group. Representative examples of alkylcarbonyl group include, but are not limited to, acetyl (—$C(O)CH_3$), propanoyl (—$C(O)CH_2CH_3$), n-butyryl (—$C(O)CH_2CH_2CH_3$), and 2,2-dimethylpropanoyl or pivaloyl (—$C(O)C(CH_3)_3$).

The term "alkylsulfonyl," as used herein, refers to an alkyl group attached to the parent molecular moiety through a sulfonyl group.

The term "allyl," as used herein, refers to the —$CH_2CH=CH_2$ group.

The term "aryl," as used herein, refers to a group derived from an aromatic carbocycle by removal of a hydrogen atom from an aromatic ring. The aryl group can be monocyclic, bicyclic or polycyclic, wherein in bicyclic or polycyclic aryl group, the aromatic carbocycle can be fused onto another four- to six-membered aromatic or non-aromatic carbocycle. Representative examples of aryl groups include, but are not limited to, phenyl, indanyl, indenyl, naphthyl, and 1,2,3,4-tetrahydronaphth-5-yl.

The term "arylalkyl," as used herein, refers to an alkyl group substituted with one, two, or three aryl groups, wherein aryl part of the arylalkyl group may optionally be substituted by one to five substituents independently selected from $C_1$ to $C_6$ alkyl, $C_1$ to $C_4$ haloalkyl, $C_1$ to $C_6$ alkoxy, halogen, cyano, and nitro groups, Represented examples of arylalkyl include, but are not limited to, benzyl, 2-phenyl-1-ethyl ($PhCH_2CH_2$—), (naphth-1-yl)methyl, and (naphth-2-yl)methyl.

The term "arylsulfonyl," as used herein, refers to an aryl group attached to the parent molecular moiety through a sulfonyl group.

The term "benzyl," as used herein, refers to a methyl group on which one of the hydrogen atoms is replaced by a phenyl group, wherein said phenyl group may optionally be substituted by one to five substituents independently selected from methyl, trifluoromethyl (—$CF_3$), methoxy (—$OCH_3$), halogen, and nitro (—$NO_2$).

Representative examples of benzyl group include, but are not limited to, $PhCH_2$—, 4-MeO—$C_6H_4CH_2$—, and 2,4,6-tri-methyl-$C_6H_4CH_2$—.

The term "bridged bicyclic ring," as used herein, refers to a ring structure comprising a bridgehead between two of the ring members, wherein the ring and the bridgehead optionally may independently comprise one or more, preferably one to two, heteroatoms independently selected from nitrogen, oxygen, and sulfur. Illustrated examples of a bridged bicyclic ring structure include, but are not limited to:

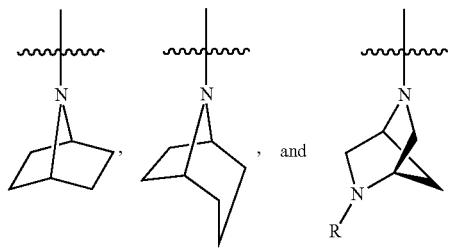

The terms "Cap" and "cap," as used herein, refer to the group which is placed on the nitrogen atom of the pyrrolidine ring in the compounds of formula (I). It should be understood that "Cap" or "cap" can also refer to the reagent which is a precursor to the final "cap" in compounds of formula (I) and is used as one of the starting materials in the reaction to append a group on the pyrrolidine nitrogen that results in the final product, a compound which contains the functionalized pyrrolidine that will be present in the compound of formula (I).

The term "carbonyl," as used herein, refers to —$C(O)$—.

The term "carboxyl," or "carboxy," as used herein, refers to —$CO2H$.

The term "cyano," as used herein, refers to —CN.

The term "cycloalkyl," as used herein, refers to a group derived from a saturated carbocycle, having preferably three to eight carbon atoms, by removal of a hydrogen atom from the saturated carbocycle, wherein the saturated carbocycle can optionally be fused onto one or two other aromatic or nonaromatic carbocycles. Representative examples of cycloalkyl groups include, but are not limited to, cyclopropyl, cyclopentyl, cyclohexyl, and 1,2,3,4-tetrahydronaphth-1-yl.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by at least one halogen atom. The haloalkyl group can be an alkyl group of which all hydrogen atoms are substituted by halogens. Representative examples of haloalkyl include, but are not limited to, trifluoromethyl ($CF_3$—), 1-chloroethyl ($ClCH_2CH_2$—), and 2,2,2-trifluoroethyl ($CF_3CH_2$—).

The term "heteroaryl," as used herein, refers to group derived from a monocyclic, bicyclic, or polycyclic compound comprising at least one aromatic ring comprising one or more, preferably one to three, heteroatoms independently selected from nitrogen, oxygen, and sulfur, by removal of a hydrogen atom from an aromatic ring thereof. As is well known to those skilled in the art, heteroaryl rings have less aromatic character than their all-carbon counterparts. Thus, for the purposes of the disclosure, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, isoxazolyl, oxazolyl, indolyl, quinolinyl, isoquinolinyl, benzisoxazolyl, benzothiazolyl, benzothienyl, and pyrrolopyridinyl.

The term "heteroarylalkyl," as used herein, refers to an alkyl group substituted with one, two, or three heteroaryl groups.

The term "heterobicyclyl," as used herein, refers to a ring structure comprising two fused or bridged rings that include carbon and one or more, preferably one to three, heteroatoms independently selected from nitrogen, oxygen, and sulfur. The heterobicyclic ring structure is a subset of heterocyclic ring and can be saturated or unsaturated. Examples of heterobicyclic ring structures include, but are not limited to, tropane, quinuclidine, and 7-azabicyclo[2.2.1]heptane.

The term "heterocyclyl," as used herein, refers to a group derived from a monocyclic, bicyclic, or polycyclic compound comprising at least one nonaromatic ring comprising one or more, preferably one to three, heteroatoms independently selected from nitrogen, oxygen, and sulfur, by removal of a hydrogen atom from the nonaromatic ring. The heterocyclyl group encompasses the heterobicyclyl group.

The heterocyclyl groups of the present disclosure can be attached to the parent molecular moiety through a carbon atom or a nitrogen atom in the group. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl.

The term "heterocyclylalkyl," as used herein, refers to an alkyl group substituted with one, two, or three heterocyclyl groups.

The terms "hydroxy" or "hydroxyl," as used herein, refer to —OH.

The term "hydroxyalkyl," as used herein, refers to an alkyl group substituted with one, two, or three hydroxy groups.

The term "nitro," as used herein, refers to —NO$_2$.

The term "—NR$^a$R$^b$," as used herein, refers to two groups, R$^a$ and R$^b$, which are attached to the parent molecular moiety through a nitrogen atom, or alternatively R$^a$ and R$^b$, together with the nitrogen atom to which they are attached, form a 5- or 6-membered ring or a fused- or bridged-bicyclic ring structure optionally containing one, two, or three additional heteroatom independently selected from nitrogen, oxygen, and sulfur. The term "—NR$^c$R$^d$" is defined similarly.

The term "(NR$^a$R$^b$)alkyl," as used herein, refers to an alkyl group substituted with one, two, or three —NR$^a$R$^b$ groups. The term "(NR$^c$R$^d$)alkyl" is defined similarly.

The term "oxo," as used herein, refers to =O.

The term "sulfonyl," as used herein, refers to —SO$_2$—.

The term "trialkylsilyl," as used herein, refers to —SiR$_3$, wherein each R is C$_1$ to C$_4$ alkyl or phenyl. The three R groups may be the same or different. Representative examples of "trialkylsilyl" include, but are not limited to, trimethylsilyl (TMS), tert-butyldiphenylsilyl (TBDMS), tert-butyldimethylsilyl (TBS or TBDMS), and triisopropylsilyl (TIPS).

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylpropionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N- dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more, preferably one to three, pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more, preferably one to three, pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use. Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles.

Liposomes can be formed from a variety of phospholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharm. Res.*, 3(6):318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology*, 38:1282 (2003); *Biochem. Biophys. Res. Commun.*, 313:42 (2004); *J. Gastroenterol.*, 38:567 (2003)).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin inhibitors | Novartis Debiopharm |
| Debio-025 | | | |
| Zadaxin | | Immunomodulator | SciClone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/ Elan Pharmaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO 2005/047288 May 26, 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co., Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novartis |
| 2'C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering-Plough |
| Zadazim | Immune modulator | Immune modulator | SciClone Pharmaceuticals Inc., San Mateo, CA |
| Ceplene | Immunomodulator | Immune modulator | Maxim Pharmaceuticals Inc., San Diego, CA |
| CELLCEPT ® | Immunosuppressant | HCV IgG immunosuppressant | F. Hoffmann-La Roche LTD, Basel, Switzerland |

TABLE 1-continued

| Brand Name | Physiological Class | Type of Inhibitor or Target | Source Company |
|---|---|---|---|
| Civacir | Immunosuppressant | HCV IgG immunosuppressant | Nabi Biopharmaceuticals Inc., Boca Raton, FL |
| Albuferon-α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| REBIF ® | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering-Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-Nucleoside NS5B polymerase inhibitor | Anadys Pharmaceuticals, Inc., San Diego, CA, USA |

TABLE 1-continued

| Brand Name | Physiological Class | Type of Inhibitor or Target | Source Company |
|---|---|---|---|
| IDX375 | Antiviral | Non-Nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | ViroChem Pharma |
| VCH-916 | Antiviral | NS5B polymerase inhibitor | ViroChem Pharma |
| GS-9190 | Antiviral | NS5B polymerase inhibitor | Gilead |
| Peg-interferon lamda | Antiviral | Interferon | ZymoGenetics/ Bristol-Myers Squibb |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition. The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials. This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative examples which follow, are well-known to those skilled in the art. Some of the abbreviations used are as follows: TFA for trifluoroacetic acid; min or min. or mins for minutes; MeCN or ACN for acetonitrile; LDA for lithium diisopropylamide; DMSO for dimethylsulfoxide; h or hr or hrs for hours; Boc or BOC for tert-butoxycarbonyl; HATU for O-(7-azabenzotriazol-1-yl)-N,N,N',N'-tetramethyluronium hexafluorophosphate; RT or Rt or rt for retention time or room temperature (context will dictate); Me for methyl; DMF for N,N-dimethylformamide; Pd(Ph$_3$P)$_4$ for tetrakistriphenyl phosphine palladium; MeOH for methanol; MeOD for CD$_4$OD; TEA for triethylamine; Ph for phenyl; TBDPS for tert-butyldiphenylsilyl; Et$_3$N or TEA for triethylamine; DMAP for N,N-dimethylaminopyridine; EtOAc for ethyl acetate; TBAF for tetrabutylammonium fluoride; THF for tetrahydrofuran; DIEA or DIPEA or iPr$_2$NEt for diisopropylethylamine; NCS for N-chlorosuccinimide; NBS for N-bromosuccinimide; DCM for dichloromethane; SEM for 2-(trimethylsilyl)ethoxymethyl; DCE for 1,2-dichloroethane; EDCI for 1-ethyl-3-(3-dimethylaminopropyl)carbodiimide; DBU for 1,8-diazabicyclo[5.4.0]undec-7-ene; Pd(t-Bu$_3$P)$_2$ for palladium bis(tributylphosphine); HMDS for hexamethyldisilazide; TMSCHN$_2$ for trimethylsilyldiazomethane; H-D-Ser-OBzl for D-serine benzyl ester; i-PrOH for isopropanol; LiHMDS for lithium hexamethyldisilazide; DIBAL or DIBALH for diisobutylaluminum hydride; TBDMS for tert-butyldimethylsilyl; CBz for carbobenzyloxy; Bn for benzyl; DEAD for diethyl azodicarboxylate; mCPBA for meta-chloroperoxybenzoic acid; TMSCN for trimethylsilyl cyanide; dpppe for 1,5-Bis(diphenylphosphino) pentane; TMEDA for tetramethylethylenediamine; OAc for acetate; DMA for N,N-dimethylacetamide; and d for days.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

EXAMPLES

Unless noted otherwise, purity assessments were conducted on Shimadzu LC system, and retention time (R$_t$) determination and low resolution mass analysis were conducted on a Shimadzu LC system coupled with Waters MICROMASS® ZQ MS system. It should be noted that retention times may vary slightly between machines.

Condition 1
Column=PHENOMENEX®, C18, 3.0×50 mm, 10 µm
Start % B=0
Final % B=100
Gradient time=2 min
Stop time=3 min
Flow Rate=4 mL/min
Wavelength=220 nm
Solvent A=0.1% TFA in 10% methanol/90% water
Solvent B=0.1% TFA in 90% methanol/10% water
Condition 2
Column=XTERRA®, C18, 3.0×50 mm, S7
Start % B=0
Final % B=100
Gradient time=2 min
Stop time=3 min
Flow Rate=5 mL/min
Wavelength=220 nm Solvent A=0.2% H₃PO₄ in 10% methanol/90% water
Solvent B=0.2% H₃PO₄ in 90% methanol/10% water
Condition 3
Column=PHENOMENEX®, C18, 3.0×50 mm, 10 μm
Start % B=0
Final % B=100
Gradient time=3 min
Stop time=4 min
Flow Rate=4 mL/min
Wavelength=220 nm
Solvent A=0.1% TFA in 10% methanol/90% water
Solvent B=0.1% TFA in 90% methanol/10% water
Condition 4
Column=XTERRA®, C18, 3.0×50 mm, S7
Start % B=0
Final % B=100
Gradient time=10 min
Stop time=11 min
Flow Rate=5 mL/min
Wavelength=220 nm
Solvent A=0.2% H₃PO₄ in 10% methanol/90% water
Solvent B=0.2% H₃PO₄ in 90% methanol/10% water
Condition 5
Column=PHENOMENEX®, C18, 3.0×50 mm, 10 μm
Start % B=0
Final % B=100
Gradient time=4 min
Stop time=5 min
Flow Rate=4 mL/min
Wavelength=220 nm
Solvent A=0.1% TFA in 10% methanol/90% water
Solvent B0.1% TFA in 90% methanol/10% water
Condition 6
Column=Phenomenex-Luna, C18, 4.6×50 mm, S10
Start % B=0
Final % B=100
Gradient time=3 min
Stop time=4 min
Flow Rate=4 mL/min
Wavelength=220 nm
Solvent A=0.1% TFA in 10% methanol/90% water
Solvent B=0.1% TFA in 90% methanol/10% water
Condition 7
Column=Phenomenex-Luna, C18, 3.0×50 mm, S10
Start % B=0
Final % B=100
Gradient time=2 min
Stop time=3 min
Flow Rate=4 mL/min
Wavelength=220 nm
Solvent A=0.1% TFA in 10% methanol/90% water
Solvent B=0.1% TFA in 90% methanol/10% water
Condition 9
Column=Waters Sunfire, C18, 4.6×150 mm, 3.5 μm
Start % B=10
Final % B=50
Gradient time=20 min
Stop time=25 min
Flow Rate=1 mL/min
Wavelength=220 & 254 nm
Slovent A=0.1% TFA in 5% CH₃CN/95% H₂O
Solvent B=0.1% TFA in 95% CH₃CN/5% H₂O
Condition 9a
Same as Condition 9 with the exception that Stop time=35 min Condition 9a.1
Column Waters Sunfire, C18, 4.6×150 mm, 3.5 μm
Start % B=30
Final % B=100
Gradient time=20 min
Stop time=25 min
Flow Rate=1 mL/min
Wavelength=220 & 254 nm
Slovent A=0.1% TFA in 5% CH₃CN/95% H₂O
Solvent B=0.1% TFA in 95% CH₃CN/5% H₂O
Condition 10
Column=Waters Xbridge phenyl, C18, 4.6×150 mm, 3 μm
Start % B=10
Final % B=50
Gradient time=20 min
Stop time=25 min
Flow Rate=1 mL/min
Wavelength=220 & 254 nm
Slovent A=0.1% TFA in 5% CH₃CN/95% H₂O
Solvent B=0.1% TFA in 95% CH₃CN/5% H₂O
Condition 10a
Same as Condition 10 with the exception that Stop time=35 min
Condition 10a.1
Column=Waters Xbridge phenyl, C18, 4.6×150 mm, 3 μm
Start % B=40
Final % B=100
Gradient time=20 min
Stop time=25 min
Flow Rate=1 mL/min
Wavelength=220 & 254 nm
Slovent A=0.1% TFA in 5% CH₃CN/95% H₂O
Solvent B=0.1% TFA in 95% CH₃CN/5% H₂O
Condition 10b
Column=Sunfire, C18, 3.0×150 mm, 3.5 μm
Start % B=10
Final % B=40
Gradient time=15 min
Stop time=18 min
Flow Rate=1 mL/min
Wavelength 1=220 nm
Wavelength 2=254 nm
Solvent A=0.1% TFA in 5% MeCN/95% water
Solvent B=0.1% TFA in 95% MeCN/5% water
Condition 10c
Column=Xbridge Phenyl, C18, 3.0×150 mm, 3.5 μm
Start % B=10
Final % B=40
Gradient time=15 min
Stop time=18 min
Flow Rate=1 mL/min
Wavelength 1=220 nm
Wavelength 2=254 nm
Solvent A=0.1% TFA in 5% MeCN/95% water
Solvent B=0.1% TFA in 95% MeCN/5% water
Condition 10d
Column=PHENOMENEX®-Luna, C18, 2.0×50 mm, 3 μm
Start % B=0
Final % B=100
Gradient time=4 min
Stop time=5 min
Flow Rate=0.8 mL/min
Wavelength=220 nm
Solvent A=0.1% TFA in 10% methanol/90% water
Solvent B=0.1% TFA in 90% methanol/10% water
Oven temp.=40° C.

Condition 10e (Agilent 1200 series LC system)
Column=Xbridge phenyl, C18, 4.6×150 mm, 3.5 μm
Solvent A=Buffer: CH₃CN (95:5)
Solvent B=Buffer: CH₃CN (5:95)
Buffer=0.05% TFA in H₂O (pH 2.5, adjusted with dilute ammonia)
Start % B=10
Final % B=100
Gradient time=12 min
Isocratic time=3 min
Stop time=23 min
Flow Rate=1 mL/min
Wavelength=220 & 254 nm
Condition 10f (Agilent LC-1200 series coupled with 6140 single quad. mass spectrometer, ESI+ve mode)
Column=Zorbax SB, C18, 4.6×50 mm, 5 μm
Slovent A=MeOH (10%)+0.1% TFA in H₂O (90%)
Solvent B=MeOH (90%)+0.1% TFA in H₂O (10%)
Start % B=0
Final % B=100
Gradient time=3 min
Isocratic time=1 min
Stop time=5 min
Flow Rate=5 mL/min
Wavelength=220 nm
Condition 10g (Agilent LC-1200 series coupled with 6140 single quad. mass spectrometer, ESI+ve mode)
Column=Ascentis Express, C-8, 2.1×5 mm, 2.7 μm
Slovent A=CH₃CN (2%)+10 mM NH₄COOH in H₂O (98%)
Solvent B=CH₃CN (98%)+10 mM NH₄COOH in H₂O (2%)
Start % B 0
Final % B=100
Gradient time=1.5 min
Isocratic time=1.7 min
Stop time=4 min
Flow Rate=1 mL/min
Wavelength=220 nm
Condition 10h
Column=PHENOMENEX®-Luna, C18, 4.6×30 mm, S10
Start % B=0
Final % B=100
Gradient time=3 min
Stop time=4 min
Flow Rate=4 mL/min
Wavelength=220 nm
Solvent A=0.1% TFA in 10% methanol/90% water
Solvent B=0.1% TFA in 90% methanol/10% water
Condition 11
Column=PHENOMENEX®-Luna, C18, 50×2 mm, 3 μm
Start % B=0
Final % B=100
Gradient time=4 min
Stop time=5 min
Flow Rate=0.8 mL/min
Wavelength=220 nm
Solvent A=5% methanol/95% water: 10 mM ammonium acetate
Solvent B=95% methanol/5% water: 10 mM ammonium acetate
Oven temperature=40° C.
Condition 12 (Waters Acquity HPLC with Waters PDA UV-Vis detection and Waters SQ MS-ESCI probe)
Column=Waters Acquity BEH, C18, 150×2.1 mm ID, 1.7 μm (at 35° C.)
Mobile phase A=0.05% TFA in water
Mobile phase B=0.05% TFA in acetonitrile
Solvent system: Hold 10% B: 0-1 min; 10-98% B: 1-32 min; Hold 98% B: 32-35 min;
98-10% B: 35-35.3 min; hold 10% B: 35.3-40 min
Flow rate=0.35 ml/min
UV detection=335 nm

EXAMPLES

Example OL-1

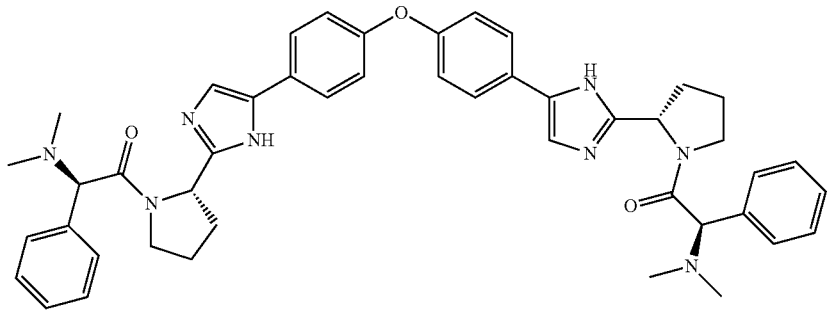 [SMILES: CN(C)[C@@H](C(=O)N1CCC[C@H]1c1ncc(-c2ccc(Oc3ccc(-c4cnc([C@@H]5CCCN5C(=O)[C@@H](c5ccccc5)N(C)C)[nH]4)cc3)cc2)[nH]1)c1ccccc1]

Example OL-1

Step a

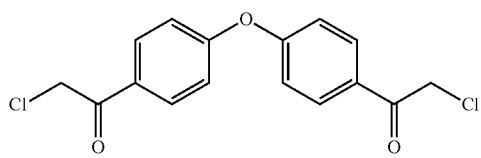 [SMILES: O=C(CCl)c1ccc(Oc2ccc(C(=O)CCl)cc2)cc1]

4,4'-Oxybis-(benzoic acid) dimethyl ester (1.5 g, 5.24 mmol) was added to a solution of chloroiodomethane (3.05 mL, 41.92 mmol) in tetrahydrofuran (50 mL) and the resulting solution was cooled to −78° C. A 1.8M solution of LDA (29 mL, 52 mmol) in tetrahydrofuran was added dropwise and the resulting brown suspension was stirred at −78° C. for 15 min. A solution of glacial acetic acid in tetrahydrofuran (10 mL in 50 mL) was then added slowly and the brown mixture was stirred at −78° C. for 10 min. before allowing it to reach room temperature. The mixture was taken up in ethyl acetate and brine (1:1, 50 mL) and the organic layer was then separated, washed with a sat. solution of sodium bicarbonate and brine, dried (MgSO₄), filtered, and concentrated in vacuo. The residue was submitted to flash chromatography (silica gel; 15% ethyl acetate/hexanes) to provide OL-1a as a pale brown solid (0.6 g). ¹H NMR (500 MHz, DMSO-d₆) δ ppm 5.17 (s, 4 H), 7.22 (d, J=8.85 Hz, 4 H), 8.06 (d, J=8.85 Hz, 4 H). LC (Cond. 2): RT=1.53 minutes, 97% homogeneity index; LCMS: Anal. Calcd. For (M−H)⁺ C₁₆H₁₁Cl₂O₃: 321.01; found: 321.30.

Example OL-1

Step b

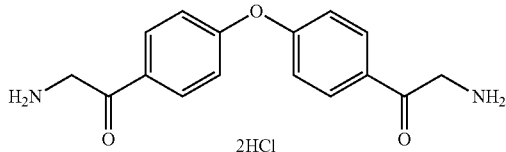 [SMILES: NCC(=O)c1ccc(Oc2ccc(C(=O)CN)cc2)cc1]

A mixture of OL-1a (0.6 g, 1.85 mmol) and sodium diformylamide (0.42 g, 4.45 mmol) in acetonitrile (20 mL) was heated to reflux for 4 h. The solvent was the removed under reduced pressure and the remaining residue was redissolved in a 5% HCl solution in ethanol (30 mL) and heated to reflux temperature for 2 h. The mixture was cooled in an ice-water bath and the resulting precipitate was filtered, washed with ethanol and ether and dried in vacuo. The recovered pale brow solid was used without further purification (0.66 g). ¹H NMR (500 MHz, DMSO-d₆) δ ppm 4.54 (s, 4 H), 7.25 (d, J=8.85 Hz, 4 H), 8.11 (d, J=8.55 Hz, 4 H), 8.52 (br. s, 6 H). LC (Cond. 1): RT=1.24 min; LRMS: Anal. Calcd. For (M+H)⁺ C₁₆H₁₇N₂O₃ 285.12; found: 285.19.

Example OL-1

Step c

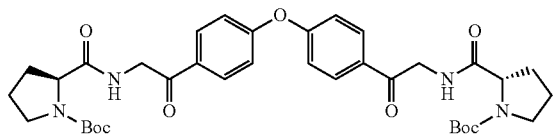 [SMILES: CC(C)(C)OC(=O)N1CCC[C@H]1C(=O)NCC(=O)c1ccc(Oc2ccc(C(=O)CNC(=O)[C@@H]3CCCN3C(=O)OC(C)(C)C)cc2)cc1]

N,N-Diisopropylethylamine (1.13 mL, 6.47 mmol) was added dropwise, over 15 minutes, to a heterogeneous mixture of N-Boc-L-proline (0.8 g, 3.73 mmol), HATU (1.48 g, 3.88 mmol), OL-1b (0.66 g, 1.85 mmol) and dimethylformamide (15 mL), and stirred at ambient condition for 4 h. Most of the volatile components were removed in vacuo, and the resulting residue was partitioned between ethyl acetate (30 mL) and water (20 mL). The organic layer was washed with water (20 mL) and brine, dried (MgSO₄), filtered, and concentrated in vacuo. A silica gel mesh was prepared from the residue and submitted to flash chromatography (silica gel; 65-85% ethyl acetate/hexanes) to provide OL-1c as a pale brown solid (0.7 g). ¹H NMR (500 MHz, DMSO-d₆) δ ppm 1.39/1.34 (rotomers, s, 18 H), 1.70-1.91 (m, 6 H), 2.00-2.25 (m, J=8.55 Hz, 2 H), 3.22-3.33 (m, 2 H), 3.32-3.47 (m, J=10.68, 10.68 Hz, 2 H), 4.08-4.26 (m, 2 H), 4.56 (ddd, J=36.93, 18.16, 5.34 Hz, 4 H), 7.19 (d, J=8.85 Hz, 4 H), 8.06 (d, J=7.93 Hz, 4 H), 8.11-8.24 (m, J=5.49 Hz, 2 H). LC (Cond. 1): RT=2.55 min; LRMS: Anal. Calcd. for (M+H)⁺ C₃₆H₄₇N₄O₉ 679.33; found: 679.44.

Example OL-1

Step d


A mixture of OL-1c (0.7 g, 1.025 mmol) and ammonium acetate (0.79 g, 10 mmol) in xylenes (5 mL) was heated in a sealed tube at 140° C. for 1.2 hours under microwave radiation. The volatile component was removed in vacuo, and the residue was partitioned carefully between ethyl acetate and water, whereby enough saturated sodium bicarbonate solution was added so as to make the pH of the aqueous phase slightly basic after the shaking of the biphasic system. The layers were separated, and the aqueous layer was extracted with additional ethyl acetate. The combined organic phase was washed with brine, dried (MgSO₄), filtered, and concentrated in vacuo. The resulting material submitted to a flash chromatography (silica gel; 15-25% acetone/dichloromethane) to provide OL-id (0.13 g). ¹H NMR (500 MHz, DMSO-d₆) δ ppm 1.17/1.48 (rotomers, s, 18 H), 1.76-1.93 (m, 4 H), 1.93-2.06 (m, J=10.07 Hz, 2 H), 2.10-2.30 (m, 2 H), 3.32-3.39 (m, 2 H), 3.45-3.62 (m, 2 H), 4.69-4.80 (m, 1 H), 4.83 (d, J=7.02 Hz, 1 H), 6.97 (d, J=7.93 Hz, 4 H), 7.00-7.22 (m, 1 H), 7.40/7.62 (rotomers, m, 2 H), 7.73 (d, J=8.55 Hz, 3 H), 11.74/11.81/12.07 (rotomers, s, 2 H). LC (Cond. 2): RT=1.53 minutes, 93% homogeneity index; LCMS: Anal. Calcd. for (M+H)⁺ C₃₆H₄₄N₆O₅: 641.34; found: 641.50.

Example OL-1

Step e

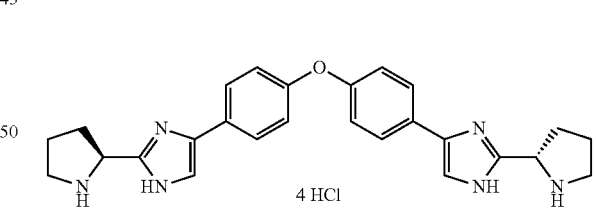

To a solution of OL-1d (0.13 g, 0.2 mmol) in 30 mL dichloromethane was added 1 mL of a 4.0M solution of HCl in dioxane. The reaction was stirred for 2 hours at room temperature and concentrated under reduced pressure. The resulting residue was redissolved in a minimum amount of methanol and the desired product was triturated with ether, filtered and dried in vacuo. A pale tan solid (0.11 g) was recovered and used without further purification. ¹H NMR (500 MHz, DMSO-d₆) δ ppm 1.92-2.07 (m, 2 H), 2.12-2.25 (m, 2 H), 2.37-2.47 (m, 4 H), 3.30-3.47 (m, 4H), 4.90-5.02 (m, 2 H), 7.15 (d, J=8.55 Hz, 4 H), 7.91 (d, J=8.24 Hz, 4 H), 7.97 (s, 2H), 9.74 (br, s, 2 H), 10.25 (br. s, 2 H). Note: the signal of the imidazole NH was too broad to assign a chemical shift. LC (Cond. 1): RT=1.68 min; LRMS: Anal. Calcd. for $(M\pm H)^+$ $C_{26}H_{29}N_6O$ 441.24; found: 441.30.

Example OL-1

HATU (52 mg, 0.137 mmol) was added to a mixture of OL-1e (35 mg, 0.06 mmol), diisopropylethylamine (58 µL, 0.33 mmol) and Cap-1 (22 mg, 0.12 mmol) in dimethylformamide (3 mL), and the resulting mixture was stirred at ambient for 3 h. The volatile component was removed in vacuo, and the residue was purified by a reverse phase HPLC system (water/methanol/TFA) to provide the TPA salt of Example OL-1 as an off-white solid (32 mg). $^1H$ NMR (500 MHz, DMSO-$D_6$) δ ppm 1.82-1.93 (m, 2 H), 1.94-2.08 (m, 4 H), 2.14-2.24 (m, 2 H), 2.29-2.40 (m, 4 H), 2.83 (s, 4 H), 2.97-3.07 (m, 4 H), 3.97 (t, J=8.24 Hz, 2 H), 4.89-5.20 (m, 2 H), 5.34-5.73 (m, 2 H), 7.00-7.22 (m, 6 H), 7.49-7.64 (m, 9 H), 7.70-7.89 (m, 5 H), 10.20 (br.s, 2 H). LC (Cond. 1): RT=2.48 min; LRMS: Anal. Calcd. for $(M+H)^+$ $C_{46}H_{51}N_8O_3$ 763.41; found: 763.56; HRMS: Anal. Calcd. for $(M+H)^+$ $C_{46}H_{51}N_8O_3$ 763.4084; found: 763.4109.

Examples OL-2 and OL-3

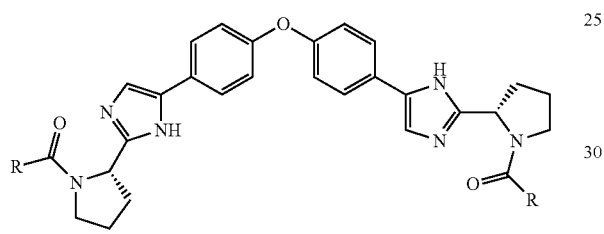

Examples OL-2 and OL-3 were prepared as TFA salts by substituting the respective acids for Cap-1 using the same method described for Example OL-1.

| Example | Acid 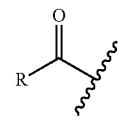 | RT (LC-Cond.); MS data |
|---|---|---|
| OL-2 | Mandelic acid (Ph, HO) | RT = 2.92 min. LC (Cond. 2); LCMS: Anal. Calcd. For $(M + H)^+$ $C_{42}H_{41}N_6O_5$ 709.31; Found: 709.41; HRMS: Anal. Calcd. for: $C_{42}H_{41}N_6O_5$ 709.3138; Found: 709.3147 $(M + H)^+$ |
| OL-3 | Cap-4 (Ph, HN, O—) | RT = 3.65 min). LC (Cond. 2); LCMS: Anal. Calcd. for $(M + H)^+$ $C_{46}H_{47}N_8O_7$ 823.35; Found: 823.66; HRMS: Anal. Calcd. for: $(M + H)^+$ $C_{46}H_{47}N_8O_7$ 823.3568; Found: 823.3574 |

Example OL-4

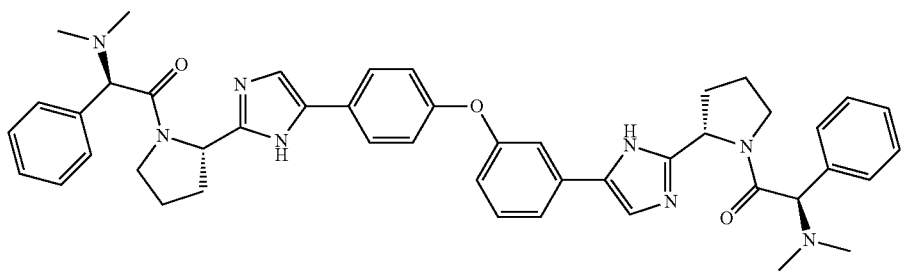 [SMILES: CN(C)[C@@H](C(=O)N1CCC[C@H]1c1ncc(-c2ccc(Oc3cccc(-c4cnc([C@@H]5CCCN5C(=O)[C@@H](c5ccccc5)N(C)C)[nH]4)c3)cc2)[nH]1)c1ccccc1]

Example OL-4

Step a

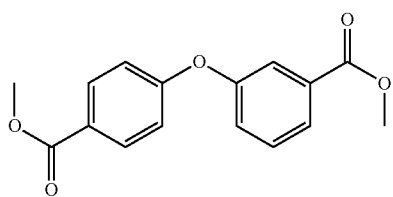 [SMILES: COC(=O)c1ccc(Oc2cccc(C(=O)OC)c2)cc1]

Methyl 3-bromobenzoate (5 g, 23.2 mmol), methyl 4-hydroxybenzoate (5.3 g, 34.87 mmol), cesium carbonate (15.12 g, 46.4 mmol), copper (1) iodide (0.44 g, 2.32 mmol) and N,N-dimethyl hydrochloride (0.97 g, 6.96 mmol) were combined in dioxane (100 ml) in a sealed tube and the resulting mixture was heated to 90° C. for 15 h. The solvent was removed under reduced pressure and the residue was taken up in ethyl acetate/water (1:1, 200 mL). The organic layer was washed with saturated aq. sodium carbonate, water and brine, dried (MgSO$_4$), filtered and concentrated in vacuo. The resulting material was purified by flash chromatography (silica gel, 5% ethyl acetate/hexanes) to provide OL-4a as a clear oil that solidified upon standing (5.8 g). $^1$H NMR (500 MHz, DMSO-d$_6$) δ ppm 3.83 (s, 6 H), 7.10 (d, J=8.55 Hz, 2 H), 7.43 (dd, J=8.09, 2.59 Hz, 1 H), 7.56 (s, 1 H), 7.61 (t, J=7.93 Hz, 1 H), 7.81 (d, J=7.63 Hz, 1 H), 7.98 (d, J=8.55 Hz, 2 H). LC (Cond. 2): RT=1.53 minutes; LCMS: Anal. Calcd. for (M+1)$^+$ C$_{16}$H$_{15}$O$_5$: 287.01; found: 287.23.

Example OL-4

Step b

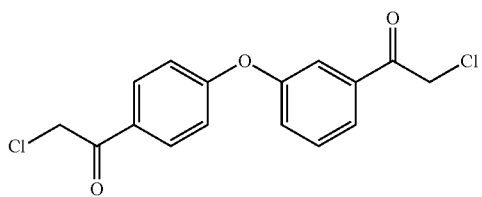 [SMILES: O=C(CCl)c1ccc(Oc2cccc(C(=O)CCl)c2)cc1]

OL-4b was prepared from OL-4a, according to the same procedure used for the preparation of OL-1a. $^1$H NMR (500 MHz, DMSO-d$_6$) δ ppm 5.14 (s, 2 H), 5.20 (s, 2H), 7.13 (d, J=8.85 Hz, 2 H), 7.43-7.49 (m, 1 H), 7.64 (t, J=8.09 Hz, 1 H), 7.66-7.68 (m, 1 H), 7.85 (d, J=7.93 Hz, 1 H), 8.02 (d, J=8.85 Hz, 2 H). LC (Cond. 1): RT=1.51 min; LRMS: Anal. Calcd. for (M+H)$^+$ C$_{16}$H$_{13}$Cl$_2$O$_3$ 323.02; found: 323.07.

Example OL-4

Step c

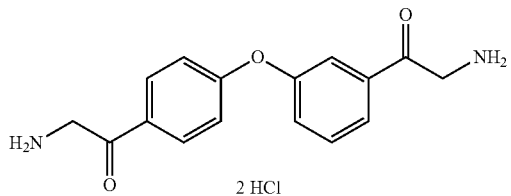 [SMILES: NCC(=O)c1ccc(Oc2cccc(C(=O)CN)c2)cc1]

OL-4c was prepared from Example OL-4b, according to the same procedure used for the preparation of Example OL-1b. $^1$H NMR (500 MHz, DMSO-d$_6$) δ ppm. 4.52 (s, 2 H), 4.56 (s, 2 H), 7.16 (d, J=8.85 Hz, 2 H), 7.51 (dd, J=8.24, 2.44 Hz, 1 H), 7.68 (t, J=7.93 Hz, 1 H), 7.71-7.75 (m, 1 H), 7.91 (d, J=7.63 Hz, 1 H), 8.07 (d, J=8.85 Hz, 2 H), 8.60 (s, 6 H). LC (Cond. 2): Anal. Calcd. for C$_{16}$H$_{17}$N$_2$O$_3$ (M+H)$^+$ 285.12; found: 285.15.

Example OL-4d

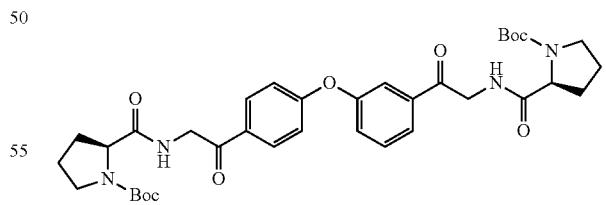

Example OL-4d was prepared from Example OL-4c, according to the same procedure used for the preparation of Example OL-1c. $^1$H NMR (500 MHz, DMSO-d$_6$) δ ppm 1.38/1.33 (rotomers, s, 18 H), 1.69-1.91 (m, 6 H), 1.95-2.19 (m, 2 H), 3.20-3.31 (m, 2 H), 3.32-3.47 (m, 2 H), 4.08-4.23 (m, 2 H), 4.43-4.68 (m, 4 H), 7.10 (d, J=8.55 Hz, 2 H), 7.42 (dd, J=8.09, 1.98 Hz, 1 H), 7.57-7.70 (m, 2 H), 7.86 (d, J=7.02 Hz, 1 H), 8.03 (d, J=7.93 Hz, 2 H), 8.08-8.24 (m, 2 H). LC (Cond. 1): RT=2.53 min; LRMS: Anal. Calcd. for $C_{36}H_{47}N_4O_9$ (M±H)+ 679.33; found: 679.42.

Example OL-4e

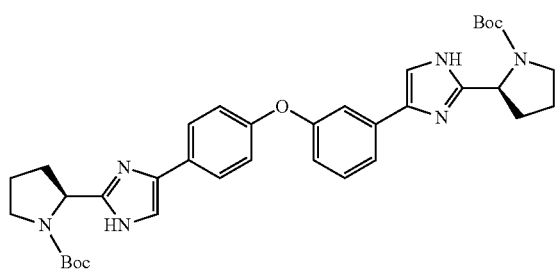 [SMILES: CC(C)(C)OC(=O)N1CCC[C@H]1c1nc(-c2ccc(Oc3cccc(-c4c[nH]c([C@@H]5CCCN5C(=O)OC(C)(C)C)n4)c3)cc2)c[nH]1]

Example OL-4e was prepared from Example OL-4d, according to the same procedure used for the preparation of Example OL-1d. $^1$H NMR (500 MHz, DMSO-$d_6$) δ ppm 1.14/1.17/1.38/1.40 (rotomers, s, 18 H), 1.71-2.06 (m, 6 H), 2.09-2.28 (m, J=25.79, 13.89 Hz, 2 H), 3.31-3.40 (m, 2 H), 3.51 (s, 2 H), 4.65-4.89 (m, 2 H), 6.80 (t, J=8.39 Hz, 1 H), 6.91-7.10 (m, 2 H), 7.28-7.55 (m, 5 H), 7.58-7.80 (m, 2 H), 11.66-12.21 (m, 2 H). LC (Cond. 1): RT=2.98 min; LRMS: Anal. Calcd. for $C_{36}H_{45}N_6O_5$ (M+H)+ 641.34; found: 641.39.

Example OL-4f

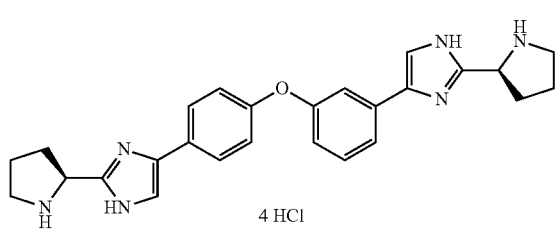 [SMILES: c1cc(Oc2ccc(-c3c[nH]c([C@@H]4CCCN4)n3)cc2)cc(-c2c[nH]c([C@@H]3CCCN3)n2)c1]

Example OL-4f was prepared from Example OL-4e, according to the same procedure used for the preparation of Example OL-1e. $^1$H NMR (500 MHz, DMSO-$d_6$) δ ppm 1.94-2.06 (m, 2 H), 2.09-2.23 (m, 2 H), 2.28-2.38 (m, 1 H), 2.37-2.47 (m, 3 H), 3.27-3.50 (m, 4 H), 4.90 (br. s, 1 H), 4.99 (br. s, 1 H), 7.00 (d, J=7.93 Hz, 1 H), 7.13 (d, J=8.55 Hz, 2 H), 7.49 (t, J=7.93 Hz, 1 H), 7.62 (s, 1 H), 7.69 (d, J=7.63 Hz, 1 H), 7.92 (d, J=8.55 Hz, 2 H), 7.99 (s, 2 H), 9.58 (br. s, 1 H), 9.84 (br. s, 1 H), 10.25 (br. d, J=22.28 Hz, 0.2 H). Note: the signal of the imidazole NH was too broad to assign a chemical shift. LC (Cond. 1): RT=1.72 min; LRMS: Anal. Calcd. for $C_{26}H_{29}N_6O$ (M+H)+ 441.24; found: 441.29.

Example OL-4

Example OL-4 was prepared from Example OL-4f according to the same procedure used for the preparation of Example OL-1. $^1$H NMR (500 MHz, DMSO-$d_6$) δ ppm 1.83-1.92 (m, 4 H), 1.95-2.09 (m, 8 H), 2.11-2.23 (m, 4 H), 2.75-2.88 (m, 2 H), 2.92 (s, 1 H), 2.96-3.12 (m, 2 H), 3.97 (t, J=8.39 Hz, 2 H), 5.14 (dd, J=17.70, 7.02 Hz, 2 H), 5.41 (s, 2 H), 6.91-7.11 (m, J=49.75 Hz, 2 H), 7.14 (d, J=7.93 Hz, 2 H), 7.44-7.68 (m, 12 H), 7.79 (d, J=8.54 Hz, 2 H), 7.84-8.02 (m, J=9.16 Hz, 2 H), 10.21 (s, 1 H). Note: the signal of the imidazole NH was too broad to assign a chemical shift. LC (Cond. 1): RT=1.78 min; LRMS: Anal. Calcd. for $C_{46}H_{51}N_8O_3$ (M+H)+ 763.41; found: 763.56. HRMS: Anal. Calcd. for $C_{46}H_{51}N_8O_3$ (M+H)+ 763.4084; found: 763.4067.

Examples OL-5 and OL-6

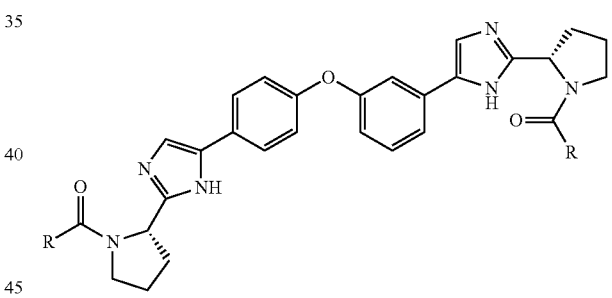

Examples OL-5 to OL-6 were prepared as TFA salts by substituting the respective acids for Cap-1 according to the same method described for Example OL-4.

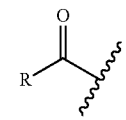

| Example | Acid | RT (LC-Cond.); MS data |
|---|---|---|
| OL-5 | 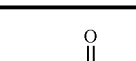<br>Mandelic acid | RT = 1.78 min. LC (Cond. 2); LCMS: Anal. Calcd. for: $C_{42}H_{41}N_6O_5$ (M + H)+ 709.31; Found: 709.42; HRMS: Anal. Calcd. for: $C_{42}H_{41}N_6O_5$ (M + H)+ 709.3138; Found: 709.3130 |

| | | |
|---|---|---|
| Example | Acid 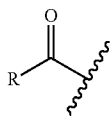 | RT (LC-Cond.); MS data |
| OL-6 | Cap-4 | RT = 1.96 min. LC (Cond. 2); LCMS: Anal. Calcd. for: $C_{46}H_{47}N_8O_7$ (M + H)⁺ 823.36; Found: 823.51; HRMS: Anal. Calcd. for: $C_{46}H_{47}N_8O_7$ (M + H)⁺ 823.3568; Found: 823.3588 |

Example OL-7

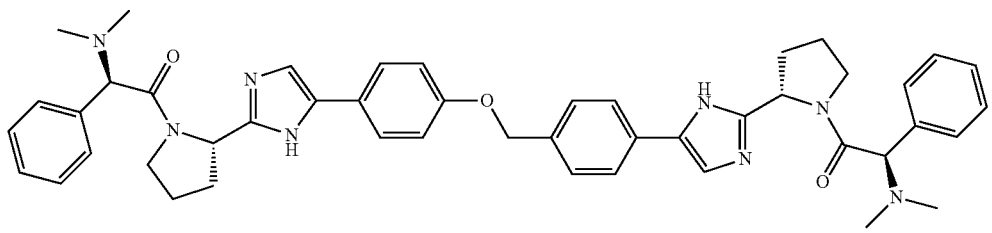 [SMILES: CN(C)[C@@H](C(=O)N1CCC[C@H]1c1ncc(-c2ccc(COc3ccc(-c4cnc([C@@H]5CCCN5C(=O)[C@@H](c5ccccc5)N(C)C)[nH]4)cc3)cc2)[nH]1)c1ccccc1]

Example OL-7a

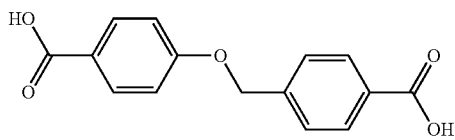 [SMILES: O=C(O)c1ccc(COc2ccc(C(=O)O)cc2)cc1]

To a solution of 4-(chloromethyl)benzoic acid (8.53 g, 50 mmol) and sodium hydroxide (10 g, 0.25 mol) in water (40 mL) was added a solution of 4-hydroxybenzoic acid (6.9 g, 50 mmol) and sodium hydroxide (6 g, 0.15 mol) in water (50 mL). The resulting mixture was heated to reflux temperature for 15 h and, after cooling to room temperature, it was filtered and acidified with a solution of sulfuric acid in water (1:1, 200 mL). The resulting precipitate was filtered off, washed with water and dried in vacuo. The off-white solid (9.3 g) was used without further purification. ¹H NMR (500 MHz, DMSO-$d_6$) δ ppm 5.27 (s, 1 H), 7.10 (d, J=8.85 Hz, 2 H), 7.56 (d, J=8.24 Hz, 2 H), 7.89 (d, J=8.85 Hz, 2 H), 7.96 (d, J=8.24 Hz, 2H), 12.36 (hr. s, 2 H). LC (Cond. 2), Note: The molecule did not ionize well in the LC/MS system and therefore an exact mass was not obtained.

Example OL-7b

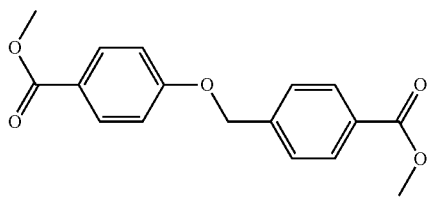 [SMILES: COC(=O)c1ccc(COc2ccc(C(=O)OC)cc2)cc1]

(Diazomethyl)trimethylsilane (15 mL, 30 mmol, 2 M in hexanes) was added dropwise to a suspension of Example OL-7a (2.04 g, 7.5 mmol) in methanol (30 mL) at 5° C. (ice-water bath). When the addition was complete, the cooling bath was removed and the mixture was stirred at ambient overnight. The solvent was removed under reduced pressure and the remaining residue was taken up in ethyl acetate, washed with water, sodium bicarbonate and brine, dried (MgSO₄), filtered and concentrated in vacuo. The resulting material was purified by flash chromatography (silica gel, 10% ethyl acetate/hexanes) to provide Example OL-7b as white solid (1.5 g). ¹H NMR (500 MHz, DMSO-$d_6$) δ ppm 3.80 (s, 3 H), 3.85 (s, 3 H), 5.29 (s, 2 H), 7.13 (d, J=8.85 Hz, 2 H), 7.59 (d, J=8.24 Hz, 2 H), 7.91 (d, J=9.16 Hz, 2 H), 7.98 (d, J=8.24 Hz, 2 H). LC (Cond. 1): RT=2.56 min; LRMS: Anal. Calcd. for $C_{17}H_{16}O_5$ (M+H)⁺ 301.11; found: 301.22.

Example OL-7c

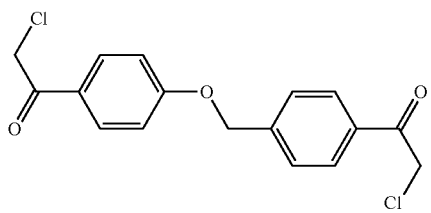 [SMILES: O=C(CCl)c1ccc(COc2ccc(C(=O)CCl)cc2)cc1]

Example OL-7c was prepared from Example OL-7b, according to the same procedure used for the preparation of Example OL-1a. ¹H NMR (500 MHz, DMSO-$d_6$) δ ppm 5.09 (s, 2 H), 5.18 (s, 2 H), 5.34 (s, 2 H), 7.15 (d, J=8.85 Hz, 2 H), 7.62 (d, J=8.55 Hz, 2 H), 7.95 (d, J=9.16 Hz, 2 H), 8.00 (d, J=8.55 Hz, 2 H). LC (Cond. 1): RT=2.36 min; LRMS: Anal. Calcd. for $C_{17}H_{15}Cl_2O_3$ (M+H)⁺ 337.04 found: 337.09.

Example OL-7d

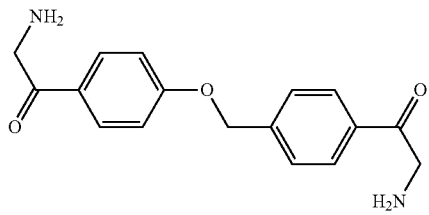 [SMILES: NCC(=O)c1ccc(COc2ccc(C(=O)CN)cc2)cc1]

Example OL-7d was prepared from Example OL-7c, according to the same procedure used for the preparation of Example OL-1b. $^1$H NMR (500 MHz, DMSO-$d_6$) δ ppm 4.49 (s, 2 H), 4.57 (s, 2 H), 5.38 (s, 2 H), 7.19 (d, J=8.85 Hz, 2 H), 7.66 (d, J=8.24 Hz, 2 H), 8.00 (d, J=8.85 Hz, 2 H), 8.05 (d, J=8.24 Hz, 2 H), 8.45 (s, 6 H). LC (Cond. 1): RT=1.26 min; LRMS: Anal. Calcd. for $C_{17}H_{19}N_{12}O_3$ (M+H)$^+$ 299.14 found: 299.19.

Example OL-7e

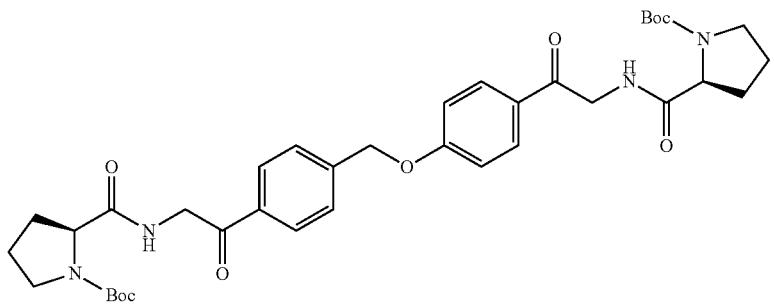 [SMILES: CC(C)(C)OC(=O)N1CCC[C@H]1C(=O)NCC(=O)c1ccc(COc2ccc(C(=O)CNC(=O)[C@@H]3CCCN3C(=O)OC(C)(C)C)cc2)cc1]

Example OL-7e was prepared from Example OL-7d, according to the same procedure used for the preparation of Example OL-1c. $^1$H NMR (500 MHz, DMSO-$d_6$) δ ppm 1.30-1.47 (m, 18 H), 1.65-1.89 (m, 6 H), 2.01-2.20 (m, 2 H), 3.24-3.34 (m, 2 H), 3.34-3.43 (m, 2 H), 4.09-4.25 (m, 2 H), 4.44-4.68 (m, 4 H), 5.33 (s, 2 H), 7.13 (d, J=8.85 Hz, 2 H), 7.60 (d, J=8.24 Hz, 2 H), 7.99 (dd, J=20.29, 8.09 Hz, 4 H), 8.04-8.22 (m, J=31.74 Hz, 2 H). LC (Cond. 2): RT=1.53 minutes, 97% homogeneity index; LCMS: Anal. Calcd. for $C_{37}H_{49}N_4O_9$(M+1)$^+$ 693.35; found: 693.32.

Example OL-7f

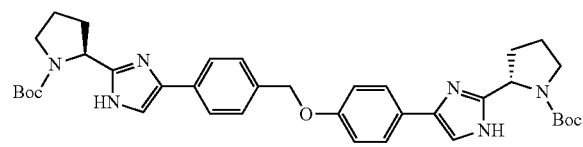 [SMILES: CC(C)(C)OC(=O)N1CCC[C@H]1c1nc(-c2ccc(COc3ccc(-c4c[nH]c([C@@H]5CCCN5C(=O)OC(C)(C)C)n4)cc3)cc2)c[nH]1]

Example OL-7f was prepared from Example OL-7e, according to the same procedure used for the preparation of Example OL-1d. $^1$H NMR (500 MHz, DMSO-$d_6$) δ ppm 1.06-1.52 (m, 18 H), 1.69-2.08 (m, 6 H), 2.08-2.30 (m, 2 H), 3.33-3.43 (m, 2 H), 3.52 (s, 2 H), 4.75 (s, 1 H), 4.83 (s, 1 H), 5.06 (s, 2 H), 6.92-7.10 (m, J=7.63 Hz, 2H), 7.20-7.33 (m, 1 H), 7.40 (d, J=7.63 Hz, 2 H), 7.46 (d, J=8.55 Hz, 1 H), 7.64 (d, J=7.63 Hz, 2 H), 7.75 (d, J=7.93 Hz, 2 H), 11.47-12.18 (m, 2 H). LC (Cond. 1): RT=2.94 min; LRMS: Anal. Calcd. for $C_{37}H_{47}N_6O_3$ (M+H)$^+$ 655.36 found: 655.39.

Example OL-7g

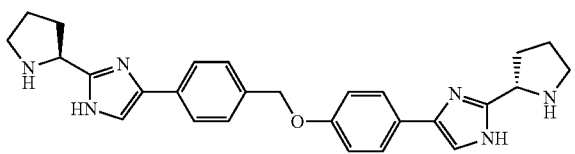 [SMILES: c1cc(-c2c[nH]c([C@@H]3CCCN3)n2)ccc1COc1ccc(-c2c[nH]c([C@@H]3CCCN3)n2)cc1]

Example OL-7g was prepared from Example OL-7fe, according to the same procedure used for the preparation of Example OL-1e. $^1$H NMR (500 MHz, DMSO-$d_6$) δ ppm 1.93-2.07 (m, 2 H), 2.13-2.26 (m, 2 H), 2.40-2.48 (m, 3 H), 3.31-3.52 (m, 5 H), 4.91-5.09 (m, 2 H), 5.21 (s, 2 H), 7.17 (d, J=8.85 Hz, 2 H), 7.57 (d, J=8.24 Hz, 2 H), 7.87 (d, J=8.85 Hz, 2 H), 7.93 (d, J=8.24 Hz, 2 H), 8.03 (d, J=16.79 Hz, 2 H), 9.78 (s, 1 H), 9.95 (s, 1 H), 10.31 (s, 2 H). Note: the signal of the imidazole NH was too broad to assign a chemical shift. LC (Cond. 2): RT=0.62 minutes; LCMS: Anal. Calcd. for $C_{27}H_{31}N_6O$ (M+1)$^+$ 455.26; found: 455.34.

Example OL-7

Example OL-7 was prepared from Example OL-7g according to the same procedure used for the preparation of Example OL-1. $^1$H NMR (500 MHz, DMSO-$d_6$) δ ppm 1.90 (d, J=2.44 Hz, 2 H), 2.04 (d, J=3.66 Hz, 4 H), 2.21 (s, 2 H), 2.36 (d, J=1.83 Hz, 2 H), 2.42-2.46 (m, 4 H), 2.83 (br. s, 4 H), 2.99-3.11 (m, 2 H), 3.98 (d, J=7.02 Hz, 2 H), 5.18 (s, 4 H), 5.42 (d, J=8.55 Hz, 2 H), 7.08-7.28 (m, 3 H), 7.50-7.67 (m, 11H), 7.73 (d, J=7.32 Hz, 2 H), 7.80 (d, J=7.93 Hz, 2 H), 7.85-7.98 (m, J=10.38 Hz, 1 H). Note: the signal of the imidazole NH was too broad to assign a chemical shift. LC (Cond. 3): RT=2.94 min; LRMS: Anal. Calcd. for $C_{47}H_{52}N_8O_3$ (M+H)$^+$ 777.42 found: 777.51; HRMS: Anal. Calcd. for $C_{47}H_{53}N_8O_3$ (M+H)$^+$ 777.4241 found: 777.4265.

Example OL-8

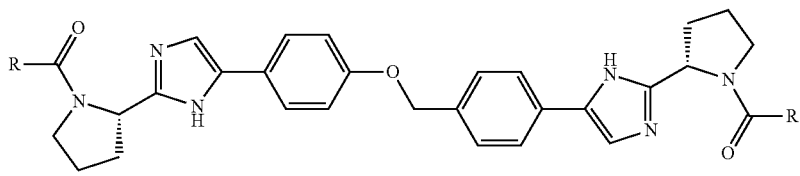

Example OL-8 was prepared as TFA salt by substituting the respective acid for Cap-1 according to the same method described for Example OL-7.

| Example | Acid | RT (LC-Cond.); MS data |
|---|---|---|
| OL-8 | Cap-4 | RT = 3.70 min. LC (Cond. 4); LCMS: Anal. Calcd. for $C_{47}H_{49}N_8O_7$ (M + H)$^+$ 837.37; Found: 837.54; HRMS: Anal. Calcd. for: $C_{47}H_{49}N_8O_7$ (M + H)$^+$ 837.3724; Found: 837.3715 |

Example OL-9

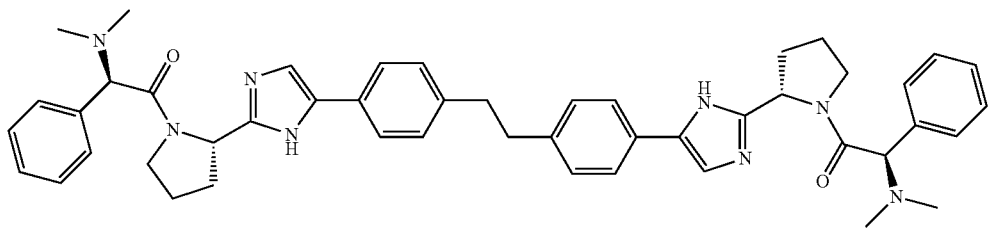 [SMILES: CN(C)[C@@H](C(=O)N1CCC[C@H]1c1ncc(-c2ccc(CCc3ccc(-c4cnc([C@@H]5CCCN5C(=O)[C@@H](c5ccccc5)N(C)C)[nH]4)cc3)cc2)[nH]1)c1ccccc1]

Example OL-9a

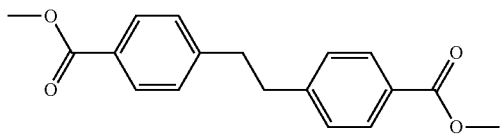

Palladium on carbon (10%, 300 mg) was added to a solution of dimethyl 4,4'-(ethene-1,2-diyl)dibenzoate (2 g, 6.76 mmol) in methanol (100 mL). The suspension was purged with $N_2$, placed under 1 atm of $H_2$ (balloon) and stirred at ambient overnight. The mixture was then filtered through a plug of diatomaceous earth (CELITE®) and the solvent was concentrated under reduced pressure. A white solid was recovered (1.42 g) and used without further purification. $^1$H NMR (500 MHz, CDCl$_3$) δ ppm 2.98 (s, 4 H), 3.90 (s, 6 H), 7.18 (d, J=7.32 Hz, 4 H), 7.93 (d, J=7.32 Hz, 4 H). LC (Cond. 1): RT=2.65 min; LRMS: Anal. Calcd. for $C_{18}H_{19}O_4$ (M+H)$^+$ 299.13 found: 299.21.

Example OL-9b

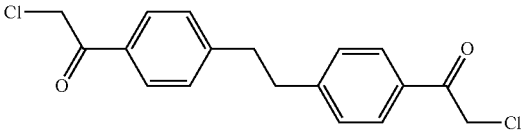 [SMILES: O=C(CCl)c1ccc(CCc2ccc(C(=O)CCl)cc2)cc1]

Example OL-9b was prepared from Example OL-9a, according to the same procedure used for the preparation of Example OL-1a. $^1$H NMR (500 MHz, CDCl$_3$) δ ppm 3.02 (s, 4 H), 4.67 (s, 4 H), 7.25 (d, J=8.24 Hz, 4 H), 7.86 (d, J=8.24 Hz, 4 H). LC (Cond. 2): RT=0.62 min; LCMS: Anal. Calcd. for $C_{18}H_{17}Cl_2O_2$ (M+1)$^+$ 335.06; found: 335.12.

Example OL-9c

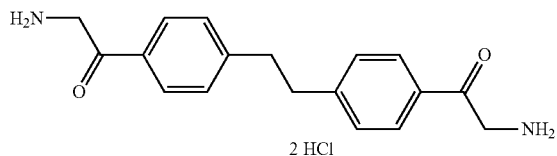 [SMILES: NCC(=O)c1ccc(CCc2ccc(C(=O)CN)cc2)cc1]

2 HCl

Example OL-9c was prepared from Example OL-9b, according to the same procedure used for the preparation of Example OL-1b. $^1$H NMR (500 MHz, DMSO-$d_6$) δ ppm 3.03 (s, 4 H), 4.51 (s, 4 H), 7.43 (d, J=8.55 Hz, 4 H), 7.92 (d, J=8.24 Hz, 4 H), 8.50 (s, 6 H). LC (Cond. 3): RT=1.90 min; LRMS: Anal. Calcd. for $C_{18}H_{21}N_2O_2$ (M+H)$^+$ 297.16 found: 297.24.

Example OL-9d

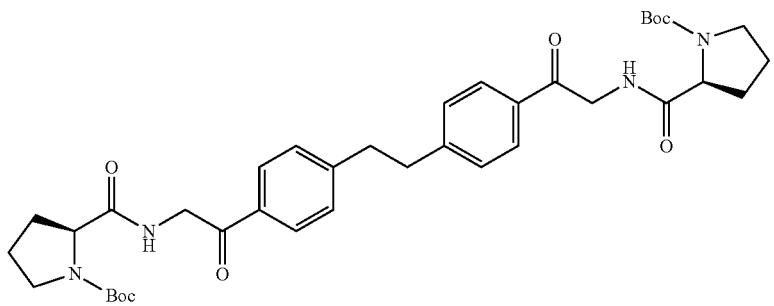 [SMILES: CC(C)(C)OC(=O)N1CCC[C@H]1C(=O)NCC(=O)c1ccc(CCc2ccc(C(=O)CNC(=O)[C@@H]3CCCN3C(=O)OC(C)(C)C)cc2)cc1]

Example OL-9d was prepared from Example OL-9c, according to the same procedure used for the preparation of Example OL-1c. $^1$H NMR (500 MHz, CDCl$_3$) δ ppm 1.38-1.56 (m, 18 H), 1.83-2.00 (m, 4 H), 2.08-2.38 (m, 4 H), 3.01 (s, 4 H), 3.32-3.65 (m, 4 H), 4.28 (br. s, 1 H), 4.39 (br. s, 1 H), 4.63-4.71 (m, 2 H), 4.72-4.84 (m, J=4.58 Hz, 2 H), 7.01 (s, 1 H), 7.18-7.33 (m, 4 H), 7.47 (s, 1 H), 7.87 (d, J=7.93 Hz, 4 H). LC (Cond. 1): RT=2.56 min; LRMS: Anal. Calcd. for $C_{38}H_{51}N_4O_8$ (M+H)$^+$ 691.37, found: 691.48.

Example OL-9e

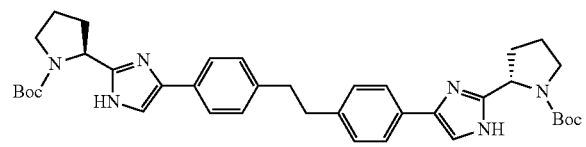 [SMILES: CC(C)(C)OC(=O)N1CCC[C@H]1c1nc(-c2ccc(CCc3ccc(-c4c[nH]c([C@@H]5CCCN5C(=O)OC(C)(C)C)n4)cc3)cc2)c[nH]1]

Example OL-9e was prepared from Example OL-9d, according to the same procedure used for the preparation of Example OL-1d. $^1$H NMR (500 MHz, DMSO-$d_5$) δ ppm 1.15/1.39 (rotomers, s, 18 H), 1.75-1.92 (m, 3 H), 1.96 (s, 3 H), 2.09-2.27 (m, J=32.04 Hz, 2 H), 2.81-2.90 (m, 4 H), 3.31-3.40 (m, 2 H), 3.52 (s, 2 H), 4.66-4.88 (m, J=35.40 Hz, 2 H), 7.14 (d, J=7.02 Hz, 4 H), 7.21 (s, 1 H), 7.31-7.41 (m, 1 H), 7.51 (d, J=6.41 Hz, 1 H), 7.61 (d, J=7.93 Hz, 3 H), 11.62-12.08 (m, 2 H). LC (Cond. 1): RT=2.20 min; LRMS: Anal. Calcd. for $C_{38}H_{49}N_6O_4$ (M+H)$^+$ 653.38, found: 653.47.

Example OL-9f

Example OL-9f was prepared from Example OL-9e, according to the same procedure used for the preparation of Example OL-1e. $^1$H NMR (500 MHz, DMSO-$d_6$) δ ppm 1.92-2.05 (m, 2 H), 2.11-2.25 (m, 2 H), 2.40-2.47 (m, 4 H), 2.89-3.03 (m, 4 H), 3.32-3.39 (m, 2 H), 3.40-3.49 (m, 2 H), 5.02 (t, J=7.78 Hz, 2 H), 7.32 (d, J=8.24 Hz, 4 H), 7.80 (d, J=8.24 Hz, 4 H), 9.91 (s, 2 H), 10.32 (s, 2 H). Note: the signal of the imidazole NH was too broad to assign a chemical shift. LC (Cond. 5): RT=2.52 min; LRMS: Anal. Calcd. for $C_{28}H_{33}N_6$ (M+H)$^+$ 453.28, found: 453.31.

Example OL-9

Example OL-9 was prepared from Example OL-9f, according to the same procedure used for the preparation of Example OL-1. $^1$H NMR (500 MHz, DMSO-$d_6$) δ ppm 1.82-1.95 (m, 2 H), 1.97-2.10 (m, 4 H), 2.15-2.27 (m, J=4.58 Hz, 2 H), 2.28-2.45 (m, 4 H), 2.72-2.88 (m, 4 H), 2.94 (s, 5 H), 2.98-3.07 (m, 2 H), 3.97 (t, J=9.77 Hz, 2 H), 5.17 (d, J=6.10 Hz, 2 H), 5.41 (s, 2 H), 7.12 (s, 1 H), 7.38 (d, J=7.32 Hz, 4H), 7.51-7.62 (m, 9 H), 7.69 (d, J=7.93 Hz, 4 H), 7.93 (s, 2 H). Note: the signal of the imidazole NH was too broad to assign a chemical shift. LC (Cond. 5): RT=2.87 min; LRMS: Anal. Calcd, for $C_{48}H_{55}N_8O_2$ (M+H)$^+$ 775.44 found: 775.51; HRMS: Anal. Calcd. for $C_{48}H_{55}N_8O_2$ (M+H)$^+$ 775.4448 found: 775.4454.

Examples OL-10 to OL-13

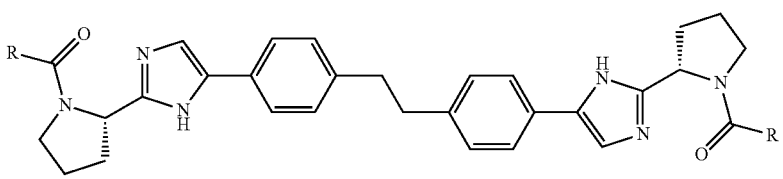

Examples OL-10 to OL-13 were prepared as TFA salts by substituting the respective acids for Cap-1 according to the same method described for Example OL-9.

| Example | Acid | RT (LC-Cond.); MS data |
|---|---|---|
| OL-10 | Mandelic acid (Ph, HO) | RT = 2.64 min. LC (Cond. 4); LCMS: Anal. Calcd. for: $C_{44}H_{45}N_6O_4$ (M + H)$^+$ 721.35; Found: 721.42; HRMS: Anal. Calcd. for: $C_{44}H_{45}N_6O_4$ (M + H)$^+$ 721.3502; Found: 721.3518 |
| OL-11 | Cap-4 | RT = 2.88 min. LC (Cond. 4); LCMS: Anal. Calcd. for: $C_{48}H_{51}N_8O_6$ (M + H)$^+$ 835.39; Found: 835.49; HRMS: Anal. Calcd. for: $C_{48}H_{50}N_8O_6$ (M + H)$^+$ 835.3932; Found: 835.3939 |
| OL-12 | Cap-46 | RT = 4.20 min. LC (Cond. 4); LCMS: Anal. Calcd. for: $C_{50}H_{57}N_{10}O_4$ (M + H)$^+$ 861.45; Found: 861.50; HRMS: Anal. Calcd. for: $C_{50}H_{57}N_{10}O_4$ (M + H)$^+$ 861.4564; Found: 861.4562 |
| OL-13 | Cap-48 | RT = 5.11 min. LC (Cond. 4); LCMS: Anal. Calcd. for: $C_{56}H_{64}N_{10}O_4$ (M + H)$^+$ 941.52; Found: 941.71; HRMS: Anal. Calcd. for: $C_{56}H_{65}N_{10}O_4$ (M + H)$^+$ 941.5190; Found: 941.5162 |

Example OL-14

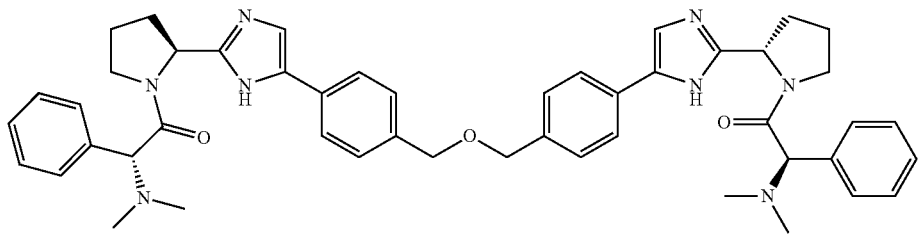 [SMILES: CN(C)[C@@H](C(=O)N1CCC[C@H]1c1ncc(-c2ccc(COCc3ccc(-c4cnc([C@@H]5CCCN5C(=O)[C@@H](c5ccccc5)N(C)C)[nH]4)cc3)cc2)[nH]1)c1ccccc1]

Example OL-14a

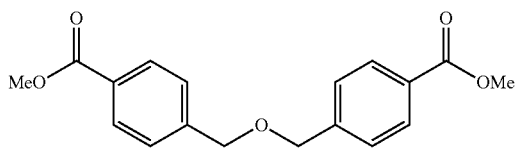 [SMILES: COC(=O)c1ccc(COCc2ccc(C(=O)OC)cc2)cc1]

Triethyl silane (5.84 mL, 36.55 mmol) was added dropwise to a solution of methyl 4-formylbenzoate (5 g, 30.46 mmol) and bismuth tribromide (0.273 g, 0.61 mmol) in acetonitrile (75 mL) and the opaque solution was stirred at ambient for 15 min. Volatiles were removed under reduced pressure and the remaining residue was taken up in ethyl acetate. The organic layer was then washed with water and brine, dried (MgSO$_4$), filtered and concentrated in vacuo. The recovered solid was then submitted to flash chromatography (silica gel; 10-20% ethyl acetate/hexanes) to provide OL-14a (3.05 g). $^1$H NMR (500 MHz, CDCl$_3$) δ ppm 3.84 (s, 6 H), 4.65 (s, 4 H), 7.51 (d, J=8.24 Hz, 4 H), 7.95 (d, J=8.24 Hz, 4 H). LC (Cond. 2): RT=1.68 min; LCMS: Anal. Calcd. for C$_{18}$H$_{19}$O$_5$ (M+H)$^+$ 315.12; found: 315.26.

Example OL-14b

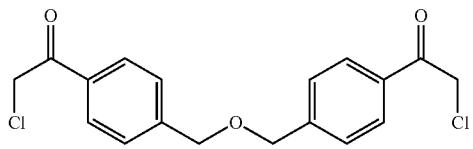 [SMILES: O=C(CCl)c1ccc(COCc2ccc(C(=O)CCl)cc2)cc1]

Example OL-14b was prepared from Example OL-14a, according to the same procedure used for the preparation of Example OL-1a. $^1$H NMR (500 MHz, DMSO-d$_6$) δ ppm 4.67 (s, 4 H), 5.19 (s, 4 H), 7.55 (d, J=8.24 Hz, 4 H), 7.98 (d, J=8.24 Hz, 4 H). LC (Cond. 5): RT=3.85 min; LRMS: Anal. Calcd. for C$_{18}$H$_{17}$Cl$_2$O$_3$ (M+H)$^+$ 351.05, found: 351.06.

Example OL-14c

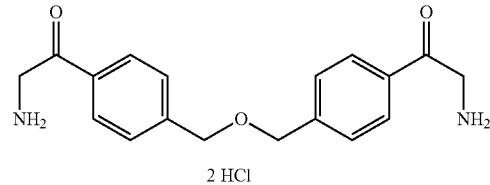 [SMILES: NCC(=O)c1ccc(COCc2ccc(C(=O)CN)cc2)cc1]

Example OL-14c was prepared from Example OL-14b, according to the same procedure used for the preparation of Example OL-1b. $^1$H NMR (500 MHz, DMSO-d$_6$) δ ppm 4.55 (s, 4 H), 4.69 (s, 4 H), 7.57 (d, J=8.24 Hz, 4 H), 8.02 (d, J=8.55 Hz, 4H), 8.53 (s, 6 H). LC (Cond. 1): RT=1.29 min; LRMS: Anal. Calcd. for C$_{18}$H$_{21}$N$_2$O$_3$ (M+H)$^+$ 313.15, found: 31121.

Example OL-14d

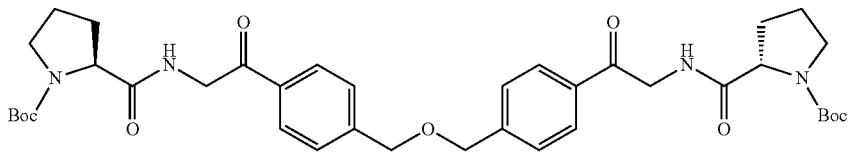 [SMILES: CC(C)(C)OC(=O)N1CCC[C@H]1C(=O)NCC(=O)c1ccc(COCc2ccc(C(=O)CNC(=O)[C@@H]3CCCN3C(=O)OC(C)(C)C)cc2)cc1]

Example OL-14d was prepared from Example OL-14c, according to the same procedure used for the preparation of Example OL-10. $^1$H NMR (500 MHz, DMSO-$d_6$) δ ppm 1.34/1.40 (rotomers, s, 18 H), 1.70-1.92 (m, 6 H), 1.99-2.20 (m, 2 H), 3.24-3.33 (m, 2 H), 3.35-3.44 (m, 2 H), 4.11-4.25 (m, 2 H), 4.50-4.65 (m, 4 H), 4.66 (s, 4 H), 7.53 (d, J=8.24 Hz, 4 H), 7.99 (d, J=7.93 Hz, 4 H), 8.09-8.23 (m, 2 H). LC (Cond. 1): RT=2.49 min; LRMS: Anal. Calcd. for $C_{38}H_{51}N_4O_9$ (M+H)$^+$ 707.36 found: 707.50.

Example OL-14e

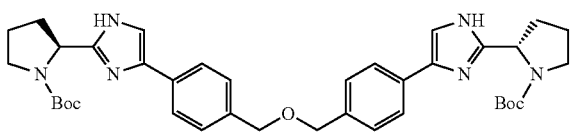 [SMILES: CC(C)(C)OC(=O)N1CCC[C@H]1c1nc(-c2ccc(COCc3ccc(-c4c[nH]c([C@@H]5CCCN5C(=O)OC(C)(C)C)n4)cc3)cc2)c[nH]1]

Example OL-14e was prepared from Example OL-14d, according to the same procedure used for the preparation of Example OL-1d. $^1$H NMR (500 MHz, DMSO-$d_6$) δ ppm 1.14/1.39 (rotomers, s, 18 H), 1.76-2.06 (m, 6 H), 2.08-2.30 (m, 2 H), 3.31-3.41 (m, 2 H), 3.52 (s, 2 H), 4.49 (s, 4 μl), 4.70-4.78 (m, 1 H), 4.79-4.90 (m, 1 H), 7.29/7.35 (rotomers, d, J=7.93 Hz, 4 H), 7.40-7.54 (m, 2 H), 7.71/7.61 (rotomers, d, J=7.93 Hz, 4 H), 11.72-12.19 (m, 2 H). LC (Cond. 1): RT=2.14 min; LRMS: Anal. Calcd. for $C_{38}H_{49}N_6O_5$ (M+H)$^+$ 669.38, found: 669.53.

Example OL-14f

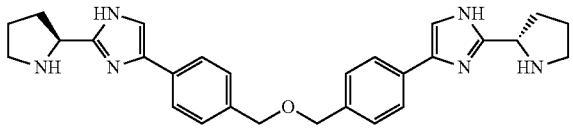 [SMILES: c1cc(-c2c[nH]c([C@@H]3CCCN3)n2)ccc1COCc1ccc(-c2c[nH]c([C@@H]3CCCN3)n2)cc1]

Example OL-14f was prepared from Example OL-14e, according to the same procedure used for the preparation of Example OL-1e. $^1$H NMR (500 MHz, DMSO-$d_6$) δ ppm 1.94-2.06 (m, 2 H), 2.11-2.25 (m, 2 H), 2.38-2.48 (m, 4 H), 3.32-3.50 (m, 4 H), 4.60 (s, 4 H), 4.92-5.06 (m, 2 H), 7.48 (d, J=7.93 Hz, 4 H), 7.89 (d, J=7.93 Hz, 4 H), 8.04 (s, 2 H), 9.78 (s, 2 H), 10.28 (s, 2 H). Note: the signal of the imidazole NH was too broad to assign a chemical shift. LC (Cond. 1): RT=1.69 min; LRMS: Anal. Calcd. for $C_{28}H_{33}N_6O$ (M+H)$^+$ 469.27 found: 469.34.

Example OL-14

Example OL-14 was prepared from Example OL-14f, according to the same procedure used for the preparation of Example OL-1. $^1$H NMR (500 MHz, DMSO-$d_6$) δ ppm 1.82-2.11 (m, 6 H), 2.18 (d, J=6.10 Hz, 2 H), 2.31-2.47 (m, 4 H), 2.98-3.10 (m, 2 H), 3.92-4.07 (m, 2 H), 4.59 (s, 4 H), 5.10-5.22 (m, 2 H), 5.42 (s, 2 H), 7.07-7.13 (m, 2 H), 7.40-7.51 (m, 4 H), 7.54-7.67 (m, 10 H), 7.75 (d, J=7.32 Hz, 4 H). Note: the signal of the imidazole NH was too broad to assign a chemical shift. The signals for the Me groups of the cap fell underneath the solvent peak. LC (Cond. 4): RT=1.83 min; LRMS: Anal. Calcd. for $C_{48}H_{55}N_8O_3$ (M+H)$^+$ 791.44; found: 791.60. HRMS: Anal. Calcd. for $C_{48}H_{55}N_8O_3$ (M+H)$^+$ 791.4397; found: 791.4406.

Examples OL-15 to OL-19

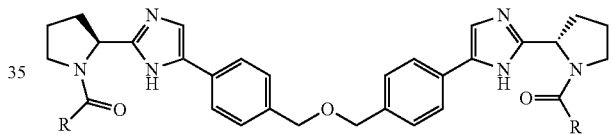

Examples OL-15 to OL-19 were prepared as TFA salts by substituting the respective acids for Cap-1 according to the same method described for Example OL-14.

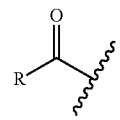

| Example | Acid | RT (LC-Cond.); MS data |
|---|---|---|
| OL-15 | ![Mandelic acid structure] Mandelic acid | RT = 2.86 min. LC (Cond. 4); LCMS: Anal. Calcd. for: $C_{44}H_{45}N_6O_4$ (M + H)$^+$ 737.34; Found: 737.38; HRMS: Anal. Calcd. for: $C_{44}H_{45}N_6O_4$ (M + H)$^+$ 737.3451; Found: 737.3452 |
| OL-16 | ![Cap-4 structure] Cap-4 | RT = 3.45 min. LC (Cond. 4); LCMS: Anal. Calcd. for: $C_{48}H_{51}N_8O_7$ (M + H)$^+$ 851.39; Found: 851.40; HRMS: Anal. Calcd. for: $C_{48}H_{51}N_8O_7$ (M + H)$^+$ 851.3881; Found: 851.3910 |

| Example | Acid | RT (LC-Cond.); MS data |
|---|---|---|
| OL-17 | Cap-45a | RT = 1.16 min. LC (Cond. 4); LCMS: Anal. Calcd. for: $C_{48}H_{53}N_{10}O_5$ $(M + H)^+$ 849.42; Found: 849.61; HRMS: Anal. Calcd. for: $C_{48}H_{53}N_{10}O_5$ $(M + H)^+$ 849.4200; Found: 849.4182 |
| OL-18 | Cap-46 | RT = 1.24 min. LC (Cond. 2); LCMS: Anal. Calcd. for: $C_{50}H_{56}N_{10}O_5$ $(M + H)^+$ 877.45; Found: 877.70; HRMS: Anal. Calcd. for: $C_{50}H_{57}N_{10}O_5$ $(M + H)^+$ 877.4513; Found: 877.4506 |
| OL-19 | Cap-48 | RT = 1.43 min. LC (Cond. 2); LCMS: Anal. Calcd. for: $C_{56}H_{65}N_{10}O_5$ $(M + H)^+$ 957.51; Found: 957.84; HRMS: Anal. Calcd. for: $C_{56}H_{65}N_{10}O_5$ $(M + H)^+$ 957.5139; Found: 957.5142 |
Example OL-20
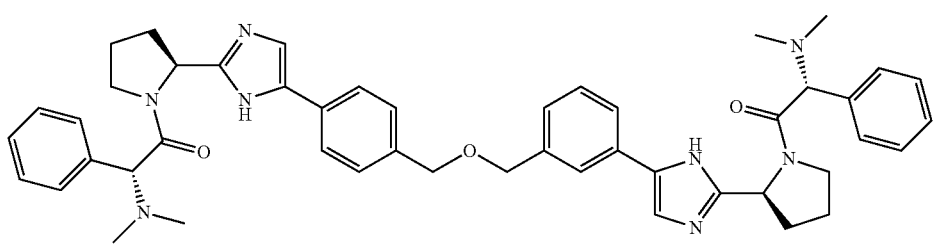 [SMILES: CN(C)[C@@H](C(=O)N1CCC[C@H]1c1ncc(-c2ccc(COCc3cccc(-c4cnc([C@@H]5CCCN5C(=O)[C@@H](c5ccccc5)N(C)C)[nH]4)c3)cc2)[nH]1)c1ccccc1]

Example OL-20a

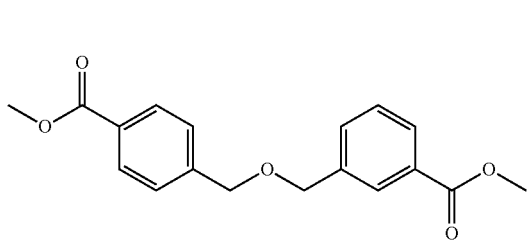

Sodium hydride (0.76 g, 18.95 mmol, 60% wt) was slowly added to a solution of methyl 4-(hydroxymethyl)benzoate (3 g, 18.05 mmol) in dimethylformamide (25 mL). The resulting dark blue solution was stirred at ambient for 15 min and methyl 3-(bromomethyl)benzoate (3.76 g, 16.41 mmol) was added in one portion. The resulting yellow solution was stirred at ambient for 1 h and then the volatiles were removed under reduced pressure. The residue was taken up in ethyl acetate and washed with water and brine, dried (MgSO$_4$), filtered and concentrated in vacuo. The residue was submitted to flash chromatography (silica gel; 20% ethyl acetate/hexanes) to provide Example OL-20a as a clear oil that solidified upon standing (2.49 g). $^1$H NMR (300 MHz, CDCl$_3$) δ ppm 3.91 (d, J=1.83 Hz, 6 H), 4.61 (d, J=2.56 Hz, 4 H), 7.39-7.49 (m, 3 H), 7.54-7.61 (m, 1 H), 7.93-8.00 (m, 1 H), 7.99-8.07 (m, 3 H). LC (Cond. 1): RT=2.56 min; LRMS: Anal. Calcd. for C$_{18}$H$_{19}$O$_5$ (M+H)$^+$ 315.12 found: 315.22.

Example OL-20b

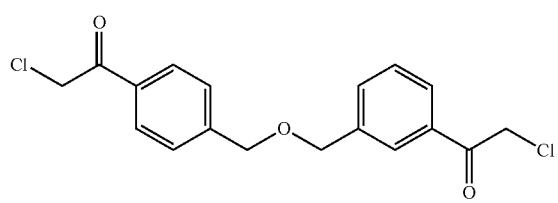 [SMILES: O=C(CCl)c1ccc(COCc2cccc(C(=O)CCl)c2)cc1]

Example OL-20b was prepared from Example OL-20a, according to the same procedure used for the preparation of Example OL-1a. $^1$H NMR (500 MHz, CDCl$_3$) δ ppm 4.65 (d, J=4.58 Hz, 4 H), 4.69 (d, J=3.36 Hz, 4 H), 7.47-7.54 (m, J=7.63, 7.63 Hz, 3 H), 7.62 (d, J=7.63 Hz, 1 H), 7.89 (d, J=7.93 Hz, 1 H), 7.93-8.00 (m, 3 H). LC (Cond. 1): RT=2.34 min; LRMS: Anal. Calcd. for C$_{18}$H$_{17}$Cl$_2$O$_3$ (M+H)$^+$ 351.05 found: 351.12.

Example OL-20c

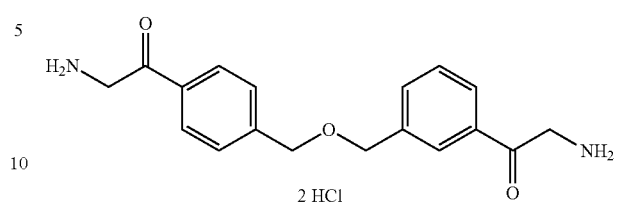

Example OL-20c was prepared from Example OL-20b, according to the same procedure used for the preparation of Example OL-1b. $^1$H NMR (300 MHz, DMSO-d$_6$) δ ppm 4.57 (d, J=2.93 Hz, 4 H), 4.68 (d, J=5.85 Hz, 4 H), 7.52-7.67 (m, J=8.60, 8.60 Hz, 3 H), 7.73 (d, J=7.68 Hz, 1 H), 7.90-8.10 (m, 4 H), 8.53 (s, 6 H). LC (Cond. 1): RT=1.32 min; LRMS: Anal. Calcd. for C$_{18}$H$_{21}$N$_2$O$_3$ (M+H)$^+$ 313.15 found: 313.24.

Example OL-20d

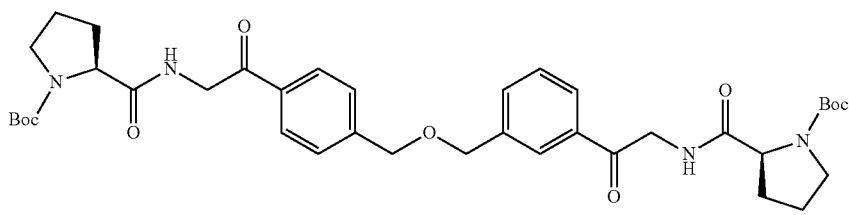 [SMILES: CC(C)(C)OC(=O)N1CCC[C@H]1C(=O)NCC(=O)c1ccc(COCc2cccc(C(=O)CNC(=O)[C@@H]3CCCN3C(=O)OC(C)(C)C)c2)cc1]

Example OL-20d was prepared from Example OL-20c, according to the same procedure used for the preparation of Example OL-1c. $^1$H NMR (500 MHz, DMSO-d$_6$) δ ppm 1.39/1.34 (rotomers, s, 18 H), 1.69-1.95 (m, 6 H), 2.00-2.18 (m, J=23.80 Hz, 2 H), 3.23-3.33 (m, 2 H), 3.34-3.43 (m, 2 H), 4.11-4.23 (m, 2 H), 4.50-4.63 (m, 4 H), 4.65 (d, J=6.71 Hz, 4 H), 7.48-7.56 (m, 3 H), 7.66 (d, J=7.63 Hz, 1 H), 7.89-8.02 (m, 4 H), 8.06-8.25 (m, 2 H). LC (Cond. 1): RT=2.53 min; LRMS: Anal. Calcd. for C$_{38}$H$_{51}$N$_4$O$_9$ (M+H)$^+$ 707.36 found: 707.44.

Example OL-20e

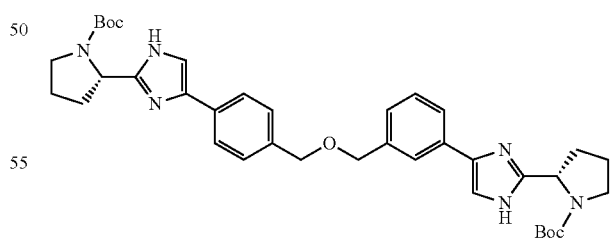

Example OL-20e was prepared from Example OL-20d, according to the same procedure used for the preparation of Example OL-1d. $^1$H NMR (500 MHz, DMSO-d$_6$) δ ppm 1.14/1.39 (rotomers, s, 18 H), 1.76-2.07 (m, 6 H), 2.08-2.29 (m, 2 H), 3.31-3.40 (m, 2 H), 3.52 (br. s, 2 H), 4.44-4.59 (m, J=8.55 Hz, 4 H), 4.75 (br. s, 1 H), 4.83 (br. s, 1 H), 7.08-7.23 (m, 2 H), 7.30 (d, J=7.63 Hz, 2 H), 7.34-7.50 (m, 2 H), 7.53-7.67 (m, 1 H), 7.68-7.79 (m, 3 H), 11.70-12.22 (m, 2 H).

LC (Cond. 1): RT=2.19 min; LRMS: Anal. Calcd. for C$_{38}$H$_{48}$N$_6$O$_5$ (M+H)$^+$ 669.39, found: 669.40.

Example OL-20f

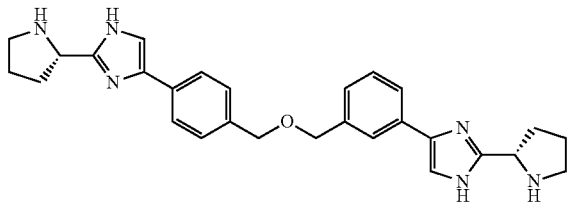 [SMILES: c1cc(COCc2ccc(-c3c[nH]c([C@@H]4CCCN4)n3)cc2)cc(-c2c[nH]c([C@@H]3CCCN3)n2)c1]

Example OL-20f was prepared from Example OL-20e, according to the same procedure used for the preparation of Example OL-1e. $^1$H NMR (500 MHz, DMSO-D6) δ ppm 1.94-2.08 (m, 2 H), 2.12-2.24 (m, 2 H), 2.39-2.48 (m, J=5.19 Hz, 4 H), 3.27-3.49 (m, 4 H), 4.61 (d, J=4.88 Hz, 4 H), 4.94-5.09 (m, J=7.93 Hz, 2 H), 7.38 (d, J=7.32 Hz, 1 H), 7.45-7.53 (m, 3 H), 7.83 (d, J=7.63 Hz, 1 H), 7.90 (d, J=7.02 Hz, 3 H), 8.07 (s, 2 H), 9.86 (br. s, 2 H), 10.33 (br. s, 2 H). Note: the signal of the imidazole NH was too broad to assign a chemical shift. LC (Cond. 1): RT=1.75 min; LRMS: Anal. Calcd. for C$_{28}$H$_{32}$N$_5$O (M+H)$^+$ 469.27, found: 469.23.

Example OL-20

Example OL-20 was prepared from Example OL-20f, according to the same procedure used for the preparation of Example OL-1. $^1$H NMR (500 MHz, DMSO-d$_6$) δ ppm 1.84-1.95 (m, J=5.19 Hz, 2 H), 1.95-2.09 (m, J=8.24 Hz, 4 H), 2.15-2.28 (m, 2 H), 3.02 (q, J=7.73 Hz, 2 H), 3.93-4.05 (m, 2 H), 4.61 (br. s, 4 H), 5.12-5.22 (m, 2 H), 5.42 (br.s, 2 H), 7.12 (br. s, 1 H), 7.39 (s, 1 H), 7.45-7.51 (m, J=7.32 Hz, 3 H), 7.53-7.64 (m, 9 H), 7.66-7.82 (m, 4 H), 7.96 (s, 2 H). Note: the signal of the imidazole NH was too broad to assign a chemical shift. The signals for the Me groups of the cap fell underneath the solvent peak. LC (Cond. 4): RT=1.93 min; LRMS: Anal. Calcd. for C$_{48}$H$_{55}$N$_8$O$_3$ (M+H)$^+$ 791.44; found: 791.57. HRMS: Anal. Calcd. for C$_{48}$H$_{55}$N$_8$O$_3$ (M+H)$^+$ . 791.4397; found: 791.4373.

Examples OL-21 to OL-25

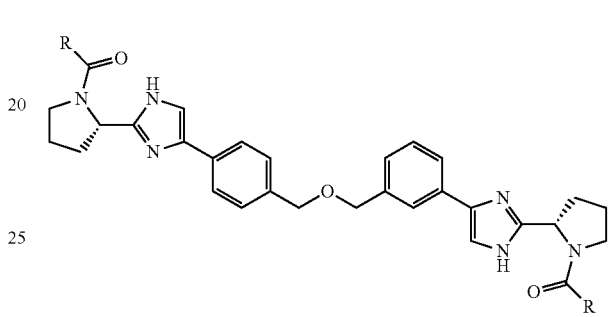

Examples OL-21 to OL-25 were prepared as TFA salts by substituting the respective acids for Cap-1 according to the same method described for Example OL-20.

| Example | Acid | RT (LC-Cond.); MS data |
|---|---|---|
| OL-21 | Mandelic acid | RT = 2.97 min. LC (Cond. 4); LCMS: Anal. Calcd. for: C$_{44}$H$_{45}$N$_6$O$_5$ (M + H)$^+$ 737.34; Found: 737.46; HRMS: Anal. Calcd. for: C$_{44}$H$_{45}$N$_6$O$_5$ (M + H)$^+$ 737.3451; Found: 737.3459 |
| OL-22 | Cap-4 | RT = 3.59 min. LC (Cond. 4); LCMS: Anal. Calcd. for: C$_{48}$H$_{51}$N$_8$O$_7$ (M + H)$^+$ 851.38; Found: 851.50; HRMS: Anal. Calcd. for: C$_{48}$H$_{51}$N$_8$O$_7$ (M + H)$^+$ 851.3881; Found: 851.3893 |
| OL-23 | Cap-45a | RT = 1.15 min. LC (Cond. 2); LCMS: Anal. Calcd. for: C$_{48}$H$_{52}$N$_{10}$O$_5$ (M + H)$^+$ 849.42; Found: 849.46; HRMS: Anal. Calcd. for: C$_{48}$H$_{53}$N$_{10}$O$_5$ (M + H)$^+$ 849.4200; Found: 849.4185 |

-continued

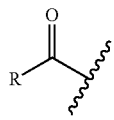

| Example | Acid | RT (LC-Cond.); MS data |
|---|---|---|
| OL-34 | Cap-46 | RT = 1.24 min. LC (Cond. 2); LCMS: Anal. Calcd. for: $C_{50}H_{56}N_{10}O_5$ (M + H)$^+$ 877.45 Found: 877.69; HRMS: Anal. Calcd. for: $C_{50}H_{57}N_{10}O_5$ (M + H)$^+$ 877.4513; Found: 877.4510 |
| OL-25 | Cap-48 | RT = 4.89 min. LC (Cond. 4); LCMS: Anal. Calcd. for: $C_{56}H_{64}N_{10}O_5$ (M + H)$^+$ 957.51; Found: 957.82; HRMS: Anal. Calcd. for: $C_{56}H_{65}N_{10}O_5$ (M + H)$^+$ 957.5139; Found: 957.5150 |

Example D-1

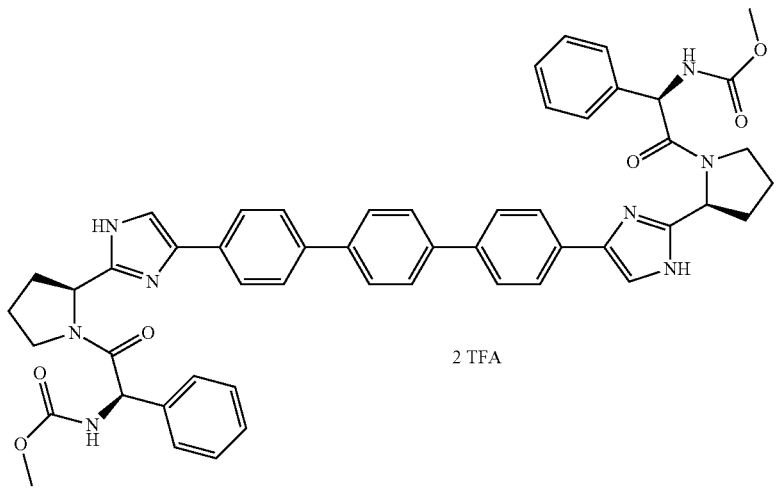 [SMILES: COC(=O)N[C@@H](C(=O)N1CCC[C@H]1c1nc(-c2ccc(-c3ccc(-c4ccc(-c5c[nH]c([C@@H]6CCCN6C(=O)[C@H](NC(=O)OC)c6ccccc6)n5)cc4)cc3)cc2)c[nH]1)c1ccccc1]

Example D-1

Step a

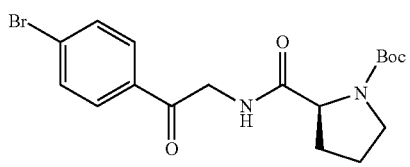 [SMILES: CC(C)(C)OC(=O)N1CCC[C@H]1C(=O)NCC(=O)c1ccc(Br)cc1]

N,N-Diisopropylethylamine (18 mL, 103.3 mmol) was added dropwise, over 15 minutes, to a heterogeneous mixture of N-Boc-L-proline (7.14 g, 33.17 mmol), HATU (13.32 g, 35.04 mmol), the HCl salt of 2-amino-1-(4-bromophenyl) ethanone (8.13 g, 32.44 mmol), and DMF (105 mL), and stirred at ambient condition for 55 minutes. Most of the volatile component was removed in vacuo, and the resulting residue was partitioned between ethyl acetate (300 mL) and water (200 mL). The organic layer was washed with water (200 mL) and brine, dried (MgSO$_4$), filtered, and concentrated in vacuo. A silica gel mesh was prepared from the residue and submitted to flash chromatography (silica gel; 50-60% ethyl acetate/hexanes) to provide D-1a as a white solid (12.8 g). $^1$H NMR (500 MHz, DMSO-d$_6$) δ ppm 1.40/ 1.34 (two app br s, 9 H), 1.90-1.70 (m, 3 H), 2.18-2.20 (m, 1 H), 3.30-3.23 (m, 1 H), 3.43-3.35 (m, 1 H), 4.22-4.12 (m, 1 H), 4.53 (dd, J=18.1, 5.6, 1 H), 4.61 (dd, J=18.3, 5.7, 1 H), 7.75 (br d, J=8.6, 2 H), 7.92 (br d, J=8.0, 2 H), 8.25-8.14 (m, 1H). LC (Cond. 7): RT=1.70 min; LRMS: Anal. Calcd. for (M+Na)$^+$ C$_{18}$H$_{23}$BrN$_2$NaO$_4$: 433.07 found 433.09.

Example D-1

Step b

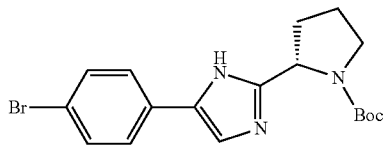 [SMILES: CC(C)(C)OC(=O)N1CCC[C@H]1c1ncc(-c2ccc(Br)cc2)[nH]1]

A mixture of D-1a (12.8 g, 31.12 mmol) and NH$_4$OAc (12.0 g, 155.7 mmol) in xylenes (155 mL) was heated in a sealed tube at 140° C. for 2 hours. The volatile component was removed in vacuo, and the residue was partitioned carefully between ethyl acetate and water, whereby enough saturated NaHCO$_3$ solution was added so as to make the pH of the aqueous phase slightly basic after the shaking of the biphasic system. The layers were separated, and the aqueous layer was extracted with additional ethyl acetate. The combined organic phase was washed with brine, dried (MgSO$_4$), filtered, and concentrated in vacuo. The resulting material was recrystallized from ethyl acetate/hexanes to provide two crops of imidazole D-1b as a light-yellow, dense solid, weighing 5.85 g. The mother liquor was concentrated in vacuo and submitted to a flash chromatography (silica gel; 30% ethyl acetate/ hexanes) to provide an additional 2.23 g of Example D-1b. $^1$H NMR (500 MHz, DMSO-d$_6$) δ ppm 1.40/1.15 (app br s, 9 H), 2.30-1.75 (m, 4 H), 3.36 (m, 1 H), 3.52 (app br s, 1 H), 4.86-4.70 (m, 1 H), 7.72-7.46/7.28 (m, 5 H), 12.17/11.92/ 11.86 (m, 1 H). LC (Cond. 7): RT=1.71 min; LRMS: Anal. Calcd. for [M+H]$^+$ C$_{18}$H$_{23}$BrN$_3$O$_2$: 392.10; found 391.96; HRMS: Anal. Calcd. for [M+H]$^+$ C$_{18}$H$_{23}$BrN$_3$O$_2$: 392.0974; found 392.0959.

The optical purity of the two samples of Example D-1b was assessed according to the chiral HPLC conditions noted below (ee>99% for the combined crops; ee=96.7% for the sample from flash chromatography):
Column: Chiralpak AD, 10 um, 4.6×50 mm
Solvent: 2% ethanol/heptane (isocratic)
Flow rate: 1 mL/min.
Wavelength: either 220 or 254 nm
Relative retention time: 2.83 minutes (R), 5.34 minutes (S).

Example D-1

Step c

Pd(Ph$_3$P)$_4$ (469 mg, 0.41 mmol) was added to a pressure tube containing a mixture of D-1b (4.01 g, 10.22 mmol), bis(pinacolato)diboron (5.42 g, 21.35 mmol), potassium acetate (2.57 g, 26.21 mmol) and 1,4-dioxane (80 mL). The pressure tube was purged with nitrogen, capped and heated in an oil bath at 80° C. for 16.5 hours. The reaction mixture was filtered and the filtrate was concentrated in vacuo. The crude residue was partitioned carefully between CH$_2$Cl$_2$ (150 mL) and an aqueous medium (50 mL water and 10 mL saturated NaHCO$_3$ solution). The aqueous layer was extracted with CH$_2$Cl$_2$, and the combined organic phase was dried (MgSO$_4$), filtered, and concentrated in vacuo. The resulting material was purified with flash chromatography (sample was loaded with eluting solvent; 20-35% ethyl acetate/CH$_2$Cl$_2$) to provide Example D-1c, contaminated with pinacol, as an off-white dense solid; the relative mole ratio of Example D-1c to pinacol was about 10:1 ($^1$H NMR). The sample weighed 3.925 g after ~2.5 days exposure to high vacuum. $^1$H NMR (500 MHz, DMSO-d$_6$) δ ppm 1.45-1.10 (m, 21H), 2.27-1.77 (m, 4H), 3.36 (m, 1H), 3.52 (app br s, 1H), 4.86-4.70 (m, 1H), 7.79-7.50/7.34-7.27 (m, 5H), 12.22/11.94/11.87 (m, 1H). LC (Cond. 7): RT=1.64 min; LRMS: Anal. Calcd. for [M+H]$^+$ C$_{24}$H$_{35}$BN$_3$O$_4$: 440.27; found 440.23.

Example D-1

Step d

Tetrakistriphenylphosphine palladium (17.5 mg, 0.015 mmol) was added in one portion to a stirred suspension of D-1e (320 mg, 0.85 mmol), 1,4-diiodobenzene (100 mg, 0.30 mmol) and sodium bicarbonate (180 mg, 2.18 mmol) in dimethoxyethane (2.4 mL) and water (7 mL) and heated to 90° C. for 2 h. The reaction was diluted with ethyl acetate and washed with saturated sodium bicarbonate. The organic layer was dried over sodium sulfate, filtered and concentrated in vacuo. The filtrate was taken up in methanol, filtered through a nylon syringe filter and then purified by preparative HPLC to provide D-1d as a white solid (101.1 mg, 20% yield). $^1$H NMR (500 MHz, DMSO-$d_6$) δ ppm 1.17 (br s, 9 H), 1.41 (br s, 9 H), 1.80-2.06 (m, 4 H), 2.13-2.32 (m, 4 H), 3.35-3.43 (m, 2 H), 3.56 (br. s., 2 H), 4.80 (br s, 2 H), 7.54 (d, J=10.07 Hz, 2 H), 7.73 (d, J=7.63 Hz, 4 H), 7.79 (s, 4 H), 7.83 (d, J=8.24 Hz, 4 H). LC (Cond. 6): RT=2.55 min; HRMS: Anal. Calcd. for (M+H)$^+$ $C_{42}H_{49}N_6O_4$ 701.3815; found: 701.3790.

Example D-1

Step e

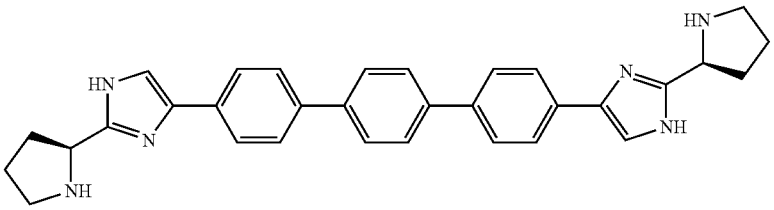 [SMILES: c1cc(-c2ccc(-c3c[nH]c([C@@H]4CCCN4)n3)cc2)ccc1-c1ccc(-c2c[nH]c([C@@H]3CCCN3)n2)cc1]

D-1e was prepared from D-1d, according to the same procedure used for the preparation of OL-1e except that methanol (1 mL) was used instead of dichloromethane. This gave D-1e as a tan solid and as a hydrochloride salt (101.5 mg, 96% yield). $^1$H NMR (500 MHz, DMSO-$d_6$) δ ppm 1.93-2.30 (m, 9 H), 2.32-2.44 (m, 3 H), 4.69-4.86 (m, 2 H), 7.68-7.87 (m, 12 H), 7.90 (d, J=8.24 Hz, 2 H), 9.48-9.75 (m, 2 H). LC (Cond. 6): RT=1.99 min; HRMS: Anal. Calcd. for (M+H)$^+$ $C_{32}H_{33}N_6$ 501.2767; found: 501.2753.

Example D-1

Example D-1 (TFA salt) was prepared from D-1e, according to the same procedure used for the preparation of Example OL-1. This gave Example D-1 as a tan solid (37.8 mg, 54% yield). $^1$H NMR (500 MHz, DMSO-$d_6$) δ ppm 2.05 (d, J=8.55 Hz, 8H), 3.49-3.57 (m, 10 H), 3.94 (br s, 2 H), 5.52 (d, J=7.63 Hz, 2 H), 7.31-7.47 (m, 10 H), 7.72 (d, J=7.02 Hz, 2 H), 7.87-8.01 (m, 12 H). LC (Cond. 6): RT=2.41 min; HRMS: Anal. Calcd. for (M+H)$^+$ $C_{52}H_{51}N_8O_6$ 883.3932; found: 883.3947.

Example D-2

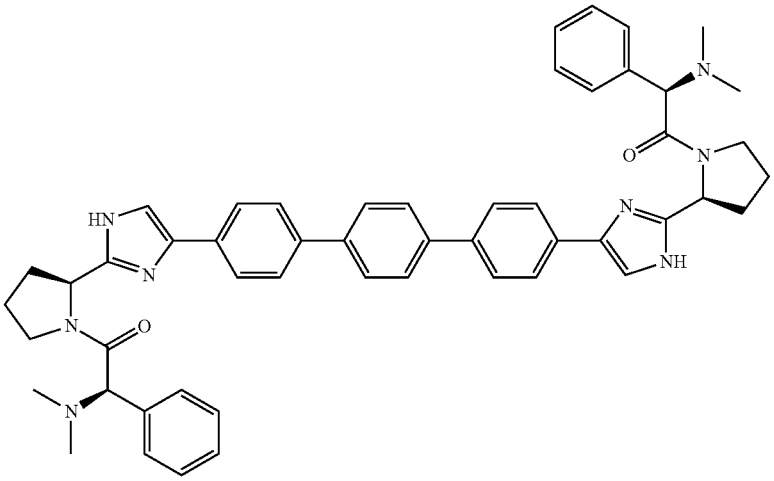 [SMILES: CN(C)[C@@H](C(=O)N1CCC[C@H]1c1nc(-c2ccc(-c3ccc(-c4ccc(-c5c[nH]c([C@@H]6CCCN6C(=O)[C@@H](c6ccccc6)N(C)C)n5)cc4)cc3)cc2)c[nH]1)c1ccccc1]

Example D-2 (TFA salt) was prepared from pyrrolidine D-1e, according to the same procedure used for the preparation of Example OL-1. This gave Example D-2 as a light yellow solid (15.4 mg, 38% yield). $^1$H NMR (500 MHz, DMSO-$d_6$) δ ppm 2.50-1.70 (m, 14 H), 2.98-2.62 (m, 6 H), 4.05-2.98 (m, 4 H), 5.79-5.12 (m, 4 H), 8.20-7.10 (m, 24 H), 10.25 (br s, 2 H). Note: The signal of the imidazole NH was too broad to assign a chemical shift. LC (Cond. 6): RT=2.08 min; HRMS: Anal. Calcd. For (M+H)$^+$ C$_{52}$H$_{55}$N$_8$O$_2$ 823.4448; found: 823.4467.

Example D-3

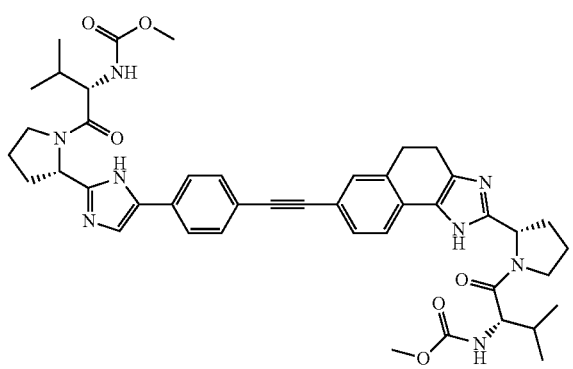 [SMILES: COC(=O)N[C@H](C(=O)N1CCC[C@H]1c1ncc(-c2ccc(C#Cc3ccc4c(c3)CCc3nc([C@@H]5CCCN5C(=O)[C@@H](NC(=O)OC)C(C)C)[nH]c3-4)cc2)[nH]1)C(C)C]

Example D-3

Step a

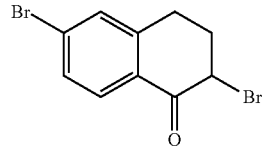 [SMILES: O=C1c2ccc(Br)cc2CCC1Br]

A solution of bromine (683 μL, 13.33 mmol) in acetic acid (7 mL) was added dropwise to a cold (10° C.) solution of 6-bromo-3,4-dihydronaphthalen-1(2 H)-one (purchased from J & W PharmLab, LLC) (3.00 g, 13.33 mmol) and 48% hydrogen bromide (20 μL, 13.33 mmol) in acetic acid (120 mL). The mixture was allowed to warm up to rt after the addition was complete and allowed to stir at rt for 1 h before it was diluted with dichloromethane and washed with water (3×), saturated sodium bicarbonate solution, dried over anhydrous sodium sulfate and concentrated. There was isolated D-3a (4.19 g, 97% yield) as a colorless oil which solidified on standing under high vacuum to a white solid. This material was used without further purification. $^1$H NMR (500 MHz, DMSO-$d_6$) δ ppm 7.85 (1 H, d, J=8.5 Hz), 7.71 (1 H, s), 7.62 (1 H, dd, J=8.5, 1.8 Hz), 5.06 (1 H, dd, J=6.1, 3.7 Hz), 2.93-3.15 (2 H, m), 2.55-2.64 (1 H, m), 2.32-2.42 (1 H,m). RT=2.67 min (Cond. 6); LC/MS: Anal. Calcd. for [M+H]$^+$ C$_{10}$H$_9$$^{79}$Br$_2$O: 304.90; found: 304.91.

Examples D-3b1 and D-3b2

Step b

D-3b1 and D-3b2 were prepared from D-3a and the appropriate Boc-protected prolines according to the same procedure used for the preparation of Example M3, step g.

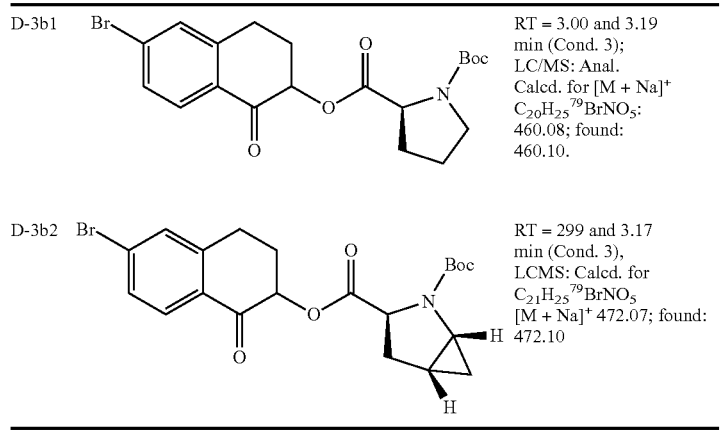

| | |
|---|---|
| D-3b1 | RT = 3.00 and 3.19 min (Cond. 3); LC/MS: Anal. Calcd. for [M + Na]$^+$ C$_{20}$H$_{25}$$^{79}$BrNO$_5$: 460.08; found: 460.10. |
| D-3b2 | RT = 299 and 3.17 min (Cond. 3), LCMS: Calcd. for C$_{21}$H$_{25}$$^{79}$BrNO$_5$ [M + Na]$^+$ 472.07; found: 472.10 |

Examples D-3c1 and D-3c2

Step c

D-3c1 and D-3c2 were prepared from D-3b1 and D-3b2 respectively according to the same procedure used for the preparation of Example M3, step h.

| | | |
|---|---|---|
| D-3c1 | 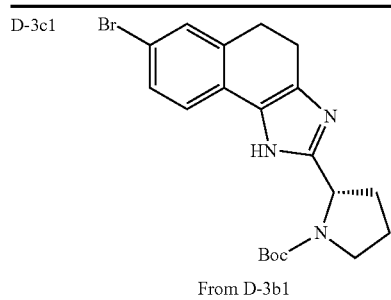<br>From D-3b1 | ¹H NMR (500 MHz, MeOD, imidazole N—H missing) δ ppm 7.32-7.43 (3H, m), 4.86-4.97 (1H, m), 3.63-3.74 (1H, m), 3.47-3.57 (1H, m), 2.98-3.07 (2H, m), 2.83 (2H, d, J = 8.2 Hz), 2.25-2.45 (1H, m), 2.00-2.11 (2H, m), 1.93-1.99 (1H, m), 1.25-1.48 (9H, 2s). RT = 2.24 min (Cond. 3); LC/MS: Anal. Calcd. for [M + H]⁺ $C_{20}H_{25}{}^{79}BrN_3O_2$: 418.13; found: 418.10. HRMS: Anal. Calcd. for [M + H]⁺ $C_{21}H_{25}{}^{79}BrN_3O_2$: 430.1125; found 430.1124. |
| D-3c2 | 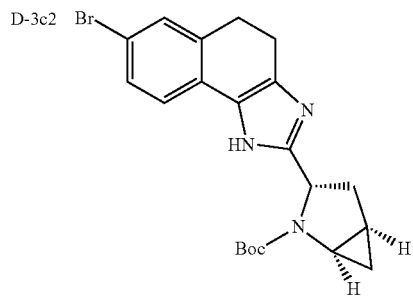<br>From D-3b2 | RT = 2.28 min (Cond. 3); LC/MS: Anal. Calcd. for [M + H]⁺ $C_{21}H_{25}{}^{79}BrN_3O_2$: 430.11; found: 430.16. HRMS: Anal. Calcd. for [M + H]⁺ $C_{21}H_{25}{}^{79}BrN_3O_2$: 430.1125; found 430.1123. |
| D-3c3 | 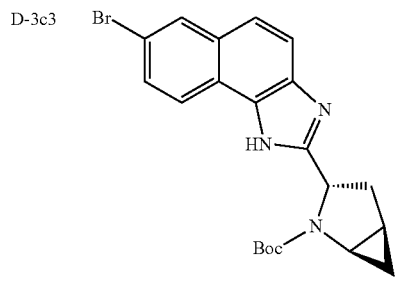<br>Prepared from D-3c2 according to the same procedure used for the preparation of D-3g1 | RT = 2.06 min (Cond. 3); LC/MS: Anal. Calcd for $C_{21}H_{23}{}^{81}BrN_3O_2$ (M + H)⁺ 430.10; found: 429.98. |

Example D-3d1

Step d

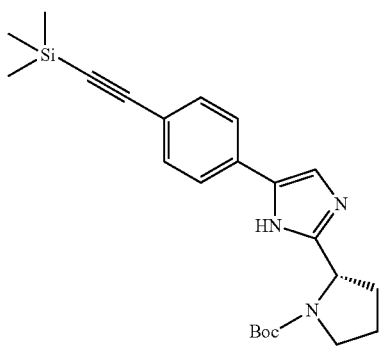 [SMILES: CC(C)(C)OC(=O)N1CCC[C@H]1c1ncc(-c2ccc(C#C[Si](C)(C)C)cc2)[nH]1]

Ethynyltrimethylsilane (0.59 mL, 4.25 mmol) was added to a solution of D-1b (1.5 g, 3.82 mmol), triphenylphosphine (0.20 g, 0.77 mmol), diethylamine (4.25 mL, 40.70 mmol), copper (I) iodide (40 mg, 0.21 mmol) and trans-dichloro(bis-triphenylphosphine)palladium (II) (149 mg, 0.21 mmol) in dry DMF (1.4 mL) at rt in a microwave vessel. The vessel was capped and irradiated for 25 min at 120° C. Two identical 1.5 g reactions were run in tandem. The reaction mixtures were diluted with ether and ethyl acetate, combined and shaken with 0.1N HCl. After standing for 20 min, the suspension was suction-filtered and the pad was washed with ether and ethyl acetate. The organic phase was then separated, washed with brine, dried over sodium sulfate, and concentrated. There was isolated the crude product (4.2 g) as a brownish-red foam which was taken up in dichloromethane and added directly to a Thompson 110 g silica gel column. Gradient elution of the residue with 20% ethyl acetate in dichloromethane to 100% ethyl acetate furnished D-3d1 (2.8 g, 40% yield) as a yellow solid after evaporation of the eluant which was taken forward directly. RT=2.37 min (Cond. 3); LC/MS: Anal. Calcd for $C_{23}H_{32}N_3O_2Si$ [M+H]⁺ 410.23; found: 410.12.

D-3d2 to D-3d4 were prepared according to the procedures described for D-3d1.

| | | |
|---|---|---|
| D-3d2 | 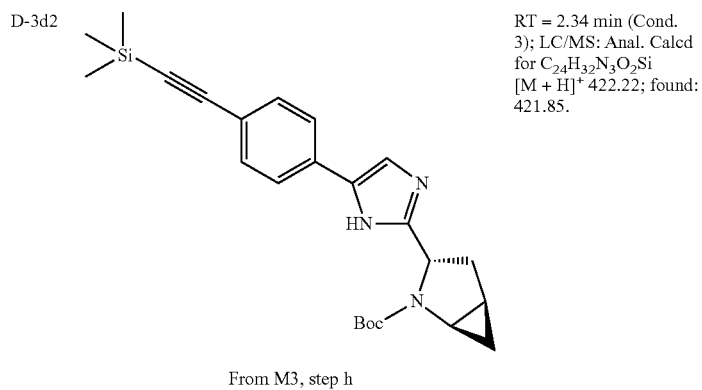<br>From M3, step h | RT = 2.34 min (Cond. 3); LC/MS: Anal. Calcd for $C_{24}H_{32}N_3O_2Si$ $[M + H]^+$ 422.22; found: 421.85. |
| D-3d3 | 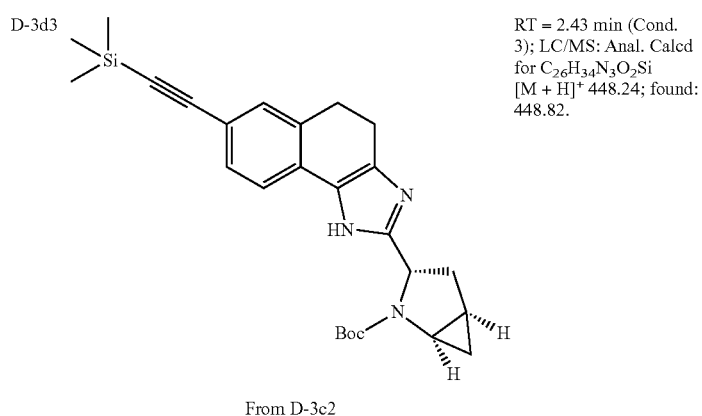<br>From D-3c2 | RT = 2.43 min (Cond. 3); LC/MS: Anal. Calcd for $C_{26}H_{34}N_3O_2Si$ $[M + H]^+$ 448.24; found: 448.82. |
| D-3d4 | 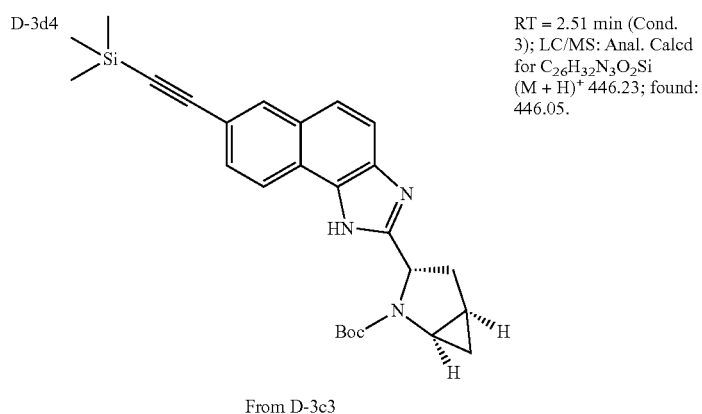<br>From D-3c3 | RT = 2.51 min (Cond. 3); LC/MS: Anal. Calcd for $C_{26}H_{32}N_3O_2Si$ $(M + H)^+$ 446.23; found: 446.05. |

Example D-3e1

Step e

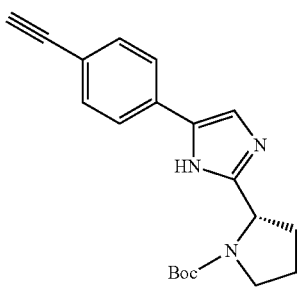 [SMILES: C#Cc1ccc(-c2cnc([C@@H]3CCCN3C(=O)OC(C)(C)C)[nH]2)cc1]

Potassium carbonate (91 mg, 0.66 mmol) was added in one portion to a stirred solution of D-3d1 (2.7 g, 6.6 mmol) in MeOH (60 mL) at rt. The mixture was stirred for 1 h before it was concentrated down in vacuo. The residue was taken up in dichloromethane and added directly to a 130 g Thompson silica gel column. Gradient elution of the residue with 15% ethyl acetate in hexanes to 100% ethyl acetate furnished D-3e1 (2.04 g, 87% yield) as a yellow foam after evaporation of the eluant. A small amount (approx. 20 mg) of the product was then subjected to preparative HPLC to afford a purer sample of D-3e1 as an off-white solid. $^1$H NMR (500 MHz, MeOD, imidazole N—H missing) δ ppm 7.68 (2 H, d, J=7.9 Hz), 7.46 (2 H, d, J=8.2 Hz), 7.34-7.40 (1 H, m), 4.89 (1 H, m), 3.64-3.73 (1 H, m), 3.49 (1 H, m), 3.49 (1 H, s), 3.31-3.34 (1 H, m), 2.25-2.44 (1 H, m), 1.99-2.11 (3 H, m), 1.25 and 1.47 (9 H, 2s). RT=1.63 min (Cond. 3), LC/MS: Anal. Calcd for $C_{20}H_{24}N_3O_2$ (M+H)$^+$ 338.19; found: 338.12.

D-3e2 to D-3e5 were prepared according to the procedures described for alkene D-3e1.

D-3e2

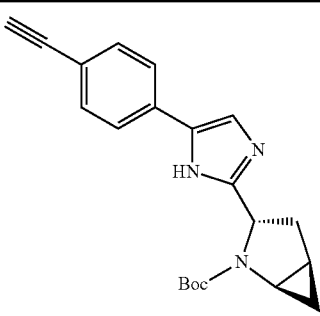

From D-3d2

RT = 1.65 min (Cond. 3); LC/MS: Anal. Calcd for $C_{21}H_{24}N_3O_2$ [M + H]$^+$ 350.19; found: 350.10.

D-3e3

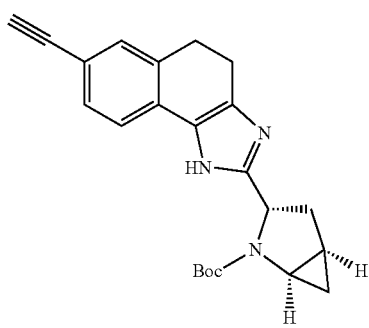 [SMILES: C#Cc1ccc2c(c1)CCc1nc([C@@H]3C[C@H]4C[C@H]4N3C(=O)OC(C)(C)C)[nH]c1-2]

From D-3d3

RT = 1.81 min (Cond. 3); LC/MS: Anal. Calcd for $C_{23}H_{26}N_3O_2$ [M + H]$^+$ 376.20; found: 376.20.

D-3e4

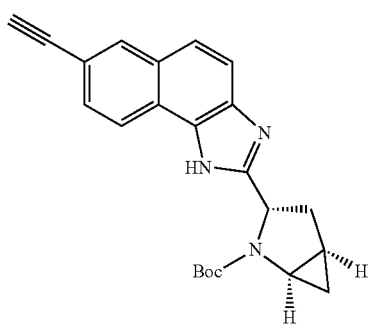 [SMILES: C#Cc1ccc2c(ccc3nc([C@@H]4C[C@H]5C[C@H]5N4C(=O)OC(C)(C)C)[nH]c32)c1]

From D-3d4

RT = 1.88 min (Cond. 3); LC/MS: Anal. Calcd for $C_{23}H_{24}N_3O_2$ (M + H)$^+$ 374.19; found: 374.04.

| D-3e5 | 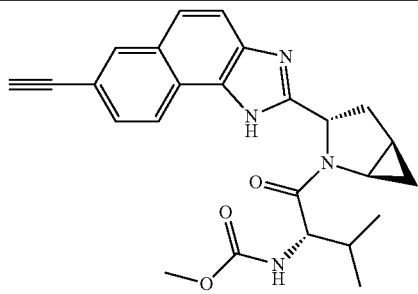 | RT = 1.75 min (Cond. 3); LC/MS: Anal. Calcd for $C_{25}H_{27}N_4O_3$ [M + H]$^+$ 431.21; found: 431.09. |
|---|---|---|
| | Prepared from D-3e4 and Cap-51 using the procedures outlined for D-3h1 and Example OL-1 | |

Example D-3f1

Step f

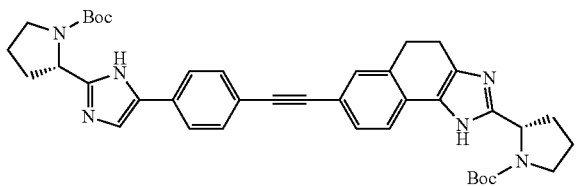 [SMILES: CC(C)(C)OC(=O)N1CCC[C@H]1c1ncc(-c2ccc(C#Cc3ccc4c(c3)CCc3nc([C@@H]5CCCN5C(=O)OC(C)(C)C)[nH]c3-4)cc2)[nH]1]

Tetrakis(triphenylphosphine)palladium (83 mg, 0.072 mmol) was added in one portion to a stirred, argon-degassed mixture of Example D-3c1 (300 mg, 0.717 mmol), D-3e1 (315 mg, 0.932 mmol), triethylamine (0.40 mL, 2.87 mmol) and copper(I) iodide (13.7 mg, 0.072 mmol) in anhydrous DMF (6 mL) at rt in a thick-walled, screw-top vial. The mixture was stirred at rt for 16 h and at 40° C. for 16 h before additional CuI (10 mg), TEA (0.4 mL) and Pd(PPh$_3$)$_4$ catalyst (40 mg) were added since the reaction was not complete after 32 h as judged by LCMS. The mixture was stirred further at 60° C. for 10 h before it was cooled to rt, diluted with ethyl acetate, THF and water and suction-filtered. The organic phase of the filtrate was separated, washed with saturated sodium bicarbonate solution and brine prior to drying over anhydrous sodium sulfate and evaporation. The residue was taken up in dichloromethane and added directly to a Thompson 80 g silica gel column. Gradient elution of the residue with 30% ethyl acetate in hexanes to 100% ethyl acetate followed by 0% methanol in ethyl acetate to 20% methanol in ethyl acetate furnished D-3f1 (366.7 mg, 68% yield) as a golden brown foam after evaporation of the eluant. A small amount (approx. 20 mg) of product was then subjected to preparative HPLC to afford a purer sample of Example D-3f1 as a tan solid. $^1$H NMR (500 MHz, MeOD, imidazole N—H's missing) δ ppm 7.73 (2 H, d, J=8.2 Hz), 7.47-7.57 (4 H, m), 7.41 (2 H, br s), 4.96-5.09 (1 H, m), 4.89-4.96 (1 H, m), 3.69 (2 H, br s), 3.54 (2 H, br s), 3.04-3.13 (2 H, m), 2.83-2.94 (2 H, m), 2.30-2.50 (2 H, m), 1.94-2.17 (6 H, m), 1.27-1.49 (18 H, 2s). RT=2.06 min (Cond. 3); LC/MS: Anal. Calcd for $C_{40}H_{47}N_6O_4$ (M+H)$^+$ 675.37; found: 675.26.

D-3f2 to D-3f4 were prepared according to the procedure described for D-3f1.

| D-3f2 | 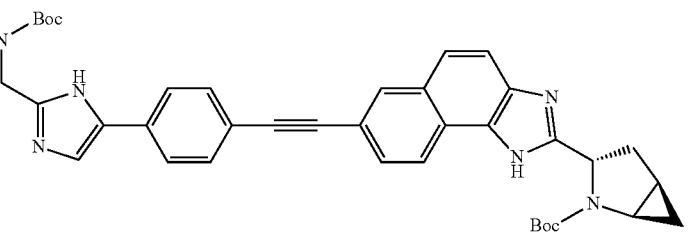 | RT = 2.12 min (Cond. 3); LC/MS: Anal. Calcd for $C_{42}H_{45}N_6O_4$ [M + H]$^+$ 697.35; found: 697.25. |
|---|---|---|
| | D-3e2 and D-3c3 | |

| D-3f3 | 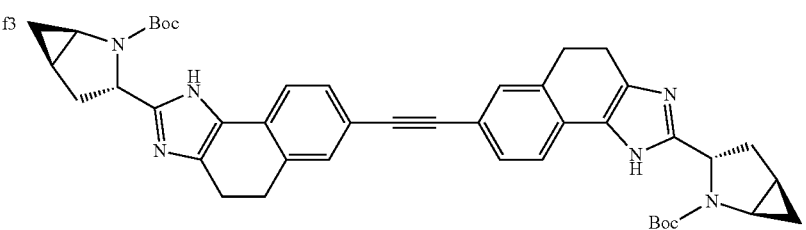 | RT = 2.14 min (Cond. 3); LC/MS: Anal. Calcd for $C_{44}H_{49}N_6O_4$ [M + H]$^+$ 725.38; found: 725.25. |
|---|---|---|
| | From D-3e3 and D-3c2 | |

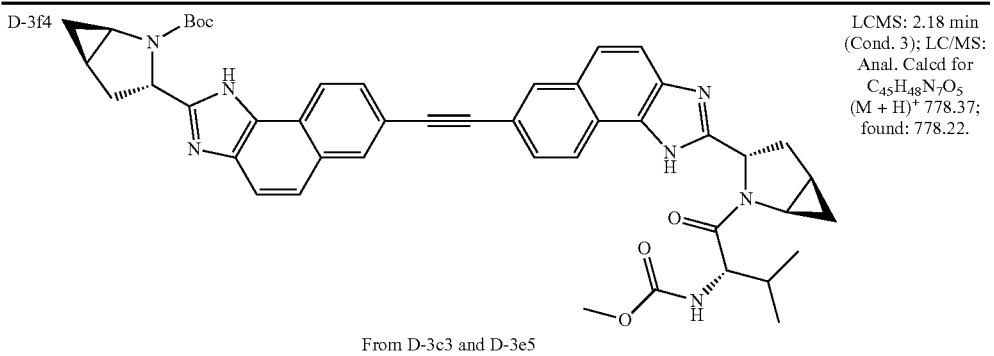

LCMS: 2.18 min (Cond. 3); LC/MS: Anal. Calcd for C$_{45}$H$_{48}$N$_7$O$_5$ (M + H)$^+$ 778.37; found: 778.22.

From D-3c3 and D-3e5

Example D-3g1

Step g

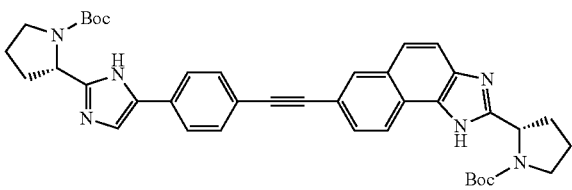 [SMILES: CC(C)(C)OC(=O)N1CCC[C@H]1c1ncc(-c2ccc(C#Cc3ccc4c(ccc5nc([C@@H]6CCCN6C(=O)OC(C)(C)C)[nH]c54)c3)cc2)[nH]1]

Activated manganese dioxide (2.0 g, 23.12 mmol) was added in one portion to a stirred solution of D-3f1 (260 mg, 0.39 mmol) in dry dichloromethane (5 mL). The suspension was stirred at rt for 6 h before additional activated manganese dioxide (1.0 g) was added. The suspension was stirred further for 14 h at rt before it suction-filtered through a pad of Celite with MeOH and the pad was washed with additional MeOH several times. The filtrate was then concentrated in vacuo to yield D-3g1 (225.1 mg, 82% yield) as a yellow solid. A small amount (approx. 20 mg) of the product was then subjected to preparative HPLC to afford a purer sample of D-3g1 as a light tan solid. $^1$H NMR (500 MHz, MeOD, imidazole N—H's missing) δ ppm 8.43 (1 H, d, J=8.5 Hz), 8.19 (1 H, br s), 7.68-7.78 (5 H, m), 7.62 (2 H, d, J=8.2 Hz), 7.54 (1 H, s), 4.90-5.27 (2 H, m), 3.76-3.85 (1 H, m), 3.66-3.74 (1 H, m), 3.51-3.66 (2 H, m), 2.35-2.60 (2 H, m), 1.94-2.21 (6 H, m), 1.49 (6 H, br s), 1.27 (6 H, br s), 1.14 (6 H, br s). RT=2.12 min (Cond. 3); LC/MS: Anal. Calcd for C$_{40}$H$_{45}$N$_6$O$_4$ (M+H)$^+$ 673.35; found: 673.30.

D-3g2 was prepared according to the procedure described for D-3g1.

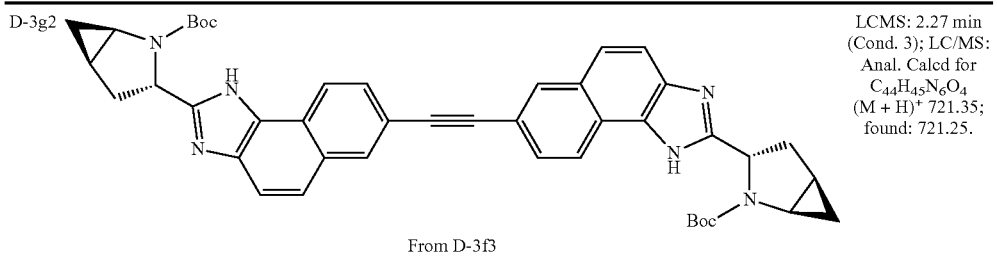

LCMS: 2.27 min (Cond. 3); LC/MS: Anal. Calcd for C$_{44}$H$_{45}$N$_6$O$_4$ (M + H)$^+$ 721.35; found: 721.25.

From D-3f3

Example D-3h1

Step h

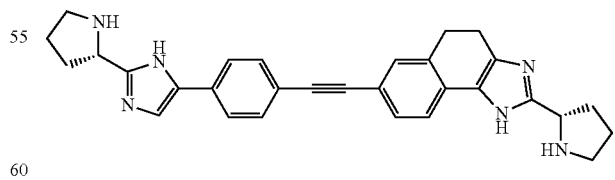

D-3h1 to D-3h6 were prepared from D-3f1, D-3g1, D-3f2, D-3f3, D-3g2 and D-3f4, respectively, according to the same procedure used for the preparation of OL-1e except that methanol (1 mL) was used instead of dichloromethane. This gave D-3h1 to D-3h6 as hydrochloride salts (or TFA salts when purified further with preparative HPLC) upon concentration of the solvent(s) in vacuo.

| | | |
|---|---|---|
| D-3h1 | 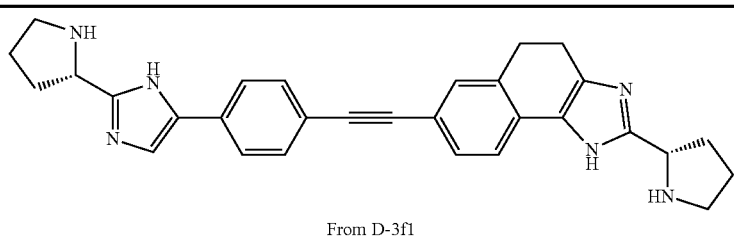<br>From D-3f1 | RT = 1.44 min (Cond. 3); LC/MS: Anal. Calcd for C$_{30}$H$_{31}$N$_6$ [M + H]$^+$ 475.26; found: 475.16. |
| D-3h2 | 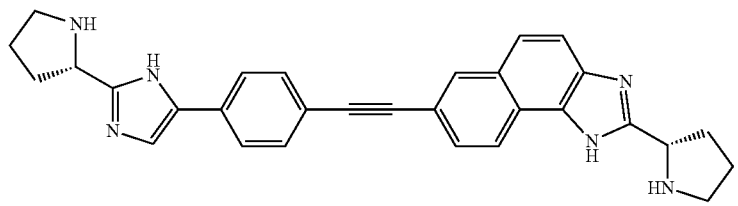 [SMILES: C(#Cc1ccc2c(ccc3nc([C@@H]4CCCN4)[nH]c32)c1)c1ccc(-c2cnc([C@@H]3CCCN3)[nH]2)cc1]<br>From D-3g1 | $^1$H NMR (500 MHz, MeOD, imidazole N-H's missing) δ ppm 8.46 (1H, d, J = 8.5 Hz), 8.21 (1H, s), 7.84 (2 H, d, J = 8.2 Hz), 7.70-7.80 (4H, m), 7.64 (2H, d, J = 8.5 Hz), 5.15 (1H, s), 4.97 (1H, s), 3.62-3.70 (1H, m), 3.56 (3H, s), 2.65-2.75 (1H, m), 2.55-2.64 (1H, m), 2.17-2.53 (6 H, series of m). RT = 1.61 min (Cond. 3); LC/MS: Calcd for C$_{30}$H$_{29}$N$_6$ (M + H)$^+$ 473.25; found: 473.13. |
| D-3h3 | 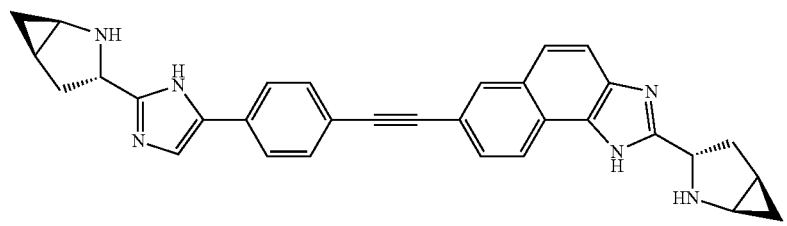 [SMILES: C(#Cc1ccc2c(ccc3nc([C@@H]4C[C@H]5C[C@H]5N4)[nH]c32)c1)c1ccc(-c2cnc([C@@H]3C[C@H]4C[C@H]4N3)[nH]2)cc1]<br>From D-3f2 | RT = 1.62 min (Cond. 3); LC/MS: Anal. Calcd for C$_{32}$H$_{29}$N$_6$ (M + H)$^+$ 497.25; found: 497.13. |
| D-3h4 | 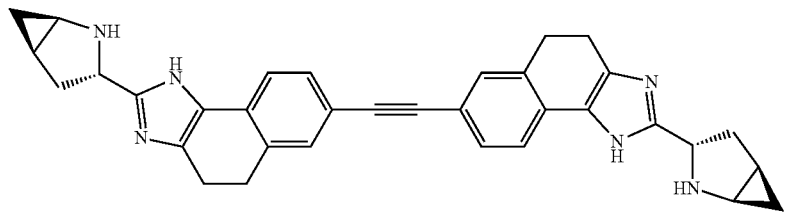 [SMILES: C(#Cc1ccc2c(c1)CCc1nc([C@@H]3C[C@H]4C[C@H]4N3)[nH]c1-2)c1ccc2c(c1)CCc1nc([C@@H]3C[C@H]4C[C@H]4N3)[nH]c1-2]<br>From D-3f3 | RT = 1.62 min (Cond. 3); LC/MS: Anal. Calcd for C$_{34}$H$_{33}$N$_6$ [M + H]$^+$ 525.28; found: 525.13. |
| D-3h5 | 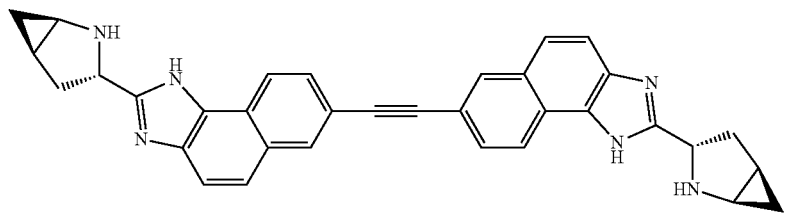 [SMILES: C(#Cc1ccc2c(ccc3nc([C@@H]4C[C@H]5C[C@H]5N4)[nH]c32)c1)c1ccc2c(ccc3nc([C@@H]4C[C@H]5C[C@H]5N4)[nH]c32)c1]<br>From D-3g2 | LCMS: 1.78 min (Cond. 3); LC/MS: Anal. Calcd for C$_{34}$H$_{29}$N$_6$ (M + H)$^+$ 521.25; found: 521.13. |
| D-3h6 | 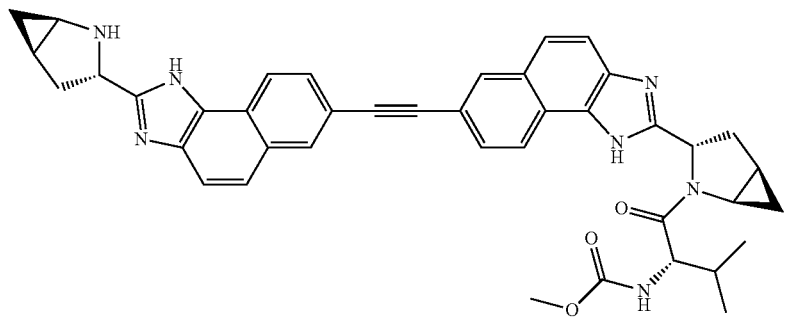 [SMILES: COC(=O)N[C@H](C(=O)N1[C@@H]2C[C@@H]2C[C@H]1c1nc2ccc3cc(C#Cc4ccc5c(ccc6nc([C@@H]7C[C@H]8C[C@H]8N7)[nH]c65)c4)ccc3c2[nH]1)C(C)C]<br>From D-3f4 | LCMS: 1.95 min (Cond. 3); LC/MS: Anal. Calcd for C$_{41}$H$_{40}$N$_7$O$_3$ (M + H)$^+$ 678.32; found: 678.45. |

Example D-3 to D-11

Final Step

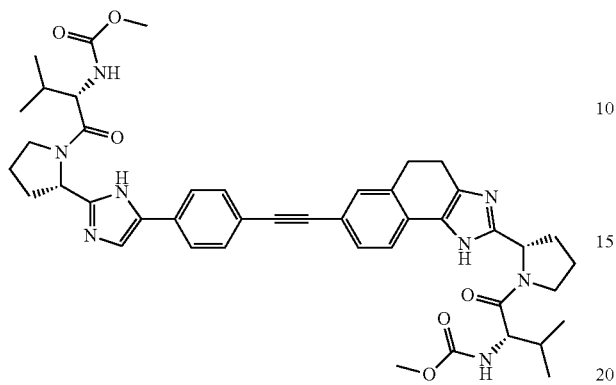

Examples D-3 to D-11 were prepared from D-3h1 to D-3h6 and the appropriate acids according to the same procedure used for the preparation of Example OL-1. This gave Examples D-3 to D-11 as TFA salts after HPLC purification.

| | | |
|---|---|---|
| D-3 | 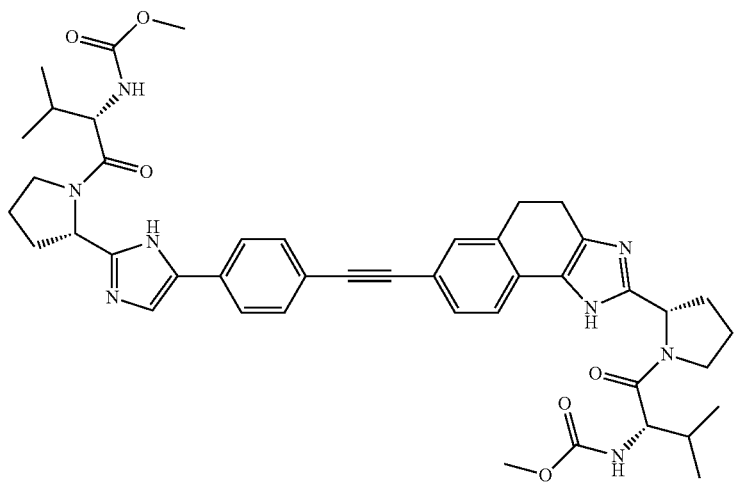<br>From D-3h1 and Cap 51 | RT = 1.80 min (Cond. 3); LC/MS: Anal. Calcd for $C_{44}H_{53}N_8O_6$ $[M + H]^+$ 789.41; found: 789.27. $^1$H NMR (500 MHz, MeOD, imidazole N-H's missing) δ ppm 7.86-7.91 (1H, m), 7.73-7.80 (2H, m), 7.64-7.71 (2H, m), 7.50-7.59 (3H, m), 5.59-5.65 and 5.16-5.31 (2H, 2m), 4.21-4.29 (2H, m), 4.06-4.16 (2H, m), 3.81-3.93 (2H, m), 3.67 (6H, s), 3.15-3.24 (2H, m), 2.95-3.07 (2H, m), 2.51-2.65 (2H, m), 2.25-2.37 (2H, m), 2.14-2.23 (4H, m), 1.99-2.11 (2H, m), 0.09-0.95 (12H, m), 0.97-1.05 (2H, m). |
| D-4 | 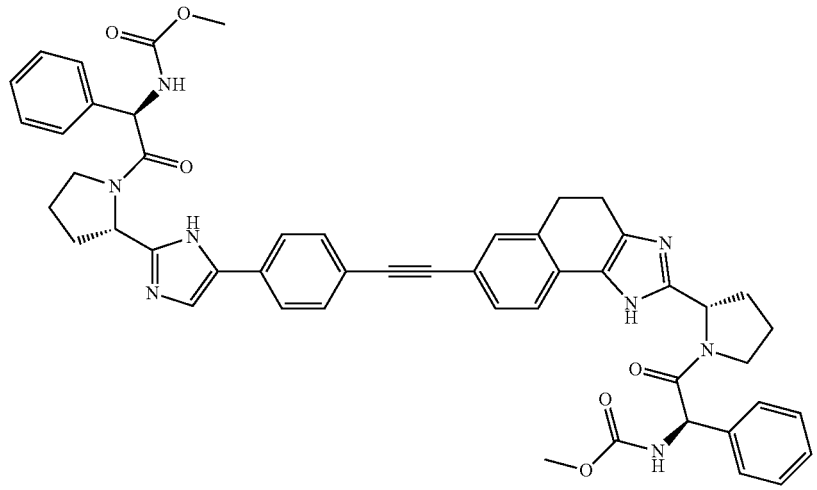 [SMILES: COC(=O)N[C@@H](C(=O)N1CCC[C@H]1c1ncc(-c2ccc(C#Cc3ccc4c(c3)CCc3nc([C@@H]5CCCN5C(=O)[C@H](NC(=O)OC)c5ccccc5)[nH]c3-4)cc2)[nH]1)c1ccccc1]<br>From D-3h1 and Cap 4 | RT = 1.88 min (Cond. 3); LC/MS: Anal. Calcd for $C_{50}H_{49}N_8O_6$ $[M + H]^+$ 857.38; found: 857.31. |

D-5
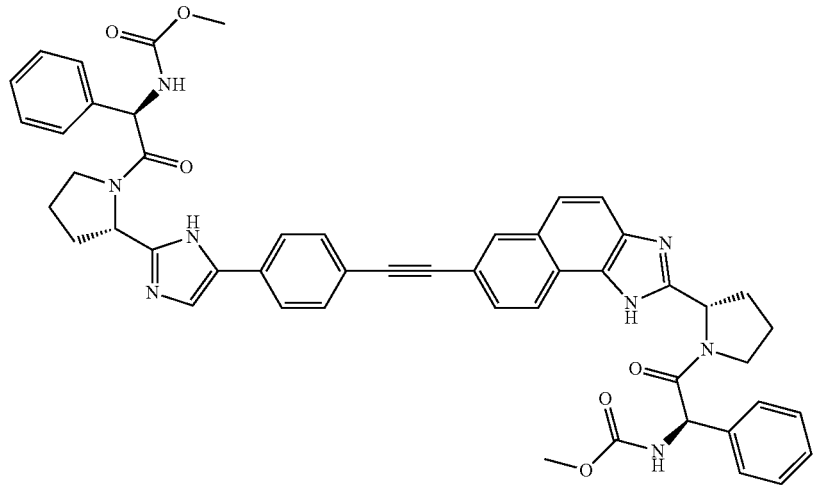 [SMILES: COC(=O)N[C@@H](C(=O)N1CCC[C@H]1c1ncc(-c2ccc(C#Cc3ccc4c(ccc5nc([C@@H]6CCCN6C(=O)[C@H](NC(=O)OC)c6ccccc6)[nH]c54)c3)cc2)[nH]1)c1ccccc1]
From D-3h2 and Cap 4
RT = 1.94 min (Cond. 3); LC/MS: Anal. Calcd for $C_{50}H_{47}N_8O_6$ $[M + H]^+$ 855.36; found: 855.28.
D-6
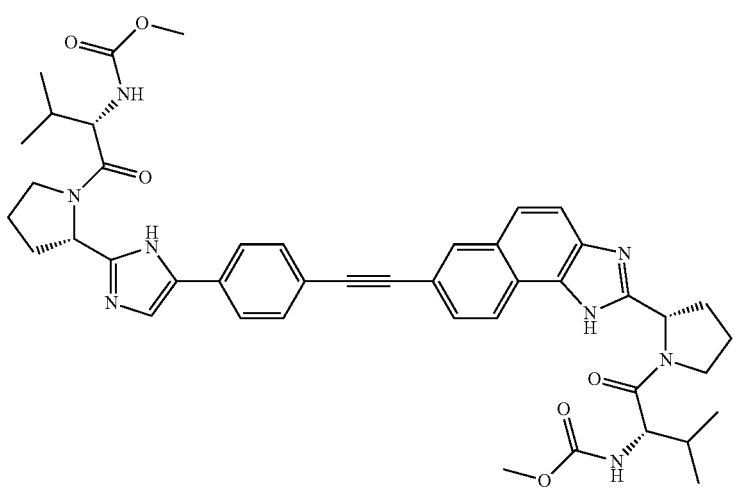 [SMILES: COC(=O)N[C@H](C(=O)N1CCC[C@H]1c1ncc(-c2ccc(C#Cc3ccc4c(ccc5nc([C@@H]6CCCN6C(=O)[C@@H](NC(=O)OC)C(C)C)[nH]c54)c3)cc2)[nH]1)C(C)C]
From D-3h2 and Cap 51
RT = 1.88 min (Cond. 3); LC/MS: Anal. Calcd for $C_{44}H_{51}N_8O_6$ $[M + H]^+$ 787.40; found: 787.30.
D-7
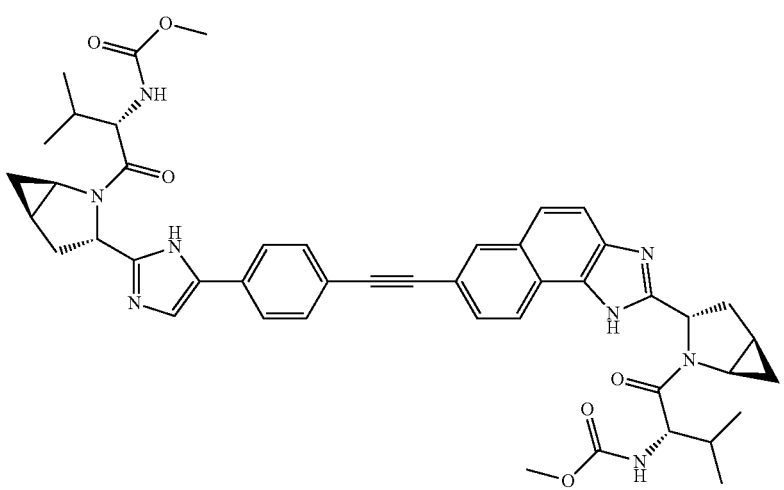 [SMILES: COC(=O)N[C@H](C(=O)N1[C@@H]2C[C@@H]2C[C@H]1c1ncc(-c2ccc(C#Cc3ccc4c(ccc5nc([C@@H]6C[C@H]7C[C@H]7N6C(=O)[C@@H](NC(=O)OC)C(C)C)[nH]c54)c3)cc2)[nH]1)C(C)C]
From D-3h3 and Cap 51
RT = 1.93 min (Cond. 3); LC/MS: Anal. Calcd for $C_{46}H_{51}N_8O_6$ $[M + H]^+$ 811.40; found: 811.26.

| | | |
|---|---|---|
| D-8 | 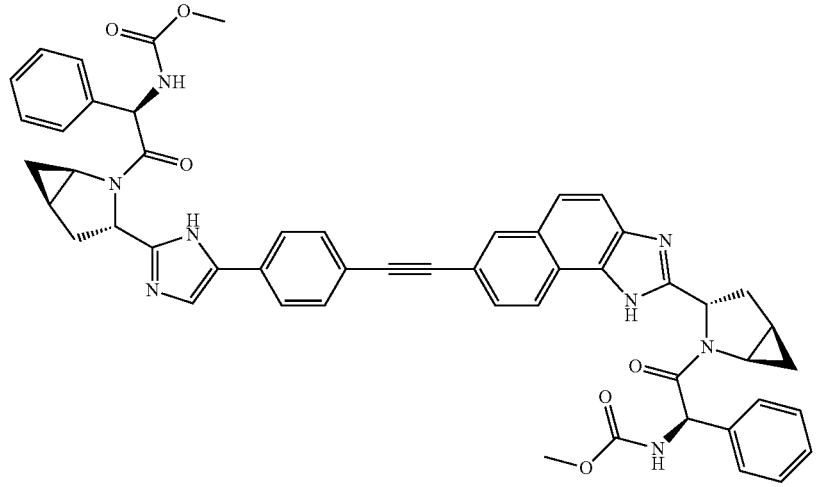 [SMILES: COC(=O)N[C@@H](C(=O)N1[C@@H]2C[C@@H]2C[C@H]1c1ncc(-c2ccc(C#Cc3ccc4c(ccc5nc([C@@H]6C[C@H]7C[C@H]7N6C(=O)[C@H](NC(=O)OC)c6ccccc6)[nH]c54)c3)cc2)[nH]1)c1ccccc1]
From D-3h3 and Cap 4 | RT = 2.01 min (Cond. 3); LC/MS: Anal. Calcd for $C_{52}H_{47}N_8O_6$ [M + H]$^+$ 879.36; found: 879.25. |
| D-9 | 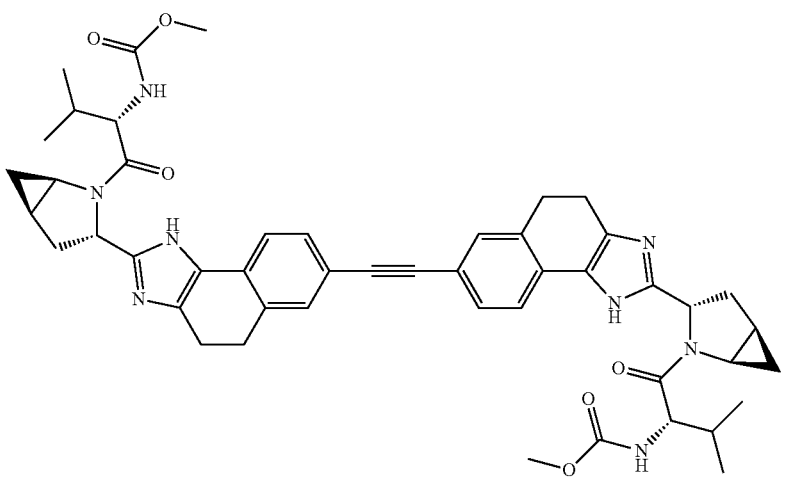 [SMILES: COC(=O)N[C@H](C(=O)N1[C@@H]2C[C@@H]2C[C@H]1c1nc2c([nH]1)-c1ccc(C#Cc3ccc4c(c3)CCc3nc([C@@H]5C[C@H]6C[C@H]6N5C(=O)[C@@H](NC(=O)OC)C(C)C)[nH]c3-4)cc1CC2)C(C)C]
From D-3h4 and Cap 51 | RT = 1.93 min (Cond. 3); LC/MS: Anal. Calcd for $C_{48}H_{55}N_8O_6$ [M + H]$^+$ 839.43; found: 839.26. |
| D-10 | 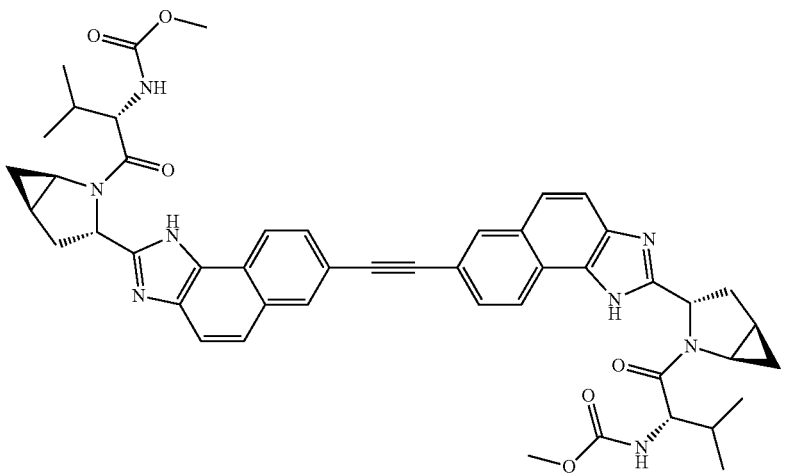 [SMILES: COC(=O)N[C@H](C(=O)N1[C@@H]2C[C@@H]2C[C@H]1c1nc2ccc3cc(C#Cc4ccc5c(ccc6nc([C@@H]7C[C@H]8C[C@H]8N7C(=O)[C@@H](NC(=O)OC)C(C)C)[nH]c65)c4)ccc3c2[nH]1)C(C)C]
From D-3h5 and Cap 51 | RT = 2.07 min (Cond. 3); LC/MS: Anal. Calcd for $C_{48}H_{51}N_8O_6$ [M + H]$^+$ 835.40; found: 835.26. |

D-11

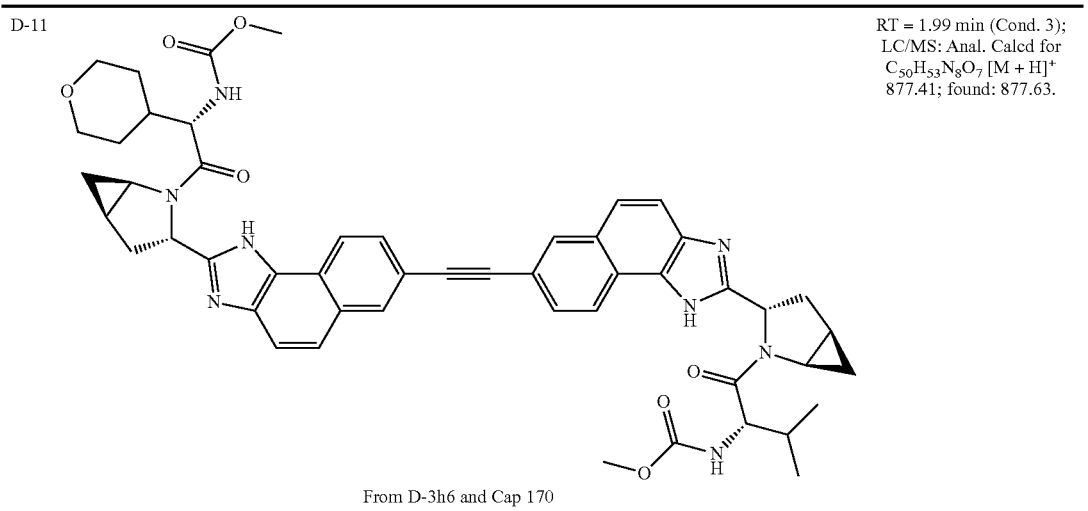

RT = 1.99 min (Cond. 3); LC/MS: Anal. Calcd for $C_{50}H_{53}N_8O_7$ [M + H]$^+$ 877.41; found: 877.63.

From D-3h6 and Cap 170

Example M1

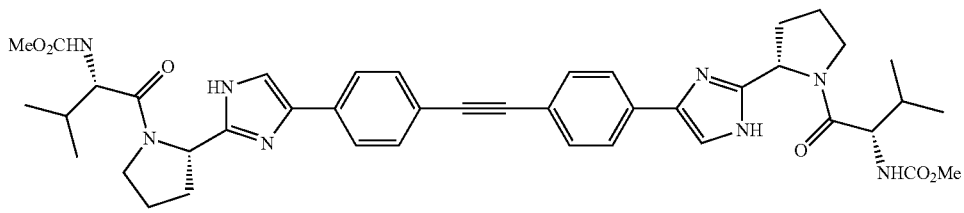

Example M1

Step a

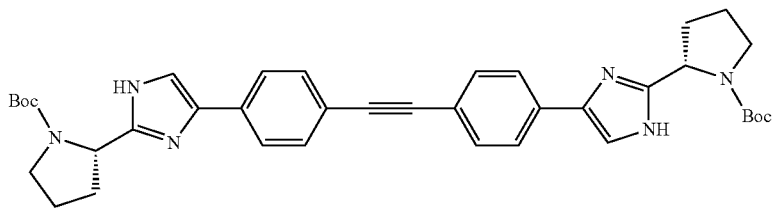 [SMILES: CC(C)(C)OC(=O)N1CCC[C@H]1c1nc(-c2ccc(C#Cc3ccc(-c4c[nH]c([C@@H]5CCCN5C(=O)OC(C)(C)C)n4)cc3)cc2)c[nH]1]

Pd(Ph$_3$P)$_4$ (0.078 g, 0.067 mmol) was added to a DMF (5 mL) solution of (S)-tert-butyl 2-(5-(4-bromophenyl)-1H-imidazol-2-yl)pyrrolidine-1-carboxylate(D-1b) (0.675 g, 1.721 mmol) and 1,2-bis(trimethylstannyl)ethyne (0.3134 g, 0.891 mmol) in a pressure tube, the mixture was flushed with nitrogen for 1 min and then heated at 90° C. for 15 h. The volatile component was removed in vacuo and the residue was directly submitted to a BIOTAGE® purification (110 g; EtOAc) to afford alkyne Mia as a yellowish orange foam containing unidentified impurity and residual solvent (430 mg). $^1$H NMR (DMSO, δ=2.50 ppm, 400 MHz): 12.23/11.98/11.91 (three br s, 2H), 7.80-735 (m, 10H), 4.84-4.76 (m, 2H), 3.54 (m, 2H), 3.39-3.33 (m, 2H), 2.28-1.78 (m, 8H), 1.40 (br s, 7.54H), 1.16 (br s, 10.46H). LC/MS: Anal. Calcd. for [M+H]$^+$ $C_{38}H_{45}N_6O_4$: 649.35; found 649.27.

Example M1

Step b

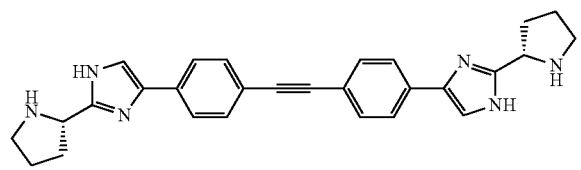 [SMILES: C(#Cc1ccc(-c2c[nH]c([C@@H]3CCCN3)n2)cc1)c1ccc(-c2c[nH]c([C@@H]3CCCN3)n2)cc1]

HCl/dioxanes (4N; 8 mL, 32.0 mmol), CH$_2$Cl$_2$ (1 mL) and MeOH (1.0 mL) were added to bis-carbamate M1a (0.427 g, 0.658 mmol), and the heterogeneous mixture was stirred for 5 hr. The volatile component was removed in vacuo, and the residue was exposed to high vacuum to afford M1b (0.4HCl) as an off-white solid (452 mg), which was submitted to the next step as such. $^1$H NMR analysis indicates that the sample may contain residual dioxane (~1 mol equiv). $^1$H NMR (DMSO, δ=2.50 ppm, 400 MHz): 10.29 (br s, 2H), 9.73 (br s, 2H), 8.11 (s, 2H), 7.96 (d, J=8.3, 4H), 7.67 (d, J=8.6, 4H), 4.97 (br m, 2H), 3.47-3.31 (m, 4H), 2.50-2.36 ('m' partially overlapped with solvent signal, 4H), 2.23-2.14 (m, 2H), 2.07-1.95 (m, 2 H). LC/MS: Anal. Calcd. for [M+H]$^+$ C$_{28}$H$_{29}$N$_6$: 449.25; found 49.23.

Example M1

HATU (0.069 g, 0.181 mmol) was added to the DMF solution of pyrrolodine M1b/4HCl (70.5 mg, 0.103 mmol), (S)-2-(methoxycarbonylamino)-3-methylbutanoic acid (36.3 mg, 0.207 mmol) and DIEA (0.1 mL, 0.573 mmol) and stirred at room temperature for 70 min. The volatile component was removed in vacuo and the residue was dissolved in MeOH and submitted to a reverse phase HPLC purification (MeOH/water/TFA) to afford the TFA salt of Example M1 as an off-white foam (68.9 mg). LC (Cond. 9 and 10): >95% homogeneity index. LC/MS (Cond. 3): R$_t$=1.78 min. $^1$H NMR (DMSO, δ=2.50 ppm, 400 MHz): 8.10 (br s, 2H), 7.88-7.83 (m, 4H), 7.71 (d, J=8.3, 3.91H), 7.34 (d, J=8.5, 2H; NHCO$_2$), 6.92 (app br s, 0.09H), 5.52 (br m, 0.17H), 5.12 (app t, 1.93H), 4.11 (app t, 2H), 3.89-3.77 (m, 4H), 3.54 (s, 5.52H), 3.33 (s, 0.48H), 2.41-2.33 (m, 2H), 2.21-1.93 (m, 8H), 0.89 (app t, 0.91H), 0.83/0.79 (two overlapping d, J=6.8/6.8, 11.09 H). LC/MS: Anal. Calcd. for [M+H]$^+$ C$_{42}$H$_{51}$N$_8$O$_6$: 763.39; found 763.33.

Example M2 to M2.1

Example M2 to M2.1 were prepared as TFA salts from pyrrolidine M1b and appropriate acids according to the procedure described for the preparation of Example M1 with a modified purification protocol noted in the table below.

| Example | R | Analytical data |
|---|---|---|
| M2 | (structure with Ph, O, NHCO$_2$Me) | Purified using two different reverse phase HPLC conditions (Column: Phenomenex Luna, 30 × 100 mm, S10; MeOH/water/TFA) and (Waters Sunfire, 30 × 100 mm, S5; CH$_3$CN/water/TFA). LC (Cond. 9 and 10): >95% homogeneity index. LC/MS (Cond. 3): R$_t$ = 2.04 min. LC/MS: Anal. Calcd. for [M + H]$^+$ C$_{48}$H$_{47}$N$_8$O$_6$: 831.36; found 841.41. |
| M2.1 | (structure with tetrahydropyran, O, NHCO$_2$Me) | Purified using two different reverse phase HPLC conditions (Column: Xbridge, 19 × 100 mm, S5; MeOH/water/TFA) and (Waters Sunfire, 30 × 100 mm, S5; CH$_3$CN/water/TFA). LC (Cond. 9 and 10): 95% homogeneity index. LC/MS (Cond. 10d): R$_t$ = 2.82 min. LC/MS: Anal. Calcd. for [M + H]$^+$ C$_{46}$H$_{55}$N$_8$O$_8$: 847.41; found 847.25. |

Example M3

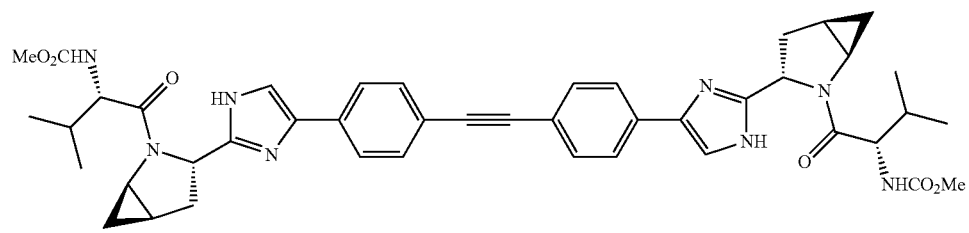

Example M3

Step a

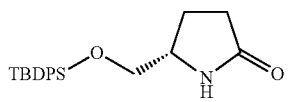

To a solution of (S)-5-(hydroxymethyl)pyrrolidin-2-one (10 g, 87 mmol) in CH$_2$Cl$_2$ (50 mL) was added tert-butylchlorodiphenylsilane (25.6 g, 93 mmol), Et$_3$N (12.1 mL, 87 mmol) and DMAP (1.06 g, 8.7 mmol). The mixture was stirred at room temperature until the starting pyrrolidinone was completely consumed, and then it was diluted with CH$_2$Cl$_2$ (50 mL) and washed with water (50 mL). The organic layer was dried (Na$_2$SO$_4$), filtered, and evaporated in vacuo, and the crude material was submitted to flash chromatography (silica gel; 30 to 100% of EtOAc/hexanes) to afford ether M3a as a colorless oil (22.7 g, 74% yield). $^1$H-NMR (400 MHz, DMSO-d$_6$, δ=2.5 ppm) 7.69 (br s, 1H), 7.64-7.61 (m, 4H), 7.50-7.42 (m, 6H), 3.67-3.62 (m, 1H), 3.58-3.51 (m, 2H), 2.24-2.04 (m, 3H), 1.87-1.81 (m, 1H), 1.00 (s, 9H). LC/MS (M+H)$^+$=354.58.

Example M3

Step b

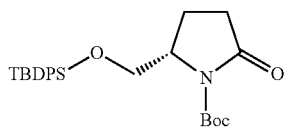

Di-tert-butyl dicarbonate (38.5 g, 177 mmol) was added in portions as a solid over 10 min to a CH$_2$Cl$_2$ (200 mL) solution of silyl ether M3a (31.2 g, 88.3 mmol), Et$_3$N (8.93 g, 88 mmol), and DMAP (1.08 g, 8.83 mmol) and stirred for 18 h at 24° C. Most of the volatile material was removed in vacuo and the crude material taken up in 20% EtOAc/Hex and applied to a 2 L funnel containing 1.3 L of silica gel and then eluted with 3 L of 20% EtOAc/hex and 2 L of 50% EtOAc). Upon concentration of the desired fractions in a rotary evaporator, a white slurry of solid formed which was filtered, washed with hexanes and dried in vacuo to afford carbamate M3b as a white solid (32.65 g, 82% yield). $^1$H-NMR (400 MHz, DMSO-d$_6$, δ=2.5 ppm) 7.61-7.59 (m, 2H), 7.56-7.54 (m, 2H), 7.50-7.38 (m, 6H), 4.18 (m, 1H), 3.90 (dd, T=10.4, 3.6, 1H), 3.68 (dd, J=10.4, 2.1, 1H), 2.68-2.58 (m, 1H), 2.40-2.33 (m, 1H), 2.22-2.12 (m, 1H), 2.01-1.96 (m, 1H), 1.35 (s, 9H), 0.97 (s, 9H). LC/MS (M-Boc+H)$^+$=354.58.

Example M3

Step c

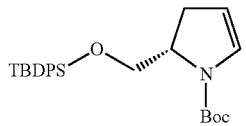

A three-necked flask equipped with a thermometer and a nitrogen inlet was charged with carbamate M3b (10.05 g, 22.16 mmol) and toluene (36 mL), and lowered into −55° C. cooling bath. When the internal temperature of the mixture reached −50° C., lithium triethylborohydride (23 mL of 1.0 M/THF, 23.00 mmol) was added dropwise over 30 min and the mixture stirred for 35 min while maintaining the internal temperature between −50° C. and −45° C. Hunig's base (16.5 mL, 94 mmol) was added dropwise over 10 min. Then, DMAP (34 mg, 0.278 mmol) was added in one batch, followed by the addition of trifluoroacetic anhydride (3.6 mL, 25.5 mmol) over 15 min, while maintaining the internal temperature between −50° C. and −45° C. The bath was removed 10 min later, and the reaction mixture was stirred for 14 h while allowing it to rise to ambient temperature. It was diluted with toluene (15 mL), cooled with an ice-water bath, and treated slowly with water (55 mL) over 5 min. The phases were separated and the organic layer washed with water (50 mL, 2×) and concentrated in vacuo. The crude material was purified by flash chromatography (silica gel; 5% EtOAc/hexanes) to afford dihydropyrrole M3c as a colorless viscous oil (7.947 g, 82% yield). LC/MS (Cond. 7): R$_f$=2.41 min. $^1$H-NMR (400 MHz, DMSO-d$_6$, δ=2.5 ppm) 7.62-7.58 (m, 4H), 7.49-7.40 (m, 6H), 6.47 (br s, 1H), 5.07/5.01 (overlapping br d, 1H), 4.18 (br s, 1H), 3.89 (br s, 0.49H), 3.69 (br s, 1.51H), 2.90-2.58 (br m, 2H), 1.40/1.26 (overlapping br s, 9H), 0.98 (s, 9H). LC/MS: [M+Na]$^+$=460.19.

Example M3

Step d

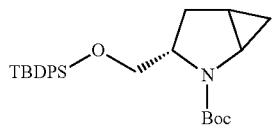

M3d-1: trans-isomer
M3d-2: cis-isomer

Diethylzinc (19 mL of ~1.1 M in toluene, 20.9 mmol) was added dropwise over 15 min to a cooled (−30° C.) toluene (27 mL) solution of dihydropyrrole M3e (3.94 g, 9.0 mmol). Chloroiodomethane (stabilized over copper; 3.0 mL, 41.2 mmol) was added dropwise over 10 min, and stirred while maintaining the bath temperature at −25° C. for 1 h and between −25° C. and −21° C. for 18.5 h. The reaction mixture was opened to the air and quenched by the slow addition of 50% saturated NaHCO$_3$ solution (40 mL), and then removed from the cooling bath and stirred at ambient temperature for 20 min. It was filtered through a filter paper and the white cake was washed with 50 mL of toluene. The organic phase of the filtrate was separated and washed with water (40 mL, 2×), dried (MgSO$_4$) and concentrated in vacuo. The crude material was purified using a BIOTAGE® system (350 g silica gel; sample was loaded with 7% EtOAc/hexanes; eluted with 7-20% EtOAc/hexanes) to afford a mixture of methanopyrrolidines M3d-1 and M3d-2 as a colorless viscous oil (3.69 g, 90.7%). [Note: the exact cis/trans-isomer ratio was not determined at this stage]. LC/MS (Cond. 7): R$_f$=2.39 min $^1$H-NMR (400 MHz, DMSO-d$_6$, δ=2.5 ppm) 7.62-7.60 (m, 4H), 7.49-7.40 (m, 6H), 3.77/3.67 (overlapping br s, 3.11-3.07 (m, 1H), 2.23 (app br s, 1H), 2.05-2.00 (m, 1H), 1.56-1.50 (m, 1H), 1.33 (very broad s, 9H), 1.00 (s, 9H), 0.80 (m, 1H), 0.30 (m, 1H). LC/MS: [M+Na]$^+$=474.14.

Example M3

Step e

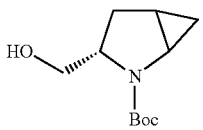

M3e-1: trans-isomer
M3e-2: cis-isomer

TBAF (7.27 mL of 1.0 M in THF, 7.27 mmol) was added dropwise over 5 min to a THF (30 mL) solution of silyl ether M3d-1/-2 (3.13 g, 6.93 mmol) and the mixture stirred at ambient temperature for 4.75 h. After the addition of saturated $NH_4Cl$ solution (5 mL), most of the volatile material was removed in vacuo and the residue partitioned between $CH_2Cl_2$ (70 mL) and 50% saturated $NH_4Cl$ solution (30 mL). The aqueous phase was extracted with $CH_2Cl_2$ (30 mL), and the combined organic phase was dried ($MgSO_4$), filtered, concentrated in vacuo and then exposed to high vacuum overnight. The crude material was purified using a BIOTAGE® (silica gel; 40-50% EtOAc/hexanes) to afford a mixture of alcohols M3e-1 and M3e-2, contaminated with traces of a lower $R_f$ spot, as a colorless oil (1.39 g, ~94% yield). [Note: the exact cis/trans isomer ratio was not determined at this stage.] $^1$H-NMR (400 MHz, DMSO-$d_6$, δ=2.5 ppm) 4.70 (t, J=5.7, 1H), 3.62-3.56 (m, 1H), 3.49-3.44 (m, 1H), 3.33-3.27 (m, 1H), 3.08-3.04 (m, 1H), 2.07 (br m, 1H), 1.93-1.87 (m, 1H), 1.51-1.44 (m, 1H), 1.40 (s, 9H), 0.76-0.71 (m, 1H), 0.26 (m, 1H). LC/MS $(M+Na)^+$=236.20.

Example M3

Step f

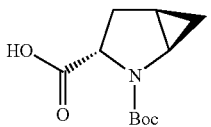

M3f-1: trans-isomer
M3f-2: cis-isomer

A semi-solution of $NaIO_4$ (6.46 g, 30.2 mmol) in $H_2O$ (31 mL) was added to a solution of alcohol M3e-1/-2 (2.15 g, 10.08 mmol) in $CH_3CN$ (20 mL) and $CCl_4$ (20 mL). $RuCl_3$ (0.044 g, 0.212 mmol) was added immediately and the heterogeneous reaction mixture was stirred vigorously for 75 min. The reaction mixture was diluted with $H_2O$ (60 mL) and extracted with $CH_2Cl_2$ (50 mL, 3×). The combined organic phase was treated with 1 mL MeOH, allowed to stand for about 5 min, and then filtered through a pad of diatomaceous earth (CELITE®). The CELITE® was washed with $CH_2Cl_2$ (50 mL), and the filtrate was concentrated in vacuo to afford a light charcoal-colored solid. $^1$H-NMR analysis of this crude material indicated a 1.00:0.04:0.18 mole ratio of trans acid M3f-1:cis acid M3f-2:presumed side product, tert-butyl 3-oxo-2-azabicyclo[3.1.0]hexane-2-carboxylate. The crude material was dissolved in EtOAc (~10 mL) with heating and allowed to stand at ambient temperature with seeding. About 15 min into the cooling phase, a rapid crystal formation was observed. About 1 h later, hexanes (~6 mL) was added and the mixture refrigerated overnight (it did not appear that additional material precipitated out). The mixture was filtered and washed with ice/water-cooled hexanes/EtOAc (2:1 ratio; 20 mL) and dried under high vacuum to afford the first crop of acid M3f-1 (off-white crystals, 1.222 g). The mother liquor was concentrated in vacuo, and the residue dissolved in ~3 mL of EtOAc with heating, allowed to stand at ambient temperature for 1 h, and then 3 mL hexanes was added and stored in a refrigerator for ~15 h. A second crop of acid M3f-1 was retrieved similarly (grey crystals, 0.133 g), for a combined yield of 59%. Acid M3f-1: Rt=1.48 min under the following HPLC conditions: Solvent gradient from 100% A:0% B to 0% A:100% B (A=0.1% TFA in 1:9 $MeOH/H_2O$; B=0.1% TFA in 9:1 $MeOH/H_2O$) over 3 min; detection @ 220 nm; PHENOMENEX®-Luna 3.0×50 mm S10 column. MP (dec.) for the first crop=147.5-149.5° C. $^1$H-NMR (400 MHz, DMSO-$d_6$, δ=2.5 ppm) 12.46 (s, 1H), 3.88 (app br s, 1H), 3.27 (app br s, 1H; overlapped with water signal), 2.28 (br m, 1H), 2.07 (app br s, 1H), 1.56 (app s, 1H), 1.40/1.34 (two overlapped s, 9H), 0.71 (m, 1H), 0.45 (m, 1H). $^{13}$C-NMR (100.6 MHz, DMSO-$d_6$, δ=39.21 ppm) 172.96, 172.60, 154.45, 153.68, 78.74, 59.88, 59.58, 36.91, 31.97, 31.17, 27.77, 27.52, 14.86, 14.53, 13.69. LC/MS $[M+Na]^+$=250.22. Anal. Calcd. for $C_{11}H_{17}NO_4$: C, 58.13; H, 7.54; N, 6.16. Found (for first crop): C, 58.24; H, 7.84; N, 6.07. Optical rotation (10 mg/mL in $CHCl_3$): $[α]_D$=−216 and −212 for the first and second crop, respectively.

Example M3

Step g

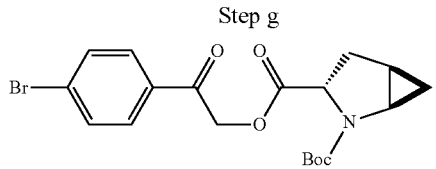

DIEA (1.3 mL, 7.44 mmol) was added dropwise over 2 min to a semi-heterogeneous mixture of acid M3f-1 (1.697 g, 7.47 mmol) and 2-bromo-1-(4-bromophenyl)ethanone (2.01 g, 7.23 mmol) in $CH_3CN$ (30 mL) and stirred at room temperature for 8 hr. The volatile component was removed in vacuo and the residue was taken up in $CH_2Cl_2$ (100 mL), washed with water (30 mL), dried ($MgSO_4$) and concentrated in vacuo to afford ketoester M3g as an off-white viscous semi-foamy oil (3.076 g). $^1$H-NMR (400 MHz, DMSO-$d_6$ δ=2.5 ppm): 7.92 (d, J=8.3, 2H), 7.78 (d, J=8.5, 2H), 5.61-5.42 (m, 2H), 4.16 (m, 1H), 3.34 ('m' partially overlapped with water signal, 1H), 2.40 (m, 2H), 1.63 (m, 1H), 1.41/1.35 (two overlapped 's', 9H), 0.74 (m, 1H), 0.53 (m, 1H). LC/MS: Anal. Calcd. for $[M+Na]^+$ $C_{19}H_{22}^{79}BrNNaO_5$: 446.06; found 446.06.

Example M3

Step h

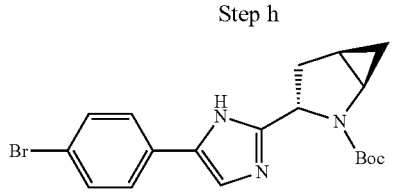

A 350 ml pressure tube was charged with keto-ester M3g (3.07 g, 7.24 mmol), ammonium acetate (5.48 g, 71.1 mmol) and Xylene (70 mL), capped and heated with an oil bath (140° C.) for 4.5 hr. The reaction mixture was allowed to cool to room temperature and the volatile component was removed in vacuo. $CH_2Cl_2$ (100 mL) and 50% saturated $NaHCO_3$ solution (30 mL) were added to the residue, vigorously stirred until gas evolution ceased, and the phases were separated. The organic layer was dried ($MgSO_4$), concentrated in vacuo, and purified with a BIOTAGE® (240 g silica gel; sample was loaded with $CH_2Cl_2$; 40-80% EtOAc/hexanes) to afford imidazole M3h as a dark yellow foam (2.40 g). $^1$H-NMR (400 MHz, DMSO-$d_6$, δ=2.5 ppm): 12.21 (s, 0.11H), 1.93 (s, 0.89H), 7.69 (d, T=8.8, 1.8H), 7.62-7.55 (m, 0.4H), 7.53 (br d, J=2, 0.87H), 7.49 (d, J=8.5, 1.8H), 7.29 (br d, T=1.6, 0.13H), 4.59 (m, 1H), 3.41 (m, 1H), 2.37-2.17 (br m, 2H), 1.62 (m, 1H), 1.21 (very broad 's', 9H), 0.75 (m, 1H), 0.54 (m, 1H). LC/MS: Anal. Calcd. for $[M+H]^+$ $C_{19}H_{23}^{81}BrN_3O_2$: 406.10; found, 406.14.

Example M3

Step i

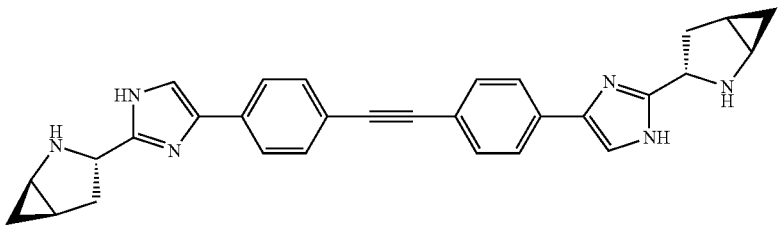 [SMILES: C(#Cc1ccc(-c2c[nH]c([C@@H]3C[C@H]4C[C@H]4N3)n2)cc1)c1ccc(-c2c[nH]c([C@@H]3C[C@H]4C[C@H]4N3)n2)cc1]

Pyrrolidine M3i (4HCl) was prepared from bromide M3h according to the procedure described for the synthesis of pyrrolidine M1b (0.4HCl) from bromide D-1b. $^1$H-NMR (400 MHz, DMSO-d$_6$, δ=2.5 ppm): 10.51 (app br s, 4H), 8.08 (s, 2H), 7.92 (d, J=7.8, 4H), 7.66 (d, J=8.5, 4H), 4.78 (m, 2H), 3.42 (m, 2H), 2.65 (m, 2H), ~2.53 ('m' partially overlapped with solvent signal, 2H), 1.94 (m, 2H), 1.10 (m, 2H), 0.86 (m, 2H). LC/MS: Anal. Calcd. for [M+H]$^+$ C$_{30}$H$_{29}$N$_6$: 473.25; found 473.21.

Example M3 (and Examples M4-M7)

Example M3, along with its analogs Examples M4-M7 highlighted in the table below, were prepared as TFA salts from pyrrolidine M3i (0.4HCl) by employing the procedure described for the synthesis of Example M1 and appropriate acids. In the case of Example M7 an equimolar mixture of (S)-2-(methoxycarbonylamino)-3-methylbutanoic acid and (S)-2-(methoxycarbonylamino)-2-(tetrahydro-2H-pyran-4-yl)acetic acid was employed for the coupling step and the resultant statistical mixture of products was separated by the HPLC technique described for Example M1. Example M3: LC (Cond. 9 and 10): >95% homogeneity index. LC/MS (Cond. 3): R$_t$=1.89 min. LC/MS: Anal. Calcd. for [M+H]$^+$ C$_{44}$H$_{51}$N$_8$O$_6$: 787.39; found 787.40.

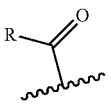

| Example | 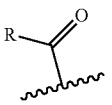 | 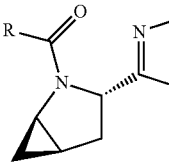 | R$_t$ (Cond. 3); % homogeneity index (Cond. 9 and 10); LC/MS data |
|---|---|---|---|
| M4 |  | 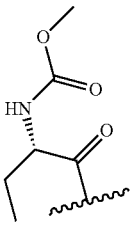 [SMILES: *C(=O)[C@H](CC)NC(=O)OC] | 1.74 min; >95%; LC/MS: Anal. Calcd. for [M + H]$^+$ C$_{42}$H$_{47}$N$_8$O$_6$: 759.36; found 759.35 |
| M5 | 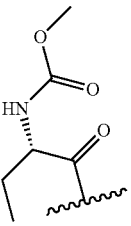 [SMILES: *C(=O)[C@H](CC)NC(=O)OC] | 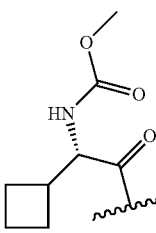 | 1.98 min; >95%; LC/MS: Anal. Calcd. for [M + H]$^+$ C$_{46}$H$_{51}$N$_8$O$_6$: 811.39; found 811.37 |

-continued

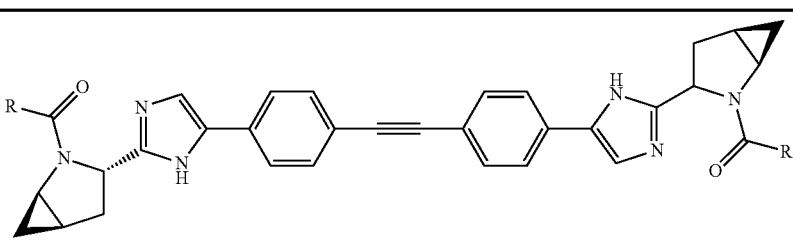

| Example | R | R | $R_t$ (Cond. 3); % homogeneity index (Cond. 9 and 10); LC/MS data |
|---|---|---|---|
| M6 | 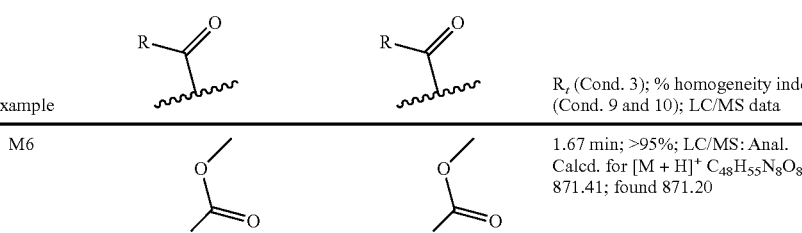 | | 1.67 min; >95%; LC/MS: Anal. Calcd. for [M + H]$^+$ C$_{48}$H$_{55}$N$_8$O$_8$: 871.41; found 871.20 |
| M7 | 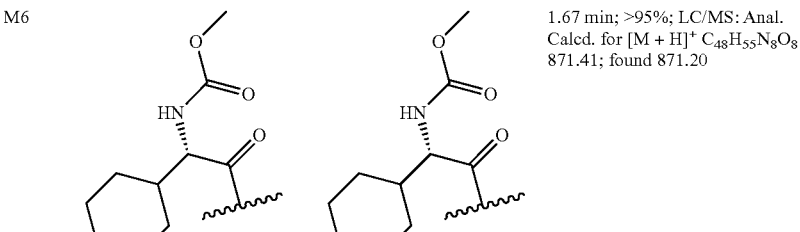 | 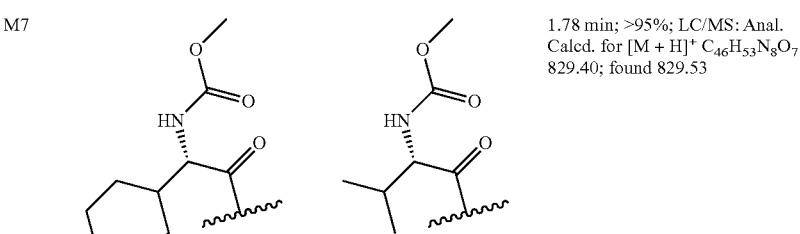 | 1.78 min; >95%; LC/MS: Anal. Calcd. for [M + H]$^+$ C$_{46}$H$_{53}$N$_8$O$_7$: 829.40; found 829.53 |

Examples M8-M9

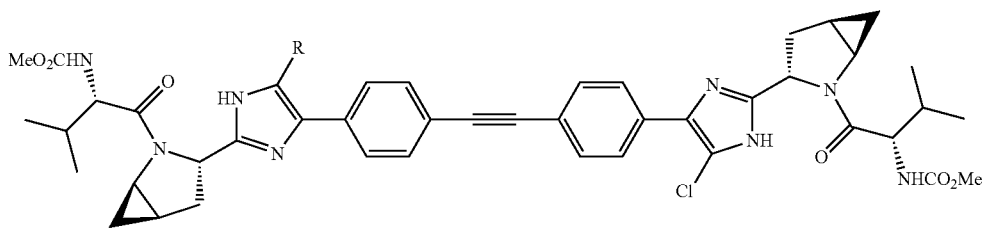

Example M8 (R = H)
Example M9 (R = Cl)

NCS (0.0195 g, 0.143 mmol) was added to a DMF (2 mL) solution of the free base form of Example M3 (obtained from the TFA salt via a standard MCX free-basing protocol; 0.109 g, 0.139 mmol), and stirred at room temperature for 16 hr and at 50° C. for 25 hr. Most of the solvent was removed in vacuo, and the residue was dissolved in MeOH and submitted to a reverse phase HPLC purification (MeOH/water/TFA) to afford the TFA salt of Example M8 (50 mg) and Example M9 (17.5 mg).

| Example | $R_t$ (Cond. 3); % homogeneity index (Cond. 9a and 10a); LC/MS data |
|---|---|
| M8 | 2.42 min; >95%; LC/MS: Anal. Calcd. for [M + H]$^+$ C$_{44}$H$_{50}$ClN$_8$O$_6$: 821.35; found 821.31 |
| M9 | 2.95 min; >95%; LC/MS: Anal. Calcd. for [M + H]$^+$ C$_{44}$H$_{49}$Cl$_2$N$_8$O$_6$: 855.32; found 855.24 |

Example M9.1-M9.2

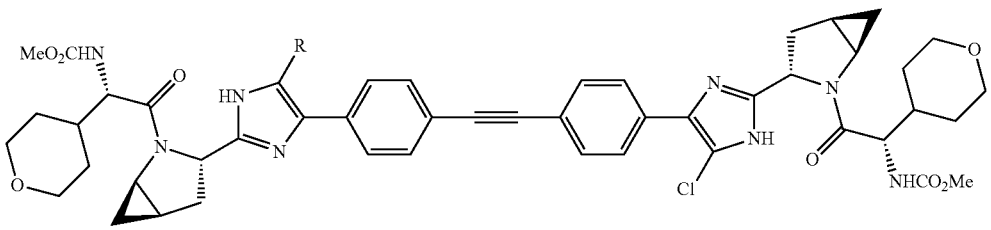

Example M9.1 (R = H)
Example M9.2 (R = Cl)

NCS (0.021 g, 0.158 mmol) was added to a DMF (1.5 mL) solution of the free base form of Example M6 (obtained from the TFA salt via a standard MCX free-basing protocol; 0.1059 g, 0.122 mmol), and stirred at 50° C. for 24 hr. The reaction mixture was diluted with MeOH (2.5 mL) and submitted to a reverse phase HPLC purification condition (XTERRA, 30×100 mm, S5; MeOH/water/TFA). The resultant sample was repurified with a different reverse phase HPLC condition (Waters-Sunfire, 30×100 mm, S5; acetonitrile/water/TFA) to afford Example M9.1 (38.8 mg) and Example M9.2 (32.6 mg) as TFA salts.

| Example | $R_f$ (Cond. 3); % homogeneity index (Cond. 9a and 10a); LC/MS data |
|---|---|
| M9.1 | 2.26 min; >95%; LC/MS: Anal. Calcd. for $[M + H]^+$ $C_{48}H_{54}ClN_8O_8$: 905.38; found 905.44 |
| M9.2 | 2.78 min; >95%; LC/MS: Anal. Calcd. for $[M + H]^+$ $C_{44}H_{53}Cl_2N_8O_8$: 939.34; found 939.40 |

Example M9.3

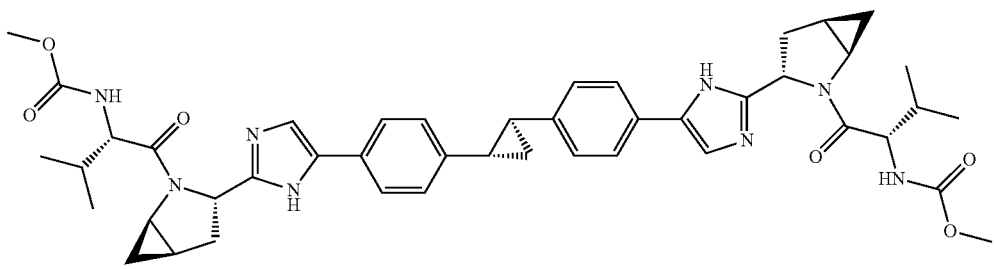

Example M9.3

Step a

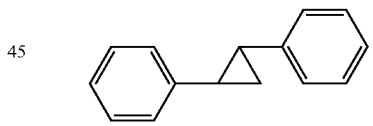

To a cooled (0° C.) $CH_2Cl_2$ (22 mL) was added diethylzinc (1M in hexanes, 60.5 mL, 60.5 mmol) under nitrogen followed by the dropwise addition of trifluoroacetic acid (5.1 mL, 66.2 mmol) in 10 mL $CH_2Cl_2$ over 15 min. The reaction was stirred for 15 min, and then diiodomethane (5.4 mL, 66.9 mmol) in 10 mL $CH_2Cl_2$ was added dropwise to the reaction. The reaction was continued to stir at 0° C. for 1 hr, and then (E)-1,2-diphenylethene (2 g, 11.10 mmol) in 10 mL $CH_2Cl_2$ was added. The mixture was removed from the cold bath and stirred at ~25° C. under nitrogen for 20 h. The reaction was quenched with 0.1N HCl (50 mL), the layers were separated, and the aqueous layer was extracted with hexanes (2×100 mL). The combined organic phase was washed with saturated $NaHCO_3$ (aq) (50 mL) and brine (50 mL), dried over $MgSO_4$, filtered, and concentrated in vacuo. The residue was submitted to a silica gel flash chromatography (hexanes) to afford biphenyl M9.3a as a colorless oil (1.6 g). $^1$H NMR (400 MHz, $CDCl_3$) δ ppm 7.34-7.31 (m, 4H), 7.24-7.17 (m, 6H), 2.22-2.18 (m, 2H), 1.51-1.47 (m, 2H).

Example M9.3

Step b

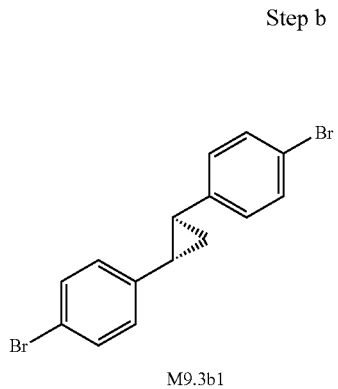

M9.3b1

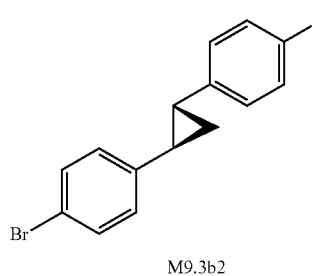

M9.3b2

To a solution of biphenyl M9.3a (3.3 g, 16.99 mmol) in 1,2-dimethoxyethane (197 mL) and water (82 mL) was added NBS (12.09 g, 67.9 mmol). The reaction flask was covered with aluminum foil and stirred at room temperature for 51 hr. The reaction was partitioned between diethyl ether and water, and the organic layer was washed with brine, dried over MgSO$_4$, filtered, and concentrated in vacuo. The residue was submitted to a flash chromatography (sample was loaded with chloroform; eluted with hexanes) to afford a stereoisomeric mixture of dibrominated product as a white solid (3.1 g). The stereoisomeric mixture was separated by chiral SFC (Chiralpak AD-H column, 30×250 mm, 5 μm; 80% CO$_2$-20% EtOH; 35° C.; 150 bar; 70 mL/min for 20 min; 220 nm) to isolate two enantiomers: M9.3b1 (white solid, 1.1 g); $^1$H NMR (400 MHz, CDCl$_3$) δ ppm 7.43 (d, J=8.6 Hz, 4H), 7.02 (d, J=8.6 Hz, 4H), 2.12-2.09 (m, 2H), 1.47-1.43 (m, 2H); OR: +361.79, 3.15 mg in 1 mL CHCl$_3$, λ=589 nm, 50 mm cell. M9.3b2 (white solid, 1.2 g); $^1$H NMR (400 MHz, CDCl$_3$) δ ppm 7.43 (d, J=8.6 Hz, 4H), 7.02 (d, J=8.6 Hz, 4H), 2.12-2.09 (m, 2H), 1.47-1.43 (m, 2H); OR: −376.70, 3.03 mg in 1 mL CHCl$_3$, λ=589 nm, 50 mm cell.

Step c

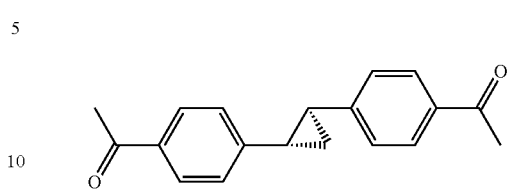

To a solution of dibromide M9.3b1 (0.8806 g, 2.501 mmol) and tributyl(1-ethoxyvinyl)stannane (2.71 g, 7.50 mmol) in 1,4-dioxane (17 mL) was added dichlorobis(triphenylphosphine)-palladium(II) (0.105 g, 0.150 mmol). The reaction was thoroughly flushed with nitrogen, sealed, and heated at 80° C. for 16 h. The reaction was removed from the heat, 1N HCl (aq) (17 mL) was added, and the mixture was stirred for 4 h. The mixture was diluted with water (20 mL) and extracted with EtOAc (3×50 mL). The combined organic layer was dried over MgSO$_4$, filtered, and concentrated in vacuo. The residue was purified with a flash chromatography (35% ethyl acetate/hexanes), and the retrieved sample was triturated with hexanes (3×50 mL) to afford ketone M9.3c as an off-white solid (412.5 mg). $^1$H NMR (400 MHz, CDCl$_3$) δ ppm 7.92 (d, J=8.5 Hz, 4H), 7.23 (d, J=8.6 Hz, 4H), 2.61 (s, 6H), 2.32-2.28 (m, 2H), 1.67-1.63 (m, 2H). LC/MS: Anal. Calcd. for [M+H]$^+$ C$_{19}$H$_{19}$O$_2$: 279.14; found 279.13.

Example M9.3

Step d

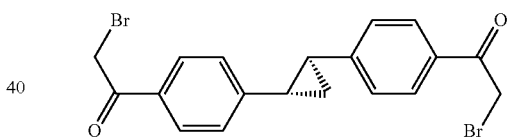

To a solution of ketone M9.3c (0.4072 g, 1.463 mmol) in THF (7 mL) was added phenyltrimethylammonium tribromide (1.10 g, 2.93 mmol), and the reaction mixture was stirred at ~25° C. for 15 h. The volatile component was removed in vacuo, and the residue was partitioned between water (25 mL) and CH$_2$Cl$_2$ (100 mL). The organic layer was dried over MgSO$_4$, filtered, and concentrated in vacuo to afford dibromide M9.3d, which was used without further purification. LC/MS: Anal. Calcd. for [M+H]$^+$ C$_{19}$H$_{17}$$^{79}$Br$_2$O$_2$: 434.96; found 434.98.

Example M9.3

Step e

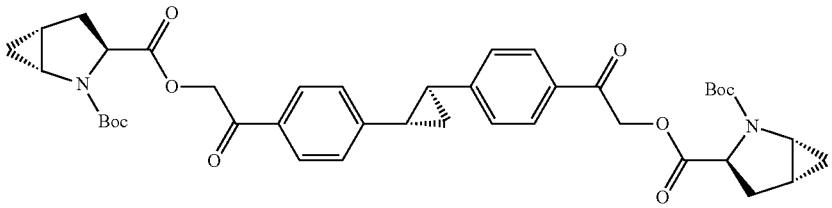 [SMILES: CC(C)(C)OC(=O)N1[C@@H]2C[C@@H]2C[C@H]1C(=O)OCC(=O)c1ccc([C@H]2C[C@@H]2c2ccc(C(=O)COC(=O)[C@@H]3C[C@H]4C[C@H]4N3C(=O)OC(C)(C)C)cc2)cc1]

To a solution of dibromide M9.3d (~1.463 mmol) and acid M3f1 (0.698 g, 3.07 mmol) in acetonitrile (10 mL) was added N,N-diisopropylethylamine (0.537 mL, 3.07 mmol), and the reaction was stirred at ~25° C. for 5 h. The volatile component was removed in vacuo, and the residue was taken up in chloroform (4 mL) and loaded onto a silica gel column and eluted with 8% ethyl acetate/methylene chloride over 1296 mL solvents to afford diketoester M9.3e as a light yellow foam containing unidentified impurities (0.723 g). $^1$H NMR (400 MHz, DMSO-$d_6$) δ ppm 7.90 (d, J=8.0 Hz, 4H), 7.37 (d, J=8.3 Hz, 4H), 5.59-5.40 (m, 3H), 4.24-4.09 (m, 2H), 3.37-3.25 (m, 2H), 2.47-2.36 (m, 5H), 1.87-1.80 (m, 2H), 1.72-1.68 (m, 2H), 1.57-1.49 (m, 2H), 1.41 (s, 7H), 1.35 (s, 11H), 0.80-0.67 (m, 2H), 0.58-0.48 (m, 2H). LC/MS: Anal. Calcd. for [M+H]$^+$ $C_{41}H_{48}N_2NaO_{10}$: 751.32; found 751.55.

Example M9.3

Step f

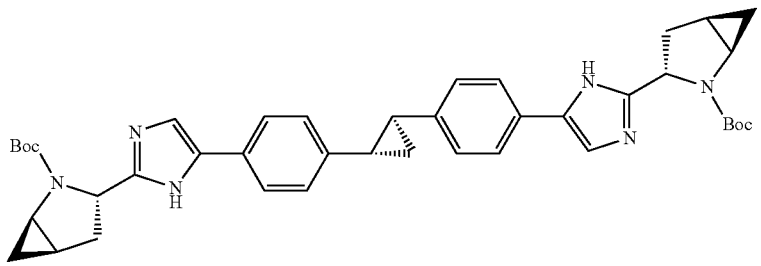 [SMILES: CC(C)(C)OC(=O)N1[C@@H]2C[C@@H]2C[C@H]1c1ncc(-c2ccc([C@H]3C[C@@H]3c3ccc(-c4cnc([C@@H]5C[C@H]6C[C@H]6N5C(=O)OC(C)(C)C)[nH]4)cc3)cc2)[nH]1]

A mixture of diketoester M9.3e (0.723 g, 0.992 mmol) and ammonium acetate (1.529 g, 19.84 mmol) in xylene (10 mL) in a sealed reaction vessel was heated at 140° C. for 2.5 h. After the reaction was allowed to cool to ambient condition, the volatile component was removed in vacuo. The residue was taken up in 20% MeOH/CHCl$_3$ (50 mL) and treated with saturated NaHCO$_3$ (aq) (20 mL), stirred and the layers were separated. The aqueous layer was extracted further with 20% MeOH/CHCl$_3$ (2×50 mL), and the combined organic phase was dried over MgSO$_4$, filtered, and concentrated in vacuo. The residue was taken up in CHCl$_3$ (4 mL), loaded onto a silica gel column and eluted with 45% ethyl acetate/methylene chloride over 1296 mL to afford imidazole M9.3f as an orange solid (261.7 mg). $^1$H NMR (400 MHz, DMSO-$d_6$) δ ppm 12.08 (s, 0.5H), 11.81 (s, 1.5H), 7.64 (d, J=8.3 Hz, 3H), 7.55 (d, J=8.3 Hz, 1H), 7.41 (d, J=1.7 Hz, 1.7H), 7.19-1.17 (m, 1.3H), 7.11 (d, J=8.3 Hz, 3H), 4.59 (app br s, 2H), 3.41 (app br s, 2H), 2.37-2.14 (m, 6H), 1.68-1.57 (m, 2H), 1.48-1.40 (m, 2H), 1.40-0.95 (br s, 18H), 0.79-0.69 (m, 2H), 0.59-0.48 (m, 2H). LC/MS: Anal. Calcd. for [M+H]$^+$ $C_{41}H_{49}N_6O_4$: 689.38; found 689.43.

Example M9.3

Step g

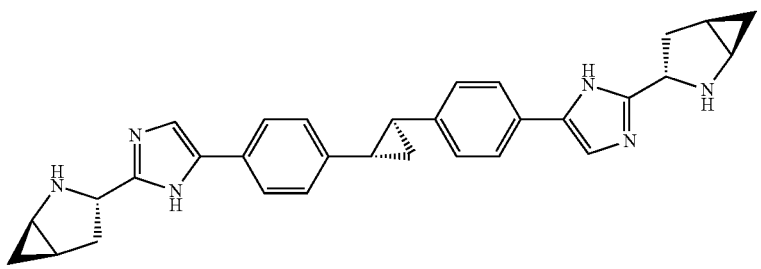 [SMILES: c1cc([C@H]2C[C@@H]2c2ccc(-c3cnc([C@@H]4C[C@H]5C[C@H]5N4)[nH]3)cc2)ccc1-c1cnc([C@@H]2C[C@H]3C[C@H]3N2)[nH]1]

A solution of carbamate M9.3f (0.2391 g, 0.347 mmol) in 25% TFA/CH²Cl² (1.7 mL) was stirred at ~25° C. for 1 h. The volatile component was removed in vacuo to afford the TFA salt of pyrrolidine M9.3 g as a tan foam (328 mg). $^1$H NMR (400 MHz, DMSO-$d_6$) δ ppm 10.01 (br s, 2H), 7.70-7.68 (m, 6H), 7.20 (d, J=8.6 Hz, 4H), 4.63-4.58 (m, 2H), 3.37-3.33 (m, 2H), 2.51-2.42 (m, 6H), 2.24-2.20 (m, 2H), 1.93-1.86 (m, 2H), 1.51-1.47 (m, 2H), 1.16-1.09 (m, 2H), 0.084-0.78 (m, 2H). LC/MS: Anal. Calcd. for [M+H]$^+$ $C_{31}H_{33}N_6$: 489.28; found 489.26.

Example M9.3

To a solution of pyrrolidine M9.3 g/TFA salt (0.0834 g, 0.088 mmol), (S)-2-(methoxycarbonylamino)-3-methylbu- Example M9.4 was prepared from pyrrolidine M9.3 g/TFA salt and (S)-2-(methoxycarbonylamino)-2-(tetrahydro-2H-pyran-4-yl)acetic acid according to the same procedure used for the preparation of Example M9.3. $^1$H NMR (400 MHz, DMSO-$d_6$) δ ppm 15-14 (bs, 6H), 7.98 (br s, 2H), 7.66 (d, J=8.3 Hz, 4H), 7.34-7.32 (m, 5H), 4.98-4.94 (m, 2H), 4.50-4.46 (m, 2H), 3.84-3.78 (m, 6H), 3.54 (s, 6H), 3.32-3.18 (m, 4H), 2.39-2.29 (m, 4H), 2.11-1.97 (m, 2H), 1.97-1.88 (m, 2H), 1.60-1.57 (m, 2H), 1.51-1.26 (m, 8H), 0.99-0.87 (m, 2H), 0.84-0.72 (m, 2H). $R_f$=1.77 min (Cond. 3); >95% homogeneity index (Cond. 9 and 10); LC/MS: Anal. Calcd. for [M+H]$^+$ $C_{49}H_{59}N_8O_8$: 887.45; found 887.50.

Examples M9.5 and M9.6

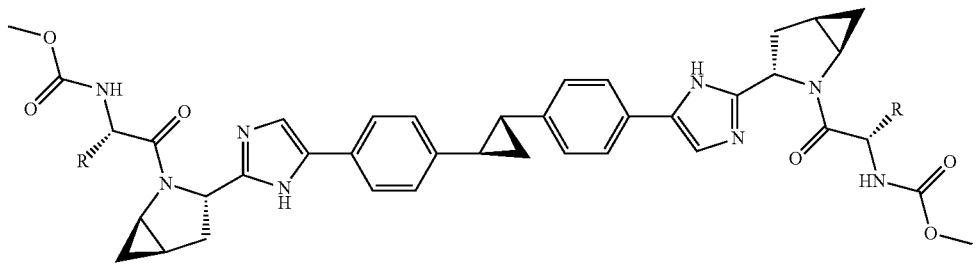

tanoic acid (0.034 g, 0.194 mmol), and N,N-diisopropylethylamine (0.123 mL, 0.706 mmol) in DMF (1.5 mL) was added HATU (0.070 g, 0.185 mmol), and the mixture was stirred at 25° C. for 4 h. The reaction mixture was diluted with MeOH (2.5 mL) and submitted to a reverse phase HPLC purification (XTERRA, 30×100 mm, 55; MeOH/H$_2$O/TFA) to afford Example M9.3 as an off-white foam (58 mg). $^1$H NMR (400 MHz, DMSO-$d_6$) δ ppm 14.90-14.20 (bs, 3H), 8.00 (br s, 2H), 7.68 (d, J=8.3 Hz, 4H), 7.34 (d, J=8.6 Hz, 4H), 7.25 (d, J=8.6 Hz, 2H), 5.00-4.96 (m, 2H), 4.42-4.39 (m, 2H), 3.79-3.69 (m, 2H), 3.54 (s, 6H), 2.38-2.31 (m, 5H), 2.16-2.07 (m, 2H), 1.95-1.88 (m, 2H), 1.61-1.58 (m, 2H), 0.97-0.90 (m, 8H), 0.80 (d, J=6.5 Hz, 8H). $R_f$=1.96 min (Cond. 3); >95% homogeneity index (Cond. 9 and 10); LC/MS: Anal. Calcd. for [M+H]$^+$ $C_{45}H_{55}N_8O_6$: 803.42; found 803.43.

Examples M9.5 and M9.6 were prepared as TFA salts starting from dibromide M9.3b2 according to the procedures described for the preparation of Examples M9.3 and M9.4 from the corresponding stereoisomer dibromide M9.3b1.

| Example | R | $R_t$ (Cond. 3); homogeneity index (Cond. 9 and 10); LC/MS data |
|---|---|---|
| M9.5 | isopropyl | 1.98 min; >95%; LC/MS: Anal. Calcd. for [M + H]$^+$ $C_{45}H_{55}N_8O_6$: 803.42; found 803.43 |
| M9.6 | tetrahydropyran-4-yl | 1.77 min; >95%; LC/MS: Anal. Calcd. for [M + H]$^+$ $C_{49}H_{59}N_8O_8$: 887.45; found 887.60 |

Example M9.4

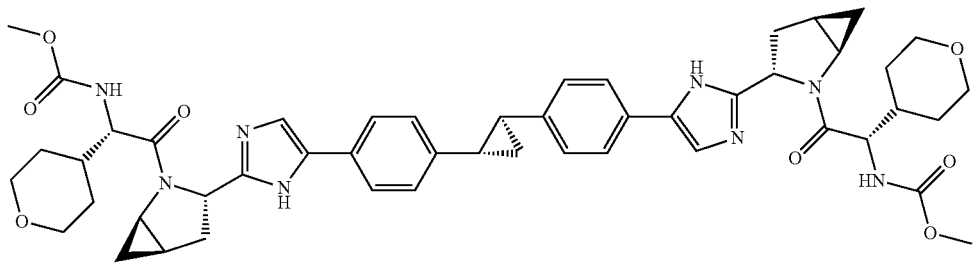

Example M9.7

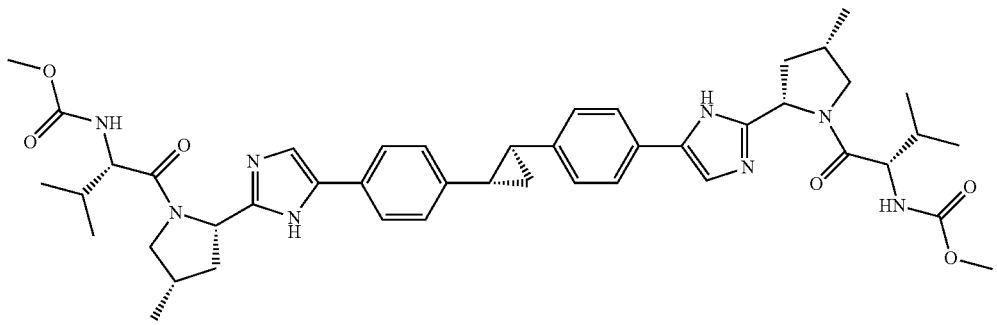

Example M9.7 (TFA salt) was prepared from dibromide M9.3d and acid M12.2c according to the procedures described for the preparation of Examples M9.3. $^1$H NMR (400 MHz, DMSO-$d_6$) δ ppm 14.90-14.42 (br s, 4H), 8.02 (br s, 2H), 7.70 (d, J=8.5 Hz, 4H), 7.36 (d, J=8.6 Hz, 4H), 7.25 (d, J=8.3 Hz, 2H), 5.07 (dd, J=10.7 Hz/7.1 Hz, 2H), 4.18-4.13 (app t, 2H), 4.12-4.08 (app t, 2H), 3.55 (s, 6H), 3.42-3.37 (app t, 2H), 2.49-2.39 (m, 2H), 2.37-2.31 (app t, 2H), 2.02-1.93 (m, 2H), 1.87-1.78 (app q, 2H), 1.62-1.59 (app t, 2H), 1.14 (d, J=6.3 Hz, 6H), 0.82 (d, J=6.5 Hz, 6H), 0.77 (d, J=6.8 Hz, 6H). $R_t$=3.12 min (Cond. 10d); >95% homogeneity index (Cond. 9 and 10); LC/MS: Anal. Calcd. for [M+H]$^+$ C$_{45}$H$_{59}$N$_8$O$_6$: 807.46; found 807.45.

Example M9.8

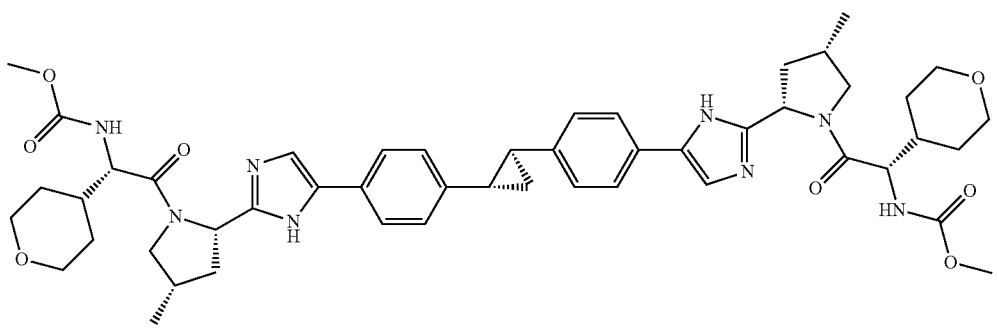

Example M9.7 (TFA salt) was prepared from dibromide M9.3d and acid M12.2c according to the procedures described for the preparation of Examples M9.4. $R_t$=3.01 min (Cond. 10d); >95% homogeneity index (Cond. 9 and 10); LC/MS: Anal. Calcd. for [M+H]$^+$ C$_{49}$H$_{63}$N$_8$O$_8$: 891.48; found 891.52.

Example M10

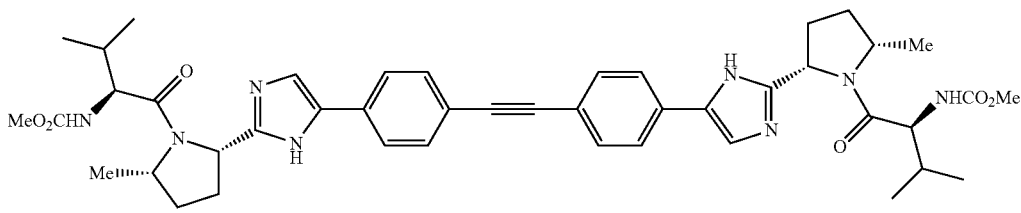

Example M10

Step a

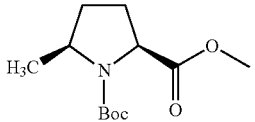

The title compound, containing a diastereomeric impurity, was prepared in 5 steps from (S)-methyl 5-oxopyrrolidine-2-carboxylate by employing the procedure described J. Med. Chem., 49:3520-3535 (2006) for the synthesis of its ethyl ester analog. $^1$H NMR (CDCl$_3$, 400 MHz): 4.35 (m, 0.5H), 4.25 (m, 0.5H), 4.05 (m, 0.5H), 3.90 (m, 0.5H), 3.73 (s, 3H), 2.20 (m, 1H), 2.00 (m, 2H), 1.65 (m, 1H), 1.50/1.40 (two overlapping br s, 9H), 1.31 (d, J=6.0, 3H).

Example M10

Step b

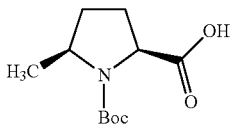 [SMILES: C[C@H]1CC[C@@H](C(=O)O)N1C(=O)OC(C)(C)C]

A solution of lithium hydroxide (0.23 g, 9.62 mmol) in water (5 mL) was added dropwise to a solution of ester M10a (1.8 g, 7.4 mmol) in ethanol (10 mL), and stirred at room temperature for 17 hr. Most of the solvent was evaporated, and the residue was diluted with water, 1 N HCl was added dropwise to bring it to pH 3. It was extracted with ethyl acetate (20 mL, 4×), dried (Na$_2$SO$_4$) and evaporated in vacuo to afford a colorless oil, which yielded crystals when dissolved in EtOAc/hexanes solvent system and allowed to stand at room temperature. The white solid was filtrated and dried in vacuo (1.42 g). $^1$H NMR (CDCl$_3$, 400 MHz, d=7.24 ppm): 4.35 (m, 1H), 3.95 (m, 1H), 2.35 (m, 1H), 2.05 (m, 2H), 1.70 (m, 1H), 1.50 (br s, 9H), 1.25 (d, J=7.1, 3H).

Example M10

Step c

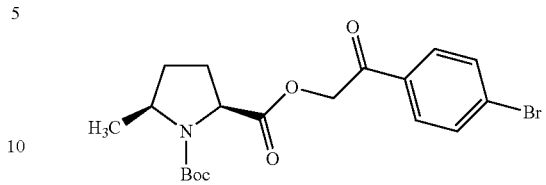

To a solution of acid M10b (2.16 g, 9.42 mmol) and 2-bromo-1-(4-bromophenyl)ethanone (2.62 g, 9.42 mmol) in acetonitrile (50 mL) was added slowly diisopropylethylamine (1.645 mL, 9.42 mmol), and the reaction mixture was stirred at room temperature for 5 hr. Solvent was removed in vacuo, and the residue was partitioned between ethyl acetate and water (1:1, 100 mL). The organic layer was washed with sat. NaHCO$_3$, dried (Na$_2$SO$_4$) and concentrated in vacuo to afford ketoester M10c as white solid (3.9 g), which was used in the next step without further purification. $^1$H NMR (400 MHz, DMSO-d$_6$, δ=2.5 ppm): 7.92 (d, J=8.3, 2H), 7.78 (d, J=8.5, 2H), 5.6-5.4 (m, 2H), 4.35 (m, 1H), 3.85 (m, 1H), 2.25 (m, 1H), 2.05 (m, 2H), 1.60 (m, 1H), 1.5/1.4 (two overlapping br s, 9H), 1.18 (d, J=6.6, 3H). LC/MS: Anal. Calcd. for [M+Na]$^+$ C$_{19}$H$_{24}$$^{81}$BrNaNO$_5$: 450.07; found: 450.00.

Example M10

Step d

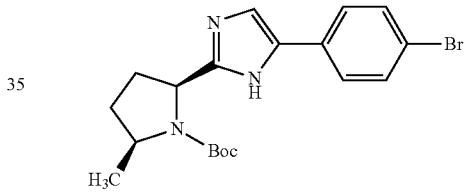

To a solution of ketoester M10c (3.9 g, 9.15 mmol) in xylene (60 mL) in a 500 mL pressure tube, ammonium acetate (7.05 g, 91 mmol) was added. The reaction vessel was sealed and heated at 140° C. for 5 hr. The solvent was removed in vacuo, and the residue was partitioned between CH$_2$Cl$_2$ (100 mL) and water (100 mL). The organic layer was washed (Sat. NaHCO$_3$), dried (Na$_2$SO$_4$), and evaporated in vacuo. The resulting crude material was purified with flash chromatograph (30-100% EtOAc/Hexane) to afford bromide M10d as a brown foam (3.0 g, yield 81%). $^1$H NMR (DMSO-d$_6$, δ=2.5 ppm, 400 MHz): 11.77 (s, 1H), 7.70 (d, J=8.5, 2H), 7.52 (br s, 1H), 7.50 (d, J=8.5, 2H), 4.80 (m, 1H), 3.85 (m, 1H), 2.10 (m, 3H), 2.70 (m, 1H), 1.5/1.3 (overlapping br s, 9H), 1.20 (m, 3H). LC/MS: Anal. Calcd. for [M+H]$^+$ C$_{19}$H$_{25}$$^{79}$BrN$_3$O$_2$: 406.11; found: 406.18.

Example M10

Step e

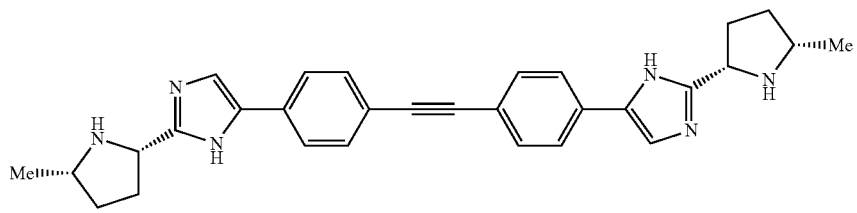 [SMILES: C[C@H]1CC[C@@H](c2ncc(-c3ccc(C#Cc4ccc(-c5cnc([C@@H]6CC[C@H](C)N6)[nH]5)cc4)cc3)[nH]2)N1]

Pyrrolidine M10e (HCl salt) was prepared bromide M10d according to the procedure described for the synthesis of pyrrolidine M1b (HCl salt) from bromide D1b.

Example M10

Example M10 (TFA salt) was prepared from bromide pyrrolidine M10e (HCl salt) according to the procedure described for the synthesis of Example M1 from pyrrolidine M31 (HCl salt). $^1$H NMR (DMSO-$d_6$, δ=2.5 ppm, 400 MHz): 8.05 (s, 2H), 7.85 (d, J=8.1, 4H), 7.69 (d, J=7.6, 4H), 7.56 (d, J=8.0, 2H), 5.5 (m, 0.4H), 5.0 (m, 1.6H), 4.75 (1.6H), 4.10 (m, 0.4H), 3.95 (m, 2H), 3.50 (s, 6H), 2.50-2.30 (m, 4H), 2.10 (m, 2H), 1.85 (m, 4H), 1.46 (d, J=6.6, 5H), 1.20 (d, J=6.8, 1H), 0.9-0.9 (m, 7.2H), 0.74 (d, J=6.8, 4.8H). LC (Cond. 9 and 10): >95% homogeneity index. LC/MS (Cond. 3): $R_t$=2.03 min. LC/MS: Anal. Calcd. for [M+H]$^+$ $C_{44}H_{55}N_8O_6$: 791.42; found: 791.39.

Examples M11-M12

The TFA salts Examples M11-M12 were prepared according to the procedure described for Example M10 and by employing appropriate acids.

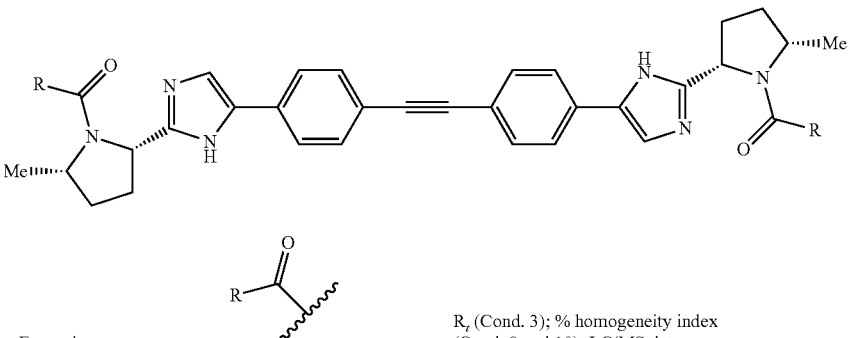

| Example | R group | $R_t$ (Cond. 3); % homogeneity index (Cond. 9 and 10); LC/MS data |
|---|---|---|
| M11 | 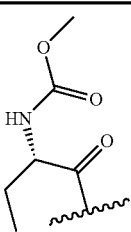 | 1.89 min.; >98%; LC/MS: Anal. Calcd. for [M + H]$^+$ $C_{42}H_{51}N_8O_6$: 763.39; found 763.40. |
| M12 | 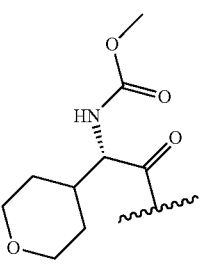 [SMILES: *C(=O)[C@@H](NC(=O)OC)C1CCOCC1] | 1.82 min.; >98%; LC/MS: Anal. Calcd. for [M + H]$^+$ $C_{48}H_{59}N_8O_8$: 875.45; found 875.42. |

Example M12.1

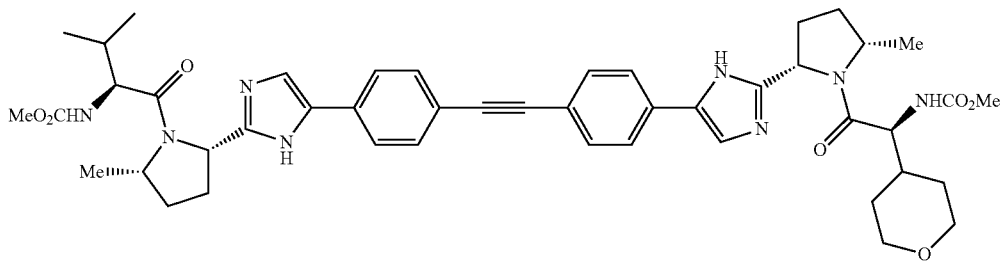

To a solution of pyrrolidine M10e/HCl salt (119 mg, 0.191 mmol), (S)-2-(methoxycarbonylamino)-2-(tetrahydro-2H-pyran-4-yl)acetic acid (49.0 mg, 0.226 mmol) and (S)-2-(methoxycarbonylamino)-3-methylbutanoic acid (40.9 mg, 0.233 mmol) in DMF (5 mL) was added DIEA (0.200 mL, 1.147 mmol) and HATU (148 mg, 0.390 mmol), and the mixture was stirred at room temperature for 1 hr. Solvent was removed in vacuo and the residue was dissolved in methanol and purified with a reverse phase HPLC (MeOH/TFA/Water) to separate the statistical mixture of products, one of which was Example M12.1 (TFA salt; light yellow foam; 55 mg). $^1$H NMR (DMSO-$d_6$, δ=2.5 ppm, 400 MHz): 8.09-7.82 (m, 6H), 7.68-7.55 (m, 6H), 5.00 (m, 2H), 4.64 (app t, 2H), 4.21-3.75 (m, 6H), 3.53 (m, 6H), 3.17 (m, 2H), 2.33-2.21 (m, 6H), 1.85 (m, 3H), 1.62-1.17 (overlay of 'd' and 'm', J for 'd'=6.6 Hz, 9H), 0.88 (m, 3.6H), 0.74 (d, J=6.8 Hz, 2.4H). LC (Cond. 9 and 10): >95% homogeneity index. LC/MS (Cond. 10h): $R_f$=1.92 min. LC/MS: Anal. Calcd. for [M+H]$^+$ $C_{46}H_{57}N_8O_7$: 833.44; found: 833.40.

Example M12.2

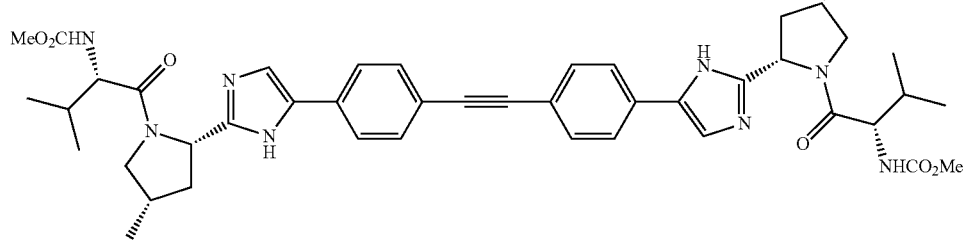

Example M12.2

Step a

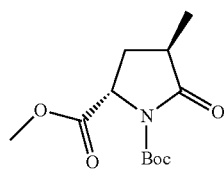

M12.2a-1

M12.2a-2

M12.2a-3

The above three esters were prepared from (S)-1-tert-butyl 2-methyl 5-oxopyrrolidine-1,2-dicarboxylate according to the procedure described in Tetrahedron Letters, 2003, 3203-3205.

Example M12.2

Step b

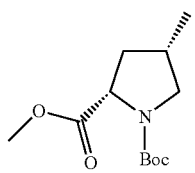

Borane-methyl sulfide complex (5.44 mL, 10.88 mmol) was added to a solution of ester M12.2a-2 (1.4 g, 5.44 mmol) in THF (25 mL), and the reaction mixture was heated at 40° C. for 7 hr. The volatile component was removed in vacuo and the residue was partitioned between EtOAc and water (50 mL each). The aqueous layer was extracted with EtOAc (30 mL), and the combined organic phase was dried with Na$_2$SO$_4$, and concentrated in vacuo. The resultant colorless oil was purified with a flash chromatography (0-50% EtOAc/Hexane) to afford ester M12.2b as a colorless oil (0.77 g). $^1$H NMR (CDCl$_3$, δ=7.24 ppm, 400 MHz): 4.29-4.18 (m, 1H), 3.78-3.66 (m, 4H), 2.99 (app t, J=10.1, 1H), 2.43-2.97 (m, 1H), 2.43-2.37 (m, 1H), 2.30-2.18 (m, 1H), 1.60-1.52 (m, 1H), 1.47/1.42 (two 's', 9H), 1.08-1.05 (m, 3H).

Example M12.2

Step c

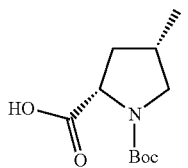

To a solution of ester M12.2b (1.69 g, 6.95 mmol) in ethanol (10 mL) was added solution of LiOH (0.250 g, 10.42 mmol) in water (5.00 mL), and the reaction mixture was stirred at room temperature for 5 hr. The organic solvent was evaporated in vacuo and the residue was diluted with water (10 mL) and washed with ether (10 mL). It was chilled in ice-water bath, and acidified to a pH range of ~2 with 1N HCl. It was then extracted with EtOAc (20 mL, 3×). The organic layer was dried with Na$_2$SO$_4$ and concentrated in vacuo to afford acid M12.2c as a colorless oil, which became a white solid upon extended exposure to high vacuum (1.38 g). $^1$H NMR (CDCl$_3$, δ=7.24 ppm, 400 MHz): 4.39-4.22 (m, 1H), 3.80-3.69 (m, 0.91H), 3.59-3.35 (m, 0.18H), 3.03-2.89 (m, 0.91H), 2.51-2.22 (m, 2H), 1.98-1.91 (m, 0.71H), 1.68-1.60 (0.29H), 1.50/1.44 (two 's', 9H), 1.09 (app m, 3H).

Example M12.2

Step d

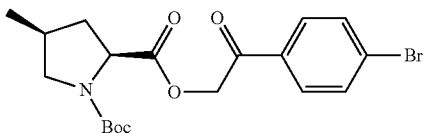 [SMILES: C[C@H]1C[C@@H](C(=O)OCC(=O)c2ccc(Br)cc2)N(C(=O)OC(C)(C)C)C1]

To a solution of M12.2c (1.38 g, 6.02 mmol) and 2-bromo-1-(4-bromophenyl)ethanone (1.673 g, 6.02 mmol) in acetonitrile (35 mL) was added DIEA (1.051 mL, 6.02 mmol). It was stirred at room temperature for 5 hrs. The solvent was evaporated in vacuo and water (50 mL) and EtOAc (70 mL) were added, organic layer was separated and washed by sat. NaHCO$_3$ (30 mL), dried with Na$_2$SO$_4$, evaporated in vacuo to give crude M12.2d as a red oil (2.71 g), which was used in the next step without further purification. $^1$H NMR (DMSO-d$_6$, δ=2.5 ppm, 400 MHz): 7.91 (m, 2H), 7.78 (d, J=8.5 Hz, 2H), 5.60-4.90 (m, 2H), 4.29 (app t, 1H), 3.61 (m, 1H), 2.85 (m, 1H), 2.35-1.80 (m, 2H), 1.65 (m, 1H), 1.40-1.32 (two s, 9H), 1.02 (d, J=6.5 Hz, 3H). LC/MS: Anal. Calcd. for [M+Na]$^+$ C$_{19}$H$_{24}$$^{81}$BrNNaO$_5$: 450.07; found: 450.11.

Example M12.2

Step e

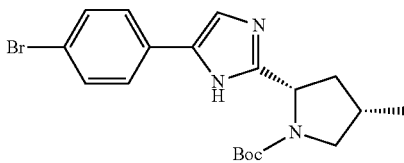 [SMILES: C[C@H]1C[C@@H](c2ncc(-c3ccc(Br)cc3)[nH]2)N(C(=O)OC(C)(C)C)C1]

To a pressure tube containing a solution of ketoester M12.2d (2.57 g, 6.03 mmol) in xylene (50 mL was added ammonium acetate (4.65 g, 60.3 mmol). The vessel was capped and heated at 140° C. for 5 hrs. The volatile component was removed in vacuo and the residue was partitioned between DCM (50 mL) and water (40 mL). The organic layer was dried with Na$_2$SO$_4$, and concentrated in vacuo. The resulting crude mixture was purified with flash chromatograph (30-100% EtOAc/Hexane) to afford imidazole M12.2.e as a brown solid (1.24 g). $^1$H NMR (DMSO-d$_6$, δ=2.5 ppm, 400 MHz): 7.69 (d, J=8.5 Hz, 2H), 7.58-7.48 (m, 3H), 4.70 (m, 1H), 3.65 (m, 1H), 3.02 (m, 11-1), 2.37 (m, 1H), 2.22 (m, 1H), 1.74-1.54 (m, 1H), 1.37-1.08 (two s, 9H), 1.03 (d, J=6.3 Hz, 3H). LC/MS: Anal. Calcd. for [M+H]$^+$ C$_{19}$H$_{25}$$^{79}$BrN$_3$O$_2$: 406.11; found: 406.18.

Example M12.2

Step f

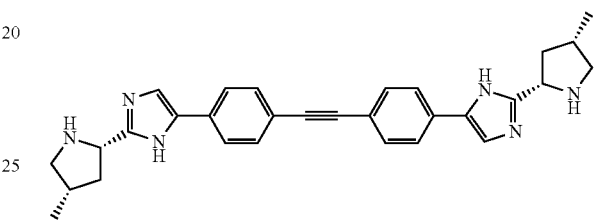

Pyrrolidine M12.2f (HCl salt) was prepared bromide M12.2e according to the procedure described for the synthesis of pyrrolidine M1b (HCl salt) from bromide D1b.

Example M12.2

To a mixture of pyrrolidine M12.2f/HCl salt (200 mg, 0.321 mmol) and (S)-2-(methoxycarbonylamino)-3-methylbutanoic acid (124 mg, 0.707 mmol) in DMF (5 mL) were added DIEA (0.337 mL, 1.928 mmol) and HATU (250 mg, 0.659 mmol), and the mixture was stirred at room temperature for 2 hrs. The volatile component was removed in vacuo and the residue was purified with a reverse phase HPLC (Phenomenex-Luna 30×100 mm, S10 Axia, MeOH/TFA/Water). The resultant sample was repurified with a different reverse phase HPLC (Water-Sunfire 30×100 mm S5, ACN/TFA/Water) to afford the TFA salt of Example M12.2 as a light yellow foam (77.1 mg). $^1$H NMR (Methanol-d$_4$, δ=3.29 ppm, 400 MHz): 7.90 (s, 2H), 7.74 (d, J=8.6 Hz, 4H), 7.67 (d, J=8.5 Hz, 4H), 5.18 (m, 2H), 4.30 (app t, 2H), 4.18 (d, J=7.3 Hz, 2H), 3.63 (s, 6H), 3.38 (m, 2H), 2.63 (m, 2H), 2.51 (m, 2H), 1.98 (m, 2H), 1.81 (m, 2H), 1.21 (d, J=6.3 Hz, 6H), 0.83-0.90 (m, 12H). LC (Cond. 9 and 10): >95% homogeneity index. LC/MS (Cond. 10h): R$_f$=2.01 min. LC/MS: Anal. Calcd. for [M+H]$^+$ C$_{44}$H$_{55}$N$_8$O$_6$: 791.42; found: 791.46.

Example M12.3

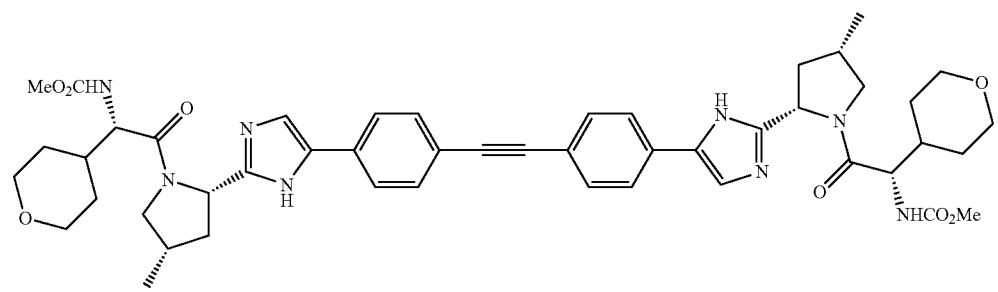

Example M12.3 (TFA salt) was prepared from pyrrolidine M12.2f/HCl and (S)-2-(methoxycarbonylamino)-2-(tetrahydro-2H-pyran-4-yl)acetic acid according to the procedure described for the preparation of Example M12.2. RT: LC (Cond. 9 and 10): >95% homogeneity index. LC/MS (Cond. 10h): $R_t$=1.89 min. LC/MS: Anal. Calcd. for $[M+H]^+$ $C_{48}H_{59}N_8O_8$: 875.45; found 875.42.

Example M12.4-M12.5

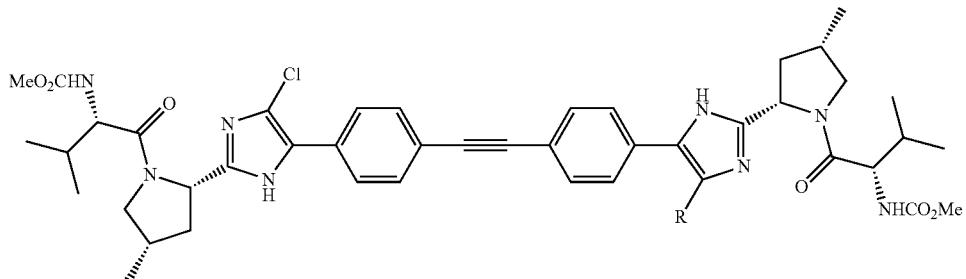

Example M12.4 (R = H)
Example M12.5 (R = Cl)

To a solution of Example M12.2 (free-based using MCX column and 2N NH$_3$/MeOH) (80 mg, 0.101 mmol) in DMF (5 mL) was added NCS (17.56 mg, 0.131 mmol), and heated at 50° C. for 3 hrs. Additional NCS (5 mg, 0.037 mmol) was added to the mixture and heating was continued for 5 more hours. The volatile component was removed in vacuo and the residue was dissolved in MeOH and submitted to a reverse phase HPLC condition (MeOH/TFA/Water) to afford Example M12.4/TFA salt (light yellow foam, 24 mg) and Example M12.5/TFA salt (light yellow foam, 28 mg). Example M12.4/TFA salt: $^1$H NMR (DMSO-d$_6$, δ=2.5 ppm, 400 MHz): 8.17 (s, 1H), 7.83-7.73 (m, 6H), 7.66 (d, J=8.6 Hz, 2H), 7.30 (d, J=8.3 Hz, 1H), 7.22 (d, J=8.3 Hz, 1H), 5.05 (m, 1H), 4.85 (m, 1H), 4.16-4.02 (m, 4H), 3.52 (s, 6H), 3.37 (m, 1H), 3.23 (m, 1H), 2.54-2.24 (m, 4H), 1.87-1.63 (m, 4H), 1.13-1.08 (m, 6H), 0.85-0.74 (m, 12H). LC (Cond. 9a.1 and 10a.1): >95% homogeneity index. LC/MS (Cond. 11): $R_t$=4.26 min. LC/MS: Anal. Calcd. for $[M+H]^+$ $C_{44}H_{54}ClN_8O_8$: 825.39; found: 825.50. Example M12.5/TFA salt: (DMSO-d$_5$, δ=2.5 ppm, 400 MHz): 7.79 (d, J=8.4 Hz, 4H), 7.66 (d, J=8.4 Hz, 4H), 7.22 (d, J=8.3 Hz, 2H), 4.85 (m, 2H), 4.13 (app t, 2H), 4.04 (app t, 2H), 3.53 (s, 6H), 3.24 (app t, 2H), 2.39 (m, 2H), 2.26 (m, 2H), 1.90 (m, 2H), 1.66 (m, 2H), 1.09 (d, J=6.5 Hz, 6H), 0.85 (d, J=6.8 Hz, 6H), 0.80 (d, J=6.5 Hz, 6H). LC (Cond. 9a and 10a.1): >95% homogeneity index. LC/MS (Cond. 11): $R_t$=4.44 min. LC/MS: Anal. Calcd. for $[M+H]^+$ $C_{44}H_{53}Cl_2N_8O_6$: 859.35; found: 859.30.

Example M12.6-M12.7

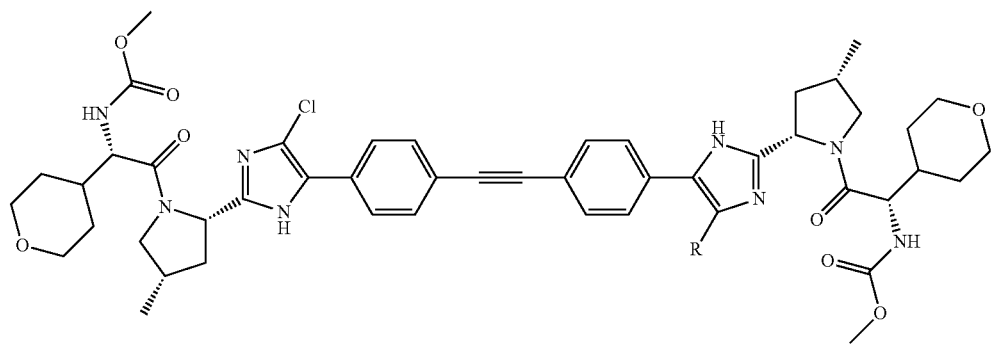

Example M12.6 (R = H)
Example M12.7 (R = Cl)

Example 12.6-12.7 were prepared as TFA salts from Example M12.3 according to the procedure described for the preparation of Example 12.4-12.5.

| Example | RT (Cond. 12); % homogeneity index (Cond. 12); MS data |
|---|---|
| M12.6 | 13.68 min.; >95%; LC/MS: Anal. Calcd. for [M + H]+ $C_{48}H_{58}ClN_8O_8$: 909.41; found 909.8 |
| M12.7 | 17.12 min; >95%; LC/MS: Anal. Calcd. for [M + H]+ $C_{48}H_{57}Cl_2N_8O_8$: 943.37; found 943.7 |

Example M12.8

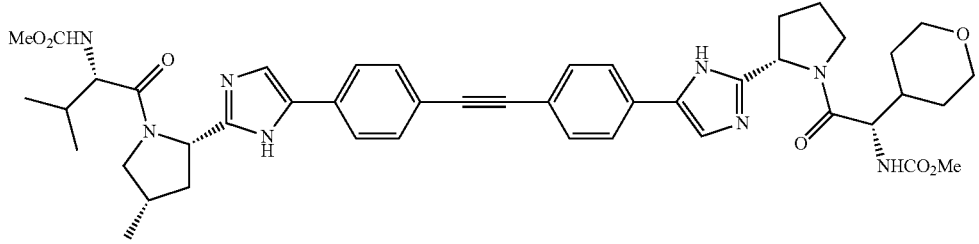

Example M12.8

Step a

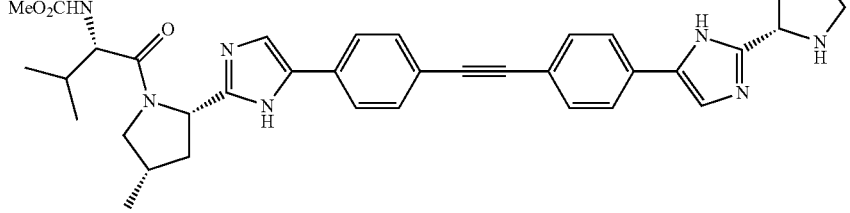

To a mixture of pyrrolidine M12.2f/HCl salt (120 mg, 0.193 mmol) and (S)-2-(methoxycarbonylamino)-3-methylbutanoic acid (35.1 mg, 0.200 mmol) in DMF (2 mL), were added DIEA (0.168 mL, 0.964 mmol) followed by HATU (70.4 mg, 0.185 mmol), and the mixture was stirred at room temperature for 1 hr. The volatile component was removed in vacuo and the residue was dissolved in MeOH and submitted to a reverse phase HPLC condition (MeOH/TFA/Water) to isolate the TFA salt of pyrrolidine M12.8a as yellow solid (36 mg). The sample was free based (MCX column; MeOH wash; 2 N NH$_3$/MeOH elution) to afford a yellow solid (22.3 mg). LC/MS: Anal. Calcd. for [M+H]+ $C_{37}H_{44}N_7O_3$: 634.35; found: 634.35.

Example M12.8

To a solution of pyrrolidine M12.8a (22.3 mg, 0.035 mmol) and (S)-2-(methoxycarbonylamino)-2-(tetrahydro-2H-pyran-4-yl)acetic acid (12.99 mg, 0.060 mmol) in DMF (2 mL) were added DIEA (0.018 mL, 0.106 mmol) and HATU (13.65 mg, 0.036 mmol), and the mixture was stirred at room temperature for 2 hrs. The volatile component was removed in vacuo and the residue was dissolved in MeOH and submitted to a reverse phase HPLC condition (Column: Phenomenex-Luna 30×100 mm, S10 Axia; MeOH/TFA/Water). The resulting sample was repurified with a second reverse phase HPLC (Column: Water-Sunfire 30×100 mm S5; ACN/TFA/Water) to afford the TFA salt of Example M12.8 as a light yellow foam (16 mg). $^1$H NMR (Methanol-d$_4$, δ=3.29 ppm, 400 MHz): 7.92 (d, J=5.0 Hz, 2H), 7.77 (d, J=8.5 Hz, 4H), 7.72-7.69 (m, 4H), 5.21 (m, 2H), 4.39-4.22 (m, 4H), 3.92 (m, 2H), 3.67 (s, 6H), 3.47-3.28 (m, 4H), 2.68 (m, 2H), 2.54 (m, 2H), 2.06-1.85 (m, 4H), 1.25 (d, J=6.5 Hz, 6H), 0.93 (d, J=6.7 Hz, 3H), 0.91 (d, J=7.3 Hz, 6H). LC (Cond. 9 and 10): >95% homogeneity index. LC/MS (Cond. 10d): R$_t$=3.10 min. LC/MS: Anal. Calcd. for [M+H]+ $C_{46}H_{57}N_8O_7$: 833.44; found: 833.47.

Example M12.9

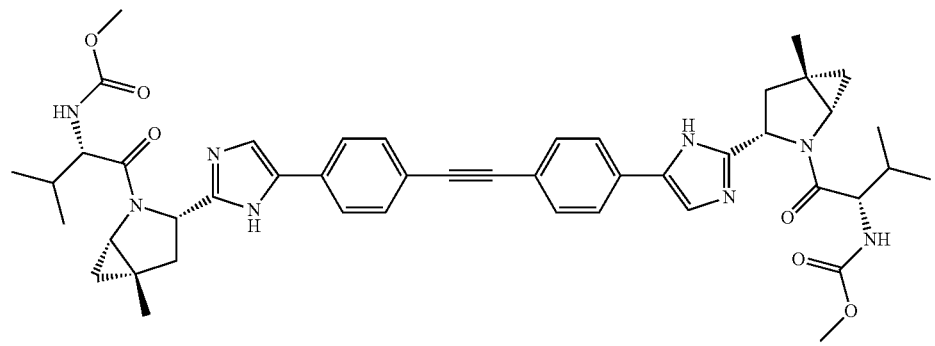 [SMILES: COC(=O)N[C@H](C(=O)N1[C@H]2C[C@@]2(C)C[C@H]1c1ncc(-c2ccc(C#Cc3ccc(-c4cnc([C@@H]5C[C@]6(C)C[C@@H]6N5C(=O)[C@@H](NC(=O)OC)C(C)C)[nH]4)cc3)cc2)[nH]1)C(C)C]

Example M12.9

Step a

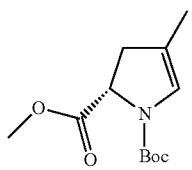

To a solution of mixture of M12.2a-1 and M12.2a-2 (4.75 g, 18.46 mmol) was added Superhydride (19.20 mL, 19.20 mmol) dropwise at −50° C. in a dry ice/acetone bath for 10 min. Hunig's base (13.58 mL, 78 mmol) was added, and stirred for 10 min and DMAP (0.122 g, 0.997 mmol) was added as a solid, stirred for 15 min, and trifluoroacetic anhydride (2.98 mL, 21.08 mmol) was added dropwise over 15 mins Then the dry ice/acetone bath was removed, and the reaction mixture was stirred for 4 hr while allowing it to thaw to room temperature. The reaction mixture was washed with water (50 mL), sat. NaCl (30 mL), and concentrated in vacuo. The resulting crude material was purified with flash chromatography (8-60% EtOAc/Hexane) to afford ester M12.9a as a yellow oil (2.85 g). $^1$H NMR (CDCl$_3$, 400 MHz): 6.36 (s, 0.5H), 6.25 (s, 0.5H), 4.70-4.57 (m, 1H), 3.78 (s, 3H), 2.96 (m, 1H), 2.54 (m, 1H), 1.70 (s, 3H), 1.50 (s, 4.5H), 1.44 (s, 4.5H).

Example M12.9

Step b

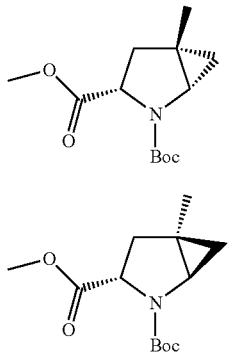

M12.9b-1

M12.9b-2

Diethylzinc (1.1 M in toluene, 59.1 mL, 65.0 mmol) was added dropwise over 20 min to a cooled (−23° C.) toluene (60 mL) solution of ester M12.9a (5.23 g, 21.68 mmol), and stirred for 10 min. Chloroiodomethane (9.44 mL, 130 mmol) was added dropwise over 10 min, and the reaction mixture was stirred at −21° C. for 16 hr. Sat. NaHCO$_3$ (60 mL) was added to the reaction mixture, the cooling bath was removed, and the mixture was stirred for 10 min. It was then filtered, and the filter cake was washed with toluene (50 mL). The filterate was partitioned, and the organic layer was dried with Na$_2$SO$_4$, and concentrated in vacuo. The resulting crude material was purified with flash chromatography (2-10% EtOAc/Hexane) to afford ester ester M12.9b-1 (first elute; colorless oil; 2.88 g) and ester M12.9b-2 (second elute; colorless oil; 1.01 g). Relative stereochemical assignment was made based on NOE studies. Ester M12.9b-1: $^1$H NMR (CDCl$_3$, 400 MHz): 4.65-4.52 (m, 1H), 3.72 (s, 3H), 3.28-3.17 (m, 1H), 2.44-2.32 (m, 1H), 2.16-2.10 (m, 1H), 1.51-1.42 (two s, 9H), 1.24 (s, 3H), 1.07 (m, 1H), 0.69-0.60 (m, 1H).

Example M12.9

Step c

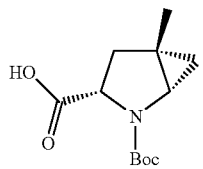

To a solution of M12.9b-1 (2.88 g, 11.28 mmol) in Ethanol (20 mL) was added a solution of LiOH (0.324 g, 13.54 mmol) in water (10.00 mL), and the mixture was stirred at room temperature for 6 hr. Most of the volatile component was removed in vacuo, and the residue was partitioned between water (20 mL) and ether (20 mL). The aqueous layer was chilled in an ice-water bath, acidified with a 1N HCl to a pH region of 2, and extracted with EtOAc (30 mL, 4×). The combined organic phase was dried with Na$_2$SO$_4$, evaporated in vacuo to give acid M12.9c as a sticky solid (2.55 g). $^1$H NMR (CDCl$_3$, 400 MHz): 4.64 (m, 1H), 3.25 (appt s, 1H), 2.70-2.40 (m, 1H), 2.14 (m, 1H), 1.54-1.44 (m, 9H), 1.27 (s, 3H), 1.10-0.80 (m, 1H), 0.67 (m, 1H).

Example M12.9

Step d

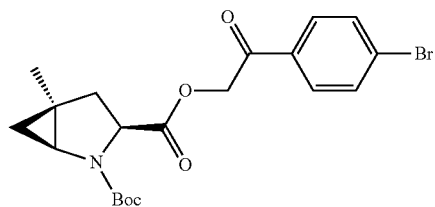 [SMILES: CC(C)(C)OC(=O)N1[C@H]2C[C@@]2(C)C[C@H]1C(=O)OCC(=O)c1ccc(Br)cc1]

To a solution of acid M12.9c (2.05 g, 8.50 mmol) in Acetonitrile (50 mL) was added 2-bromo-1-(4-bromophenyl)ethanone (2.361 g, 8.50 mmol) followed by DIEA (1.484 mL, 8.50 mmol), and the reaction mixture was stirred at room temperature for 16 hr. Most of the volatile component was removed in vacuo, and the residue was partitioned between EtOAc (50 mL) and water (50 mL). The organic layer was washed with sat. NaHCO$_3$ (30 mL) and sat. NaCl (20 mL), dried with Na$_2$SO$_4$, and evaporated in vacuo to afford ketoester M12.9d as white foam (3.5 g). LC/MS: Anal. Calcd. for [M+Na]$^+$ C$_{20}$H$_{24}$$^{81}$BrNNaO$_5$: 462.07; found: 461.91.

Example M12.9

Step e

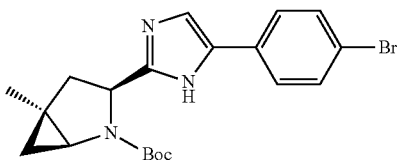 [SMILES: CC(C)(C)OC(=O)N1[C@H]2C[C@@]2(C)C[C@H]1c1ncc(-c2ccc(Br)cc2)[nH]1]

To a mixture of ketoester M12.9e (3.5 g, 7.99 mmol) and xylene (80 mL) in a pressure tube was added ammonium acetate (6.16 g, 80 mmol), and the reaction mixture was capped and heated at 140° C. for 4.5 hr. The volatile component was removed in vacuo and the residue was partitioned between DCM (70 mL) and water (70 mL). The organic layer was washed with sat. NaHCO$_3$ (30 mL), and concentrated in vacuo. The resulting crude material was purified with flash chromatograph (40-100% EtOAc/Hexane) to afford imidazole M12.9e as a brown solid (2.8 g). $^1$H NMR (DMSO-d$_6$, δ=2.5 ppm, 400 MHz): 7.68 (m, 2H), 7.57-7.49 (m, 3H), 5.08 (m, 1H), 3.20 (m, 1H), 2.45-2.09 (M, 2H), 1.69-1.52 (m, 1H), 1.42-1.16 (m, 12H), 0.62 (m, 1H). LC/MS: Anal. Calcd. for [M+H]$^+$ C$_{20}$H$_{25}$$^{81}$BrN$_3$O$_2$: 420.11; found: 420.02.

Example M12.9

Step f

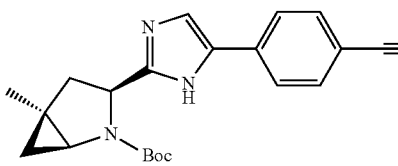

To a pressure tube containing a solution of bromide M12.9e (0.354 g, 1.007 mmol) and 1,2-bis(trimethylstannyl)ethyne (0.354 g, 1.007 mmol) in DMF (15 mL) was added Pd(Ph$_3$P)$_4$ (0.070 g, 0.060 mmol), and the reaction mixture was degassed for 10 min and the reaction vessel was capped and heated at 90° C. for 14 hr. Most of the volatile component was removed in vacuo, and the residue was partitioned between DCM (60 mL) and water (40 mL). The organic layer was dried with Na$_2$SO$_4$, and evaporated in vacuo. The resulting crude material was purified with flash chromatograph (40-100% EtOAc/hexanes) to afford alkyne M12.9f as a red solid (0.3 g). LC/MS: Anal. Calcd. for [M+H]$^+$ C$_{42}$H$_{49}$N$_6$O$_4$: 701.38; found: 701.43.

Example M12.9

Step g

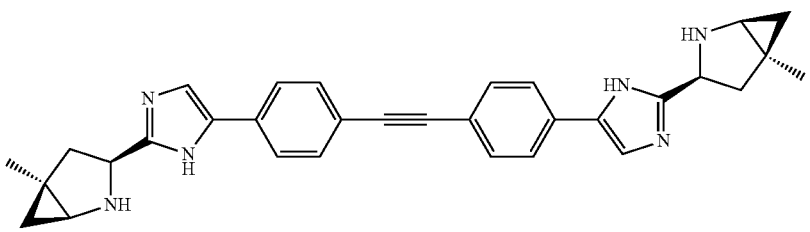

4N HCl in dioxane (3.90 mL, 128 mmol) was added to carbamate M12.9f (0.3 g, 0.428 mmol), and the mixture was stirred at room temperature for 5 hr. The volatile component was removed in vacuo and the residue was dried under high vacuum overnight to afford the HCl salt of pyrrolidine M12.9 g as a yellow solid (0.27 g). LC/MS: Anal. Calcd. for [M+H]$^+$ C$_{32}$H$_{33}$N$_6$: 501.28; found: 501.22.

Example M12.9

To a mixture of M12.9 g/HCl salt (60 mg, 0.093 mmol) and (S)-2-(methoxycarbonylamino)-3-methylbutanoic acid (35.8 mg, 0.204 mmol) in DMF (2 mL) were added DIEA (0.097 mL, 0.557 mmol) and HATU (72.7 mg, 0.191 mmol), and the reaction mixture was stirred at room temperature for 2 hr. The volatile component was removed in vacuo and the residue was dissolved in MeOH and submitted to a reverse phase HPLC purification (Phenomenex-Luna 30×100 mm, S10 Axia, MeOH/TFA/Water). The resulting sample was repurified with a second reverse phase HPLC (Water-Sunfire 30×150 mm OBD, ACN/TFA/Water) to afford the TPA salt of Example M12.9 as light yellow foam (37 mg). LC/MS (Cond. 10d): R$_t$=3.08 min. LC (Cond. 9 and 10): >95% homogeneity index. LC/MS: Anal. Calcd. for [M+H]$^+$ C$_{46}$H$_{55}$N$_8$O$_6$: 815.42; found: 815.46.

Example M13

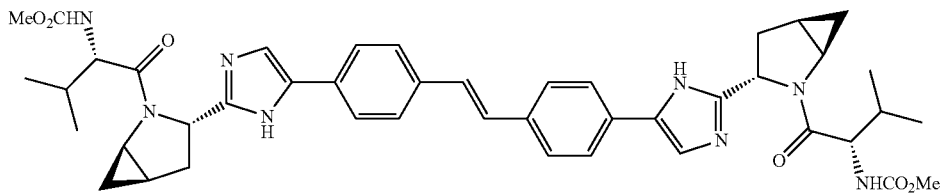

Example M13

Step a

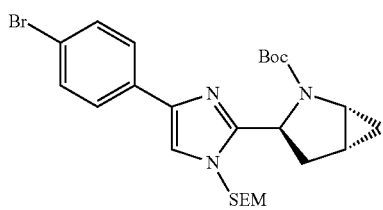

(SEM regiochemistry was not determined)

Example M13

Step b

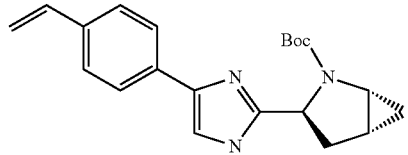

(SEM regiochemistry was not determined)

To a solution of bromide M3h (1.0 g, 2.47 mmol) in DMF (25 mL) was added sodium hydride (60%; 0.109 g, 2.72 mmol), and the reaction mixture was stirred at room temperature for 20 min. Then (2-(chloromethoxy)ethyl)trimethylsilane (0.482 mL, 2.72 mmol) was added dropwise, and the reaction was stirred for 21 h. The volatile component was removed in vacuo, and the residue was partitioned between ethyl acetate (25 mL) and water (25 mL). The aqueous layer was extracted with ethyl acetate (2×25 mL), and the combined organic phase was washed with brine (25 mL), dried over MgSO$_4$, filtered, and concentrated in vacuo. The residue was taken up in CHCl$_3$ (2 mL) and loaded on a Thomson's silica gel cartridge eluting with 25% ethyl acetate/hexanes to afford bromide M13a of unknown regio-chemical make up as light yellow foam (1.171 g). NMR (DMSO-d$_6$, δ=2.5 ppm, 400 MHz): 7.71 (s, 1H), 7.69 (d, J=8.6, 2H), 7.52 (d, J=8.6, 2H), 5.62-5.31 (br s, 1H), 5.26 (d, J=10.8, 1H), 4.84-4.66 (app br s, 1H), 3.57-3.36 (app br s, 1H), 3.50 (t, J=8.1, 2H), 2.44-2.20 (app br s, 2H), 1.77-1.60 (app br s, 1H), 1.52-1.23 (br s, 4H), 1.23-0.96 (br s, 5H), 0.92-0.79 (m, 2H), 0.78-0.69 (m, 1H), 0.64-0.55 (app br s, 1H), 0.00 (s, 9H). LC/MS: Anal. Calcd. for [M+H]$^+$ C$_{25}$H$_{37}$$^{79}$BrN$_3$O$_3$Si: 534.18; found: 533.99.

To a solution of bromide M13a (0.5542 g, 1.037 mmol) and triethylamine (0.434 mL, 3.11 mmol) in 2-propanol (2.000 mL) and water (1 mL) in a sealed reaction vessel was added potassium vinyltrifluoroborate (0.181 g, 1.348 mmol) followed by 1,1'-bis(diphenylphosphino)ferrocene-palladium (II)dichloride dichloromethane complex (0.085 g, 0.104 mmol). The reaction mixture was flushed with nitrogen, capped and heated at 100° C. for 17 h. The volatile component was removed in vacuo, and the residue was partitioned between ethyl acetate (25 mL) and water (25 mL), and the aqueous phase was extracted with ethyl acetate (2×25 mL). The combined organic phase was dried over MgSO$_4$, filtered, and concentrated in vacuo. The residue was taken up in CHCl$_3$ (4 mL) and loaded onto a Thomson's silica gel cartridge eluting with 25% ethyl acetate/hexanes to afford alkene M13b as a light yellow viscous oil (345.4 mg). $^1$H NMR (DMSO-d$_6$, δ=2.5 ppm, 400 MHz): 7.71 (d, J=8.3, 2H), 7.67 (s, 1H), 7.45 (d, J=8.3, 2H), 6.72 (dd, J=17.6, 11.1, 1H), 5.8 (dd, J=0.8, 17.6, 1H), 5.60-5.29 (app br s, 1H), 5.26 (d, J=10.8, 1H), 5.22 (d, J=11.8, 1H), 4.83-4.67 (app br s, 1H), 3.59-3.35 (app br s, 1H), 3.51 (t, J=8.1, 2H), 2.41-2.23 (app br s, 2H), 1.76-1.59 (app br s, 1H), 1.51-1.22 (app br s, 4H), 1.22-0.97 (app br s, 5H), 0.93-0.80 (m, 2H), 0.80-0.71 (m, 1H), 0.65-0.56 (app br s, 1H), 0.00 (s, 9H). LC/MS: Anal. Calcd. for [M+H]$^+$ C$_{27}$H$_{40}$N$_3$O$_3$Si: 482.28; found: 482.24.

Example M13

Step c

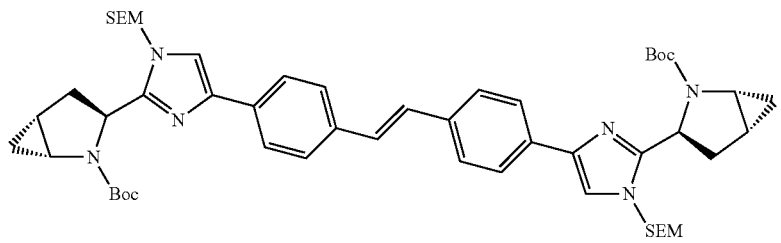

(SEM regiochemistry was not determined)

To a solution of alkene M13b (0.748 g, 1.552 mmol) in CH$_2$Cl$_2$ (2 mL) was added Grubbs 2nd Generation Catalyst (0.132 g, 0.155 mmol), and stirred at room temperature under nitrogen for 18 hr. The reaction was loaded onto a Thomson's silica gel cartridge eluting with 30% ethyl acetate/hexanes to afford M13c as a tan foam (0.50 g). $^1$H NMR (DMSO-d$_6$, δ=2.5 ppm, 400 MHz): 7.74 (d, J=8.4, 4H), 7.68 (s, 2H), 7.58 (d, J=8.3, 4H), 7.22 (s, 2H), 5.72-5.34 (bs, 3H), 5.34-5.21 (m, 2H), 4.94-4.63 (app br s, 3H), 3.52 (t, J=7.8, 4H), 2.45-2.20 (app br s, 4H), 1.88-1.57 (app br s, 2H), 1.57-1.26 (br s, 8H), 1.26-0.98 (br s, 10H), 0.93-0.80 (m, 4H), 0.80-0.69 (m, 2H), 0.69-0.51 (app bs, 2H), 0.00 (s, 18H).

Example M13

Step d

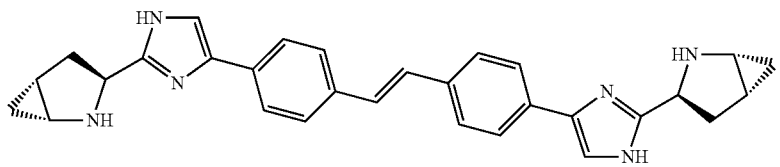 [SMILES: C(=C\c1ccc(-c2c[nH]c([C@@H]3C[C@H]4C[C@H]4N3)n2)cc1)/c1ccc(-c2c[nH]c([C@@H]3C[C@H]4C[C@H]4N3)n2)cc1]

4N HCl/Dioxane (13 mL) was carefully added to a flask containing M13c (0.4799 g, 0.513 mmol) that was cooled with an ice/water bath. A mixture of water (4 mL) and 12N HCl (2 mL) was added to the above mixture and the cooling bath was removed and stirring of the reaction mixture continued for 24 h. MeOH (2 mL) was added to the reaction, and stirring was continued for 17 h. All solvents were removed in vacuo to afford pyrrolidine M13d (0.4HCl) as a yellow/tan solid (317 mg). $^1$H NMR (DMSO-d$_6$, δ=2.5 ppm, 400 MHz): 10.78-9.87 (very br s, ~3H), 8.01 (s, 2H), 7.87 (d, J=8.4, 4H), 7.71 (d, J=8.6, 4H), 7.35 (s, 2H), 4.76 (app t, J=8.8, 2H), 3.43 (app t, J=5.1, 2H), 2.64 (m, 2H), 2.55-2.52 (m, 2H), 1.95 (m, 2H), 1.16-1.05 (m, 2H), 0.86 (m, 2H). LC/MS: Anal. Calcd. for [M+H]$^+$ C$_{30}$H$_{31}$N$_6$: 475.26; found: 475.26.

Example M13

The TFA salt of Example M13 was prepared from pyrrolidine M13d (0.4HCl) and (S)-2-(methoxycarbonylamino)-3-methylbutanoic acid according to the procedure described for the preparation of Example M1. $^1$H NMR (DMSO-d$_6$, δ=2.5 ppm, 400 MHz): 8.14-7.95 (br s, 2H), 7.80-7.74 (m, 8H), 7.40 (s, 2H), 7.25 (d, J=8.3, 2H), 5.0 (app t, J=7.3, 2H), 4.41 (app t, J=7.6, 2H), 3.81-3.67 (m, 2H), 3.54 (s, 6H), 2.57-2.46 (overlapped with DMSO-$_{d6}$) (m, 2H), 2.44-2.31 (m, 2H), 2.19-2.05 (m, 2H), 1.98-1.87 (m, 2H), 1.02-0.89 (m, 7.5H), 0.89-0.70 (m, 8.5H). LC (Cond. 3): R$_t$=1.92 min; LC/MS: Anal. Calcd. for [M+H]$^+$ C$_{44}$H$_{53}$N$_8$O$_6$: 789.41; found: 789.46.

Examples M14-M15

Example M14 (TFA salt) was prepared from pyrrolidine M13d and appropriate acid by employing the procedure described for the synthesis of Example M1. In the case of Example M15 an equimolar mixture of (S)-2-(methoxycarbonylamino)-3-methylbutanoic acid and (S)-2-(methoxycarbonylamino)-2-(tetrahydro-2H-pyran-4-yl)acetic acid was employed for the coupling step and the resultant statistical mixture of products was separated by the HPLC technique described for Example M1.

| Example | R$_1$ | R$_2$ | Rt (Cond. 3); % homogeneity index (Cond. 9 and 10); LC/MS data |
|---|---|---|---|
| M14 | ![R1] | ![R2] | 1.72 min.; >98%; LC/MS: Anal. Calcd. for [M + H]$^+$ C$_{48}$H$_{57}$N$_8$O$_8$: 873.43; found 873.48 |

-continued

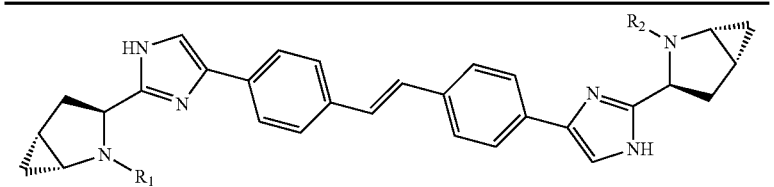

| Example | $R_1$ | $R_2$ | Rt (Cond. 3); % homogeneity index (Cond. 9 and 10); LC/MS data |
|---|---|---|---|
| M15 | 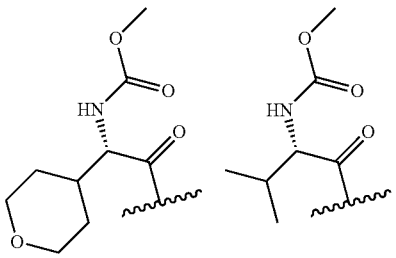 | | 1.82 min.; >98%; LC/MS: Anal. Calcd. for $[M + H]^+$ $C_{46}H_{55}N_8O_7$: 831.42; found 831.47 |

Example N1

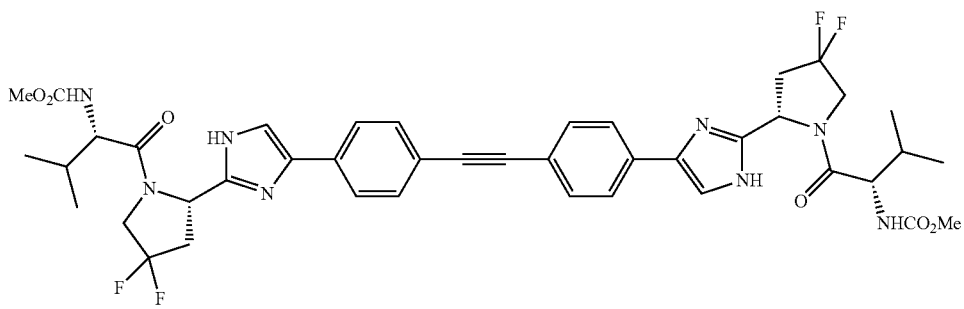

Example N1

Step a

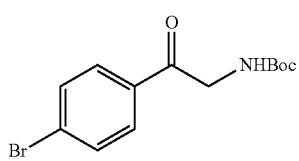

To a suspension of 2-amino-1-(4-bromophenyl)ethanone, HCl (4.0 g, 15.97 mmol) in DCM (50.0 mL) was added sodium bicarbonate (4.02 g, 47.9 mmol). Then Boc-anhydride (3.89 mL, 16.77 mmol) was added to the solution and the reaction mixture was warmed to rt and stirred for 18 hrs. Then DIEA (3 mL, 17.18 mmol) was added and the reaction mixture was stirred at rt for 2 hrs, LCMS showed that the reaction was complete. The reaction mixture was diluted with EtOAc and water, the organic phase was washed with 5% citric acid, water and sat. NaCl, dried over anhydrous $Na_2SO_4$, filtered and concentrated to yield bromide N1A (5.0 g) as a yellow solid, which was used in the next step without further purification. $^1$H NMR (400 MHz, MeOD) ppm 7.89 (2 H, m), 7.68 (2 H, m, J=8.53 Hz), 4.52 (2 H, s), 1.38-1.51 (9 H, m). LC/MS (Cond. 10d): $R_f$=3.56 min. LC/MS: Anal. Calcd. For $[M+Na]^+$ $C_{13}H_{16}BrNaNO_3$: 336.03; found: 335.97.

Example N1

Step b

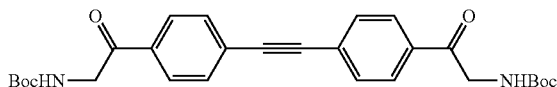

To a solution of carbamate N1a (2.0 g, 6.37 mmol) in DMF (5 mL) was added 1,2-bis(trimethylstannyl)ethyne (1.119 g, 3.18 mmol). The reaction mixture was degassed, tetrakis (triphenylphosphine)palladium(0) (0.184 g, 0.159 mmol) was added, and the mixture was heated at 90° C. for 4 hrs. The crude reaction mixture was charged to a 90 g silica gel cartridge which was eluted with a 20 min gradient of 0-60% EtOAc in hexane. Alkyne N1b (0.83 g) was collected as a yellow solid. LC/MS (Cond. 10d): $R_f$=4.1 min. LC/MS: Anal. Calcd. For $[M+Na]^+$ $C_{28}H_{32}NaN_2O_6$: 515.23; found: 515.10.

Example N1

Step c

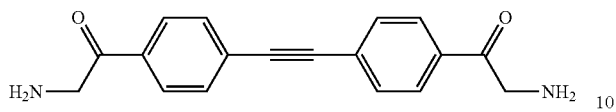

To a solution of alkyne N1b (1.13 g, 2.294 mmol) in 1,4-dioxane (5 mL) was added 4 M HCl in dioxane (4 mL, 16.00 mmol). The reaction mixture was stirred at rt for 2 hrs. The reaction mixture was concentrated to dryness to yield a yellow solid. The solid was washed with hexane and EtOAc, then dried to yield aminoketone N1c, 2 HCl (0.508 g). $^1$H NMR (400 MHz, MeOD) ppm 8.10 (4 H, d, J=8.53 Hz), 7.78 (4 H, d, J=8.53 Hz), 4.64 (4 H, s). LC/MS (Cond. 10d): $R_t$=1.94 min. LC/MS: Anal. Calcd. For [M+H]$^+$ $C_{18}H_{17}N_2O_2$: 293.12; found: 293.07.

Example N1

Step d

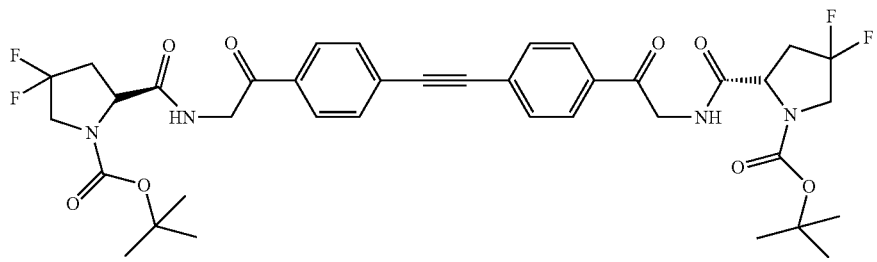

To a mixture of (S)-1-(tert-butoxycarbonyl)-4,4-difluoro-pyrrolidine-2-carboxylic acid (0.25 g, 0.995 mmol), aminoketone N1c, 2 HCl (0.182 g, 0.498 mmol), HATU (0.189 g, 0.498 mmol) in DMF (2 mL) was added DIEA (0.521 mL, 2.99 mmol). The reaction mixture was stirred at rt for 3 hrs. The crude mixture was charged to an 80 g silica gel cartridge which was eluted with a 20 min gradient of 0-100% EtOAc in hexane. ketoamide N1d (0.12 g) was collected as a yellow solid. LC/MS (Cond. 10d): $R_t$=4.08 min. LC/MS: Anal. Calcd. For [M+H]$^+$ $C_{38}H_{43}F_4N_4O_8$: 759.29; found: 759.03.

Example N1

Step e

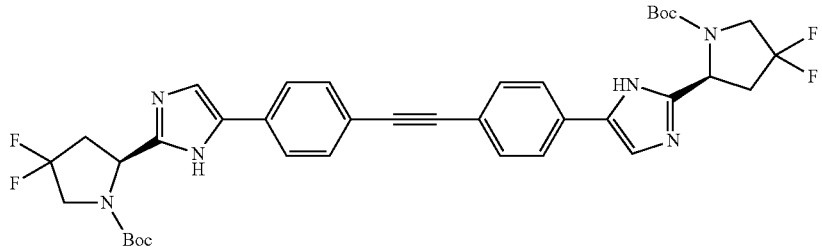 [SMILES: CC(C)(C)OC(=O)N1CC(F)(F)C[C@H]1c1ncc(-c2ccc(C#Cc3ccc(-c4cnc([C@@H]5CC(F)(F)CN5C(=O)OC(C)(C)C)[nH]4)cc3)cc2)[nH]1]

In a sealed tube, a mixture of ketoamide N1d (0.12 g, 0.158 mmol) and ammonium acetate (0.122 g, 1.582 mmol) in xylene (2 mL) was heated at 140° C. for 4 hrs. The reaction mixture was partitioned between EtOAc and water, the organic layer was washed with sat. NaHCO$_3$ and sat. NaCl, dried over anhydrous Na$_2$SO$_4$, filtered and concentrated. The residue was dissolved in a small amount of methylene chloride and charged to a 40 g silica gel cartridge which was eluted with a 20 min gradient of 0-100% EtOAc in hexane. Imidazole N1e (0.054 g) was collected as a yellow solid. LC/MS (Cond. 10d): $R_t$=3.3 min. LC/MS: Anal, Calcd. For [M+H]$^+$ $C_{38}H_{41}F_4N_6O_4$: 721.3; found: 721.10.

Example N1

Step f

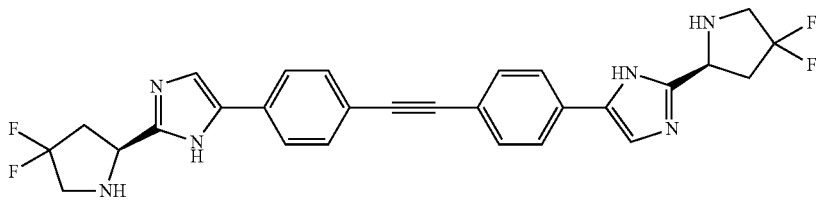 [SMILES: FC1(F)CN[C@H](c2ncc(-c3ccc(C#Cc4ccc(-c5cnc([C@@H]6CC(F)(F)CN6)[nH]5)cc4)cc3)[nH]2)C1]

To a solution of imidazole N1e (0.054 g, 0.075 mmol) in 1,4-Dioxane was added 4 M HCl in dioxane (0.5 mL, 2.0 mmol) plus a few drops of MeOH. The reaction mixture was stirred at rt for 4 hrs, and concentrated to yield pyrrolidine N1f, 4 HCl (0.055 g) as a pale yellow solid. LC/MS (Cond. 10d): $R_t$=2.94 min. LC/MS: Anal. Calcd. For $[M+H]^+$ $C_{28}H_{25}F_4N_6$: 520.2; found: 521.10.

Example N1

To a mixture of (S)-2-(methoxycarbonylamino)-3-methylbutanoic acid (0.014 g, 0.079 mmol), pyrrolidine N1f, 4 HCl (0.025 g, 0.038 mmol), HATU (0.030 g, 0.079 mmol) in DMF (2 mL) was added DIEA (0.039 mL, 0.225 mmol). The reaction mixture was stirred at rt for 18 hrs, diluted with MeOH, filtered and purified by reverse phase HPLC to yield TFA salt of Example N1 (0.026 g) as a white solid. LC (Cond. 10b and 10c): >95% homogeneity index. LC/MS (Cond. 10d): $R_t$=3.11 min. LC/MS: Anal. Calcd. For $[M+H]^+$ $C_{42}H_{47}F_4N_8O_6$: 835.35; found: 835.16.

Example N2

Pyrrolidine N1f was coupled with 2-(methoxycarbonylamino)-2-(tetrahydro-2H-pyran-4-yl)acetic acid by employing the procedure described for the synthesis of Example N1. The resultant three diastereomers (TFA salts) were separated by employing the following condition: Column=Waters-Sunfire 30×100 mm S5; Start % B=0; Final % B=32; Gradient time=25 min; Stop time=25 min; Flow Rate=40 mL/min; Wavelength=220 nm; Solvent A=0.1% TFA in 10% MeCN/90% water; Solvent B=0.1% TFA in 90% MeCN/10% water.

| Example | Analytical conditions |
|---|---|
| N2 | LC (Cond. 10b and 10c): >95% homogeneity index. LC/MS (Cond. 10d): $R_t$ = 2.90 min. LC/MS: Anal. Calcd. For $[M + H]^+$ $C_{46}H_{51}F_4N_8O_8$: 919.37; found: 919.41. |
| N3 | LC (Cond. 10b and 10c): >95% homogeneity index. LC/MS (Cond. 10d): $R_t$ = 2.96 min. LC/MS: Anal. Calcd. For $[M + H]^+$ $C_{46}H_{51}F_4N_8O_8$: 919.37; found: 919.41. |
| N4 | LC (Cond. 10b and 10c): >95% homogeneity index. LC/MS (Cond. 10d): $R_t$ = 3.00 min. LC/MS: Anal. Calcd. For $[M + H]^+$ $C_{46}H_{51}F_4N_8O_8$: 919.37; found: 919.41. |

Example N5-N7

Example N5-N7 (TFA salt) were prepared starting from aminoketone N1c and appropriate starting materials, obtained from commercial sources, by employing the procedures described for the synthesis of Example N1.

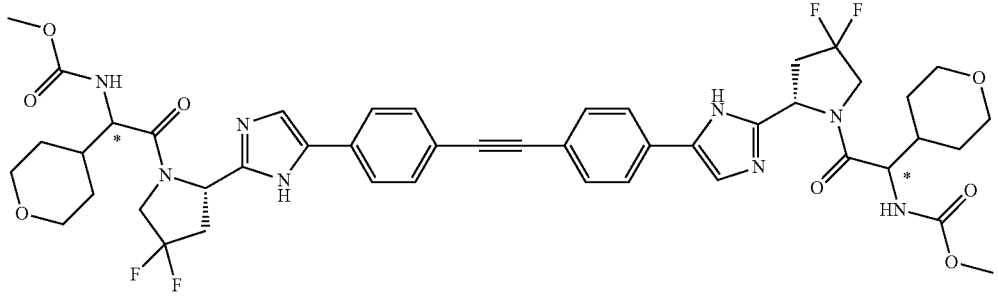

Example N2: (S, S)
Example N3: (S, R)
Example N4: (R, R)

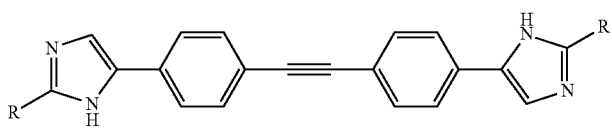

| Example | R | Analytical conditions |
|---|---|---|
| N5 | (morpholine with valine-methylcarbamate substituent) | LC (Cond. 10b and 10c): >95% homogeneity index. LC/MS (Cond. 10d): $R_t$ = 3.05 min. LC/MS: Anal. Calcd. For [M + H]$^+$ C$_{42}$H$_{51}$N$_5$O$_8$: 795.38; found: 795.23. |
| N6 | (piperidine with valine-methylcarbamate substituent) | LC (Cond. 10b and 10c): >95% homogeneity index. LC/MS (Cond. 10d): $R_t$ = 3.23 min. LC/MS: Anal. Calcd. For [M + H]$^+$ C$_{44}$H$_{55}$N$_8$O$_6$: 791.42; found: 791.54. |
| N7 | (4-hydroxypyrrolidine with valine-methylcarbamate substituent) | LC (Cond. 10b and 10c): 93% homogeneity index. LC/MS (Cond. 10d): $R_t$ = 3.06 min. LC/MS: Anal. Calcd. For [M + H]$^+$ C$_{42}$H$_{51}$N$_8$O$_8$: 795.38; found: 795.4. |
| N7.1 | (4-methylenepyrrolidine with valine-methylcarbamate substituent) | LC (Cond. 10b and 10c): 97% homogeneity index. LC/MS (Cond. 10d): $R_t$ = 3.056 min. LC/MS: Anal. Calcd. For [M + H]$^+$ C$_{44}$H$_{51}$N$_8$O$_6$: 787.39; found: 787.4. |
| N7.2 | (4-hydroxypyrrolidine isomer with valine-methylcarbamate substituent) | LC (Cond. 10b and 10c): 98% homogeneity index. LC/MS (Cond. 10d): $R_t$ = 2.878 min. LC/MS: Anal. Calcd. For [M + H]$^+$ C$_{42}$H$_{51}$N$_8$O$_8$: 795.38; found: 795.41. |

Example N8

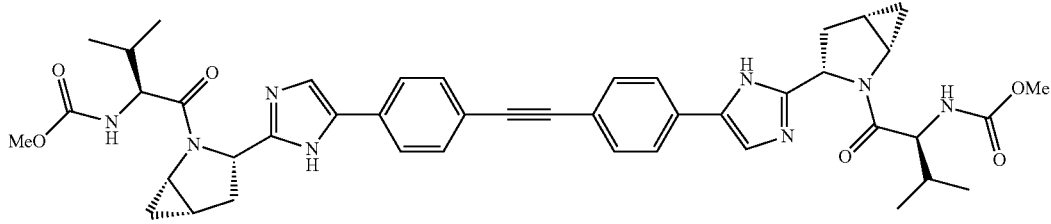 [SMILES: COC(=O)N[C@H](C(=O)N1[C@H](c2ncc(-c3ccc(C#Cc4ccc(-c5cnc([C@@H]6C[C@@H]7C[C@@H]7N6C(=O)[C@@H](NC(=O)OC)C(C)C)[nH]5)cc4)cc3)[nH]2)C[C@@H]2C[C@@H]21)C(C)C]

Example N8

Step a

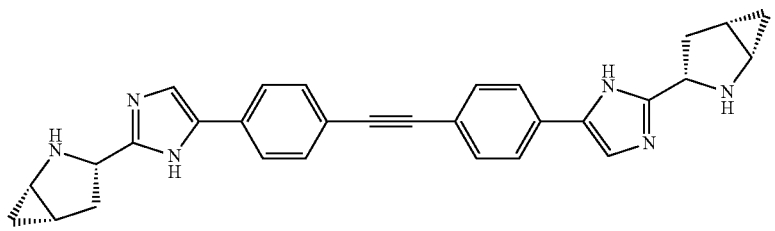 [SMILES: C(#Cc1ccc(-c2cnc([C@@H]3C[C@@H]4C[C@@H]4N3)[nH]2)cc1)c1ccc(-c2cnc([C@@H]3C[C@@H]4C[C@@H]4N3)[nH]2)cc1]

Pyrrolidine N8a (HCl salt) was prepared staring from aminoketone N1c and (1S,3S,5S)-2-(tert-butoxycarbonyl)-2-azabicyclo[3.1.0]hexane-3-carboxylic acid (for its preparative method, see WO2004/052850) according to the procedures described for the preparation of pyrrolidine N1f. NMR (MeOD, δ=3.33 ppm, 400 MHz): 7.98 (s, 2H), 7.87 (d, J=8.4, 4H), 7.69 (d, J=8.4, 4H), 5.59 (dd, J=10.2, 5.4, 2H), 3.61-3.56 (m, 2H), 3.05-2.98 (m, 2H), 2.67 (dd, J=14.2, 5.4, 2H), 2.20-2.14 (m, 2H), 1.28-1.22 (m, 2H), 1.19-1.13 (m, 2H). LC/MS: Anal. Calcd. for [M+H]$^+$ C$_{30}$H$_{29}$N$_6$: 473.24; found 473.2.

Example N8

Example N8 was prepared from pyrrolidine N8a according to the procedure described for the preparation of Example N1 with the exception that the purification was conducted under a modified reverse phase HPLC condition (ACN/water/NH$_4$OAc). Example N8 was retrieved as a pale-yellow solid. LC (Cond. 10e): >99% homogeneity index. LC/MS (Cond. 10f): R$_t$=2.21 min. $^1$H NMR (DMSO, δ=2.50 ppm, 400 MHz): 12.33 (s, 0.28H), 11.86 (s, 1.72H), 7.74 (d, J=8.4, 3.42H), 7.65 (d, J=8.4, 0.58H), 7.55 (d, J=8.4, 0.58H), 7.51 (s, 2H), 7.49 (d, J=8.4, 3.42H), 7.31 (d, J=8.8, 2H), 5.39 (app d, 0.15H), 3.34 (dd, J=10.8, 2.4, 3.85H), 4.29 (app t, 2H), 3.90 (br m, 2H), 3.55 (s, 6H), 2.64-2.56 (m, 2H), 2.17 (app d, 2H), 2.08-1.98 (m, 2H), 1.79-1.74 (m, 4H), 0.92-0.83 (m, 14H). LC/MS: Anal. Calcd. for [M+H]$^+$ C$_{44}$H$_{51}$N$_8$O$_6$: 787.39; found 787.8.

Example N9

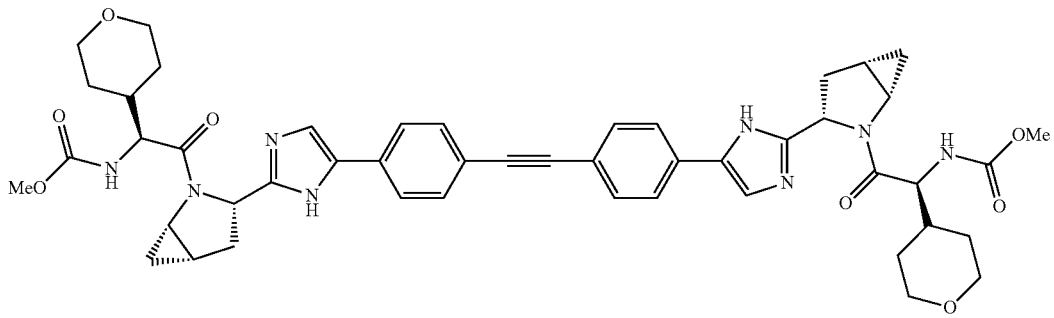 [SMILES: COC(=O)N[C@H](C(=O)N1[C@H](c2ncc(-c3ccc(C#Cc4ccc(-c5cnc([C@@H]6C[C@@H]7C[C@@H]7N6C(=O)[C@@H](NC(=O)OC)C6CCOCC6)[nH]5)cc4)cc3)[nH]2)C[C@@H]2C[C@@H]21)C1CCOCC1]

Compound N9 (TFA salt) was prepared from pyrrolidine N8a and (S)-2-(methoxycarbonylamino)-2-(tetrahydro-2H-pyran-4-yl)acetic acid according to the procedure described for the preparation of Example N1 with the exception that ACN/water/TFA solvent system was employed in its purification. LC (Cond. 10e): >97% homogeneity index. LC/MS (Cond. 10g): R$_t$=1.82 min. LC/MS: Anal. Calcd. for [M+H]$^+$ C$_{48}$H$_{55}$N$_8$O$_8$: 871.41; found 871.6.

Example J1 to J1.1

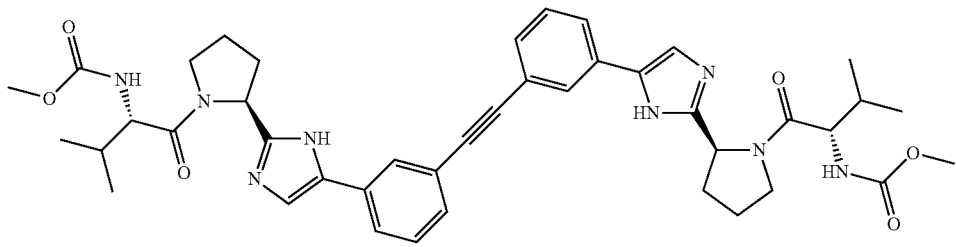

Example J1

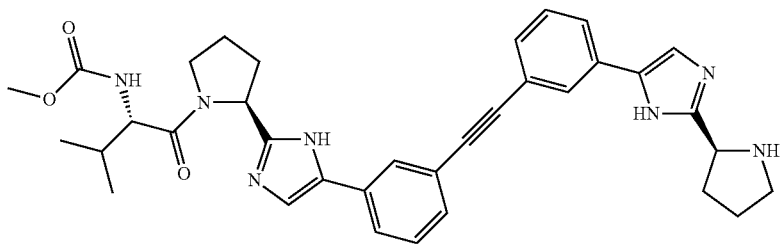

Example J1.1

Example J1

Step a

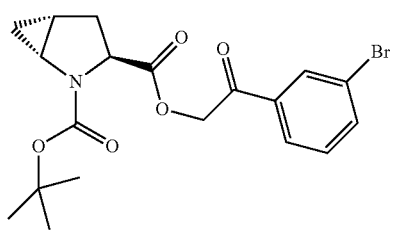 [SMILES: CC(C)(C)OC(=O)N1[C@@H]2C[C@@H]2C[C@H]1C(=O)OCC(=O)c1cccc(Br)c1]

DIPEA (2.8 mL, 16 mmol) was added to a slurry of acid M3f (2.00 g, 8.80 mmol) and 2-bromo-1-(3-bromophenyl)ethanone (2.22 g, 8.00 mmol) in acetonitrile (25 mL) and the reaction mixture was stirred overnight at rt. The reaction mixture was concentrated and purified with a Biotage Horizon (80 g SiO$_2$, 10-25% EtOAc/hexanes) to yield ketoester J1a (3.37 g) as a viscous light yellow oil. LC-MS retention time 1.853 min; m/z 423 and 425.98 (1:1) (MH+). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (400 MHz, CDCl$_3$) δ ppm 8.04 (t, J=1.8 Hz, 1H), 7.83 (d, J=7.8 Hz, 1H), 7.75 (d, J=8.0 Hz, 1H), 7.38 (t, J=7.9 Hz, 1H), 5.33-5.59 (m, 1H), 5.13-5.32 (m, 1H), 4.22 (br s, 1H), 3.40-3.63 (m, 1H), 2.52-2.63 (m, 1H), 2.46 (dd, J=13.1, 9.3 Hz, 1H), 1.63-1.73 (m, 1H), 1.47 (br s, 9H), 0.86 (br s, 1H), 0.51 (br s, 1H).

Example J1

Step b

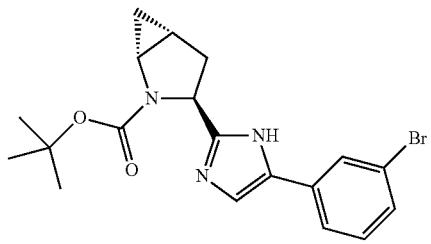 [SMILES: C[C@@H]1C[C@@H](c2ncc(-c3cccc(Br)c3)[nH]2)N(C(=O)OC(C)(C)C)[C@@H]1C]

A solution of ketoester J1a (3.33 g, 7.85 mmol) in xylene (75 mL) was added to ammonium acetate (5.94 g, 77 mmol) in a pressure vessel and the reaction mixture was stirred under nitrogen for 5 min. The reaction vessel was sealed and then placed into an oil bath which had been preheated to 140° C. and the reaction was held at that temperature for 6 h. The reaction was cooled to rt, stirred overnight and reheated at 140° C. for 5 hr. Additional ammonium acetate (3.0 g) was added and the reaction was stirred at 145 C for 8 hrs, cooled to rt and concentrated under high vacuum to a brown oil. The oil was partitioned between DCM (~200 mL) and ½ sat. sodium bicarbonate (~200 mL). The organic layer was dried (MgSO$_4$), filtered and concentrated. The crude orange solidified foam was purified on a Biotage Horizon (20-50% EtOAc/hexanes, 160 g SiO$_2$) to yield imidazole J1b (2.03 g) as a yellow solidified foam.

LC-MS retention time 2.450 min; m/z 404 and 406.06 (1:1) (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/ruin, a gradient of 100% solvent A/0% solvent B to 0% solvent A/100% solvent B, a gradient time of 3 min, a hold time of 1 min, and an analysis time of 4 min where solvent A was 5% MeOH/95% H₂O/10 mM ammonium acetate and solvent B was 5% H₂O/95% MeOH/10 mM ammonium acetate. MS data was determined using a Micromass Platform for LC in electrospray mode. $^1$H NMR (400 MHz, MeOD) δ ppm 7.89 (br s, 1H), 7.65 (d, J=6.5 Hz, 1H), 7.32-7.44 (m, 2H), 7.26 (t, J=7.8 Hz, 1H), 4.66 (br s, 1H), 3.52-3.63 (m, 1H), 2.51 (dd, J=13.1, 8.8 Hz, 1H), 2.25-2.37 (m, 1H), 1.66-1.75 (m, 1H), 1.29 (br s, 9H), 0.84 (ddd, 6.0, 5.8 Hz, 1H), 0.56-0.63 (m, 1H).

Example J1

Step c

TFA (3 mL, 38.9 mmol) was added to a stirred solution of carbamate J1c (238 mg, 0.367 mmol) in DCE (7 mL) and the reaction was stirred at rt for 1 h. The reaction mixture was concentrated under vacuum to yield a TFA salt of pyrrolidine J1d (260 mg) as a yellow solid.

LC-MS retention time 2.505 min; m/z 449.22 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H₂O/10 mM ammonium acetate and solvent B was 5% H₂O/95% MeOH/10 mM ammonium acetate. MS data was determined using a Micro-

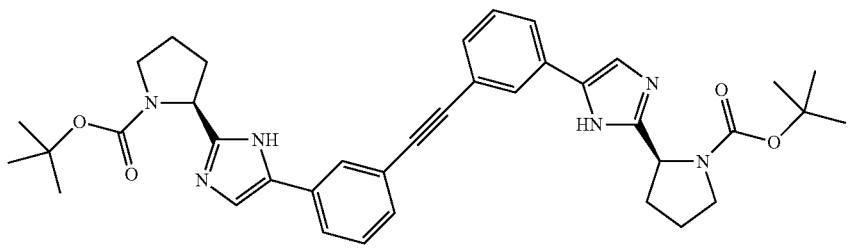 [SMILES: CC(C)(C)OC(=O)N1CCC[C@H]1c1ncc(-c2cccc(C#Cc3cccc(-c4cnc([C@@H]5CCCN5C(=O)OC(C)(C)C)[nH]4)c3)c2)[nH]1]

Nitrogen was bubbled through a stirred solution of bromide J1b (854 mg, 2.18 mmol) and 1,2-bis(trimethylstannyl) ethyne (403 mg, 1.15 mmol) in DMF (10 mL) for 10 minutes. Then Pd(PPh₃)₄ (79 mg, 0.069 mmol) was added, nitrogen was bubbled through the reaction for 1 min and then the reaction was heated at 90° C. under nitrogen for 17 h. The reaction mixture was cooled to rt, concentrated to a viscous oil and purified on a Biotage Horizon (40 g SiO₂, 70-100% EtOAc/hexanes, loaded with DCM)) to yield alkyne J1c (500 mg) as a yellow solidified foam. LC-MS retention time 2.876 min; m/z 649.51 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H₂O/10 mM ammonium acetate and solvent B was 5% H₂O/95% MeOH/10 mM ammonium acetate. MS data was determined using a Micromass Platform for LC in electrospray mode. $^1$H NMR (400 MHz, MeOD) δ ppm 7.89 (s, 2H), 7.67-7.74 (m, 2H), 7.35-7.44 (m, 6H), 4.85-5.04 (m, 2H), 3.64-3.74 (m, 2H), 3.47-3.56 (m, 2H), 2.29-2.45 (m, 2H), 1.90-2.13 (m, 6H), 1.48 (br s, 6H), 1.26 (br s, 12H).

Example J1

Step d mass Platform for LC in electrospray mode. $^1$H NMR (400 MHz, MeOD) δ ppm 7.96-8.00 (m, 2H), 7.79 (dt, J=6.6, 2.1 Hz, 2H), 7.65 (s, 2H), 7.41-7.48 (m, 4H), 4.91 (t, J=7.8 Hz, 2H), 3.44-3.61 (m, 4H), 2.51-2.62 (m, 2H), 2.27-2.45 (m, 4H), 2.16-2.24 (m, 2H).

Example J1 to J1.1

HATU (61.8 mg, 0.162 mmol) was added to a stirred solution of a TFA salt of pyrrolidine J1d (110 mg, 0.12 mmol) and (S)-2-(methoxycarbonylamino)-3-methylbutanoic acid (28.5 mg, 0.162 mmol) in DMF (0.7 mL) and Hunig's Base (0.10 mL, 0.54 mmol). The reaction mixture was stirred at rt for 3 hours and then concentrated under a stream of nitrogen. The reaction was purified in two injections by preparative HPLC (MeOH/water/10 mM ammonium acetate) to yield Example J1 (31.5 mg) as a light yellow solid and Example J1.1 (41.1 mg) as a light yellow solid.

Example J1

LC-MS retention time 2.605 min; m/z 763.36 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H₂O/10 mM ammonium acetate and solvent B was 5% H₂O/95% MeOH/10 mM ammonium acetate. MS data was determined using a Micromass Platform for LC in electrospray mode. The $^1$H NMR presents as a 4:1 mixture of rotamers. The major rotamer is: NMR (400 MHz, MeOD) δ ppm 7.86 (s, 2H), 7.64-7.70 (m, 2H), 7.36-7.43 (m, 4H), 7.34 (s, 2H), 5.17 (dd, J=7.8, 5.3 Hz, 2H), 4.24 (d, J=7.3 Hz, 2H), 3.95-4.04 (m, 2H), 3.84-3.92 (m, 2H), 3.66 (s, 6H), 2.17-2.42 (m, 6H), 2.00-2.13 (m, 4H), 0.96 (d, J=6.8 Hz, 6H), 0.91 (d, J=6.8 Hz, 6H).

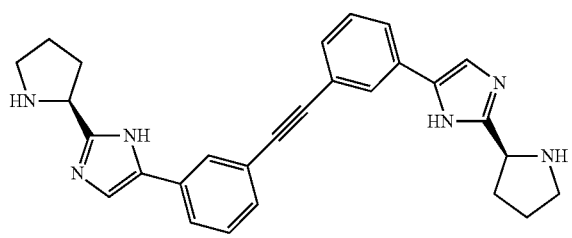 [SMILES: C(#Cc1cccc(-c2cnc([C@@H]3CCCN3)[nH]2)c1)c1cccc(-c2cnc([C@@H]3CCCN3)[nH]2)c1]

Example J1.1

LC-MS retention time 2.620 min; m/z 606.23 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode. The $^1$H NMR presents as a 3:1 mixture of rotamers. $^1$H NMR (400 MHz, MeOD) δ ppm 7.94 (s, 1H), 7.87 (s, 1H), 7.74 (ddd, J=5.6, 3.4, 1.8 Hz, 1H), 7.65-7.70 (m, 1H), 7.51 (s, 1H), 7.36-7.44 (m, 6H), 7.35 (s, 1H), 5.18 (dd, J=7.7, 5.4 Hz, 1H), 4.68 (t, J=7.8 Hz, 1H), 4.24 (d, J=7.5 Hz, 1H), 3.95-4.06 (m, 1H), 3.85-3.92 (m, 1H), 3.66 (s, 3H), 3.35-3.52 (m, 2H), 2.01-2.50 (m, 9H), 0.96 (d, J=6.8 Hz, 3H), 0.91 (d, J=6.8 Hz, 3H).

Example J2

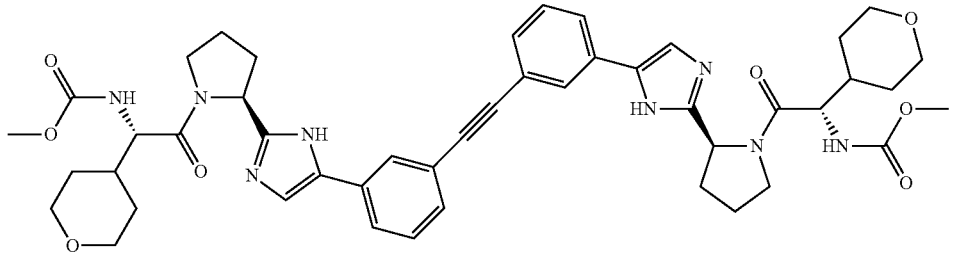

HATU (118 mg, 0.310 mmol) was added to a stirred solution of a TFA salt of pyrrolidine J1d (93.4 mg, 0.103 mmol) and (S)-2-(methoxycarbonylamino)-2-(tetrahydro-2H-pyran-4-yl)acetic acid (67.3 mg, 0.310 mmol) in DIPEA (0.18 mL, 1.0 mmol) and DMF (1 mL) and the reaction was stirred at rt for 2 h. The reaction was concentrated under a stream of nitrogen, dissolved into MeOH and purified by preparative HPLC (MeOH/water 10 mM ammonium acetate) to yield Example J2 (18.1 mg) as a light pink solid LC-MS retention time 2.428 min; m/z 847.39 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode. The $^1$H NMR exhibits as a 4:1 mixture of rotamers. The major rotamer is: $^1$H NMR (400 MHz, MeOD) δ ppm 7.83 (s, 2H), 7.62-7.67 (m, 2H), 7.33-7.42 (m, 6H), 5.15 (dd, J=7.5, 5.5 Hz, 2H), 4.32 (d, J=8.3 Hz, 2H), 3.89-4.08 (m, 6H), 3.66 (s, 6H), 3.33-3.50 (m, 6H), 2.23-2.40 (m, 4H), 2.13-2.22 (m, 2H), 1.92-2.10 (m, 4H), 1.61-1.71 (m, 4H), 1.32-1.56 (m, 4H).

Example J3

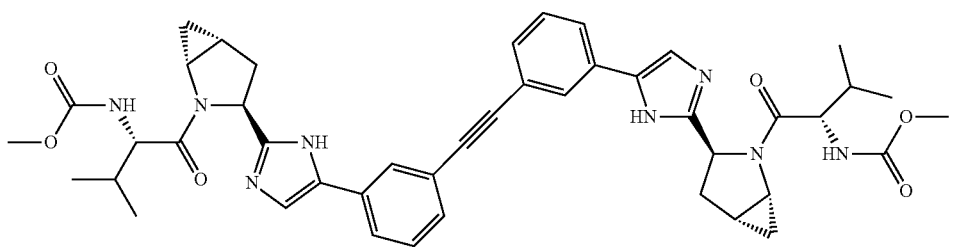

Example J3

Step a

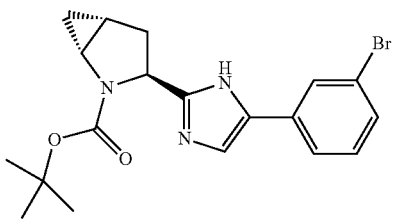 [SMILES: CC(C)(C)OC(=O)N1[C@@H]2C[C@@H]2C[C@H]1c1ncc(-c2cccc(Br)c2)[nH]1]

Bromide J3a was prepared from acid M3f according to the procedure described for bromide J1b.

Example J3

Step b

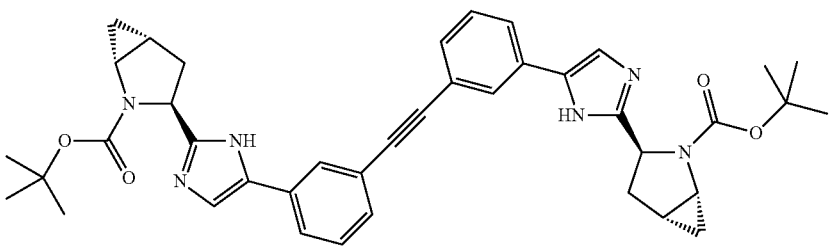 [SMILES: CC(C)(C)OC(=O)N1[C@@H]2C[C@@H]2C[C@H]1c1ncc(-c2cccc(C#Cc3cccc(-c4cnc([C@@H]5C[C@H]6C[C@H]6N5C(=O)OC(C)(C)C)[nH]4)c3)c2)[nH]1]

Nitrogen was bubbled through a stirred solution of bromide J3a (825 mg, 2.041 mmol) and 1,2-bis(trimethylstannyl)ethyne (378 mg, 1.074 mmol) in DMF (10 mL) for 10 minutes. Then, Pd(PPh$_3$)$_4$ (74.5 mg, 0.064 mmol) was added to the reaction mixture, nitrogen was bubbled through the reaction for 1 min and then the reaction was heated at 90° C. under nitrogen for 17 h. The reaction mixture was cooled to rt, concentrated to a thick black oil, diluted with DCM and purified on a Biotage Horizon (40 g SiO$_2$, 60-100% EtOAc/hexanes) to yield alkyne J3b (312 mg) as a yellow solid.

LC-MS retention time 2.800 min; m/z 671.53 (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (400 MHz, MeOD) δ ppm 7.89 (s, 2H), 7.70 (ddd, J=5.6, 3.3, 1.9 Hz, 2H), 7.38-7.43 (m, 6H), 4.69 (br s, 2H), 3.59 (br s, 2H), 2.53 (dd, J=13.2, 8.9 Hz, 2H), 2.28-2.39 (m, 2H), 1.68-1.77 (m, 2H), 1.29-1.31 (m, 18H), 0.85 (dt, J=8.5, 5.8 Hz, 2H), 0.58-0.64 (m, 2H).

Example J3

Step c

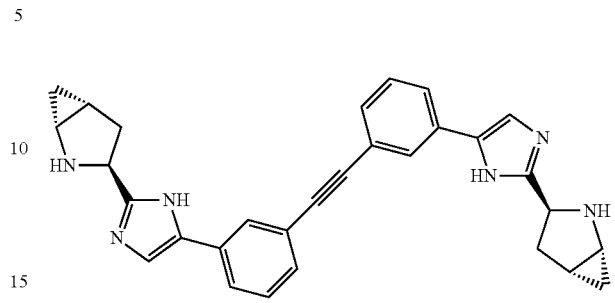

TFA (3 mL, 38.9 mmol) was added to a stirred solution of carbamate J3b (316 mg, 0.470 mmol) in DCE (7 mL) and the reaction was stirred at rt for 1 h. The reaction mixture was concentrated under vacuum to yield a TFA salt of pyrrolidine J3c (360 mg) as a yellow solid.

LC-MS retention time 2.711 min; m/z 473.24 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Example J3

HATU (69.6 mg, 0.183 mmol) was added to a stirred solution of a TEA salt of pyrrolidine J3e (56.7 mg, 0.061 mmol) and (S)-2-(methoxycarbonylamino)-3-methylbutanoic acid (32.1 mg, 0.183 mmol) in DMF (0.7 mL) and Hunig's Base (0.11 mL, 0.61 mmol) and the reaction mixture was stirred at rt for 3 h. The reaction was concentrated under a stream of nitrogen, dissolved into MeOH and purified in two injections by preparative HPLC (MeOH/water 10 mM ammonium acetate) to yield Example J3 (31.8 mg) as a light yellow solid.

LC-MS retention time 2.605 min; m/z 787.36 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode. $^1$H NMR (400 MHz, MeOD) δ ppm 7.87 (s, 2H), 7.65-7.71 (m, 2H), 7.37-7.43 (m, 4H), 7.36 (s, 2H), 5.16 (dd, J=8.8, 4.8 Hz, 2H), 4.59 (d, J=6.5 Hz, 2H), 3.67 (s, 6H), 3.63-3.68 (m, 2H), 2.49-2.58 (m, 2H), 2.37-2.45 (m, 2H), 2.10-2.21 (m, 2H), 1.98-2.07 (m, 2H), 1.12 (ddd, J=8.7, 5.6, 5.5 Hz, 2H), 1.01 (d, J=6.8 Hz, 6H), 0.93 (d, J=6.8 Hz, 6H), 0.78 (br s, 2H).

Example J4

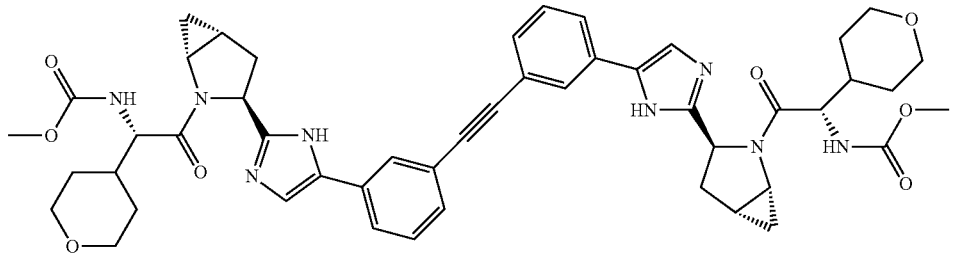

HATU (120 mg, 0.317 mmol) was added to a stirred solution of a TFA salt of pyrrolidine J3c (98 mg, 0.106 mmol) and (S)-2-(methoxycarbonylamino)-2-(tetrahydro-2H-pyran-4-yl)acetic acid (68.8 mg, 0.317 mmol) in DIPEA (0.18 mL, 1.1 mmol) and DMF (1 mL) and the reaction was stirred at rt for 3 h. The reaction was concentrated under a stream of nitrogen, dissolved into MeOH and purified in by preparative HPLC (MeOH/water 10 mM ammonium acetate) and then repurified by prep HPLC (MeOH/water 0.1% TFA) to yield a TFA salt of Example J4 (18 mg) as a white solid.

LC-MS retention time 2.463 min; m/z 869.40 (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode. $^1$H NMR (400 MHz, MeOD) δ ppm 7.89-7.92 (m, 2H), 7.87 (s, 2H), 7.74 (dt, J=7.8, 1.5 Hz, 2H), 7.61-7.66 (m, 2H), 7.54-7.60 (m, 2H), 5.11 (dd, J=9.0, 7.0 Hz, 2H), 4.59 (d, J=7.5 Hz, 2H), 3.91-3.99 (m, 4H), 3.83 (t, J=4.8 Hz, 2H), 3.67 (s, 6H), 3.33-3.45 (m, 4H), 2.67 (dd, J=13.7, 9.4 Hz, 2H), 2.43-2.52 (m, 2H), 2.02-2.14 (m, 4H), 1.39-1.63 (m, 8H), 1.03-1.11 (m, 2H), 0.83-0.90 (m, 2H).

Example J5

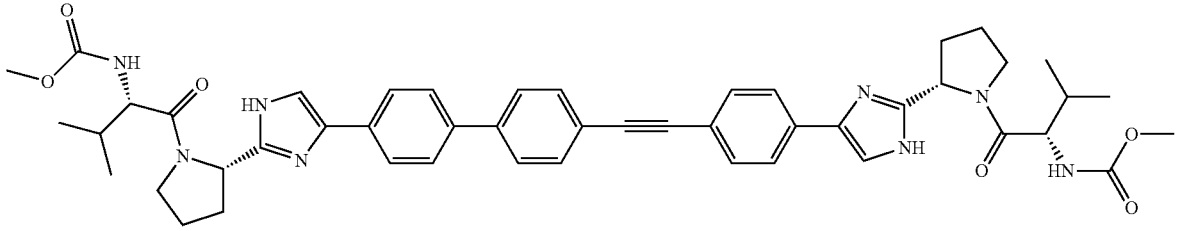

Example J5

Step a

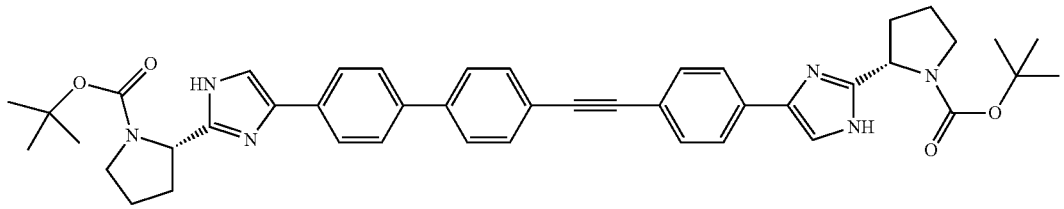 [SMILES: CC(C)(C)OC(=O)N1CCC[C@H]1c1nc(-c2ccc(C#Cc3ccc(-c4ccc(-c5c[nH]c([C@@H]6CCCN6C(=O)OC(C)(C)C)n5)cc4)cc3)cc2)c[nH]1]

Nitrogen was bubbled through a stirred solution of (S)-tert-butyl 2-(4-(4-bromophenyl)-1H-imidazol-2-yl)pyrrolidine-1-carboxylate (bromide D-1b) (400 mg, 1.02 mmol), 4-ethynylphenylboronic acid (149 mg, 1.02 mmol) and sodium bicarbonate (214 mg, 2.55 mmol) in DME (8 mL) and water (2 mL) for 15 min. Then Pd(PPh$_3$)$_4$ (58.9 mg, 0.051 mmol) was added and the nitrogen bubbling was continued for 5 min. before the reaction vessel was sealed and heated at 90° C. overnight. The reaction was cooled, diluted with THF, washed with brine and concentrated to dryness. The residue was purified by Biotage Horizon (60-90% EtOAc/hexanes) to yield carbamate J5a (85 mg) as a yellow solid.

LC-MS retention time 2.911 min; m/z 723.64 (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (400 MHz, MeOD) δ ppm 7.78 (d, J=8.0 Hz, 2H), 7.72 (d, J=8.0 Hz, 2H), 7.64-7.69 (m, 4H), 7.58 (d, J=8.3 Hz, 2H), 7.52 (d, J=8.3 Hz, 2H), 7.31-7.41 (m, 2H), 4.86-5.03 (m, 2H), 3.68 (br s, 2H), 3.46-3.57 (m, 2H), 2.37 (br s, 2H), 1.89-2.13 (m, 6H), 1.47 (br s, 6H), 1.25 (br s, 12H).

Example 35

Step b

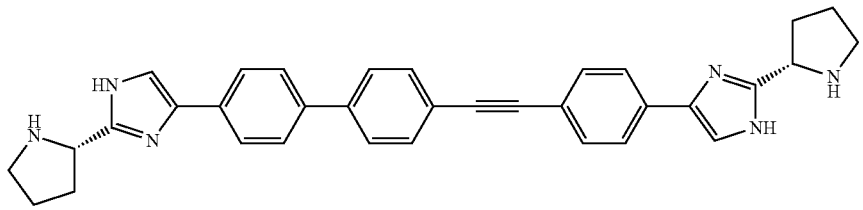 [SMILES: C(#Cc1ccc(-c2c[nH]c([C@@H]3CCCN3)n2)cc1)c1ccc(-c2ccc(-c3c[nH]c([C@@H]4CCCN4)n3)cc2)cc1]

TFA (250 µL, 3.24 mmol) was added to a solution of carbamate J5a in DCE (1 mL) and the reaction was stirred at rt for 1.5 hr. The reaction was concentrated under a stream of nitrogen to provide a TFA salt of pyrrolidine J5b (45 mg). LC-MS retention time 2.928 min; m/z 525.32 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Example J5

HATU (53 mg, 0.14 mmol) was added to a solution of a TFA salt of J5b (45 mg, 0.046 mmol) and (S)-2-(methoxycarbonylamino)-3-methylbutanoic acid (24.2 mg, 0.138 mmol) in DMF (0.7 mL) and TEA (0.038 mL, 0.28 mmol) and the reaction was stirred for 30 min. The reaction was diluted with MeOH, filtered and purified by prep HPLC (MeOH/water with 10 mM ammonium acetate) to yield Example J5 (14.7 mg) as a light yellow solid. LC-MS retention time 2.728 min; m/z 839.57 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (400 MHz, MeOD) δ ppm 7.73-7.78 (m, 2H), 7.65-7.71 (m, 6H), 7.57-7.62 (m, 2H), 7.52 (d, J=8.5 Hz, 2H), 7.33-7.36 (m, 2H), 5.18 (dt, J=7.6, 5.2 Hz, 2H), 4.21-4.27 (m, 2H), 3.96-4.05 (m, 2H), 3.84-3.92 (m, 2H), 3.66 (s, 6H), 2.17-2.42 (m, 6H), 2.00-2.13 (m, 4H), 0.95 (dd, J=6.8, 1.3 Hz, 6H), 0.91 (dd, J=6.8, 1.0 Hz, 6H).

Synthesis of Common Caps

Compound analysis conditions: Purity assessment and low resolution mass analysis were conducted on a Shimadzu LC system coupled with Waters Micromass ZQ MS system. It should be noted that retention times may vary slightly between machines. Additional LC conditions applicable to the current section, unless noted otherwise.

Cond.-MS-W1
Column=XTERRA 3.0×50 mm S7
Start % B=0
Final % B=100
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Cond.-MS-W2
Column=XTERRA 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Cond.-MS-W5
Column=XTERRA 3.0×50 mm S7
Start % B=0
Final % B=30
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Cond.-D.1
Column=XTERRA C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Cond.-D2
Column=Phenomenex-Luna 4.6×50 mm S10
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Cond.-MD1
Column=XTERRA 4.6×50 mm S5
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Cond.-M3
Column=XTERRA C18 3.0×50 mm S7
Start % B=0
Final % B=40
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Condition OL1
Column=Phenomenex-Luna 3.0×50 mm S10
Start % B=0
Final % B=100
Gradient time=4 min
Stop time=5 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition OL2
Column=Phenomenex-Luna 50×2 mm 3 u
Start % B=0
Final % B=100
Gradient time=4 min
Stop time=5 min
Flow Rate=0.8 mL/min
Oven Temp=40° C.
Wavelength=220 nm
Solvent A=0.1% TFA in 10% Acetonitrile/90% $H_2O$
Solvent B=0.1% TFA in 90% Acetonitrile/10% $H_2O$
Condition I
Column=Phenomenex-Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition II
Column=Phenomenex-Luna 4.6×50 mm S10
Start % B=0
Final % B=100
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Condition III
Column=XTERRA C18 3.0×50 mm S7
Start % B=0
Final % B=100
Gradient time=3 min
Stop time=4 min Flow Rate=4 mL/min
Wavelength=220 nm
Solvent A=0.1% TFA in 10% methanol/90% $H_2O$
Solvent B=0.1% TFA in 90% methanol/10% $H_2O$ Cap-1

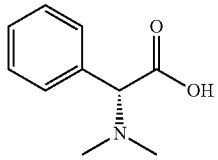

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to $H_2$ (60 psi) for 3 hours. The reaction mixture was filtered through diatomaceous earth (Celite®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in $H_2O$; λ=589 nm]. $^1$H NMR (DMSO-$d_6$, δ=2.5 ppm, 500 MHz): δ 7.43-7.34 (m, 5H), 4.14 (s, 1H), 2.43 (s, 6H); LC (Cond. I): RT=0.25; LC/MS: Anal. Calcd. for $[M+H]^+$ $C_{10}H_{14}NO_2$ 180.10; found 180.17; HRMS: Anal. Calcd. for $[M+H]^+$ $C_{10}H_{14}NO_2$ 180.1025; found 180.1017.

Cap-2

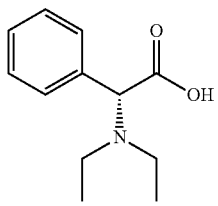

$NaBH_3CN$ (6.22 g, 94 mmol) was added in portions over a few minutes to a cooled (ice/water) mixture of (R)-2-Phenylglycine (6.02 g, 39.8 mmol) and methanol (100 mL), and stirred for 5 minutes. Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). $^1$H NMR (DMSO-$d_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: $[α]^{25}$−102.21° (c=0.357, $H_2O$); crop-2: $[α]^{25}$−99.7° (c=0.357, $H_2O$). LC (Cond. I): RT=0.43 min; LC/MS: Anal. Calcd. for $[M+H]^+$ $C_{12}H_{18}NO_2$: 208.13; found 208.26.

Cap-3

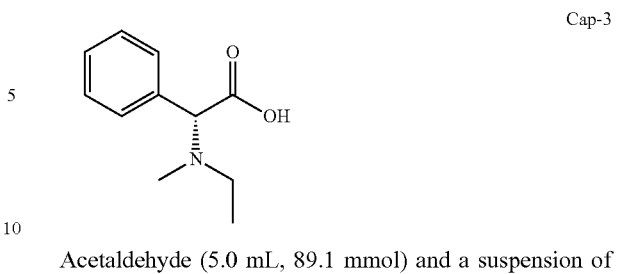

Acetaldehyde (5.0 mL, 89.1 mmol) and a suspension of 10% Pd/C (720 mg) in methanol/$H_2O$ (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of $H_2$ for 17 hours. An additional acetaldehyde (10 mL, 178.2 mmol) was added and stirring continued under $H_2$ atmosphere for 24 hours [Note: the supply of $H_2$ was replenished as needed throughout the reaction]. The reaction mixture was filtered through diatomaceous earth (Celite®), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-$d_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. I): RT=0.39 min; >95% homogeneity index; LC/MS: Anal. Calcd. for $[M+H]^+$ $C_{10}H_{14}NO_2$: 180.10; found 180.18.

A suspension of 10% Pd/C (536 mg) in methanol/$H_2O$ (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of $H_2$ for ~72 hours, where the $H_2$ supply was replenished as needed. The reaction mixture was filtered through diatomaceous earth (Celite®) and the filtrate was concentrated in vacuo. The resulting crude material was recrystallized from isopropanol (50 mL) to provide the HCl salt of Cap-3 as a white solid (985 mg). $^1$H NMR (DMSO-$d_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Cond. I): RT=0.39 min; >95% homogeneity index; LC/MS: Anal. Calcd. for $[M+H]^+$ $C_{11}H_{16}NO_2$: 194.12; found 194.18; HRMS: Anal. Calcd. for $[M+H]^+$ $C_{11}H_{16}NO_2$: 194.1180; found 194.1181.

Cap-4

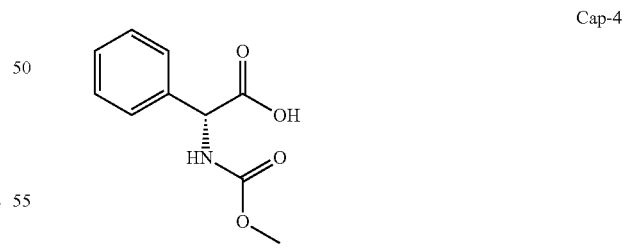

$ClCO_2Me$ (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated $NaHCO_3$ solution (30 mL), dried ($MgSO_4$), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1$H NMR (DMSO-d$_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. I): RT=1.53 min; ~90% homogeneity index; LC/MS: Anal. Calcd. for [M+Na]$^+$ C$_{14}$H$_{19}$NNaO$_4$: 288.12; found 288.15.

TFA (16 mL) was added dropwise to a cooled (ice/water) CH$_2$Cl$_2$ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in H$_2$O; λ=589 nm]. $^1$H NMR (DMSO-d$_6$, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Cond. I): RT=1.01 min; >95% homogeneity index; LC/MS: Anal. Calcd. for [M+H]$^+$ C$_{10}$H$_{12}$NO$_4$ 210.08; found 210.17; HRMS: Anal. Calcd. for [M+H]$^+$ C$_{10}$H$_{12}$NO$_4$ 210.0766; found 210.0756.

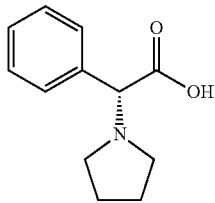

Cap-5

A mixture of (R)-2-phenylglycine (1.0 g, 6.62 mmol), 1,4-dibromobutane (1.57 g, 7.27 mmol) and Na$_2$CO$_3$ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-d$_6$, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 minutes (Cond. I); >98% homogeneity index; LC/MS: Anal. Calcd. for [M+H]$^+$ C$_{12}$H$_{16}$NO$_2$: 206.12; found 206.25.

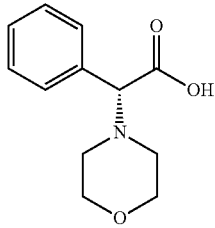

Cap-6

The TFA salt of Cap-6 was synthesized from (R)-2-phenylglycine and 1-bromo-2-(2-bromoethoxy)ethane by using the method of preparation of Cap-5. $^1$H NMR (DMSO-d$_6$, δ=2.5, 500 MHz) δ 12.20 (br s, 1H), 7.50 (m, 5H), 4.92 (s, 1H), 3.78 (app br s, 4H), 3.08 (app br 5, 2H), 2.81 (app br s, 2H); RT=0.32 minutes (Cond. I); >98%; LC/MS: Anal. Calcd. for [M+H]$^+$ C$_{12}$H$_{16}$NO$_3$: 222.11; found 222.20; HRMS: Anal. Calcd. for [M+H]$^+$ C$_{12}$H$_{16}$NO$_3$: 222.1130; found 222.1121.

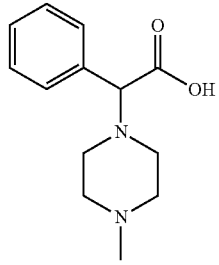

Cap-7

Cap-7a: enantiomer-1
Cap-7b: enantiomer-2

A CH$_2$Cl$_2$ (200 mL) solution of p-toluenesulfonyl chloride (8.65 g, 45.4 mmol) was added dropwise to a cooled (−5° C.) CH$_2$Cl$_2$ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO$_4$), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-d$_6$, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. III); >90% homogeneity index; LC/MS: Anal. Calcd. for [M+H]$^+$ C$_{22}$H$_{20}$NaO$_5$S: 419.09; found 419.04.

A THF (75 mL) solution of benzyl 2-phenyl-2-(tosyloxy) acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO$_4$), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (Chiralcel OD-H) indicated that the sample is a mixture of enantiomers in a 38.2 to 58.7 ratio. The separation of the enantiomers were effected as follow: the product was dissolved in 120 mL of ethanol/heptane (1:1) and injected (5 mL/injection) on chiral HPLC column (Chiracel OJ, 5 cm ID×50 cm L, 20 μm) eluting with 85:15 Heptane/ethanol at 75 mL/min, and monitored at 220 mm Enantiomer-1 (1.474 g) and enantiomer-2 (2.2149 g) were retrieved as viscous oil. $^1$H NMR (CDCl$_3$, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. III); >98% homogeneity index; LC/MS: Anal. Calcd. for [M+H]$^+$ C$_{20}$H$_{25}$N$_2$O$_2$: 325.19; found 325.20.

A methanol (10 mL) solution of either enantiomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (Celite®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-$d_6$, δ=2.5, 500 MHz) δ 7.44-7.37 (m, 2H), 7.37-7.24 (m, 3H), 3.92 (s, 1H), 2.63-2.48 (app. br 5, 2H), 2.48-2.32 (m, 6H), 2.19 (s, 3H); RT=0.31 (Cond. II); >90% homogeneity index; LC/MS: Anal. Calcd. for [M+H]$^+$ $C_{13}H_{19}N_2O_2$: 235.14; found 235.15; HRMS: Anal. Calcd. for [M+H]$^+$ $C_{13}H_{19}N_2O_2$: 235.1447; found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermediates, as described below.

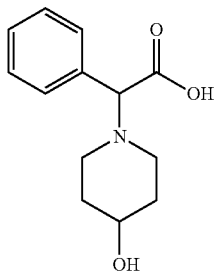

Cap-8

8a: enantiomer-1
8b: enantiomer-2

The enantiomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 μm) eluting with 80:20 heptane/ethanol at 10 mL/min, monitored at 220 nm, to provide 186.3 mg of enantiomer-1 and 209.1 mg of enantiomer-2 as light-yellow viscous oils. These benzyl ester was hydrogenolysed according to the preparation of Cap-7 to provide Cap-8: $^1$H NMR (DMSO-$d_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Cond. II); >98% homogeneity index; LC/MS: Anal. Calcd. for [M+H]$^+$ $C_{13}H_{18}NO_3$: 236.13; found 236.07; HRMS: Calcd. for [M+H]$^+$ $C_{13}H_{18}NO_3$: 236.1287; found 236.1283.

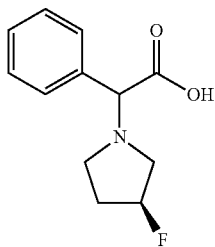

Cap-9

9a: diastereomer-1
9b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% CO$_2$/5% methanol with 0.1% TFA, at 10 bar pressure, 70 mL/min flow rate, and a temperature of 35° C. The HPLC elute for the respective stereoisomers was concentrated, and the residue was dissolved in CH$_2$Cl$_2$ (20 mL) and washed with an aqueous medium (10 mL water+1 mL saturated NaHCO$_3$ solution). The organic phase was dried (MgSO$_4$), filtered, and concentrated in vacuo to provide 92.5 mg of fraction-1 and 59.6 mg of fraction-2. These benzyl esters were hydrogenolysed according to the preparation of Cap-7 to prepare Caps 9a and 9b. Cap-9a (diastereomer-1; the sample is a TFA salt as a result of purification on a reverse phase HPLC using H$_2$O/methanol/TFA solvent): $^1$H NMR (DMSO-$d_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Cond. I); >95% homogeneity index; LC/MS: Anal. Calcd. for [M+H]$^+$ $C_{12}H_{15}FNO_2$: 224.11; found 224.14; Cap-9b (diastereomer-2): $^1$H NMR (DMSO-$d_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. I); LC/MS: Anal. Calcd. for [M+H]$^+$ $C_{12}H_{15}FNO_2$: 224.11; found 224.14.

Cap-10

To a solution of D-proline (2.0 g, 17 mmol) and formaldehyde (2.0 mL of 37% wt. in H$_2$O) in methanol (15 mL) was added a suspension of 10% Pd/C (500 mg) in methanol (5 mL). The mixture was stirred under a balloon of hydrogen for 23 hours. The reaction mixture was filtered through diatomaceous earth (Celite®) and concentrated in vacuo to provide Cap-10 as an off-white solid (2.15 g). $^1$H NMR (DMSO-$d_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. II); >98% homogeneity index; LC/MS: Anal. Calcd. for [M+H]$^+$ $C_6H_{12}NO_2$: 130.09; found 129.96.

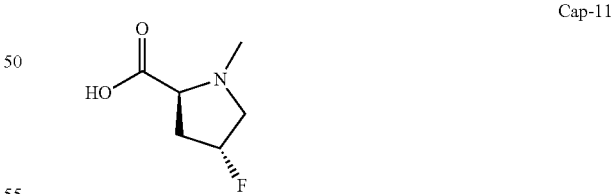

Cap-11

A mixture of (2S,4R)-4-fluoropyrrolidine-2-carboxylic acid (0.50 g, 3.8 mmol), formaldehyde (0.5 mL of 37% wt. in H$_2$O), 12 N HCl (0.25 mL) and 10% Pd/C (50 mg) in methanol (20 mL) was stirred under a balloon of hydrogen for 19 hours. The reaction mixture was filtered through diatomaceous earth (Celite®) and the filtrate was concentrated in vacuo. The residue was recrystallized from isopropanol to provide the HCl salt of Cap-11 as a white solid (337.7 mg). $^1$H NMR (DMSO-$d_5$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26

(m, 1H). RT=0.28 (Cond. II); >98% homogeneity index; LC/MS: Anal. Calcd. for [M+H]$^+$ C$_6$H$_{11}$FNO$_2$: 148.08; found 148.06.

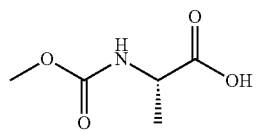

Cap-12 (same as cap 52)

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH~2-3. The resulting solutions was extracted with ethyl acetate (3×100 mL), and the combined organic phase was dried (Na$_2$SO$_4$), filtered, and concentrated in vacuo to provide a colorless oil (2.58 g). 500 mg of this material was purified by a reverse phase HPLC(H$_2$O/methanol/TFA) to provide 150 mg of Cap-12 as a colorless oil. $^1$H NMR (DMSO-d$_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

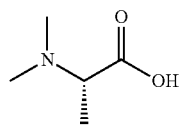

Cap-13

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (Celite®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-d$_6$, δ=2.5, 500 MHz) δ 12.1 (br s, 1H), 4.06 (q, J=7.4, 1H), 2.76 (s, 6H), 1.46 (d, J=7.3, 3H).

mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O-0.1% TFA) to give the intermediate ester (2.70 g, 56%) as a clear oil. $^1$H NMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for C$_{17}$H$_{25}$NO$_2$: 275; found: 276 (M+H)$^+$.

Step 2: To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; CH$_3$CN—H$_2$O-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-d$_6$) δ 7.50 (s, 5H), 5.13 (s, 1H), 3.09 (br s, 2H), 2.92-2.89 (m, 2H), 1.74 (m, 4H), 1.48 (br s, 2H). LC/MS: Anal. Calcd. for C$_{13}$H$_{17}$NO$_2$: 219; found: 220 (M+H)$^+$.

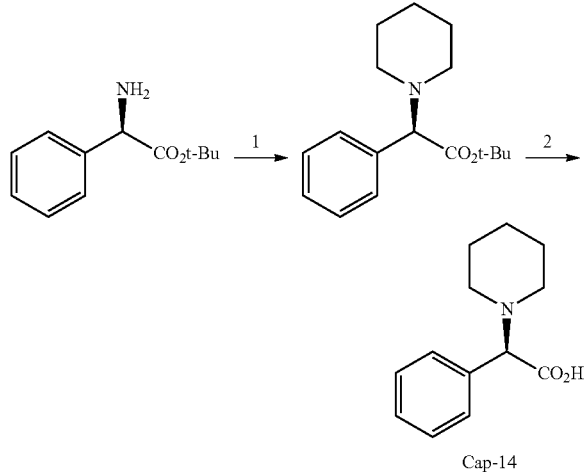

Cap-14

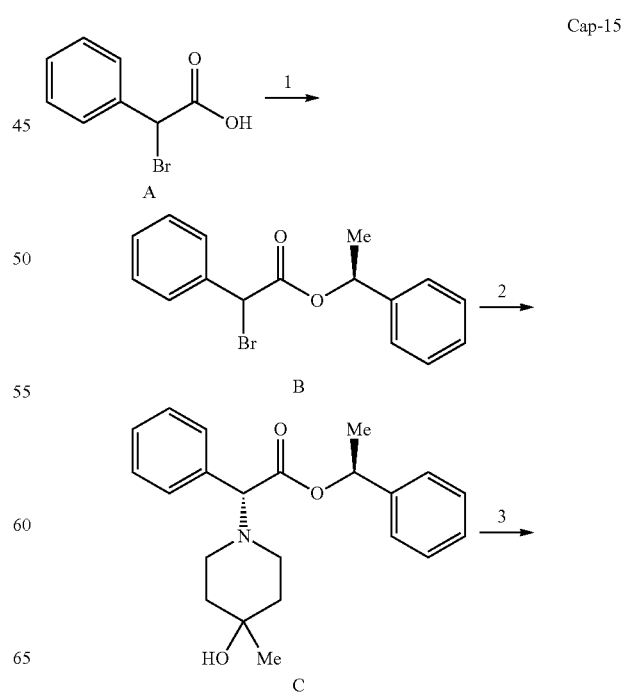

Cap-15

Step 1: A mixture of (R)-(−)-D-phenylglycine tert-butyl ester (3.00 g, 12.3 mmol), NaBH$_3$CN (0.773 g, 123 mmol), KOH (0.690 g, 12.3 mmol) and acetic acid (0.352 mL, 6.15

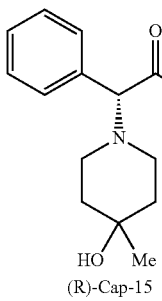

(R)-Cap-15

Step 1: (S)-1-Phenylethyl 2-bromo-2-phenylacetate: To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed (H$_2$O×2, brine), dried (Na$_2$SO$_4$), filtered, and concentrated to give a pale yellow oil. Flash chromatography (SiO$_2$/hexane-ethyl acetate, 4:1) of this oil provided the title compound (11.64 g, 73%) as a white solid. $^1$H NMR (400 MHz, CDCl$_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2: (S)-1-Phenylethyl (R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed (H$_2$O×2, brine), dried (MgSO$_4$), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: $^1$H NMR (CD$_3$OD) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LCMS: Anal. Calcd. for C$_{22}$H$_{27}$NO$_3$: 353; found: 354 (M+H)$^+$. (S,S)-isomer: $^1$H NMR (CD$_3$OD) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for C$_{22}$H$_{27}$NO$_3$: 353; found: 354 (M+H)$^+$.

Step 3: (R)-2-(4-Hydroxy-4-methylpiperidin-1-yl)-2-phenylacetic acid: To a solution of (S)-1-phenylethyl (R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; CH$_3$CN—H$_2$O-0.1% TFA) to give the title compound (as TFA salt) as a pale bluish solid (0.128 g, 98%). LCMS: Anal. Calcd. for C$_{14}$H$_{19}$NO$_3$: 249; found: 250 (M+H)$^+$.

Cap-16

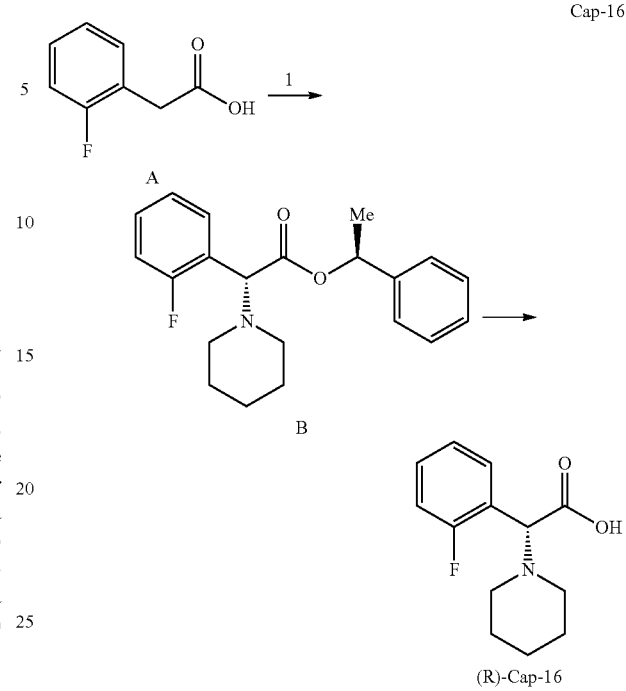

(R)-Cap-16

Step 1: (S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in CH$_2$Cl$_2$ (100 mL) was stirred at room temperature for 12 hours. The solvent was then concentrated and the residue partitioned with H$_2$O-ethyl acetate. The phases were separated and the aqueous layer back-extracted with ethyl acetate (2×). The combined organic phases were washed (H$_2$O, brine), dried (Na$_2$SO$_4$), filtered, and concentrated in vacuo. The residue was purified by silica gel chromatography (Biotage/0-20% ethyl acetate-hexane) to provide the title compound as a colorless oil (8.38 g, 92%). $^1$H NMR (400 MHz, CD$_3$OD) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2: (R)-((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of CBr$_4$ (13.5 g, 40.7 mmol) in THF (100 mL) was added and the mixture was allowed to warm to −10° C. and stirred at this temperature for 2 hours. The reaction mixture was quenched with saturated aq. NH$_4$Cl and the layers were separated. The aqueous layer was back-extracted with ethyl acetate (2×) and the combined organic phases were washed (H$_2$O, brine), dried (Na$_2$SO$_4$), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (Biotage/0-30% diethyl ether-hexane) to provide a pure mixture of diastereomers (2:1 ratio by $^1$H NMR) as a yellow oil (2.07 g, 31%), along with unreacted starting material (2.53 g, 51%).

Further chromatography of the diastereomeric mixture (Biotage/0-10% diethyl ether-toluene) provided the title compound as a colorless oil (0.737 g, 11%). $^1$H NMR (400 MHz, CD$_3$OD) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for C$_{21}$H$_{24}$FNO$_2$: 341; found: 342 (M+H)$^+$.

Step 3: (R)-2-(2-fluorophenyl)-2-(piperidin-1-yl)acetic acid: A mixture of (R)-((S)-1-phenylethyl) 2-(2-fluorophenyl)-2-(piperidin-1-yl)acetate (0.737 g, 2.16 mmol) and 20% Pd(OH)$_2$/C (0.070 g) in ethanol (30 mL) was hydrogenated at room temperature and atmospheric pressure (H$_2$ balloon) for 2 hours. The solution was then purged with Ar, filtered through diatomaceous earth (Celite®), and concentrated in vacuo. This provided the title compound as a colorless solid (0.503 g, 98%). $^1$H NMR (400 MHz, CD$_3$OD) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for C$_{13}$H$_{16}$FNO$_2$: 237; found: 238 (M+H)$^+$.

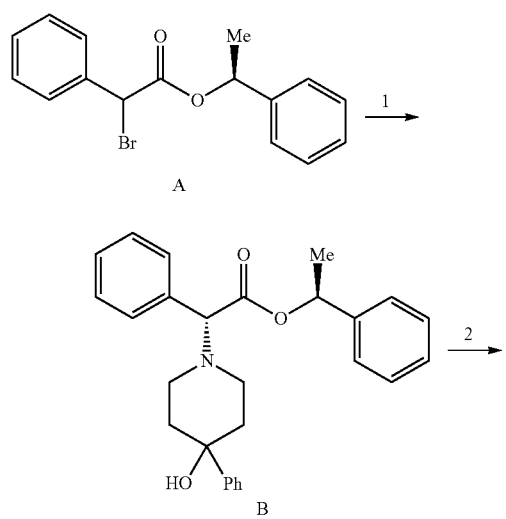

Cap-17

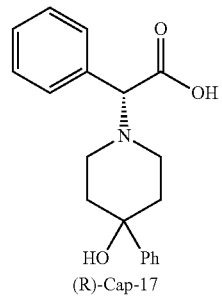

(R)-Cap-17

Step 1: (S)-1-Phenylethyl (R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed (H$_2$O×2, brine), dried (MgSO$_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (Chiralcel OJ-H, 30×250 mm; 20% ethanol in CO$_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, CD$_3$OD) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for C$_{27}$H$_{29}$NO$_3$: 415; found: 416 (M+H)$^+$; (S,S)-isomer: H$^1$NMR (400 MHz, CD$_3$OD) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for C$_{27}$H$_{29}$NO$_3$: 415; found: 416 (M±H)$^+$.

The following esters were prepared in similar fashion:

| Intermediate -17a | | |
|---|---|---|
| 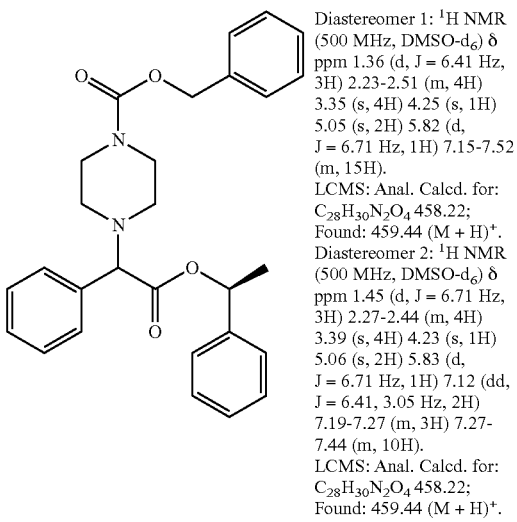 | Diastereomer 1: $^1$H NMR (500 MHz, DMSO-d$_6$) δ ppm 1.36 (d, J = 6.41 Hz, 3H) 2.23-2.51 (m, 4H) 3.35 (s, 4H) 4.25 (s, 1H) 5.05 (s, 2H) 5.82 (d, J = 6.71 Hz, 1H) 7.15-7.52 (m, 15H). LCMS: Anal. Calcd. for: C$_{28}$H$_{30}$N$_2$O$_4$ 458.22; Found: 459.44 (M + H)$^+$. Diastereomer 2: $^1$H NMR (500 MHz, DMSO-d$_6$) δ ppm 1.45 (d, J = 6.71 Hz, 3H) 2.27-2.44 (m, 4H) 3.39 (s, 4H) 4.23 (s, 1H) 5.06 (s, 2H) 5.83 (d, J = 6.71 Hz, 1H) 7.12 (dd, J = 6.41, 3.05 Hz, 2H) 7.19-7.27 (m, 3H) 7.27-7.44 (m, 10H). LCMS: Anal. Calcd. for: C$_{28}$H$_{30}$N$_2$O$_4$ 458.22; Found: 459.44 (M + H)$^+$. | |

-continued

| | | |
|---|---|---|
| Intermediate -17b | 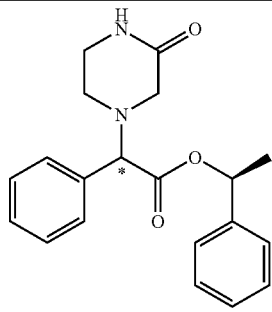 | Diasteromer 1: RT = 11.76 minutes (Cond'n II); LCMS: Anal. Calcd. for: $C_{20}H_{22}N_2O_3$ 338.16 Found: 339.39 (M + H)⁺; Diastereomer 2: RT = 10.05 minutes (Cond'n II); LCMS: Anal. Calcd. for: $C_{20}H_{22}N_2O_3$ 338.16; Found: 339.39 (M + H)⁺. |
| Intermediate -17c | 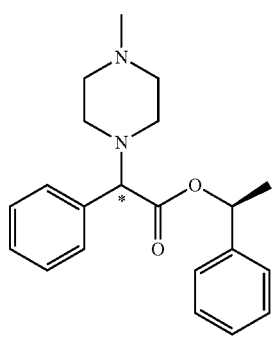 [SMILES: C[C@H](OC(=O)C(c1ccccc1)N1CCN(C)CC1)c1ccccc1] | Diastereomer 1: $T_R$ = 4.55 minutes (Cond'n I); LCMS: Anal. Calcd. for: $C_{21}H_{26}N_2O_2$ 338.20 Found: 339.45 (M + H)⁺; Diastereomer 2: $T_R$ = 6.00 minutes (Cond'n I); LCMS: Anal. Calcd. for: $C_{21}H_{26}N_2O_2$ 338.20 Found: 339.45 (M + H)⁺. |
| Intermediate -17d | 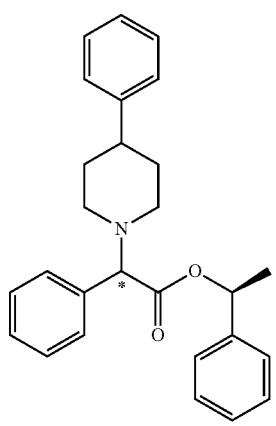 [SMILES: C[C@H](OC(=O)C(c1ccccc1)N1CCC(c2ccccc2)CC1)c1ccccc1] | Diastereomer 1: RT = 7.19 minutes (Cond'n I); LCMS: Anal. Calcd. for: $C_{27}H_{29}NO_2$ 399.22 Found: 400.48 (M + H)⁺; Diastereomer 2: RT = 9.76 minutes (Cond'n I); LCMS: Anal. Calcd. for: $C_{27}H_{29}NO_2$ 399.22 Found: 400.48 (M + H)⁺. |

Chiral SFC Conditions for determining retention time
Condition I
Column: Chiralpak AD-H Column, 4.62×50 mm, 5 μm
Solvents: 90% CO2-10% methanol with 0.1% DEA
Temp: 35° C.
Pressure: 150 bar
Flow rate: 2.0 mL/min.
UV monitored @ 220 nm
Injection: 1.0 mg/3 mL methanol
Condition II
Column: Chiralcel OD-H Column, 4.62×50 mm, 5 μm
Solvents: 90% CO2-10% methanol with 0.1% DEA
Temp: 35° C.
Pressure: 150 bar
Flow rate: 2.0 mL/min.
UV monitored @ 220 nm
Injection: 1.0 mg/mL methanol Cap 17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LCMS: Anal. Calcd. for $C_{19}H_{21}NO_3$: 311.15; found: 312 (M+H)⁺.

The following carboxylic acids were prepared in optically pure form in a similar fashion:

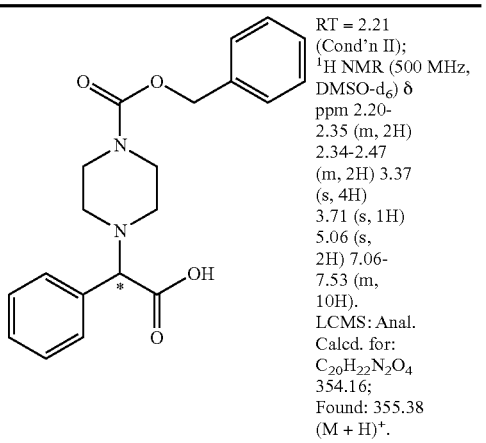

| | | |
|---|---|---|
| Cap-17a | | RT = 2.21 (Cond'n II); ¹H NMR (500 MHz, DMSO-d₆) δ ppm 2.20-2.35 (m, 2H) 2.34-2.47 (m, 2H) 3.37 (s, 4H) 3.71 (s, 1H) 5.06 (s, 2H) 7.06-7.53 (m, 10H). LCMS: Anal. Calcd. for: $C_{20}H_{22}N_2O_4$ 354.16; Found: 355.38 $(M + H)^+$. |

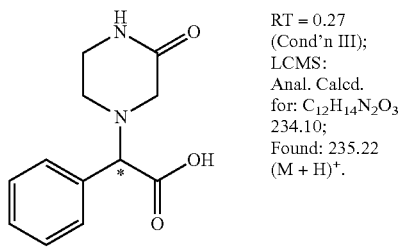

Cap-17b — RT = 0.27 (Cond'n III); LCMS: Anal. Calcd. for: $C_{12}H_{14}N_2O_3$ 234.10; Found: 235.22 $(M + H)^+$.

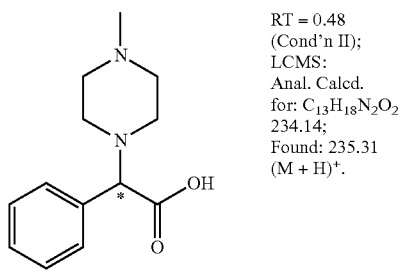

Cap-17c — RT = 0.48 (Cond'n II); LCMS: Anal. Calcd. for: $C_{13}H_{18}N_2O_2$ 234.14; Found: 235.31 $(M + H)^+$.

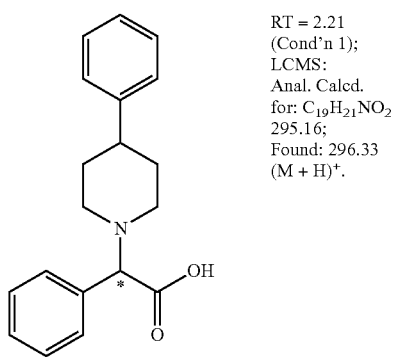

Cap-17d — RT = 2.21 (Cond'n 1); LCMS: Anal. Calcd. for: $C_{19}H_{21}NO_2$ 295.16; Found: 296.33 $(M + H)^+$.

LCMS Conditions for determining retention time
Condition I
Column: Phenomenex-Luna 4.6×50 mm S10
Start % B=0
Final % B=100
Gradient Time=4 min
Flow Rate=4 mL/min
Wavelength=220
Solvent A=10% methanol–90% H₂O–0.1% TFA
Solvent B=90% methanol–10% H₂O–0.1% TFA Condition II
Column: Waters-Sunfire 4.6×50 mm S5
Start % B=0
Final % B=100
Gradient Time=2 min
Flow Rate=4 mL/min
Wavelength=220
Solvent A=10% methanol–90% H₂O–0.1% TFA
Solvent B=90% methanol–10% H₂O–0.1% TFA
Condition III
Column: Phenomenex 10µ 3.0×50 mm
Start % B=0
Final % B=100
Gradient Time=2 min
Flow Rate=4 mL/min
Wavelength=220
Solvent A=10% methanol–90% H₂O–0.1% TFA
Solvent B=90% methanol–10% H₂O–0.1% TFA

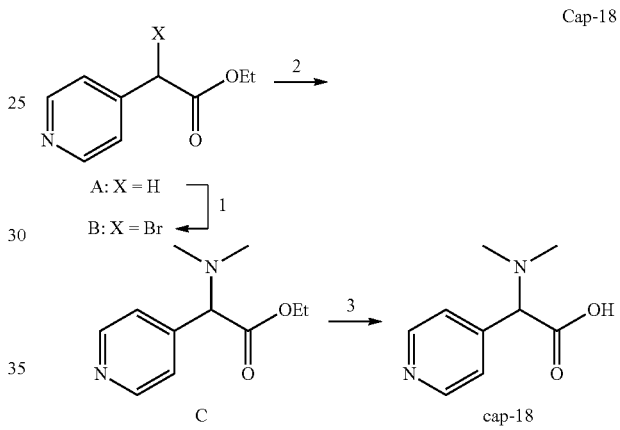

Cap-18

Step 1; (R,S)-Ethyl 2-(4-pyridyl)-2-bromoacetate: To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added CBr₄ (2.21 g, 6.66 mmol) and stirring was continued at −78° C. for 2 hours. The reaction mixture was then quenched with sat. aq. NH₄Cl and the phases were separated. The organic phase was washed (brine), dried (Na₂SO₄), filtered, and concentrated in vacuo. The resulting yellow oil was immediately purified by flash chromatography (SiO₂/hexane-ethyl acetate, 1:1) to provide the title compound (1.40 g, 95%) as a somewhat unstable yellow oil. ¹H NMR (400 MHz, CDCl₃) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for $C_9H_{10}BrNO_2$: 242, 244; found: 243, 245 $(M+H)^+$.

Step 2; (R,S)-Ethyl 2-(4-pyridyl)-2-(N,N-dimethylamino) acetate: To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (Biotage, 40+M SiO₂ column; 50%-100% ethyl acetate-hexane) to provide the title compound (0.539 g, 31%) as a light yellow oil. ¹H NMR (400 MHz, CDCl₃) δ 8.58 (d, J=6.0 Hz, 2H), 7.36 (d, J=6.0 Hz, 2H), 4.17 (m, 2H), 3.92 (s, 1H), 2.27

(s, 6H), 1.22 (t, J=7.0 Hz). LCMS: Anal. Calcd. for C₁₁H₁₆N₂O₂: 208; found: 209 (M+H)⁺.

Step 3; (R,S)-2-(4-Pyridyl)-2-(N,N-dimethylamino)acetic acid: To a solution of (R,S)-ethyl 2-(4-pyridyl)-2-(N,N-dimethylamino)acetate (0.200 g, 0.960 mmol) in a mixture of THF-methanol-H₂O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. ¹H NMR (400 MHz, DMSO-d₆) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above;

| | | |
|---|---|---|
| Cap-19 | 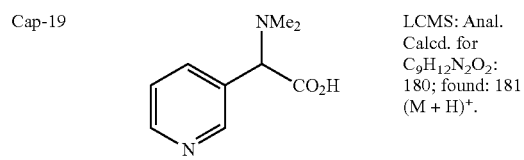 | LCMS: Anal. Calcd. for C₉H₁₂N₂O₂: 180; found: 181 (M + H)⁺. |
| Cap-20 | 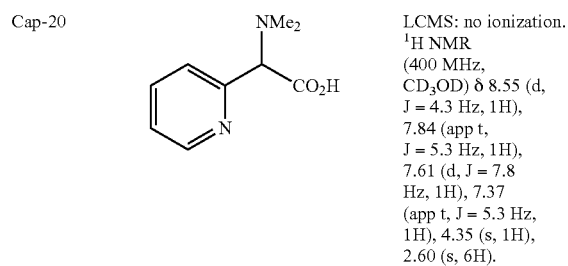 | LCMS: no ionization. ¹H NMR (400 MHz, CD₃OD) δ 8.55 (d, J = 4.3 Hz, 1H), 7.84 (app t, J = 5.3 Hz, 1H), 7.61 (d, J = 7.8 Hz, 1H), 7.37 (app t, J = 5.3 Hz, 1H), 4.35 (s, 1H), 2.60 (s, 6H). |
| Cap-21 | 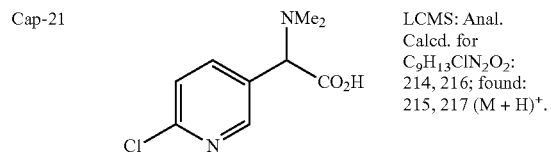 | LCMS: Anal. Calcd. for C₉H₁₃ClN₂O₂: 214, 216; found: 215, 217 (M + H)⁺. |
| Cap-22 | 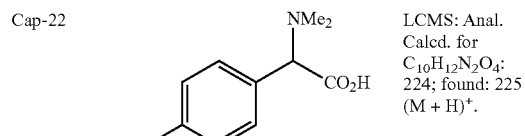 | LCMS: Anal. Calcd. for C₁₀H₁₂N₂O₄: 224; found: 225 (M + H)⁺. |
| Cap-23 | 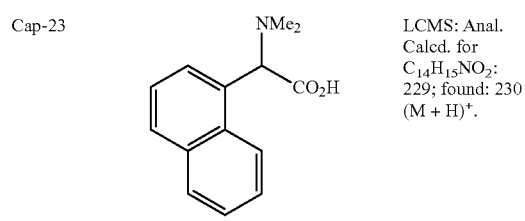 | LCMS: Anal. Calcd. for C₁₄H₁₅NO₂: 229; found: 230 (M + H)⁺. |
| Cap-24 | 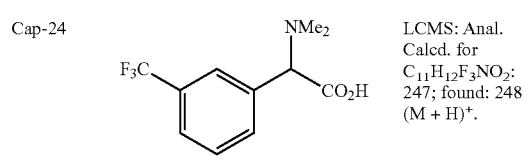 | LCMS: Anal. Calcd. for C₁₁H₁₂F₃NO₂: 247; found: 248 (M + H)⁺. |
| Cap-25 | 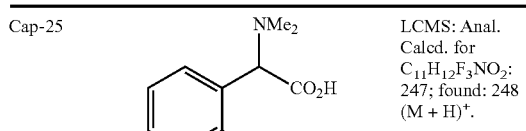 | LCMS: Anal. Calcd. for C₁₁H₁₂F₃NO₂: 247; found: 248 (M + H)⁺. |
| Cap-26 | 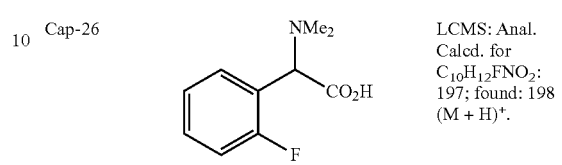 | LCMS: Anal. Calcd. for C₁₀H₁₂FNO₂: 197; found: 198 (M + H)⁺. |
| Cap-27 | 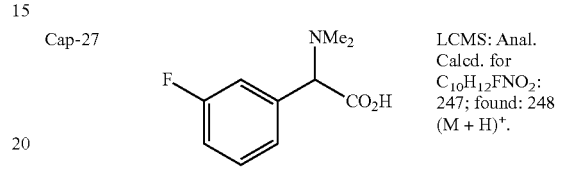 | LCMS: Anal. Calcd. for C₁₀H₁₂FNO₂: 247; found: 248 (M + H)⁺. |
| Cap-28 | 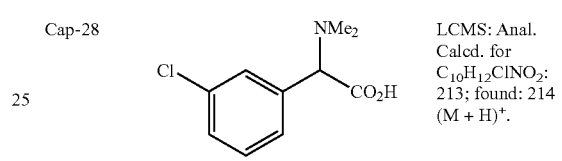 | LCMS: Anal. Calcd. for C₁₀H₁₂ClNO₂: 213; found: 214 (M + H)⁺. |
| Cap-29 | 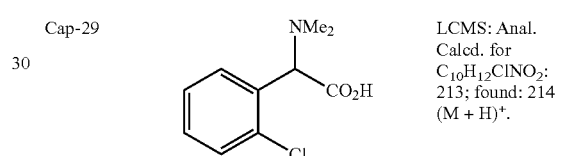 | LCMS: Anal. Calcd. for C₁₀H₁₂ClNO₂: 213; found: 214 (M + H)⁺. |
| Cap-30 | 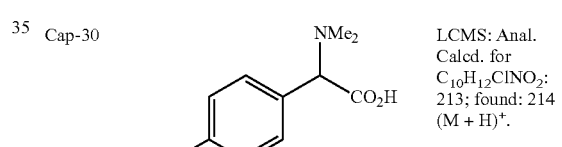 | LCMS: Anal. Calcd. for C₁₀H₁₂ClNO₂: 213; found: 214 (M + H)⁺. |
| Cap-31 | 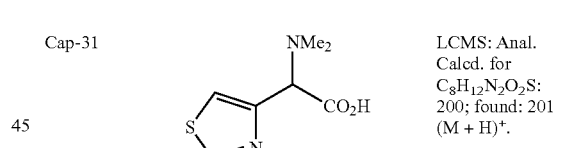 | LCMS: Anal. Calcd. for C₈H₁₂N₂O₂S: 200; found: 201 (M + H)⁺. |
| Cap-32 | 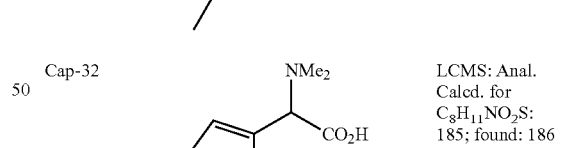 | LCMS: Anal. Calcd. for C₈H₁₁NO₂S: 185; found: 186 (M + H)⁺. |
| Cap-33 | 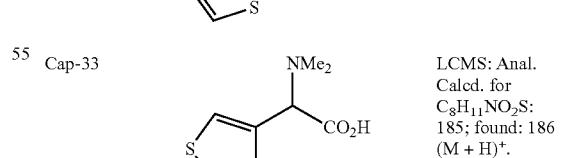 | LCMS: Anal. Calcd. for C₈H₁₁NO₂S: 185; found: 186 (M + H)⁺. |
| Cap-34 | 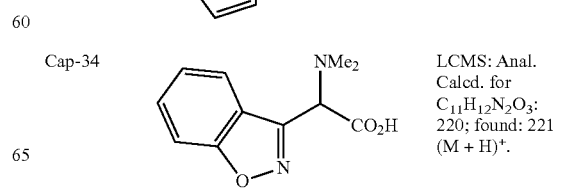 | LCMS: Anal. Calcd. for C₁₁H₁₂N₂O₃: 220; found: 221 (M + H)⁺. |

| | | |
|---|---|---|
| Cap-35 | 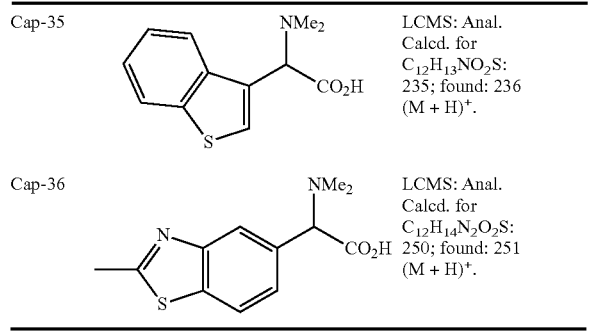 | LCMS: Anal. Calcd. for $C_{12}H_{13}NO_2S$: 235; found: 236 $(M+H)^+$. |
| Cap-36 | | LCMS: Anal. Calcd. for $C_{12}H_{14}N_2O_2S$: 250; found: 251 $(M+H)^+$. |

Cap-37

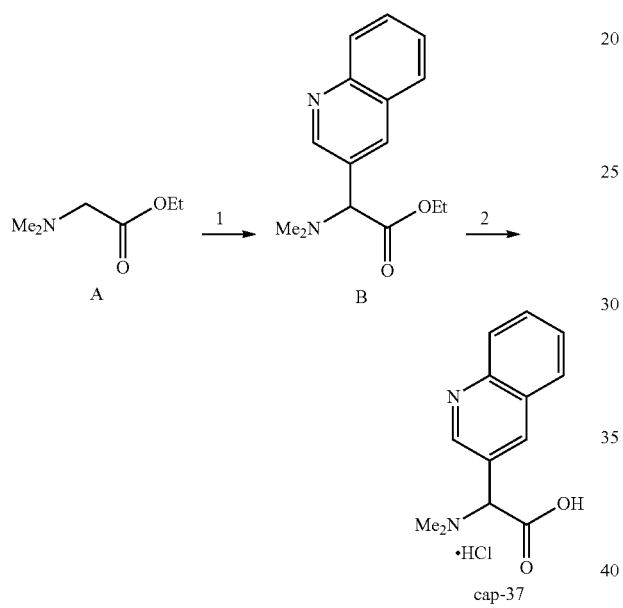

cap-37 title compound (0.169 g, >100%) as a light yellow foam. The unpurified material was used in subsequent steps without further purification. LCMS: Anal. Calcd. for $C_{13}H_{14}N_2O_2$: 230; found: 231 $(M+H)^+$.

Cap-38

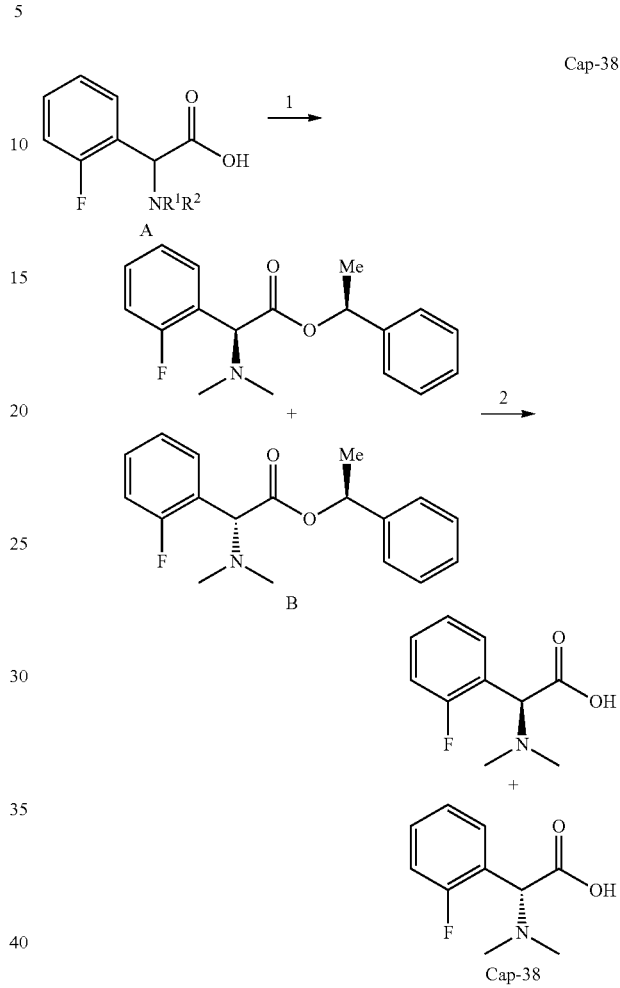

Cap-38

Step 1; (R,S)-Ethyl 2-(quinolin-3-yl)-2-(N,N-dimethylamino)-acetate: A mixture of ethyl N,N-dimethylaminoacetate (0.462 g, 3.54 mmol), $K_3PO_4$ (1.90 g, 8.95 mmol), $Pd(t-Bu_3P)_2$ (0.090 g, 0.176 mmol) and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 min; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1$H NMR (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for $C_{15}H_{18}N_2O_2$: 258; found: 259 $(M+H)^+$.

Step 2; (R,S) 2-(Quinolin-3-yl)-2-(N,N-dimethylamino) acetic acid: A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the Step 1; (R)-((S)-1-phenylethyl) 2-(dimethylamino)-2-(2-fluorophenyl)acetate and (S)-((S)-1-phenylethyl) 2-(dimethylamino)-2-(2-fluorophenyl)acetate: To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried ($Na_2SO_4$), filtered, and concentrated in vacuo. The residue was purified by silica gel chromatography (Biotage/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl (R)-2-(dimethylamino)-2-(2-fluorophenyl)acetate (0.501 g, 13%) and then (S)-1-phenethyl (S)-2-(dimethylamino)-2-(2-fluorophenyl)-acetate (0.727 g. 18%), both as their TFA salts. (S,R)-isomer: $^1$H NMR (400 MHz, $CD_3OD$) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LCMS: Anal. Calcd.

$C_{18}H_{20}FNO_2$: 301; found: 302 (M+H)$^+$; (S,S)-isomer: $^1$H NMR (400 MHz, CD$_3$OD) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for $C_{18}H_{20}FNO_2$: 301; found: 302 (M+H)$^+$.

Step 2; (R)-2-(dimethylamino)-2-(2-fluorophenyl)acetic acid: A mixture of (R)-((S)-1-phenylethyl) 2-(dimethylamino)-2-(2-fluorophenyl)acetate TFA salt (1.25 g, 3.01 mmol) and 20% Pd(OH)$_2$/C (0.125 g) in ethanol (30 mL) was hydrogenated at room temperature and atmospheric pressure (H$_2$ balloon) for 4 hours. The solution was then purged with Ar, filtered through diatomaceous earth (Celite®) and concentrated in vacuo. This gave the title compound as a colorless solid (0.503 g, 98%). $^1$H NMR (400 MHz, CD$_3$OD) δ 7.53-7.63 (m, 2H), 7.33-7.38 (m, 2H), 5.36 (s, 1H), 2.86 (s, 6H). LCMS: Anal. Calcd. for $C_{10}H_{12}FNO_2$: 197; found: 198 (M+H)$^+$.

The S-isomer could be obtained from (S)-((S)-1-phenylethyl) 2-(dimethylamino)-2-(2-fluorophenyl)acetate TFA salt in similar fashion.

Cap-39

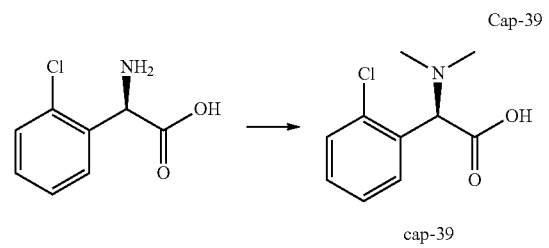

cap-39

A mixture of (R)-(2-chlorophenyl)glycine (0.300 g, 1.62 mmol), formaldehyde (35% aqueous solution, 0.80 mL, 3.23 mmol) and 20% Pd(OH)$_2$/C (0.050 g) was hydrogenated at room temperature and atmospheric pressure (H$_2$ balloon) for 4 hours. The solution was then purged with Ar, filtered through diatomaceous earth (Celite®) and concentrated in vacuo. The residue was purified by reverse-phase preparative HPLC (Primesphere C-18, 30×100 mm; CH$_3$CN—H$_2$O-0.1% TFA) to give the TFA salt of the title compound (R)-2-(dimethylamino)-2-(2-chlorophenyl)acetic acid as a colorless oil (0.290 g, 55%). $^1$H NMR (400 MHz, CD$_3$OD) δ 7.59-7.65 (m, 2H), 7.45-7.53 (m, 2H), 5.40 (s, 1H), 2.87 (s, 6H). LCMS: Anal. Calcd. for $C_{10}H_{12}ClNO_2$: 213; found: 214 (M+H)$^+$.

Cap-40

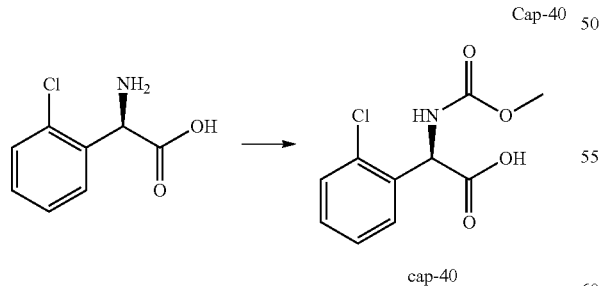

cap-40

To an ice-cold solution of (R)-(2-chlorophenyl)glycine (1.00 g, 5.38 mmol) and NaOH (0.862 g, 21.6 mmol) in H$_2$O (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed (H$_2$O, brine), dried (Na$_2$SO$_4$), filtered, and concentrated in vacuo to give the title compound (R)-2-(methoxycarbonylamino)-2-(2-chlorophenyl)acetic acid as a yellow-orange foam (1.31 g, 96%). $^1$H NMR (400 MHz, CD$_3$OD) δ 7.39-7.43 (m, 2H), 7.29-7.31 (m, 2H), 5.69 (s, 1H), 3.65 (s, 3H). LCMS: Anal. Calcd. for $C_{10}H_{10}ClNO_4$: 243; found: 244 (M+H)$^+$.

Cap-41

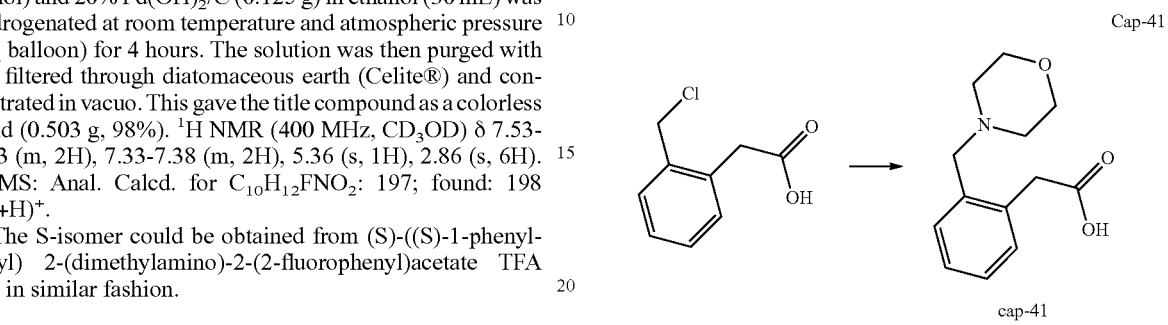

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with H$_2$O (2×). The aqueous phase was lyophilized and the residue was purified by silica gel chromatography (Biotage/0-10% methanol-CH$_2$Cl$_2$) to give the title compound 2-(2-(Morpholinomethyl)phenyl)acetic acid as a colorless solid (2.22 g, 87%). $^1$H NMR (400 MHz, CD$_3$OD) δ 7.37-7.44 (m, 3H), 7.29-7.33 (m, 1H), 4.24 (s, 2H), 3.83 (br s, 4H), 3.68 (s, 2H), 3.14 (br s, 4H). LCMS: Anal. Calcd. for $C_{13}H_{17}NO_3$: 235; found: 236 (M+H)$^+$.

The following examples were similarly prepared using the method described for Cap-41:

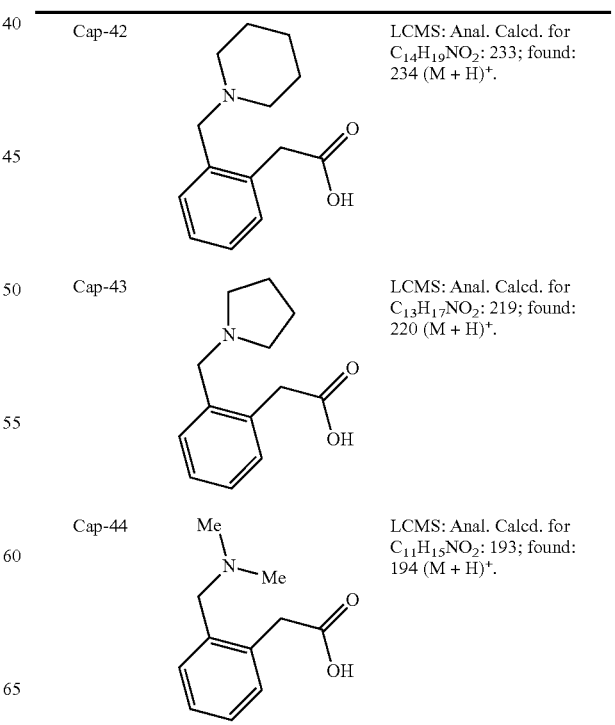

| Cap-42 | LCMS: Anal. Calcd. for $C_{14}H_{19}NO_2$: 233; found: 234 (M + H)$^+$. |
|---|---|
| Cap-43 | LCMS: Anal. Calcd. for $C_{13}H_{17}NO_2$: 219; found: 220 (M + H)$^+$. |
| Cap-44 | LCMS: Anal. Calcd. for $C_{11}H_{15}NO_2$: 193; found: 194 (M + H)$^+$. |

| | |
|---|---|
| Cap-45 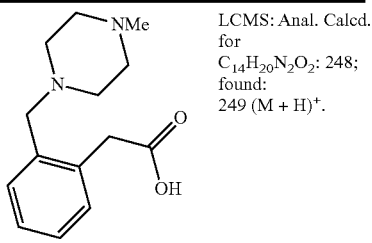 | LCMS: Anal. Calcd. for $C_{14}H_{20}N_2O_2$: 248; found: 249 (M + H)$^+$. |

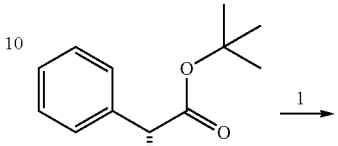

Cap-45a

HMDS (1.85 mL, 8.77 mmol) was added to a suspension of (R)-2-amino-2-phenylacetic acid p-toluenesulfonate (2.83 g, 8.77 mmol) in CH$_2$Cl$_2$ (10 mL) and the mixture was stirred at room temperature for 30 minutes. Methyl isocyanate (0.5 g, 8.77 mmol) was added in one portion stirring continued for 30 minutes. The reaction was quenched by addition of H$_2$O (5 mL) and the resulting precipitate was filtered, washed with H$_2$O and n-hexanes, and dried under vacuum. (R)-2-(3-methylureido)-2-phenylacetic acid (1.5 g; 82%) was recovered as a white solid and it was used without further purification. $^1$H NMR (500 MHz, DMSO-d$_6$) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for $C_{10}H_{12}N_2O_3$ 208.08 found 209.121 (M+H)$^+$; HPLC Phenomenex C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

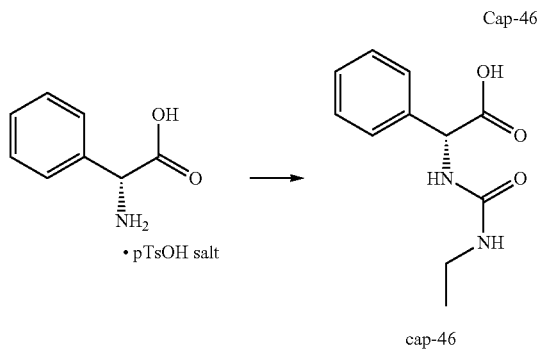 [SMILES: N[C@@H](C(=O)O)c1ccccc1 ; CCNC(=O)N[C@@H](C(=O)O)c1ccccc1]

cap-46

The desired product was prepared according to the method described for Cap-45a. $^1$H NMR (500 MHz, DMSO-d$_6$) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for $C_{11}H_{14}N_2O_3$ 222.10 found 223.15 (M+H)$^+$. HPLC XTERRA C-18 3.0×506 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=0.87 min, 90% homogeneity index.

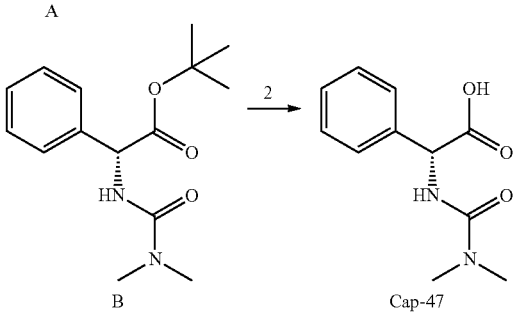

Step 1; (R)-tert-butyl 2-(3,3-dimethylureido)-2-phenylacetate: To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with H$_2$O, 1N aq. HCl and brine, dried (MgSO$_4$), filtered and concentrated under reduced pressure. (R)-tert-butyl 2-(3,3-dimethylureido)-2-phenylacetate was obtained as a white solid (0.86 g; 75%) and used without further purification. $^1$H NMR (500 MHz, DMSO-d$_6$) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for $C_{15}H_{22}N_2O_3$ 278.16 found 279.23 (M+H)$^+$; HPLC Phenomenex LUNA C-18 4.6×50 mm, 0 to 100% B over 4 minutes, 1 minute hold time, A=90% water, 10% methanol, 0.1% TFA, B=10% water, 90% methanol, 0.1% TFA, RT=2.26 min, 97% homogeneity index.

Step 2; (R)-2-(3,3-dimethylureido)-2-phenylacetic acid: To a stirred solution of ((R)-tert-butyl 2-(3,3-dimethylureido)-2-phenylacetate (0.86 g, 3.10 mmol) in CH$_2$Cl$_2$ (250 mL) was added TFA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. $^1$H NMR (500 MHz, DMSO-d$_6$) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LCMS: Anal. Calcd. for $C_{11}H_{14}N_2O_3$: 222.24; found: 223.21 (M+H)$^+$. HPLC XTERRA C-18 3.0× 50 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=0.75 min, 93% homogeneity index.

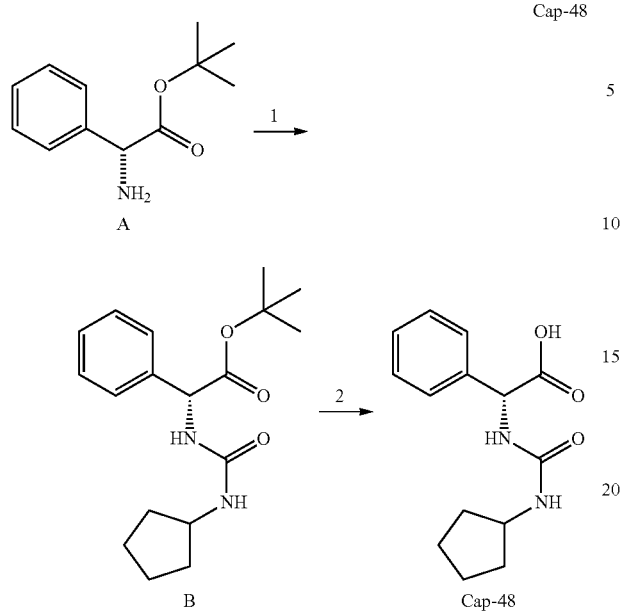

Step 1; (R)-tert-butyl 2-(3-cyclopentylureido)-2-phenylacetate: To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with $H_2O$ and brine, dried ($MgSO_4$), filtered, and concentrated under reduced pressure. (R)-tert-butyl 2-(3-cyclopentylureido)-2-phenylacetate was obtained as an opaque oil (1.32 g; 100%) and used without further purification. $^1$H NMR (500 MHz, $CD_3Cl$-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LCMS: Anal. Calcd. for $C_{18}H_{26}N_2O_3$ 318.19 found 319.21 (M+H)$^+$; HPLC XTERRA C-18 3.0×50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2; (R)-2-(3-cyclopentylureido)-2-phenylacetic acid: To a stirred solution of (R)-tert-butyl 2-(3-cyclopentylureido)-2-phenylacetate (1.31 g, 4.10 mmol) in $CH_2Cl_2$ (25 mL) was added TFA (4 mL) and triethylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). $^1$H NMR (500 MHz, DMSO-$d_6$) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for $C_{14}H_{18}N_2O_3$: 262.31; found: 263.15 (M+H)$^+$. HPLC XTERRA C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=1.24 min, 100% homogeneity index.

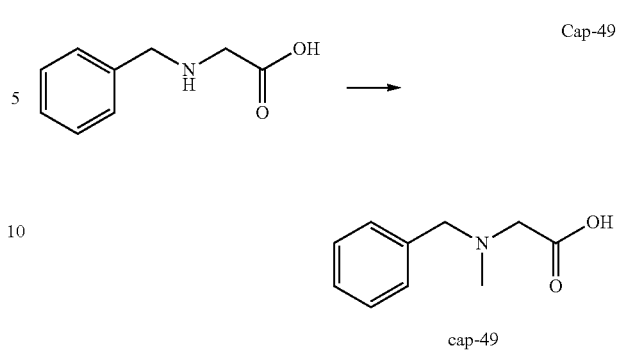

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (Xterra 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl (methyl)-amino)acetic acid as its TFA salt (723 mg, 33%) as a colorless wax. $^1$H NMR (300 MHz, DMSO-$d_6$) δ ppm 2.75 (s, 3H) 4.04 (s, 2H) 4.34 (s, 2H) 7.29-7.68 (m, 51-1). LCMS: Anal. Calcd. for: $C_{10}H_{13}NO_2$ 179.09; Found: 180.20 (M+H)$^+$.

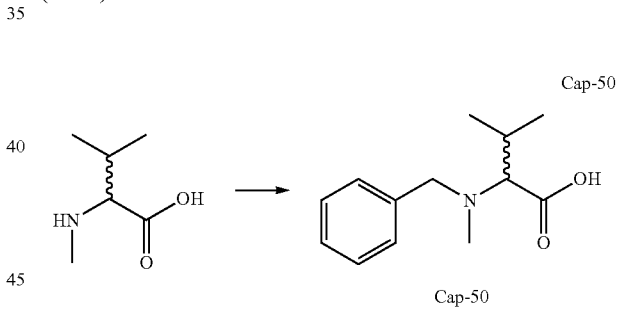

To a stirred solution of 3-methyl-2-(methylamino)butanoic acid (0.50 g, 3.81 mmol) in water (30 mL) was added $K_2CO_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (Xterra 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1$H NMR (500 MHz, DMSO-$d_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LCMS: Anal. Calcd. for: $C_{13}H_{19}NO_2$ 221.14; Found: 222.28 (M+H)$^+$.

Cap-51

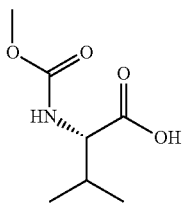

Na$_2$CO$_3$ (1.83 g, 17.2 mmol) was added to NaOH (33 mL of 1M/H$_2$O, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with CH$_2$Cl$_2$ (50 mL, 3×). The organic phase was dried (MgSO$_4$) and evaporated in vacuo to afford Cap-51 as a white solid (6 g). $^1$H NMR for the dominant rotamer (DMSO-d$_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]$^+$ C$_7$H$_{14}$NO$_4$: 176.0923; found 176.0922.

Cap 51 (alternate route)

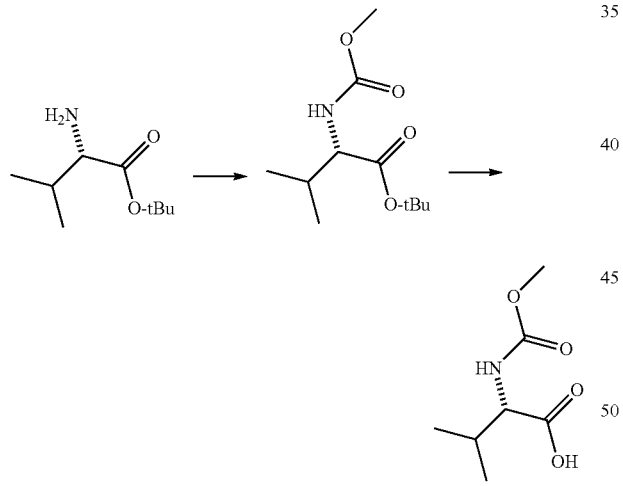

DIEA (137.5 mL, 0.766 mol) was added to a suspension of (S)-tert-butyl 2-amino-3-methylbutanoate hydrochloride (75.0 g, 0.357 mol) in THF (900 mL), and the mixture was cooled to 0° C. (ice/water bath). Methyl chloroformate (29.0 mL, 0.375 mol) was added dropwise over 45 min, the cooling bath was removed and the heterogeneous mixture was stirred at ambient temperature for 3 h. The solvent was removed under diminished pressure and the residue partitioned between EtOAc and water (1 L each). The organic layer was washed with H$_2$O (1 L) and brine (1 L), dried (MgSO$_4$), filtered and concentrated under diminished pressure. The crude material was passed through a plug of silica gel (1 kg), eluting with hexanes (4 L) and 15:85 EtOAc/hexanes (4 L) to afford (S)-tert-butyl 2-(methoxycarbonylamino)-3-methylbutanoate as a clear oil (82.0 g, 99% yield). $^1$H-NMR (500 MHz, DMSO-d$_6$, δ=2.5 ppm) 7.34 (d, J=8.6, 1H), 3.77 (dd, J=8.6, 6.1, 1H), 3.53 (s, 3H), 1.94-2.05 (m, 1H), 1.39 (s, 9H), 0.83-0.92 (m, 6H). $^{13}$C-NMR (126 MHz, DMSO-d$_6$, δ=39.2 ppm) 170.92, 156.84, 80.38, 60.00, 51.34, 29.76, 27.62, 18.92, 17.95. LC/MS: [M+Na]$^+$ 254.17.

Trifluoroacetic acid (343 mL, 4.62 mol) and Et$_3$SiH (142 mL, 0.887 mol) were added sequentially to a solution of (S)-tert-butyl 2-(methoxycarbonylamino)-3-methylbutanoate (82.0 g, 0.355 mol) in CH$_2$Cl$_2$ (675 mL), and the mixture was stirred at ambient temperature for 4 h. The volatile component was removed under diminished pressure and the resultant oil triturated with petroleum ether (600 mL) to afford a white solid, which was filtered and washed with hexanes (500 mL) and petroleum ether (500 mL). Recrystallization from EtOAc/petroleum ether afforded Cap-51 as white flaky crystals (54.8 g, 88% yield). MP=108.5-109.5° C. $^1$H NMR (500 MHz, DMSO-d$_6$, δ=2.5 ppm) 12.52 (s, 1H), 7.31 (d, J=8.6, 1H), 3.83 (dd, J=8.6, 6.1, 1H), 3.53 (s, 3H), 1.94-2.07 (m, 1H), 0.86 (dd, J=8.9, 7.0, 6H). $^{13}$C NMR (126 MHz, DMSO-d$_6$, δ=39.2 ppm) 173.30, 156.94, 59.48, 51.37, 29.52, 19.15, 17.98. LC/MS: [M+H]$^+$=176.11. Anal. Calcd. for C$_7$H$_{13}$NO$_4$: C, 47.99; H, 7.48; N, 7.99. Found: C, 48.17; H, 7.55; N, 7.99. Optical Rotation: [α]$_D$=−4.16 (12.02 mg/mL; MeOH). Optical purity: >99.5% ee. Note: the optical purity assessment was made on the methyl ester derivative of Cap-51, which was prepared under a standard TMSCHN$_2$ (benzene/MeOH) esterification protocol. HPLC analytical conditions: column, ChiralPak AD-H (4.6×250 mm, 5 μm); solvent, 95% heptane/5% IPA (isocratic); flow rate, 1 mL/min; temperature, 35° C.; UV monitored at 205 nm.
[Note: Cap 51 could also be purchased from Flamm.]

Cap-52 (Same as Cap-12)

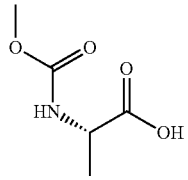

Cap-52 was synthesized from L-alanine according to the procedure described for the synthesis of Cap-51. For characterization purposes, a portion of the crude material was purified by a reverse phase HPLC(H$_2$O/methanol/TFA) to afford Cap-52 as a colorless viscous oil. $^1$H NMR (DMSO-d$_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to -64 were prepared from appropriate starting materials according to the procedure described for the synthesis of Cap-51, with noted modifications if any.

| Cap | Structure | Data |
|---|---|---|
| Cap-53a: (R) Cap-53b: (S) | | ¹H NMR (DMSO-d₆, δ = 2.5 ppm, 500 MHz): δ 12.51 (br s, 1H), 7.4 (d, J = 7.9, 0.9H), 7.06 (app s, 0.1H), 3.86-3.82 (m, 1H), 3.53 (s, 3H), 1.75-1.67 (m, 1H), 1.62-1.54 (m, 1H), 0.88 (d, J = 7.3, 3H). RT = 0.77 minutes (Cond. 2); LC/MS: Anal. Calcd. for [M + Na]⁺ C₆H₁₁NNaO₄: 184.06; found 184.07. HRMS Calcd. for [M + Na]⁺ C₆H₁₁NNaO₄: 184.0586; found 184.0592. |
| Cap-54a: (R) Cap-54b: (S) | | ¹H NMR (DMSO-d₆, δ = 2.5 ppm, 500 MHz): δ 12.48 (s, 1H), 7.58 (d, J = 7.6, 0.9H), 7.25 (app s, 0.1H), 3.52 (s, 3H), 3.36-3.33 (m, 1H), 1.10-1.01 (m, 1H), 0.54-0.49 (m, 1H), 0.46-0.40 (m, 1H), 0.39-0.35 (m, 1H), 0.31-0.21 (m, 1H). HRMS Calcd. for [M + H]⁺ C₇H₁₂NO₄: 174.0766; found 174.0771 |
| Cap-55 | 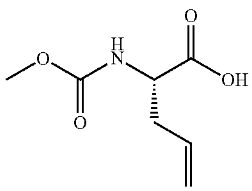 | ¹H NMR (DMSO-d₆, δ = 2.5 ppm, 500 MHz): δ 12.62 (s, 1H), 7.42 (d, J = 8.2, 0.9H), 7.07 (app s, 0.1H), 5.80-5.72 (m, 1H), 5.10 (d, J = 17.1, 1H), 5.04 (d, J = 10.4, 1H), 4.01-3.96 (m, 1H), 3.53 (s, 3H), 2.47-2.42 (m, 1H), 2.35-2.29 (m, 1H). |
| Cap-56 | 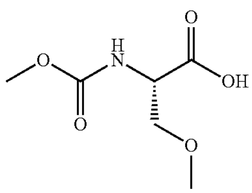 | ¹H NMR (DMSO-d₆, δ = 2.5 ppm, 500 MHz): δ 12.75 (s, 1H), 7.38 (d, J = 8.3, 0.9H), 6.96 (app s, 0.1H), 4.20-4.16 (m, 1H), 3.60-3.55 (m, 2H), 3.54 (s, 3H), 3.24 (s, 3H). |
| Cap-57 | 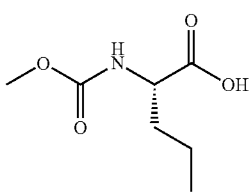 | ¹H NMR (DMSO-d₆, δ = 2.5 ppm, 500 MHz): δ 12.50 (s, 1H), 8.02 (d, J = 7.7, 0.08H), 7.40 (d, J = 7.9, 0.76H), 7.19 (d, J = 8.2, 0.07H), 7.07 (d, J = 6.7, 0.09H), 4.21-4.12 (m, 0.08H), 4.06-3.97 (m, 0.07H), 3.96-3.80 (m, 0.85H), 3.53 (s, 3H), 1.69-1.51 (m, 2H), 1.39-1.26 (m, 2H), 0.85 (t, J = 7.4, 3H). LC (Cond. 2): RT = 1.39 LC/MS: Anal. Calcd. for [M + H]⁺ C₇H₁₄NO₄: 176.09; found 176.06. |
| Cap-58 | 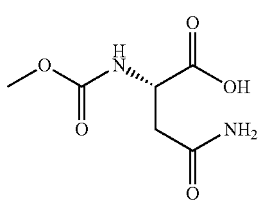 | ¹H NMR (DMSO-d₆, δ = 2.5 ppm, 500 MHz): δ 12.63 (br s, 1H), 7.35 (s, 1H), 7.31 (d, J = 8.2, 1H), 6.92 (s, 1H), 4.33-4.29 (m, 1H), 3.54 (s, 1H), 2.54 (dd, J = 15.5 5.4, 1H), 2.43 (dd, J = 15.6, 8.0, 1H).RT = 0.16 min (Cond. 2); LC/MS: Anal. Calcd. for [M + H]⁺ C₆H₁₂N₂O₅: 191.07; found 191.14. |
| Cap-59a: (R) Cap-59b: (S) | | ¹H NMR (DMSO-d₆, δ = 2.5 ppm, 400 MHz): δ 12.49 (br s, 1H), 7.40 (d, J = 7.3, 0.89H), 7.04 (br s, 0.11H), 4.00-3.95 (m, 3H), 1.24 (d, J = 7.3, 3H), 1.15 (t, J = 7.2, 3H). HRMS: Anal. Calcd. for [M + H]⁺ C₆H₁₂NO₄: 162.0766; found 162.0771. |
| Cap-60 | 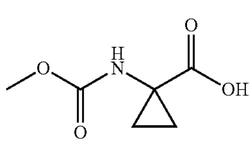 | The crude material was purified with a reverse phase HPLC (H₂O/MeOH/TFA) to afford a colorless viscous oil that crystallized to a white solid upon exposure to high vacuum. ¹H NMR (DMSO-d₆, δ = 2.5 ppm, 400 MHz): δ 12.38 (br s, 1H), 7.74 (s, 0.82H), 7.48 (s, 0.18H), 3.54/3.51 (two s, 3H), 1.30 (m, 2H), 0.98 (m, 2H). HRMS: Anal. Calcd. for [M + H]⁺ C₆H₁₀NO₄: 160.0610; found 160.0604. |

| Cap | Structure | Data |
|---|---|---|
| Cap-61 | 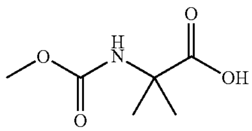 | ¹H NMR (DMSO-d₆, δ = 2.5 ppm, 400 MHz): δ 12.27 (br s, 1H), 7.40 (br s, 1H), 3.50 (s, 3H), 1.32 (s, 6H). HRMS: Anal. Calcd. for [M + H]⁺ C₆H₁₂NO₄: 162.0766; found 162.0765. |
| Cap-62 | 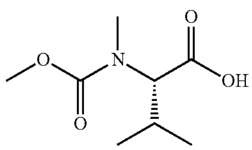 | ¹H NMR (DMSO-d₆, δ = 2.5 ppm, 400 MHz): δ 12.74 (br s, 1H), 4.21 (d, J = 10.3, 0.6H), 4.05 (d, J = 10.0, 0.4H), 3.62/3.60 (two singlets, 3H), 3.0 (s, 3H), 2.14-2.05 (m, 1H), 0.95 (d, J = 6.3, 3H), 0.81 (d, J = 6.6, 3H). LC/MS: Anal. Calcd. for [M − H]⁻ C₈H₁₄NO₄: 188.09; found 188.05. |
| Cap-63 | 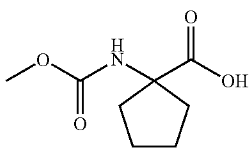 | [Note: the reaction was allowed to run for longer than what was noted for the general procedure.] ¹H NMR (DMSO-d₆, δ = 2.5 ppm, 400 MHz): 12.21 (br s, 1H), 7.42 (br s, 1H), 3.50 (s, 3H), 2.02-1.85 (m, 4H), 1.66-1.58 (m, 4H). LC/MS: Anal. Calcd. for [M + H]⁺ C₈H₁₄NO₄: 188.09; found 188.19. |
| Cap-64 | 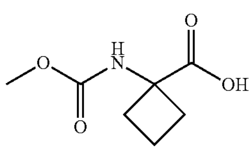 | [Note: the reaction was allowed to run for longer than what was noted for the general procedure.] ¹H NMR (DMSO-d₆, δ = 2.5 ppm, 400 MHz): 12.35 (br s, 1H), 7.77 (s, 0.82H), 7.56/7.52 (overlapping br s, 0.18H), 3.50 (s, 3H), 2.47-2.40 (m, 2H), 2.14-2.07 (m, 2H), 1.93-1.82 (m, 2H). |

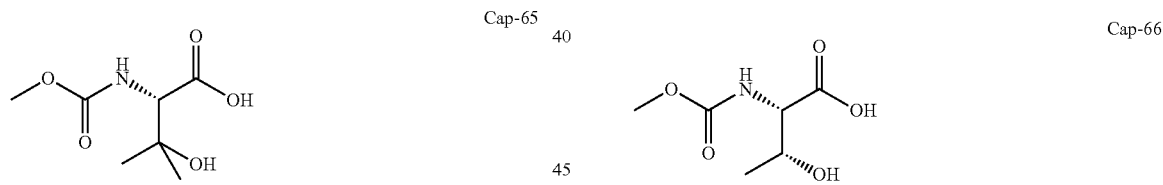

Cap-65

Cap-66

Cap-67

Methyl chloroformate (0.65 mL, 8.39 mmol) was added dropwise over 5 min to a cooled (ice-water) mixture of Na₂CO₃ (0.449 g, 4.23 mmol), NaOH (8.2 mL of 1M/H₂O, 8.2 mmol) and (5)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with CH₂Cl₂, and the aqueous phase was cooled with ice-water bath and acidified with concentrated HCl to a pH region of 1-2. The volatile component was removed in vacuo and the residue was taken up in a 2:1 mixture of MeOH/CH₂Cl₂ (15 mL) and filtered, and the filtrate was rotervaped to afford Cap-65 as a white semi-viscous foam (1.236 g). ¹H NMR (DMSO-d₆, δ=2.5 ppm, 400 MHz): δ 6.94 (d, J=8.5, 0.9 H), 6.53 (br s, 0.1H), 3.89 (d, J=8.8, 1H), 2.94 (s, 3H), 1.15 (s, 3H), 1.13 (s, 3H).

Cap-66 and -67 were prepared from appropriate commercially available starting materials by employing the procedure described for the synthesis of Cap-65.

¹H NMR (DMSO-d₆, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

¹H NMR (DMSO-d₆, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted].

Cap-68

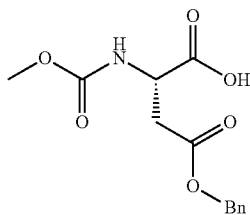

Cap-69a and -69b

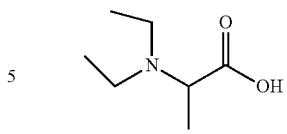

Cap-69a: (R)-enantiomer
Cap-69b: (S)-enantiomer

Methyl chloroformate (0.38 ml, 4.9 mmol) was added drop-wise to a mixture of 1N NaOH (aq) (9.0 ml, 9.0 mmol), 1M NaHCO$_3$ (aq) (9.0 ml, 9.0 mol), L-aspartic acid β-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH~1-2, and extracted with ethyl acetate (3×50 ml). The combined organic layers were washed with brine, dried (Na$_2$SO$_4$), filtered, and concentrated in vacuo to afford Cap-68 as a light yellow oil (1.37 g; mass is above theoretical yield, and the product was used without further purification). $^1$H NMR (DMSO-d$_6$, δ=2.5 ppm, 500 MHz): δ 12.88 (br s, 1H), 7.55 (d, =8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC/MS: Anal. Calcd. For [M+H]$^+$ C$_{13}$H$_{16}$NO$_6$: 282.10; found 282.12.

NaCNBH$_3$ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a Dowex® 50WX8-100 ion-exchange resin (column was washed with water, and the compound was eluted with dilute NH$_4$OH, prepared by mixing 18 ml of NH$_4$OH and 282 ml of water) to afford Cap-69 (2.0 g) as an off-white soft hygroscopic solid. $^1$H NMR (DMSO-d$_6$, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to -74x were prepared according to the procedure described for the synthesis of Cap-69 by employing appropriate starting materials.

| | | |
|---|---|---|
| Cap-70a: (R) Cap-70b: (S) | 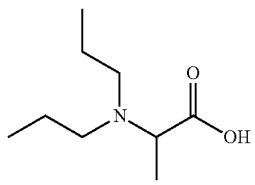 | $^1$H NMR (DMSO-d$_6$, δ = 2.5 ppm, 400 MHz): δ 3.42 (q, J = 7.1, 1H), 2.68-2.60 (m, 4H), 1.53-1.44 (m, 4H), 1.19 (d, J = 7.3, 3H), 0.85 (t, J = 7.5, 6H). LC/MS: Anal. Calcd. for [M + H]$^+$ C$_9$H$_{20}$NO$_2$: 174.15; found 174.13. |
| Cap-71a: (R) Cap-71b: (S) | 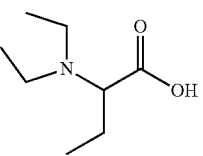 | $^1$H NMR (DMSO-d$_6$, δ = 2.5 ppm, 500 MHz): δ 3.18-3.14 (m, 1H), 2.84-2.77 (m, 2H), 2.76-2.68 (m, 2H), 1.69-1.54 (m, 2H), 1.05 (t, J = 7.2, 6H), 0.91 (t, J = 7.3, 3H). LC/MS: Anal. Calcd. for [M + H]$^+$ C$_8$H$_{18}$NO$_2$: 160.13; found 160.06. |
| Cap-72 | 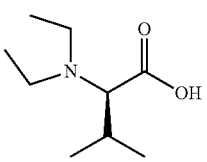 | $^1$H NMR (DMSO-d$_6$, δ = 2.5 ppm, 400 MHz): δ 2.77-2.66 (m, 3H), 2.39-2.31 (m, 2H), 1.94-1.85 (m, 1H), 0.98 (t, J = 7.1, 6H), 0.91 (d, J = 6.5, 3H), 0.85 (d, J = 6.5, 3H). LC/MS: Anal. Calcd. for [M + H]$^+$ C$_9$H$_{20}$NO$_2$: 174.15; found 174.15. |
| Cap-73 | 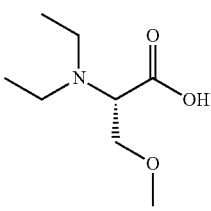 | $^1$H NMR (DMSO-d$_6$, δ = 2.5 ppm, 500 MHz): δ 9.5 (br s, 1H), 3.77 (dd, J = 10.8, 4.1, 1H), 3.69-3.61 (m, 2H), 3.26 (s, 3H), 2.99-2.88 (m, 4H), 1.13 (t, J = 7.2, 6H). |

Cap-74 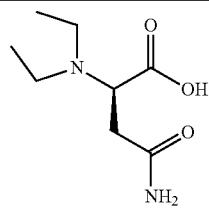

¹H NMR (DMSO-d₆, δ = 2.5 ppm, 500 MHz): δ 7.54 (s, 1H), 6.89 (s, 1H), 3.81 (t, J = 6.6, k, 1H), 2.82-2.71 (m, 4H), 2.63 (dd, J = 15.6, 7.0, 1H), 2.36 (dd, J = 15.4, 6.3, 1H), 1.09 (t, J = 7.2, 6H). RT = 0.125 minutes (Cond. 2); LC/MS: Anal. Calcd. for [M + H]⁺ $C_8H_{17}N_2O_3$: 189.12; found 189.13.

Cap-74x 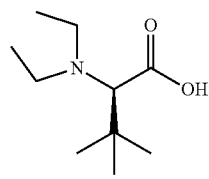

LC/MS: Anal. Calcd. for [M + H]⁺ $C_{10}H_{22}NO_2$: 188.17; found 188.21

Cap-75 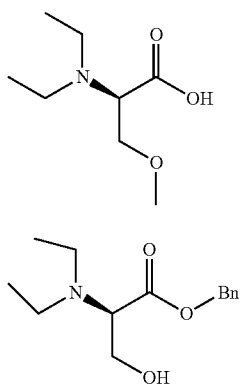

Cap-75, step a

NaBH₃CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H₂O/TFA) to afford the TFA salt of (R)-benzyl 2-(diethylamino)-3-hydroxypropanoate as a colorless viscous oil (1.9 g). ¹H NMR (DMSO-d₆, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC/MS (Cond. 2): RT=1.38 min; LC/MS: Anal. Calcd. for [M+H]⁺ $C_{14}H_{22}NO_3$: 252.16; found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 µL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH₃/Methanol. Removal of the volatile component in vacuo afforded Cap-75, contaminated with (R)-2-(diethylamino)-3-hydroxypropanoic acid, as a yellow semi-solid (100 mg). The product was used as is without further purification.

Cap-76 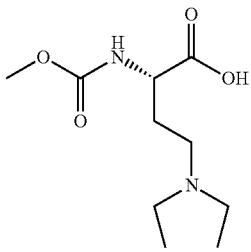

NaCNBH₃ (1.60 g, 24.2 mmol) was added in batches to a chilled (~15° C.) water/MeOH (12 mL each) solution of (S)-4-amino-2-(tert-butoxycarbonylamino)butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with Dowex® 50WX8-100 ion-exchange resin (column was washed with water and the compound was eluted with dilute NH₄OH, prepared from 18 ml of NH₄OH and 282 ml of water) to afford intermediate (S)-2-amino-4-(diethylamino)butanoic acid as an off-white solid (1.73 g).

Methyl chloroformate (0.36 mL, 4.65 mmol) was added drop-wise over 11 min to a cooled (ice-water) mixture of Na₂CO₃ (0.243 g, 2.29 mmol), NaOH (4.6 mL of 1M/H₂O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH₂Cl₂ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M NH$_3$/MeOH) to afford impure Cap-76 as an off-white solid (704 mg). $^1$H NMR (MeOH-d$_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]$^+$ C$_{10}$H$_{21}$N$_2$O$_4$: 233.15; found 233.24.

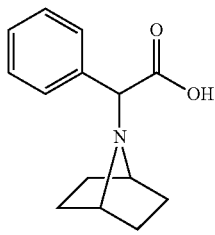

Cap-77a and -77b

Cap-77a: enantiomer-1
Cap-77b: enantiomer-2

The synthesis of Cap-77 was conducted according to the procedure described for Cap-7 by using 7-azabicyclo[2.2.1] heptane for the SN$_2$ displacement step, and by effecting the enantiomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% CO$_2$-10% EtOH at 70 mL/min, and a temperature of 35° C. to provide 124.5 mg of enantiomer-1 and 133.8 mg of enantiomer-2. These benzyl esters were hydrogenolysed according to the preparation of Cap-7 to provide Cap-77: $^1$H NMR (DMSO-d$_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4 H), 1.57-1.46 (m, 4H). LC (Cond. 1): RT=0.67 min; LC/MS: Anal. Calcd. for [M+H]$^+$ C$_{14}$H$_{18}$NO$_2$: 232.13; found 232.18. HRMS: Anal. Calcd. for [M+H]$^+$ C$_{14}$H$_{18}$NO$_2$: 232.1338; found 232.1340.

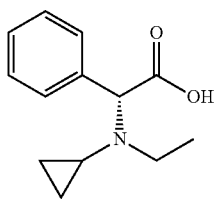

Cap-78

NaCNBH$_3$ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH$_3$ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC (H$_2$O/MeOH/TFA) to afford the TFA salt of Cap-78 as a colorless viscous oil (353 mg). $^1$H NMR (DMSO-d$_6$, δ=2.5 ppm, 400 MHz; after D$_2$O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC/MS: Anal. Calcd. for [M+H]$^+$ C$_{13}$H$_{18}$NO$_2$: 220.13; found 220.21. HRMS: Anal. Calcd. for [M+H]$^+$ C$_{13}$H$_{18}$NO$_2$: 220.1338; found 220.1343.

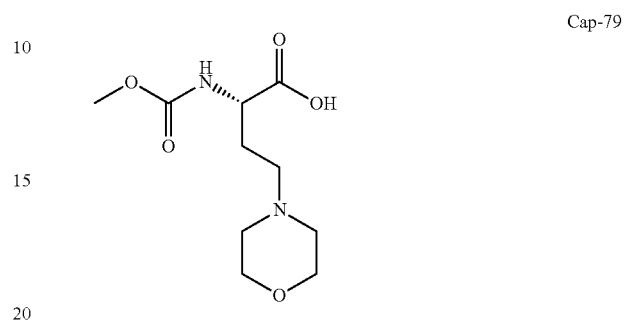

Cap-79

Ozone was bubbled through a cooled (−78° C.) CH$_2$Cl$_2$ (5.0 mL) solution Cap-55 (369 mg, 2.13 mmol) for about 50 min until the reaction mixture attained a tint of blue color. Me$_2$S (10 pipette drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH$_3$CN (149 mg, 2.25 mmol) was added to a MeOH (5.0 mL) solution of the above crude material and morpholine (500 µL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH$_3$/MeOH elution) and a reverse phase HPLC (H$_2$O/MeOH/TFA) to afford Cap-79 containing unknown amount of morpholine.

In order to consume the morpholine contaminant, the above material was dissolved in CH$_2$Cl$_2$ (1.5 mL) and treated with Et$_3$N (0.27 mL, 1.94 mmol) followed by acetic anhydride (0.10 mL, 1.06 mmol) and stirred at ambient condition for 18 hr. THF (1.0 mL) and H$_2$O (0.5 mL) were added and stirring continued for 1.5 hr. The volatile component was removed in vacuo, and the resultant residue was passed through MCX resin (MeOH wash; 2.0 N NH$_3$/MeOH elution) to afford impure Cap-79 as a brown viscous oil, which was used for the next step without further purification.

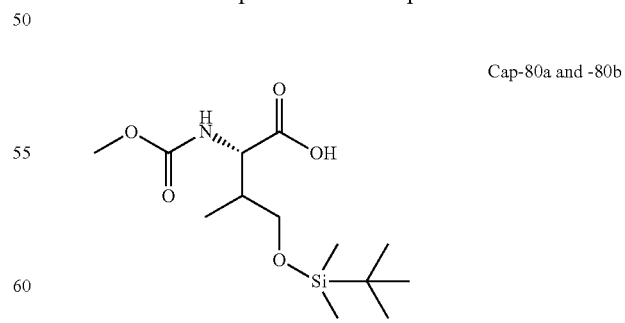

Cap-80a and -80b

Cap-80a: S/S-diastereomer
Cap-80b: S/R-diastereomer

SOCl$_2$ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO$_3$ solution. The aqueous phase was extracted with EtOAc (150 mL, 2×), and the combined organic phase was dried (MgSO$_4$), filtered, and concentrated in vacuo to afford (S)-1-benzyl 4-methyl 2-aminosuccinate as a colorless oil (9.706 g). $^1$H NMR (DMSO-d$_6$, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]$^+$ C$_{12}$H$_{16}$NO$_4$: 238.11; found 238.22.

Pb(NO$_3$)$_2$ (6.06 g, 18.3 mmol) was added over 1 min to a CH$_2$Cl$_2$ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et$_3$N (3.0 mL, 21.5 mmol), and the heterogeneous mixture was stirred at ambient condition for 48 hr. The mixture was filtered and the filtrate was treated with MgSO$_4$ and filtered again, and the final filtrate was concentrated. The resulting crude material was submitted to a Biotage purification (350 g silica gel, CH$_2$Cl$_2$ elution) to afford (S)-1-benzyl 4-methyl 2-(9-phenyl-9H-fluoren-9-ylamino)succinate as highly viscous colorless oil (7.93 g). $^1$H NMR (DMSO-d$_6$, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]$^+$ C$_{31}$H$_{28}$NO$_4$: 478.20; found 478.19.

LiHMDS (9.2 mL of 1.0 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for ~1 hr. MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a Biotage (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ 4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ 4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC/MS: Anal. Calcd. for [M+H]$^+$ C$_{32}$H$_{30}$NO$_4$: 492.22; found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-d$_5$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]$^+$ C$_{31}$H$_{30}$NO$_3$: 464.45; found 464.22. (2S,3R) isomer: $^1$H NMR (DMSO-d$_5$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC/MS: Anal. Calcd. for [M+H]$^+$ C$_{31}$H$_{30}$NO$_3$: 464.45; found 464.52.

The relative stereochemical assignments of the DIBAL-reduction products were made based on NOE studies conducted on lactone derivatives prepared from each isomer by employing the following protocol: LiHMDS (50 μL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a Biotage purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for [M+Na]$^+$ C$_{24}$H$_{21}$NNaO$_2$: 378.15; found 378.42. (3S,4R)-lactone isomer: $^1$H NMR (DMSO-d$_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for [M+Na]$^+$ C$_{24}$H$_{21}$NNaO$_2$: 378.15; found 378.49.

TBDMS-Cl (48 mg, 0.312 mmol) followed by imidazole (28.8 mg, 0.423 mmol) were added to a CH$_2$Cl$_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH$_2$Cl$_2$ (30 mL) and washed with water (15 mL), and the organic layer was dried (MgSO$_4$), filtered, and concentrated in vacuo. The resultant crude material was purified with a Biotage (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-d$_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for [M+H]$^+$ C$_{37}$H$_{44}$NO$_3$Si: 578.31; found 578.40. (2S,3R)-silyl ether isomer: $^1$H NMR (DMSO-d$_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S,3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H$_2$ as necessary. The reaction mixture was diluted with CH$_2$Cl$_2$ and filtered through a pad of diatomaceous earth (Celite-545®), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/H$_2$O) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S,3R)-2-amino-4-(tert-butyldimethylsilyloxy)-3-methylbutanoic acid. (2S,3S)-amino acid isomer: $^1$H NMR (Methanol-d$_4$, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC/MS: Anal. Calcd. for [M+H]$^+$ C$_{11}$H$_{26}$NO$_3$Si: 248.17; found 248.44. (2S,3R)-amino acid isomer: $^1$H NMR (Methanol-d$_4$, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal, Calcd. for [M+H]$^+$ C$_{11}$H$_{26}$NO$_3$Si: 248.17; found 248.44.

Water (1 mL) and NaOH (0.18 mL of 1.0 M/H$_2$O, 0.18 mmol) were added to a mixture of (2S,3S)-2-amino-4-(tert-butyldimethylsilyloxy)-3-methylbutanoic acid (41.9 mg, 0.169 mmol) and Na$_2$CO$_3$ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH$_2$Cl$_2$ (15 mL, 2×). The combined organic phase was dried (MgSO$_4$), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: $^1$H NMR (DMSO-d$_6$, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for [M+Na]$^+$ C$_{13}$H$_{27}$NNaO$_5$Si: 328.16; found 328.46. Cap-80b: $^1$H NMR (CDCl$_3$, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for [M+Na]$^+$ C$_{13}$H$_{27}$NNaO$_5$Si: 328.16; found 328.53. The crude products were utilized without further purification.

Cap-81

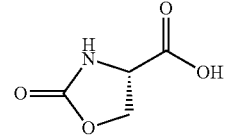

Prepared according to the protocol described by Falb et al. *Synthetic Communications* 1993, 23, 2839.

Cap-82 to Cap-85

Cap-82 to Cap-85 were synthesized from appropriate starting materials according to the procedure described for Cap-51 or Cap-13. The samples exhibited similar spectral profiles as that of their enantiomers (i.e., Cap-4, Cap-13, Cap-51 and Cap-52, respectively).

Cap-82

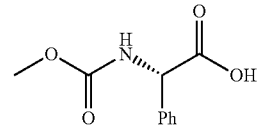

Cap-83

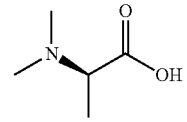

Cap-84

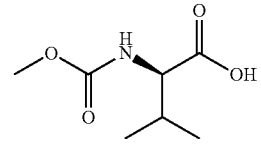

Cap-85

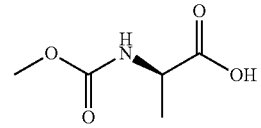

Cap-86

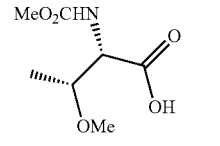

To a mixture of O-methyl-L-threonine (3.0 g, 22.55 mmol), NaOH (0.902 g, 22.55 mmol) in H$_2$O (15 mL) was added ClCO$_2$Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH$_2$Cl$_2$ (250 mL) and the combined organic phases were concentrated under in vacuo to afford a colorless oil (4.18 g, 97%) which was of sufficient purity for use in subsequent steps. ¹HNMR (400 MHz, CDCl₃) δ 4.19 (s, 1H), 3.92-3.97 (m, 1H), 3.66 (s, 3H), 1.17 (d, J=7.7 Hz, 3H). LCMS: Anal. Calcd. for C₇H₁₃NO₅: 191; found: 190 (M−H)⁻.

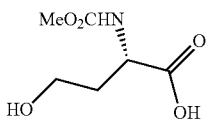

Cap-87

To a mixture of L-homoserine (2.0 g, 9.79 mmol), Na₂CO₃ (2.08 g, 19.59 mmol) in H₂O (15 mL) was added ClCO₂Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated in vacuo to afford a colorless solid (0.719 g, 28%) which was of sufficient purity for use in subsequent steps. ¹HNMR (400 MHz, CDCl₃) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for C₇H₁₃NO₅: 191; found: 192 (M+H)⁺.

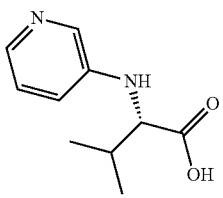

Cap-88

A mixture of L-valine (1.0 g, 8.54 mmol), 3-bromopyridine (1.8 mL, 18.7 mmol), K₂CO₃ (2.45 g, 17.7 mmol) and CuI (169 mg, 0.887 mmol) in DMSO (10 mL) was heated at 100° C. for 12 h. The reaction mixture was cooled to rt, poured into H₂O (ca. 150 mL) and washed with EtOAc (×2). The organic layers were extracted with a small amount of H₂O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H₂O (200 mL), MeOH (200 mL), and then NH₃ (3M in MeOH, 2×200 mL). The appropriate fractions was concentrated in vacuo and the residue (ca. 1.1 g) was dissolved in H₂O, frozen and lyophylized. The title compound was obtained as a foam (1.02 g, 62%). ¹HNMR (400 MHz, DMSO-d₆) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for C₁₀H₁₄N₂O₂: 194; found: 195 (M+H)⁺.

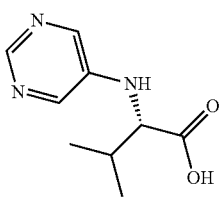

Cap-89

A mixture of L-valine (1.0 g, 8.54 mmol), 5-bromopyrimidine (4.03 g, 17.0 mmol), K₂CO₃ (2.40 g, 17.4 mmol) and CuI (179 mg, 0.94 mmol) in DMSO (10 mL) was heated at 100° C. for 12 h. The reaction mixture was cooled to RT, poured into H₂O (ca. 150 mL) and washed with EtOAc (×2). The organic layers were extracted with a small amount of H₂O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H₂O (200 mL), MeOH (200 mL), and then NH₃ (3M in MeOH, 2×200 mL). The appropriate fractions was concentrated in vacuo and the residue (ca. 1.1 g) was dissolved in H₂O, frozen and lyophylized. The title compound was obtained as a foam (1.02 g, 62%). ¹HNMR (400 MHz, CD₃OD) showed the mixture to contain valine and the purity could not be estimated. The material was used as is in subsequent reactions. LCMS: Anal. Calcd. for C₉H₁₃N₃O₂: 195; found: 196 (M+H)⁺.

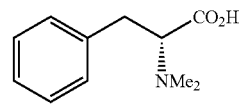

Cap-90

Cap-90 was prepared according to the method described for the preparation of Cap-1. The crude material was used as is in subsequent steps. LCMS: Anal, Calcd. for C₁₁H₁₅NO₂: 193; found: 192 (M−H)⁻.

The following caps were prepared according to the method used for preparation of cap 51 unless noted otherwise:

| Cap | Structure | LCMS |
|---|---|---|
| Cap-91 | NHCO₂Me, CO₂H | LCMS: Anal. Calcd. for C₁₁H₁₃NO₄: 223; found: 222 (M − H)⁻. |
| Cap-92 | NHCO₂Me, CO₂H | LCMS: Anal. Calcd. for C₁₁H₁₃NO₄: 223; found: 222 (M − H)⁻. |
| Cap-93 | 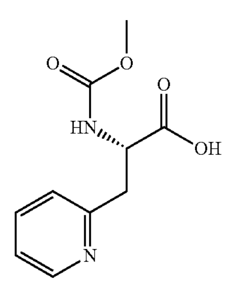 [SMILES: COC(=O)N[C@@H](Cc1ccccn1)C(=O)O] | LCMS: Anal. Calcd. for C₁₀H₁₂N₂O₄: 224; found: 225 (M + H)⁺. |
| Cap-94 | 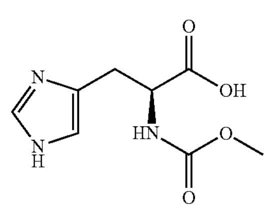 | LCMS: Anal. Calcd. for C₈H₁₁N₃O₄: 213; found: 214 (M + H)⁺. |

-continued

| Cap | Structure | LCMS |
|---|---|---|
| Cap-95 | (methyl carbamate of 3-amino-5-phenylpentanoic acid) | LCMS: Anal. Calcd. for $C_{13}H_{17}NO_4$: 251; found: 250 $(M - H)^-$. |
| Cap-96 | (methyl carbamate of 3-amino-4-phenylbutanoic acid) | LCMS: Anal. Calcd. for $C_{12}H_{15}NO_4$: 237; found: 236 $(M - H)^-$. |
| Cap-97 | (methyl carbamate of cis-2-aminocyclohexanecarboxylic acid) | LCMS: Anal. Calcd. for $C_9H_{15}NO_4$: 201; found: 200 $(M - H)^-$. |
| Cap-98 | (methyl carbamate of trans-2-aminocyclohexanecarboxylic acid) | LCMS: Anal. Calcd. for $C_9H_{15}NO_4$: 201; found: 202 $(M + H)^+$. |
| Cap-99 | (methyl carbamate of 3-aminocyclopentanecarboxylic acid, one enantiomer) | $^1$HNMR (400 MHz, $CD_3OD$) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-99a | (methyl carbamate of 3-aminocyclopentanecarboxylic acid, other enantiomer) | $^1$HNMR (400 MHz, $CD_3OD$) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |

-continued

| Cap | Structure | LCMS |
|---|---|---|
| Cap-100 | (methyl carbamate of 3-amino-4-(2-fluorophenyl)butanoic acid) | LCMS: Anal. Calcd. for $C_{12}H_{14}NO_4F$: 255; found: 256 $(M + H)^+$. |
| Cap-101 | (methyl carbamate of phenylalanine, one enantiomer) | LCMS: Anal. Calcd. for $C_{11}H_{13}NO_4$: 223; found: 222 $(M - H)^-$. |
| Cap-102 | (methyl carbamate of phenylalanine, other enantiomer) | LCMS: Anal. Calcd. for $C_{11}H_{13}NO_4$: 223; found: 222 $(M - H)^-$. |
| Cap-103 | (methyl carbamate of 3-(pyridin-2-yl)alanine) | LCMS: Anal. Calcd. for $C_{10}H_{12}N_2O_4$: 224; found: 225 $(M + H)^+$. |
| Cap-104 | (methyl carbamate of trans-4-aminocyclohexanecarboxylic acid) | $^1$HNMR (400 MHz, $CD_3OD$) δ 3.60 (s, 3H), 3.50-3.53 (m, 1H), 2.66-2.69 and 2.44-2.49 (m, 1H), 1.91-2.01 (m, 2H), 1.62-1.74 (m, 4H), 1.51-1.62 (m, 2H). |

| Cap | Structure | LCMS |
|---|---|---|
| Cap-105 | 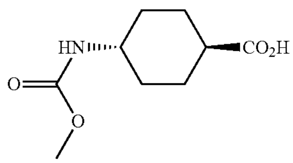 | ¹HNMR (400 MHz, CD₃OD) δ 3.60 (s, 3H), 3.33-3.35 (m, 1H, partially obscured by solvent), 2.37-2.41 and 2.16-2.23 (m, 1H), 1.94-2.01 (m, 4H), 1.43-1.53 (m, 2H), 1.17-1.29 (m, 2H). |
| Cap-106 | 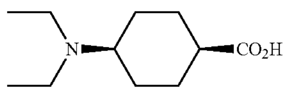 | ¹HNMR (400 MHz, CD₃OD) δ 3.16 (q, J = 7.3 Hz, 4H), 2.38-2.41 (m, 1H), 2.28-2.31 (m, 2H), 1.79-1.89 (m, 2H), 1.74 (app, ddd J = 3.5, 12.5, 15.9 Hz, 2H), 1.46 (app dt J = 4.0, 12.9 Hz, 2H), 1.26 (t, J = 7.3 Hz, 6H) |
| | Prepared from cis-4-aminocyclohexane carboxylic acid and acetaldehyde by employing a similar procedure described for the synthesis of Cap-2. The crude HCl salt was passed through MCX (MeOH/H₂O/CH₂Cl₂ wash; 2N NH₃/MeOH elution) to afford an oil, which was dissolved in CH₃CN/H₂O and lyophilized to afford a tan solid. | |
| Cap-107 | 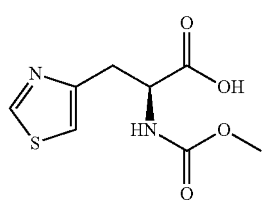 | LCMS: Anal. Calcd. for C₈H₁₀N₂O₄S: 230; found: 231 (M + H)⁺. |
| Cap-108 | 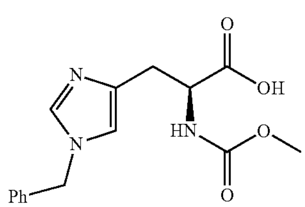 [SMILES: COC(=O)N[C@@H](Cc1cn(Cc2ccccc2)cn1)C(=O)O] | LCMS: Anal. Calcd. for C₁₅H₁₇N₃O₄: 303; found: 304 (M + H)⁺. |
| Cap-109 | 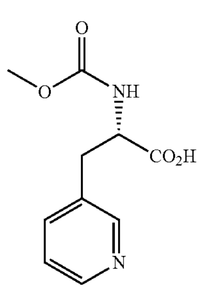 [SMILES: COC(=O)N[C@@H](Cc1cccnc1)C(=O)O] | LCMS: Anal. Calcd. for C₁₀H₁₂N₂O₄: 224; found: 225 (M + H)⁺. |
| Cap-110 | | LCMS: Anal. Calcd. for C₁₀H₁₂N₂O₄: 224; found: 225 (M + H)⁺. |
| Cap-111 | | LCMS: Anal. Calcd. for C₁₂H₁₆NO₈P: 333; found: 334 (M + H)⁺. |
| Cap-112 | | LCMS: Anal. Calcd. for C₁₃H₁₄N₂O₄: 262; found: 263 (M + H)⁺. |
| Cap-113 | | LCMS: Anal. Calcd. for C₁₈H₁₉NO₅: 329; found: 330 (M + H)⁺. |

| Cap | Structure | LCMS |
|---|---|---|
| Cap-114 | (azetidine with CO2Me on N and CO2H on C2) | ¹HNMR (400 MHz, CDCl₃) δ 4.82-4.84 (m, 1H), 4.00-4.05 (m, 2H), 3.77 (s, 3H), 2.56 (s, br, 2H) |
| Cap-115 | MeO₂CHN-CH(CH₃)-CH₂-CO₂H | ¹HNMR (400 MHz, CDCl₃) δ 5.13 (s, br, 1H), 4.13 (s, br, 1H), 3.69 (s, 3H), 2.61 (d, J = 5.0 Hz, 2H), 1.28 (d, J = 9.1 Hz, 3H). |
| Cap-116 | iPr-CH(NHCO₂Me)-CH₂-CO₂H | ¹HNMR (400 MHz, CDCl₃) δ 5.10 (d, J = 8.6 Hz, 1H), 3.74-3.83 (m, 1H), 3.69 (s, 3H), 2.54-2.61 (m, 2H), 1.88 (sept, J = 7.0 Hz, 1H), 0.95 (d, J = 7.0 Hz, 6H). |

Cap-117 to Cap-123

For the preparation of Cap-117 to Cap-123 the Boc amino acids were obtained from commercially sources and were deprotected by treatment with 25% TFA in $CH_2Cl_2$. After complete reaction as judged by LCMS the solvents were removed in vacuo and the corresponding TFA salt of the amino acid was carbamoylated with methyl chloroformate according to the procedure described for Cap-51.

| Cap | Structure | LCMS |
|---|---|---|
| Cap-117 | (N-methoxycarbonyl-β-homophenylalanine) | LCMS: Anal. Calcd. for $C_{12}H_{15}NO_4$: 237; found: 238 $(M + H)^+$. |
| Cap-118 | (N-methoxycarbonyl-β-homo(2-thienyl)alanine) | LCMS: Anal. Calcd. for $C_{10}H_{13}NO_4S$: 243; found: 244 $(M + H)^+$. |
| Cap-119 | (N-methoxycarbonyl-β-homo(2-thienyl)alanine, enantiomer) | LCMS: Anal. Calcd. for $C_{10}H_{13}NO_4S$: 243; found: 244 $(M + H)^+$. |

| Cap | Structure | LCMS |
|---|---|---|
| Cap-120 | 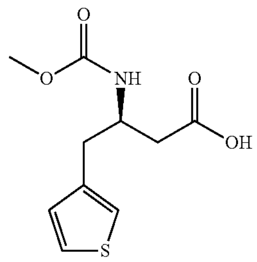 [SMILES: COC(=O)N[C@@H](CC(=O)O)Cc1ccsc1] | LCMS: Anal. Calcd. for $C_{10}H_{13}NO_4S$: 243; found: 244 $(M + H)^+$. |
| Cap-121 | 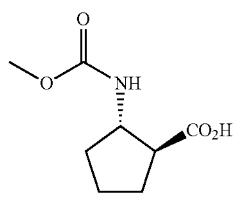 | $^1$HNMR (400 MHz, CDCl$_3$) δ 4.06-4.16 (m, 1H), 3.63 (s, 3H), 3.43 (s, 1H), 2.82 and 2.66 (s, br, 1H), 1.86-2.10 (m, 3H), 1.64-1.76 (m, 2H), 1.44-1.53 (m, 1H). |
| Cap-122 | 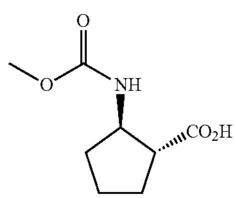 | $^1$HNMR profile is similar to that of its enantiomer, Cap-121. |
| Cap-123 | 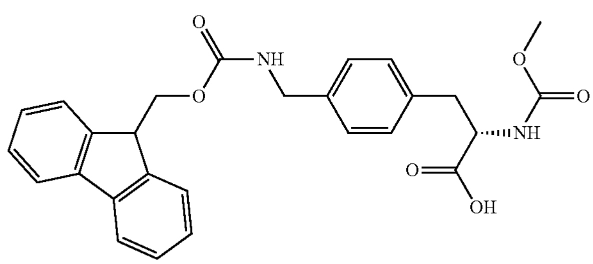 [SMILES: COC(=O)N[C@@H](Cc1ccc(CNC(=O)OCC2c3ccccc3-c3ccccc32)cc1)C(=O)O] | LCMS: Anal. Calcd. for $C_{27}H_{26}N_2O_6$: 474; found: 475 $(M + H)^+$. |

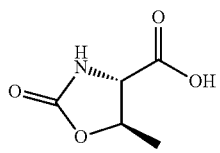

Cap-124

The hydrochloride salt of L-threonine tert-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc—CH$_2$Cl$_2$-MeOH (1:1:0.1) and then the organic phase concentrated in vacuo to give a colorless oil which was shown by LCMS to be the desired product. Both crops were combined to give 0.52 g of a solid. $^1$HNMR (400 MHz, CD$_3$OD) δ 4.60 (m, 1H), 4.04 (d, J=5.0 Hz, 1H), 1.49 (d, J=6.3 Hz, 3H). LCMS: Anal. Calcd. for $C_5H_7NO_4$: 145; found: 146 $(M+H)^+$.

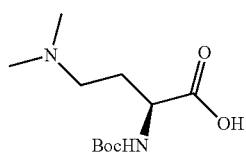

Cap-125

To a suspension of Pd(OH)$_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temp. The reaction mixture was filtered through a pad of diatomaceous earth (Celite®), and the volatile component was removed in vacuo. The resulting crude material was used as is for the next step. LC/MS: Anal. Calcd. for $C_{11}H_{22}N_2O_4$: 246; found: 247 $(M+H)^+$.

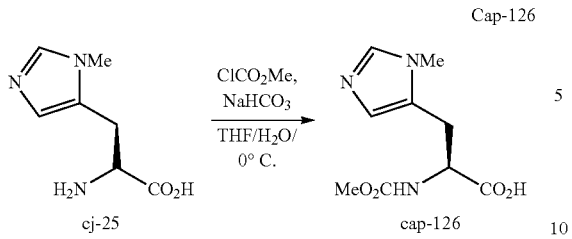

Cap-126

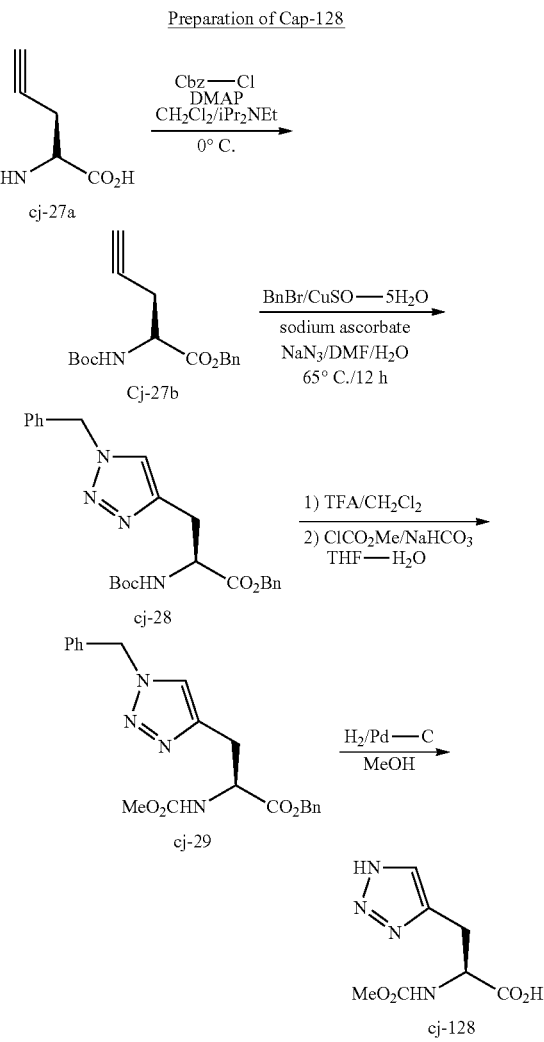

Preparation of Cap-128

This procedure is a modification of that used to prepare Cap-51. To a suspension of 3-methyl-L-histidine (0.80 g, 4.70 mmol) in THF (10 mL) and H$_2$O (10 mL) at 0° C. was added NaHCO$_3$ (0.88 g, 10.5 mmol). The resulting mixture was treated with ClCO$_2$Me (0.40 mL, 5.20 mmol) and the mixture allowed to stir at 0° C. After stirring for ca. 2h LCMS showed no starting material remaining. The reaction was acidified to pH 2 with 6 N HCl.

The solvents were removed in vacuo and the residue was suspended in 20 mL of 20% MeOH in CH$_2$Cl$_2$. The mixture was filtered and concentrated to give a light yellow foam (1.21 g,). LCMS and $^1$HNMR showed the material to be a 9:1 mixture of the methyl ester and the desired product. This material was taken up in THF (10 mL) and H$_2$O (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and $^1$H NMR confirm the absence of the ester. The title compound was obtained as its HCl salt contaminated with inorganic salts (1.91 g, >100%). The compound was used as is in subsequent steps without further purification. $^1$HNMR (400 MHz, CD$_3$OD) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H). LCMS: Anal. Calcd. for C$_9$H$_{13}$N$_3$O$_4$: 227.09; found: 228.09 (M+H)$^+$.

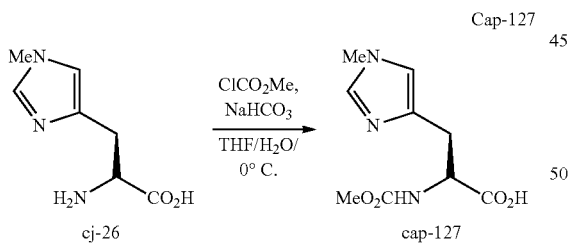

Cap-127

Cap-127 was prepared according to the method for Cap-126 above starting from (S)-2-amino-3-(1-methyl-1H-imidazol-4-yl)propanoic acid (1.11 g, 6.56 mmol), NaHCO$_3$ (1.21 g, 14.4 mmol) and ClCO$_2$Me (0.56 mL, 7.28 mmol). The title compound was obtained as its HCl salt (1.79 g, >100%) contaminated with inorganic salts. LCMS and $^1$H NMR showed the presence of ca. 5% of the methyl ester. The crude mixture was used as is without further purification. $^1$HNMR (400 MHz, CD$_3$OD) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H); LCMS: Anal. Calcd. for C$_9$H$_{13}$N$_3$O$_4$: 227.09; found: 228 (M+H)$^+$, Step 1. Preparation of (S)-benzyl 2-(tert-butoxycarbonylamino)pent-4-ynoate (cj-27b).

To a solution of cj-27a (1.01 g, 4.74 mmol), DMAP (58 mg, 0.475 mmol) and iPr$_2$NEt (1.7 mL, 9.8 mmol) in CH$_2$Cl$_2$ (100 mL) at 0° C. was added Cbz-Cl (0.68 mL, 4.83 mmol). The solution was allowed to stir for 4 h at 0° C., washed (1N KHSO$_4$, brine), dried (Na$_2$SO$_4$), filtered, and concentrated in vacuo. The residue was purified by flash column chromatography (TLC 6:1 hex:EtOAc) to give the title compound (1.30 g, 91%) as a colorless oil. $^1$HNMR (400 MHz, CDCl$_3$) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LCMS: Anal. Calcd. for $C_{17}H_{21}NO_4$: 303; found: 304 $(M+H)^+$.

Step 2. Preparation of (S)-benzyl 3-(1-benzyl-1H-1,2,3-triazol-4-yl)-2-(tert-butoxycarbonylamino)propanoate (cj-28).

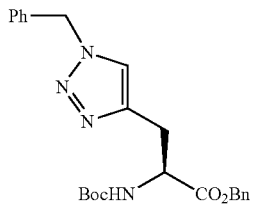

cj-28

To a mixture of (S)-benzyl 2-(tert-butoxycarbonylamino)pent-4-ynoate (0.50 g, 1.65 mmol), sodium ascorbate (0.036 g, 0.18 mmol), $CuSO_4 \cdot 5H_2O$ (0.022 g, 0.09 mmol) and $NaN_3$ (0.13 g, 2.1 mmol) in $DMF-H_2O$ (5 mL, 4:1) at rt was added BnBr (0.24 mL, 2.02 mmol) and the mixture was warmed to 65° C. After 5 h LCMS indicated low conversion. A further portion of $NaN_3$ (100 mg) was added and heating was continued for 12 h. The reaction was poured into EtOAc and $H_2O$ and shaken. The layers were separated and the aqueous layer extracted 3× with EtOAc and the combined organic phases washed ($H_2O \times 3$, brine), dried ($Na_2SO_4$), filtered, and concentrated. The residue was purified by flash (Biotage, 40+M 0-5% MeOH in $CH_2Cl_2$; TLC 3% MeOH in $CH_2Cl_2$) to afford a light yellow oil which solidified on standing (748.3 mg, 104%) The NMR was consistent with the desired product but suggests the presence of DMF. The material was used as is without further purification. $^1$HNMR (400 MHz, DMSO-$d_6$) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H).

LCMS: Anal. Calcd. for $C_{24}H_{28}N_4O_4$: 436; found: 437 $(M+H)^+$.

Step 3. Preparation of (S)-benzyl 3-(1-benzyl-1H-1,2,3-triazol-4-yl)-2-(methoxycarbonylamino)propanoate (cj-29).

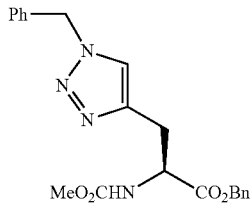

cj-29

A solution of (S)-benzyl 3-(1-benzyl-1H-1,2,3-triazol-4-yl)-2-(tert-butoxycarbonylamino)propanoate (0.52 g, 1.15 mmol) in $CH_2Cl_2$ was added TFA (4 mL). The mixture was allowed to stir at room temperature for 2 h. The mixture was concentrated in vacuo to give a colorless oil which solidified on standing. This material was dissolved in $THF—H_2O$ and cooled to 0° C. Solid $NaHCO_3$ (0.25 g, 3.00 mmol) was added followed by $ClCO_2Me$ (0.25 mL, 3.25 mmol). After stirring for 1.5 h the mixture was acidified to pH~2 with 6N HCl and then poured into $H_2O$-EtOAc. The layers were separated and the aq phase extracted 2× with EtOAc. The combined org layers were washed ($H_2O$, brine), dried ($Na_2SO_4$), filtered, and concentrated in vacuo to give a colorless oil (505.8 mg, 111%, NMR suggested the presence of an unidentified impurity) which solidified while standing on the pump. The material was used as is without further purification. $^1$HNMR (400 MHz, DMSO-$d_6$) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LCMS: Anal. Calcd. for $C_{21}H_{22}N_4O_4$: 394; found: 395 $(M+H)^+$.

Step 4. Preparation of (S)-2-(methoxycarbonylamino)-3-(1H-1,2,3-triazol-4-yl)propanoic acid (Cap-128).

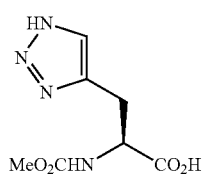

Cap-128

(S)-benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (Celite®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification. $^1$HNMR (400 MHz, DMSO-$d_6$) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LCMS: Anal. Calcd. for $C_7H_{10}N_4O_4$: 214; found: 215 $(M+H)^+$.

Preparation of Cap-129

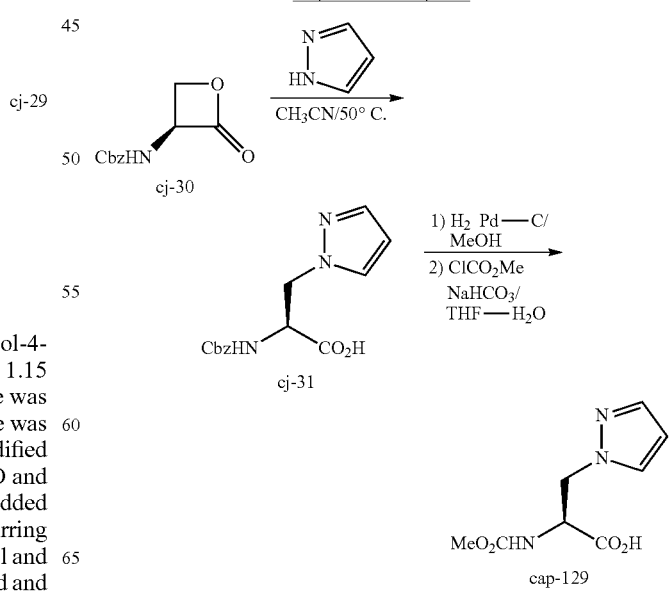

Step 1. Preparation of (S)-2-(benzyloxycarbonylamino)-3-(1H-pyrazol-1-yl)propanoic acid (cj-31).

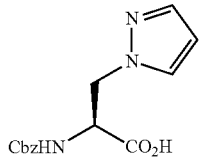

cj-31

A suspension of (S)-benzyl 2-oxooxetan-3-ylcarbamate (0.67 g, 3.03 mmol), and pyrazole (0.22 g, 3.29 mmol) in $CH_3CN$ (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of $CH_3CN$ (ca. 4 mL) to afford a second crop (43.5 mg). Total yield 3704 mg (44%). m.p. 165.5-168° C. lit m.p. 168.5-169.5 [Vederas et al. J. Am. Chem. Soc. 1985, 107, 7105]. $^1$HNMR (400 MHz, $CD_3OD$) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for $C_{14}H_{15}N_3O_4$: 289; found: 290 $(M+H)^+$.

Step 2. Preparation of (S)-2-(methoxycarbonylamino)-3-(1H-pyrazol-1-yl)propanoic acid (Cap-129).

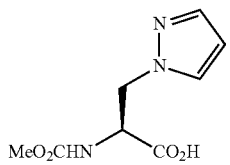

cap-129

(S)-2-(benzyloxycarbonylamino)-3-(1H-pyrazol-1-yl) propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL $H_2O$ and a few drops of 6N HCl. The homogeneous solution was filtered through diatomaceous earth (Celite®), and the MeOH removed in vacuo. The remaining solution was frozen and lyophilized to give a yellow foam (188.9 mg). This material was suspended in THF—$H_2O$ (1:1, 10 mL) and then cooled to 0° C. To the cold mixture was added $NaHCO_3$ (146.0 mg, 1.74 mmol) carefully (evolution of $CO_2$). After gas evolution had ceased (ca. 15 min) $ClCO_2Me$ (0.06 mL, 0.78 mmol) was added dropwise. The mixture was allowed to stir for 2 h and was acidified to pH~2 with 6N HCl and poured into EtOAc. The layers were separated and the aqueous phase extracted with EtOAC (×5). The combined organic layers were washed (brine), dried ($Na_2SO_4$), filtered, and concentrated to give the title compound as a colorless solid (117.8 mg, 79%). $^1$HNMR (400 MHz, DMSO-$d_6$) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for $C_8H_{11}N_3O_4$: 213; found: 214 $(M+H)^+$.

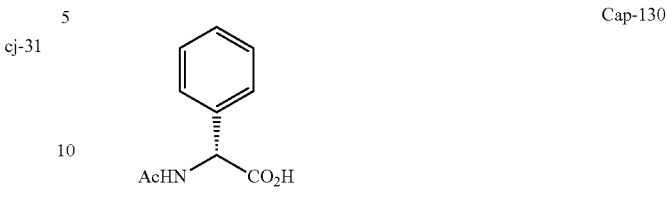

Cap-130

Cap-130 was prepared by acylation of commercially available (R)-phenylglycine analogous to the procedure given in: Calmes, M.; Daunts, J.; Jacquier, R.; Verducci, J. Tetrahedron, 1987, 43(10), 2285.

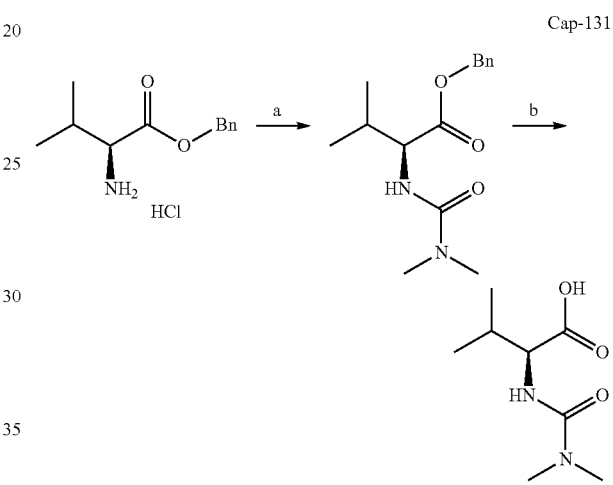

Cap-131

Step a: Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried ($MgSO_4$), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. $^1$H NMR (300 MHz, DMSO-$d_6$) δ ppm 0.84 (d, J=6.95 Hz, 3H), 0.89 (d, J=6.59 Hz, 3H), 1.98-2.15 (m, 1H), 2.80 (s, 6H), 5.01-5.09 (m, J=12.44 Hz, 1H), 5.13 (d, J=12.44 Hz, 1H), 6.22 (d, J=8.05 Hz, 1H), 7.26-7.42 (m, 5H). LC (Cond. 1): RT=1.76 min; MS: Anal. Calcd. for $[M+H]^+$ $C_{16}H_{22}N_2O_3$: 279.17; found 279.03.

Step b: To a MeOH (50 mL) solution of the intermediate prepared above (2.35 g; 8.45 mmol) was added Pd/C (10%; 200 mg) and the resulting black suspension was flushed with $N_2$ (3×) and placed under 1 atm of $H_2$. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. $^1$H NMR (500 MHz, DMSO-$d_6$) δ ppm 0.87 (d, J=4.27 Hz, 3H), 0.88 (d, J=3.97 Hz, 3H), 1.93-2.11

(m, 1H), 2.80 (s, 6H), 3.90 (dd, J=8.39, 6.87 Hz, 1H), 5.93 (d, J=8.54 Hz, 1H), 12.36 (s, 1H). LC (Cond. 1): RT=0.33 min; MS: Anal. Calcd. for [M+H]+ C8H17N2O3: 189.12; found 189.04.

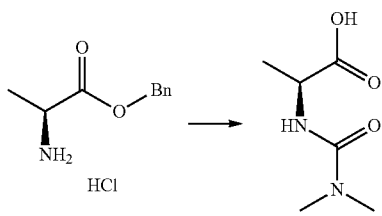

Cap-132

Cap-132 was prepared from (S)-benzyl 2-aminopropanoate hydrochloride according to the method described for Cap-131. 1H NMR (500 MHz, DMSO-d6) δ ppm 1.27 (d, J=7.32 Hz, 3H), 2.80 (s, 6H), 4.06 (qt, 1H), 6.36 (d, J=7.32 Hz, 1H), 12.27 (s, 1H). LC (Cond. 1): RT=0.15 min; MS: Anal. Calcd. for [M+H]+ C6H13N2O3: 161.09; found 161.00.

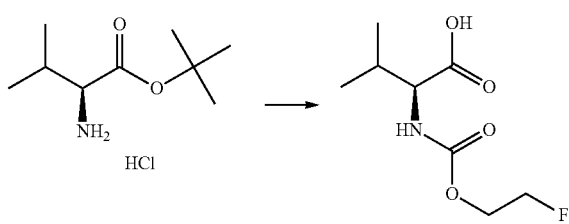

Cap-133

Cap-133 was prepared from (S)-tert-butyl 2-amino-3-methylbutanoate hydrochloride and 2-fluoroethyl chloroformate according to the method described for Cap-47. 1H NMR (500 MHz, DMSO-d6) δ ppm 0.87 (t, J=6.71 Hz, 6H), 1.97-2.10 (m, 1H), 3.83 (dd, J=8.39, 5.95 Hz, 1H), 4.14-4.18 (m, 1H), 4.20-4.25 (m, 1H), 4.50-4.54 (m, 1H), 4.59-4.65 (m, 1H), 7.51 (d, J=8.54 Hz, 1H), 12.54 (s, 1H).

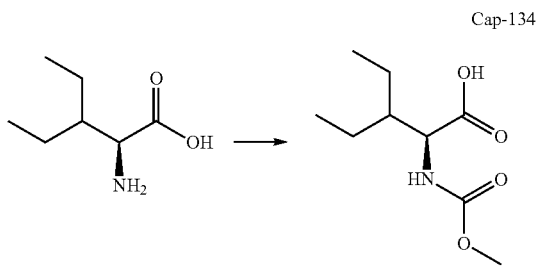

Cap-134

Cap-134 was prepared from (S)-diethyl alanine and methyl chloroformate according to the method described for Cap-51. 1H NMR (500 MHz, DMSO-d6) δ ppm 0.72-0.89 (m, 6H), 1.15-1.38 (m, 4H), 1.54-1.66 (m, 1H), 3.46-3.63 (m, 3H), 4.09 (dd, J=8.85, 5.19 Hz, 1H), 7.24 (d, J=8.85 Hz, 1H), 12.55 (s, 1H). LC (Cond. 2): RT=0.66 min; LC/MS: Anal. Calcd. for [M+H]+ C9H18NO4: 204.12; found 204.02.

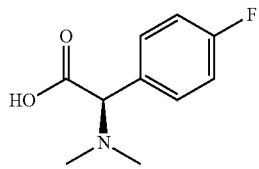

Cap-135

A solution of D-2-amino-(4-fluorophenyl)acetic acid (338 mg, 2.00 mmol), 1N HCl in diethylether (2.0 mL, 2.0 mmol) and formalin (37%, 1 mL) in methanol (5 mL) was subjected to balloon hydrogenation over 10% palladium on carbon (60 mg) for 16 h at 25° C. The mixture was then filtered through Celite to afford the HCl salt of Cap-135 as a white foam (316 mg, 80%). 1H NMR (300 MHz, MeOH-d4) δ 7.59 (dd, J=8.80, 5.10 Hz, 2H), 7.29 (t, J=8.6 Hz, 2H), 5.17 (s, 1H), 3.05 (v br s, 3H), 2.63 (v br s, 3H); Rf=0.19 min (Cond.-MS-W5); 95% homogeneity index; LRMS: Anal. Calcd. for [M+H]+ C10H13FNO2: 198.09; found: 198.10.

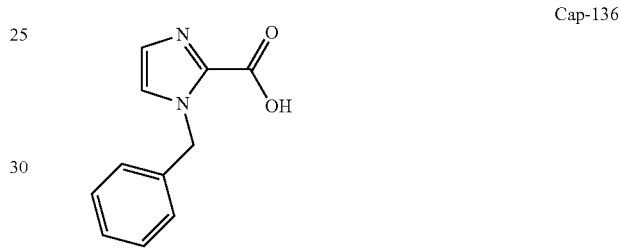

Cap-136

To a cooled (−50° C.) suspension of 1-benzyl-1H-imidazole (1.58 g, 10.0 mmol) in anhydrous diethyl ether (50 mL) under nitrogen was added n-butyl lithium (2.5 Min hexanes, 4.0 mL, 10.0 mmol) dropwise. After being stirred for 20 min at −50° C., dry carbon dioxide (passed through Drierite) was bubbled into the reaction mixture for 10 min before it was allowed to warm up to 25° C. The heavy precipitate which formed on addition of carbon dioxide to the reaction mixture was filtered to yield a hygroscopic, white solid which was taken up in water (7 mL), acidified to pH=3, cooled, and induced to crystallize with scratching. Filtration of this precipitate gave a white solid which was suspended in methanol, treated with 1N HCl/diethyl ether (4 mL) and concentrated in vacuo. Lyophilization of the residue from water (5 mL) afforded the HCl salt of Cap-136 as a white solid (817 mg, 40%). 1H NMR (300 MHz, DMSO-d6) δ 7.94 (d, J=1.5 Hz, 1H), 7.71 (d, J=1.5 Hz, 1H), 7.50-7.31 (m, 5H), 5.77 (s, 2H); Rf=0.51 min (Cond.-MS-W5); 95% homogeneity index; LRMS: Anal. Calc. for [M+H]+ C11H12N2O2: 203.08; found: 203.11.

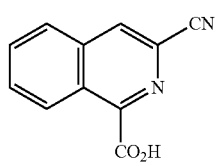

Cap-137

-continued

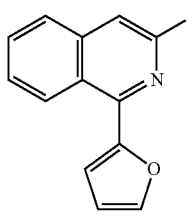

Cap-137, step a

A suspension of 1-chloro-3-cyanoisoquinoline (188 mg, 1.00 mmol; prepared according to the procedure in WO 2003/099274) (188 mg, 1.00 mmol), cesium fluoride (303.8 mg, 2.00 mmol), bis(tri-tert-butylphosphine)palladium dichloride (10 mg, 0.02 mmol) and 2-(tributylstannyl)furan (378 µL, 1.20 mmol) in anhydrous dioxane (10 mL) under nitrogen was heated at 80° C. for 16 h before it was cooled to 25° C. and treated with saturated, aqueous potassium fluoride solution with vigorous stirring for 1 h. The mixture was partitioned between ethyl acetate and water and the organic phase was separated, washed with brine, dried over $Na_2SO_4$, filtered and concentrated. Purification of the residue on silica gel (elution with 0% to 30% ethyl acetate/hexanes) afforded Cap-137, step a (230 mg, 105%) as a white solid which was carried forward directly. $R_f$=1.95 min (Cond.-MS-W2); 90% homogeneity index; LRMS: Anal. Calc. for $[M+H]^+$ $C_{14}H_8N_2O$: 221.07; found: 221.12.

Cap-137

To a suspension of Cap 137, step a, (110 mg, 0.50 mmol) and sodium periodate (438 mg, 2.05 mmol) in carbon tetrachloride (1 mL), acetonitrile (1 mL) and water (1.5 mL) was added ruthenium trichloride hydrate (2 mg, 0.011 mmol). The mixture was stirred at 25° C. for 2 h and then partitioned between dichloromethane and water. The aqueous layer was separated, extracted twice more with dichloromethane and the combined dichloromethane extracts were dried over $Na_2SO_4$, filtered and concentrated. Trituration of the residue with hexanes afforded Cap-137 (55 mg, 55%) as a grayish-colored solid. $R_f$=1.10 min (Cond.-MS-W2); 90% homogeneity index; LCMS: Anal. Calc. for $[M+H]^+$ $C_{11}H_8N_2O_2$: 200.08; found: 200.08, Caps 138 to 158

Synthetic Strategy. Method A.

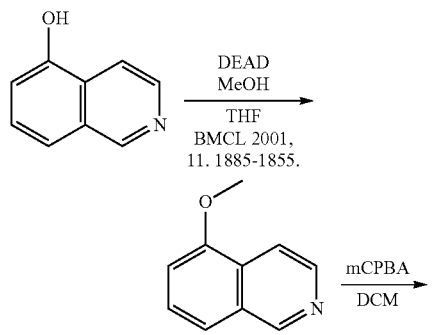

-continued

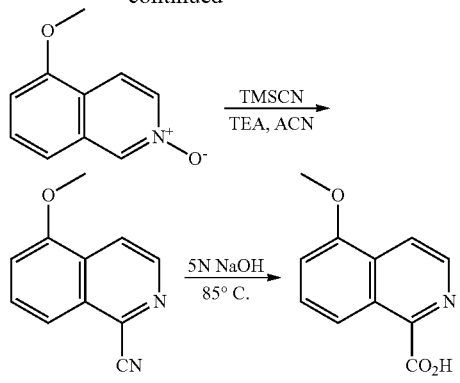

Cap-138

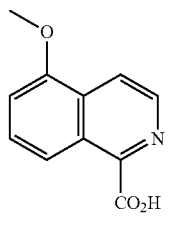

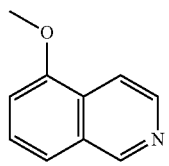

Cap-138, step a

To a stirred suspension of 5-hydroxyisoquinoline (prepared according to the procedure in WO 2003/099274) (2.0 g, 13.8 mmol) and triphenylphosphine (4.3 g, 16.5 mmol) in dry tetrahydrofuran (20 mL) was added dry methanol (0.8 mL) and diethyl azodicarboxylate (3.0 mL, 16.5 mmol) portionwise. The mixture was stirred at room temperature for 20 h before it was diluted with ethyl acetate and washed with brine, dried over $Na_2SO_4$, filtered and concentrated. The residue was preabsorbed onto silica gel and chromatographed (elution with 40% ethyl acetate/hexanes) to afford Cap-138, step a (1.00 g, 45%) as a light yellow solid. $^1$H NMR (CDCl$_3$, 500 MHz) δ 9.19 (s, 1H), 8.51 (d, J=6.0 Hz, 1H), 7.99 (d, J=6.0 Hz, 1H), 7.52-7.50 (m, 2H), 7.00-6.99 (m, 1H), 4.01 (s, 3H); $R_f$=0.66 min (Cond.-D2); 95% homogeneity index; LCMS: Anal. Calc. for $[M+H]^+$ $C_{10}H_{10}NO$: 160.08; found 160.1.

Cap-138, step b

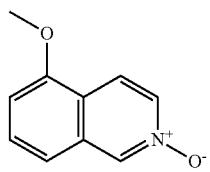

To a stirred solution of Cap 138, step a (2.34 g, 14.7 mmol) in anhydrous dichloromethane (50 mL) at room temperature was added meta-chloroperbenzoic acid (77%, 3.42 g, 19.8 mmol) in one portion. After being stirred for 20 h, powdered potassium carbonate (2.0 g) was added and the mixture was stirred for 1 h at room temperature before it was filtered and concentrated in vacuo to afford Cap-138, step b (2.15 g, 83%) as a pale, yellow solid which was sufficiently pure to carry forward directly. $^1$H NMR (CDCl$_3$, 400 MHz) δ 8.73 (d, J=1.5 Hz, 1H), 8.11 (dd, J=7.3, 1.7 Hz, 1H), 8.04 (d, J=7.1 Hz, 1H), 7.52 (t, J=8.1 Hz, 1H), 7.28 (d, J=8.3 Hz, 1H), 6.91 (d, J=7.8 Hz, 1H), 4.00 (s, 3H); R$_f$=0.92 min, (Cond.-D1); 90% homogeneity index; LCMS: Anal. Calc. for [M+H]$^+$ C$_{10}$H$_{10}$NO$_2$: 176.07; found: 176.0.

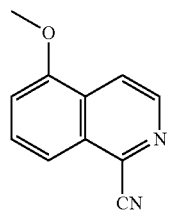

Cap-138, step c

To a stirred solution of Cap 138, step b (0.70 g, 4.00 mmol) and triethylamine (1.1 mL, 8.00 mmol) in dry acetonitrile (20 mL) at room temperature under nitrogen was added trimethylsilylcyanide (1.60 mL, 12.00 mmol). The mixture was heated at 75° C. for 20 h before it was cooled to room temperature, diluted with ethyl acetate and washed with saturated sodium bicarbonate solution and brine prior to drying over Na$_2$SO$_4$ and solvent concentration. The residue was flash chromatographed on silica gel (gradient elution with 5% ethyl acetate in hexanes to 25% ethyl acetate in hexanes) to afford Cap-138, step c (498.7 mg, 68%) as a white, crystalline solid along with 223 mg (30%) of additional Cap-138, step c recovered from the filtrate. $^1$H NMR (CDCl$_3$, 500 MHz) δ 8.63 (d, J=5.5 Hz, 1H), 8.26 (d, J=5.5 Hz, 1H), 7.88 (d, J=8.5 Hz, 1H), 7.69 (t, J=8.0 Hz, 1H), 7.08 (d, J=7.5 Hz, 1H), 4.04 (s, 3H); R$_f$=1.75 min, (Cond.-D1); 90% homogeneity index; LCMS: Anal. Calc. for [M+H]$^+$ C$_{11}$H$_9$N$_2$O: 185.07; found: 185.10.

Cap-138

Cap-138, step c (0.45 g, 2.44 mmol) was treated with 5N sodium hydroxide solution (10 mL) and the resulting suspension was heated at 85° C. for 4 h, cooled to 25° C., diluted with dichloromethane and acidified with 1N hydrochloric acid. The organic phase was separated, washed with brine, dried over Na$_2$SO$_4$, concentrated to ¼ volume and filtered to afford Cap-138 (0.44 g, 88.9%) as a yellow solid. $^1$H NMR (DMSO-d$_6$, 400 MHz) δ 13.6 (br s, 1H), 8.56 (d, J=6.0 Hz, 1H), 8.16 (d, J=6.0 Hz, 1H), 8.06 (d, J=8.8 Hz, 1H), 7.71-7.67 (m, 1H), 7.30 (d, J=8.0 Hz, 1H), 4.02 (s, 3H); R$_f$=0.70 min (Cond.-D1); 95% homogeneity index; LCMS: Anal. Calc. for [M+H]$^+$ C$_{11}$H$_{10}$NO$_3$: 204.07; found: 204.05.

Synthetic Strategy. Method B (derived from *Tetrahedron Letters*, 2001, 42, 6707).

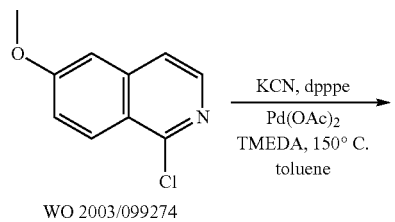

WO 2003/099274

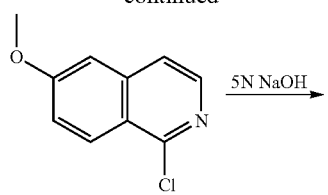

5N NaOH

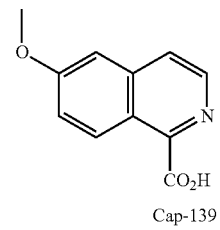

Cap-139

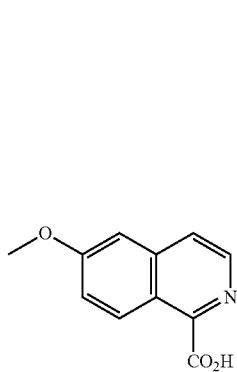

Cap-139, step a

To a thick-walled, screw-top vial containing an argon-degassed suspension of 1-chloro-6-methoxyisoquinoline (1.2 g, 6.2 mmol; prepared according to the procedure in WO 2003/099274), potassium cyanide (0.40 g, 6.2 mmol), 1,5-bis(diphenylphosphino)pentane (0.27 g, 0.62 mmol) and palladium (II) acetate (70 mg, 0.31 mmol) in anhydrous toluene (6 mL) was added N,N,N',N'-tetramethylethylenediamine (0.29 mL, 2.48 mmol). The vial was sealed, heated at 150° C. for 22 h and then allowed to cool to 25° C. The reaction mixture was diluted with ethyl acetate, washed with water and brine, dried over Na$_2$SO$_4$, filtered and concentrated. The residue was purified on silica gel (gradient elution with 5% ethyl acetate/hexanes to 25% ethyl acetate/hexanes) to afford Cap-139, step a (669.7 mg, 59%) as a white solid. $^1$H NMR (CDCl$_3$, 500 MHz) δ 8.54 (d, J=6.0 Hz, 1H), 8.22 (d, J=9.0 Hz, 1H), 7.76 (d, J=5.5 Hz, 1H), 7.41-7.39 (m, 1H), 7.13 (d, J=2.0 Hz, 1H), 3.98 (s, 3H); R$_f$=1.66 min (Cond.-D1); 90% homogeneity index; LCMS: Anal. Calc. for [M+H]$^+$ C$_{11}$H$_9$N$_2$O: 185.07; found: 185.2.

Cap-139

Cap-139 was prepared from the basic hydrolysis of Cap-139, step a with 5N NaOH according to the procedure described for Cap 138. $^1$H NMR (400 MHz, DMSO-d$_6$) δ 13.63 (v br s, 1H), 8.60 (d, J=9.3 Hz, 1H), 8.45 (d, J=5.6 Hz, 1H), 7.95 (d, J=5.9 Hz, 1H), 7.49 (d, J=2.2 Hz, 1H), 7.44 (dd, J=9.3, 2.5 Hz, 1H), 3.95 (s, 3H); R$_f$=0.64 min (Cond.-D1); 90% homogeneity index; LCMS: Anal. Calc. for [M+H]$^+$ C$_{11}$C$_{10}$NO$_3$: 204.07; found: 204.05.

Cap-140

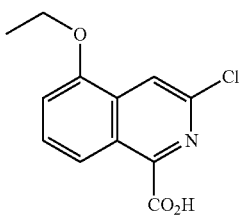

Cap-140, step a

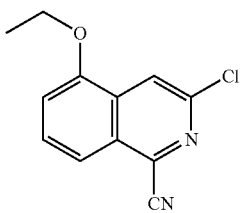

To a vigorously-stirred mixture of 1,3-dichloro-5-ethoxy-isoquinoline (482 mg, 2.00 mmol; prepared according to the procedure in WO 2005/051410), palladium (II) acetate (9 mg, 0.04 mmol), sodium carbonate (223 mg, 2.10 mmol) and 1,5-bis(diphenylphosphino)pentane (35 mg, 0.08 mmol) in dry dimethylacetamide (2 mL) at 25° C. under nitrogen was added N,N,N',N'-tetramethylethylenediamine (60 mL, 0.40 mmol). After 10 min, the mixture was heated to 150° C., and then a stock solution of acetone cyanohydrin (prepared from 457 µL of acetone cyanohydrin in 4.34 mL DMA) was added in 1 mL portions over 18 h using a syringe pump. The mixture was then partitioned between ethyl acetate and water and the organic layer was separated, washed with brine, dried over $Na_2SO_4$, filtered and concentrated. The residue was purified on silica gel (gradient elution with 10% ethyl acetate in hexanes to 40% ethyl acetate in hexanes) to afford Cap-140, step a (160 mg, 34%) as a yellow solid. $R_f$=2.46 min (Cond.-MS-W2); 90% homogeneity index; LCMS: Anal. Calc. for $[M+H]^+$ $C_{12}H_9ClN_2O$: 233.05; found: 233.08.

Cap-140

Cap-140 was prepared by the acid hydrolysis of Cap-140, step a with 12N HCl as described in the procedure for the preparation of Cap 141, described below. $R_f$=2.24 min (Cond.-MS-W2); 90% homogeneity index; LCMS: Anal. Calc. for $[M+H]^+$ $C_{12}H_{11}ClNO_3$: 252.04; found: 252.02.

Cap-141

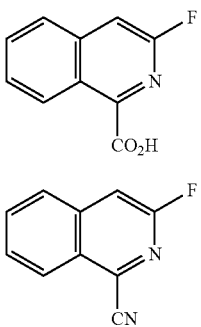

Cap-141, step a

Cap-141, step a was prepared from 1-bromo-3-fluoroisoquinoline (prepared from 3-amino-1-bromoisoquinoline using the procedure outlined in *J. Med. Chem.* 1970, 13, 613) as described in the procedure for the preparation of Cap-140, step a (vide supra). $^1$H NMR (500 MHz, $CDCl_3$) δ 8.35 (d, J=8.5 Hz, 1H), 7.93 (d, J=8.5 Hz, 1H), 7.83 (t, J=7.63 Hz, 1H), 7.77-7.73 (m, 1H), 7.55 (s, 1H); $R_f$=1.60 min (Cond.-D1); 90% homogeneity index; LCMS: Anal. Calc. for $[M+H]^+$ $C_{10}H_6FN_2$: 173.05; found: 172.99.

Cap-141

Cap-141, step a (83 mg, 0.48 mmol) was treated with 12N HCl (3 mL) and the resulting slurry was heated at 80° C. for 16 h before it was cooled to room temperature and diluted with water (3 mL). The mixture was stirred for 10 min and then filtered to afford Cap-141 (44.1 mg, 48%) as an off-white solid. The filtrate was diluted with dichloromethane and washed with brine, dried over $Na_2SO_4$, and concentrated to afford additional Cap-141 (29.30 mg, 32%) which was sufficiently pure to be carried forward directly. $^1$H NMR (DMSO-$d_6$, 500 MHz) δ 14.0 (br s, 1H), 8.59-8.57 (m, 1H), 8.10 (d, J=8.5 Hz, 1H), 7.88-7.85 (m, 2H), 7.74-7.71 (m, 1H); $R_f$=1.33 min (Cond.-D1); 90% homogeneity index; LCMS: Anal. Calc. for $[M+H]^+$ $C_{10}H_7FNO_2$: 192.05; found: 191.97.

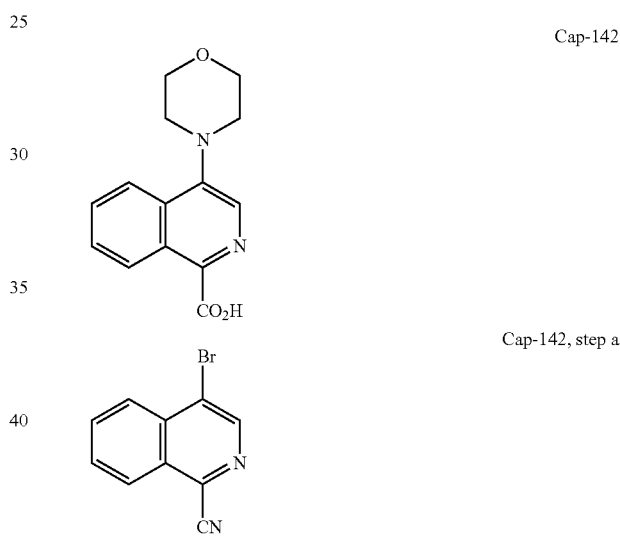

Cap-142

Cap-142, step a

Cap-142, step a was prepared from 4-bromoisoquinoline N-oxide as described in the two-step procedure for the preparation of Cap-138, steps b and c. $R_f$=1.45 min (Cond.-MS-W1); 90% homogeneity index; LCMS: Anal. Calc. for $[M+H]^+$ $C_{10}H_6BrN_2$: 232.97; found: 233.00.

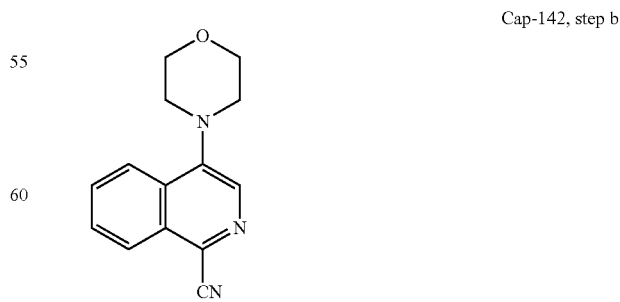

Cap-142, step b

To an argon-degassed suspension of Cap-142, step a (116 mg, 0.50 mmol), potassium phosphate tribasic (170 mg, 0.80 mmol), palladium (II) acetate (3.4 mg, 0.015 mmol) and 2-(dicyclohexylphosphino)biphenyl (11 mg, 0.03 mmol) in anhydrous toluene (1 mL) was added morpholine (61 μL, 0.70 mmol). The mixture was heated at 100° C. for 16 h, cooled to 25° C., filtered through diatomaceous earth (Celite®) and concentrated. Purification of the residue on silica gel (gradient elution with 10% to 70% ethyl acetate in hexanes) afforded Cap-142, step b (38 mg, 32%) as a yellow solid which was carried forward directly. $R_f$=1.26 min (Cond.-MS-W1); 90% homogeneity index; LCMS: Anal. Calc. for $[M+H]^+$ $C_{14}H_{14}N_3O$: 240.11; found: 240.13.

Cap-142

Cap-142 was prepared from Cap-142, step b with 5N sodium hydroxide as described in the procedure for Cap 138. $R_f$=0.72 min (Cond.-MS-W1); 90% homogeneity index; LCMS: Anal. Calc. for $[M+H]^+$ $C_{14}H_{15}N_2O_3$: 259.11; found: 259.08.

Cap-143

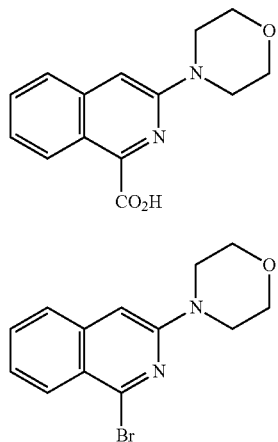

Cap-143, step a

To a stirred solution of 3-amino-1-bromoisoquinoline (444 mg, 2.00 mmol) in anhydrous dimethylformamide (10 mL) was added sodium hydride (60%, unwashed, 96 mg, 2.4 mmol) in one portion. The mixture was stirred at 25° C. for 5 min before 2-bromoethyl ether (90%, 250 μL, 2.00 mmol) was added. This mixture was stirred further at 25° C. for 5 h and at 75° C. for 72 h before it was cooled to 25° C., quenched with saturated ammonium chloride solution and diluted with ethyl acetate. The organic layer was separated, washed with water and brine, dried over $Na_2SO_4$, filtered and concentrated. Purification of the residue on silica gel (gradient elution with 0% to 70% ethyl acetate in hexanes) afforded Cap-143, step a (180 mg, 31%) as a yellow solid. $R_f$=1.75 min (Cond.-MS-W1); 90% homogeneity index; LCMS: Anal. Calc. for $[M+H]^+$ $C_{13}H_{14}BrN_2O$: 293.03; found: 293.04.

Cap-143

To a cold (−60° C.) solution of Cap-143, step a (154 mg, 0.527 mmol) in anhydrous tetrahydrofuran (5 mL) was added a solution of n-butyllithium in hexanes (2.5 M, 0.25 mL, 0.633 mmol). After 10 min, dry carbon dioxide was bubbled into the reaction mixture for 10 min before it was quenched with 1N HCl and allowed to warm to 25° C. The mixture was then extracted with dichloromethane (3×30 mL) and the combined organic extracts were concentrated in vacuo. Purification of the residue by reverse phase HPLC (MeOH/water/

TFA) afforded Cap-143 (16 mg, 12%). $R_f$=1.10 min (Cond.-MS-W1); 90% homogeneity index; LCMS: Anal. Calc. for $[M+H]^+$ $C_{14}H_{15}N_2O_3$: 259.11; found: 259.08.

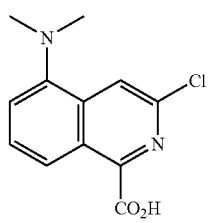

Cap-144

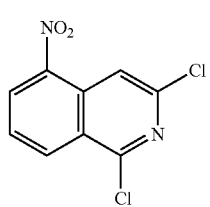

Cap-144, step a 1,3-Dichloroisoquinoline (2.75 g, 13.89 mmol) was added in small portions to a cold (0° C.) solution of fuming nitric acid (10 mL) and concentrated sulfuric acid (10 mL). The mixture was stirred at 0° C. for 0.5 h before it was gradually warmed to 25° C. where it stirred for 16 h. The mixture was then poured into a beaker containing chopped ice and water and the resulting suspension was stirred for 1 h at 0° C. before it was filtered to afford Cap-144, step a (2.73 g, 81%) as a yellow solid which was used directly. $R_f$=2.01 min (Cond.-D1); 95% homogeneity index; LCMS: Anal. Calc. for $[M+H]^+$ $C_9H_5Cl_2N_2O_2$: 242.97; found: 242.92.

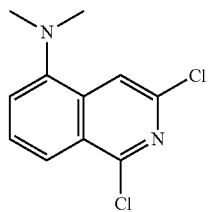

Cap-144, step b

Cap-144, step a (0.30 g, 1.23 mmol) was taken up in methanol (60 mL) and treated with platinum oxide (30 mg), and the suspension was subjected to Parr hydrogenation at 7 psi $H_2$ for 1.5 h before formalin (5 mL) and additional platinum oxide (30 mg) were added. The suspension was resubjected to Parr hydrogenation at 45 psi $H_2$ for 13 h before it was suction-filtered through diatomaceous earth (Celite®) and concentrated down to ¼ volume. Suction-filtration of the ensuing precipitate afforded the title compound as a yellow solid which was flash chromatographed on silica gel (gradient elution with 5% ethyl acetate in hexanes to 25% ethyl acetate in hexanes) to afford Cap-144, step b (231 mg, 78%) as a pale, yellow solid. $R_f$=2.36 min (Cond.-D1); 95% homogeneity index; $^1$H NMR (400 MHz, $CDCl_3$) δ 8.02 (s, 1H), 7.95 (d, J=8.6 Hz, 1H), 7.57-7.53 (m, 1H), 7.30 (d, J=7.3 Hz, 1H), 2.88 (s, 6H); LCMS: Anal. Calc. for $[M+H]^+$ $C_{11}H_{11}Cl_2N_2$: 241.03; found: 241.02. HRMS: Anal. Calc. for $[M+H]^+$ $C_{11}H_{11}Cl_2N_2$: 241.0299; found: 241.0296.

Cap-144, step c

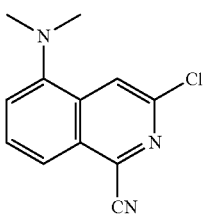

Cap-144, step c was prepared from Cap-144, step b according to the procedure described for the preparation of Cap-139, step a. $R_t$=2.19 min (Cond.-D1); 95% homogeneity index; LCMS: Anal. Calc. for $[M+H]^+$ $C_{12}H_{11}ClN_3$: 232.06; found: 232.03. HRMS: Anal. Calc. for $[M+H]^+$ $C_{12}H_{11}ClN_3$: 232.0642; found: 232.0631.

Cap-144

Cap-144 was prepared according to the procedure described for Cap-141. $R_t$=2.36 min (Cond.-D1); 90%; LCMS: Anal. Calc. for $[M+H]^+$ $C_{12}H_{12}ClN_2O_2$: 238.01; found: 238.09.

Caps-145 to -162

Caps-145 to 162 were prepared from the appropriate 1-chloroisoquinolines according to the procedure described for the preparation of Cap-138 (Method A) or Cap-139 (Method B) unless noted otherwise as outlined below.

| Cap # | Cap | Method | Hydrolysis | $R_t$ (LC-Cond.); % homogeneity index; MS data |
|---|---|---|---|---|
| Cap-145 | (structure) Prepared from commercially available 1,3-dichloroisoquinoline | B | 12N HCl | 1.14 min (Cond.-MS-W1); 90%; LCMS: Anal. Calc. for $[M+H]^+$ $C_{10}H_7ClNO_2$: 208.02; found: 208.00. |
| Cap-146 | (structure) Prepared from commercially available 3-hydroxyisoquinoline | A | 5N NaOH | 1.40 min (Cond.-D1); 95%; LCMS: Anal. Calc. for $[M+H]^+$ $C_{11}H_{10}NO_3$: 204.07; found: 204.06. |
| Cap-147 | (structure) Prepared from commercially available 1-chloro-4-hydroxyisoquinoline | B | 5N NaOH | 0.87 min (Cond.-D1); 95%; LCMS: Anal. Calc. for $[M+H]^+$ $C_{11}H_{10}NO_3$: 204.07; found: 204.05. |
| Cap-148 | (structure) Prepared from commercially available 7-hydroxyisoquinoline | A | 5N NaOH | 0.70 min (Cond.-D1); 95%; LCMS: Anal. Calc. for $[M+H]^+$ $C_{11}H_{10}NO_3$: 204.07; found: 204.05. |

-continued

| Cap # | Cap | Method | Hydrolysis | $R_f$ (LC-Cond.); % homogeneity index; MS data |
|---|---|---|---|---|
| Cap-149 | 5-methoxyisoquinoline-1-carboxylic acid<br><br>Prepared from commercially available 5-hydroxyisoquinoline | A | 5N NaOH | 0.70 min (Cond.-D1); 95%; LCMS: Anal. Calc. for [M + H]$^+$ C$_{11}$H$_{10}$NO$_3$: 204.07; found: 204.05. |
| Cap-150 | 8-methoxyisoquinoline-1-carboxylic acid · TFA<br><br>Prepared from 8-methoxy-1-chloroisoquinoline, which can be synthesized following the procedure in WO 2003/099274 | A | 12N HCl | 0.26 min (Cond.-D1); 95%; LCMS: Anal. Calc. for [M + H]$^+$ C$_{11}$H$_{10}$NO$_3$: 204.07; found: 204.04. |
| Cap-151 | 3-chloro-5-methoxyisoquinoline-1-carboxylic acid<br><br>Prepared from 5-methoxy-1,3-dichloroisoquinoline, which can be synthesized following the procedure in WO 2005/051410. | B | 12N HCl | 1.78 min (Cond.-D1); 90%; LCMS: Anal. Calc. for [M + H]$^+$ C$_{11}$H$_9$ClNO$_3$: 238.03; found: 238.09. |
| Cap-152 | 3-chloro-6-methoxyisoquinoline-1-carboxylic acid<br><br>Prepared from commercially available 6-methoxy-1,3-dichloroisoquinoline | B | 12N HCl | 1.65 min (Cond.-D1); 95%; LCMS: Anal. Calc. for [M + H]$^+$ C$_{11}$H$_9$ClNO$_3$: 238.00; found: 238.09. |
| Cap-153 | 4-bromoisoquinoline-1-carboxylic acid<br><br>Prepared from 4-bromoisoquinoline, which can be synthesized following the procedure in WO 2003/062241 | A | 6N HCl | 1.18 min (Cond.-MS-W1); 95%; LCMS: Anal. Calc. for [M + H]$^+$ C$_{10}$H$_7$BrNO$_2$: 251.97; found: 251.95. |

| Cap # | Cap | Method | Hydrolysis | $R_f$ (LC-Cond.); % homogeneity index; MS data |
|---|---|---|---|---|
| Cap-154 | 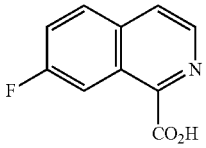<br>Prepared from 7-fluoro-1-chloroisoquinoline, which can be synthesized following the procedure in WO 2003/099274 | B | 5N NaOH | 0.28 min (Cond.-MS-W1); 90%; LCMS: Anal. Calc. for $[M + H]^+$ $C_{10}H_7FNO_2$: 192.05; found: 192.03. |
| Cap-155 | 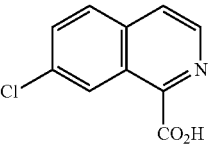<br>Prepared from 1,7-dichloroisoquinoline, which can be synthesized following the procedure in WO 2003/099274 | B | 5N NaOH | 0.59 min (Cond.-MS-W1); 90%; LCMS: Anal. Calc. for $[M + H]^+$ $C_{10}H_7ClNO_2$: 208.02; found: 208.00. |
| Cap-156 | 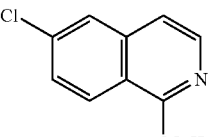<br>Prepared from 1,6-dichloroisoquinoline, which can be synthesized following the procedure in WO 2003/099274 | B | 5N NaOH | 0.60 min (Cond.-MS-W1); 90%; LCMS: Anal. Calc. for $[M + H]^+$ $C_{10}H_7ClNO_2$: 208.02; found: 208.03. |
| Cap-157 | 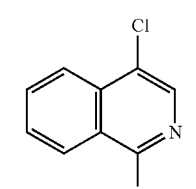<br>Prepared from 1,4-dichloroisoquinoline, which can be synthesized following the procedure in WO 2003/062241 | B | 12N HCl | 1.49 min (Cond.-D1); 95%; LCMS: Anal. Calc. for $[M + H]^+$ $C_{10}H_{17}ClNO$: 208.02; found: 208.00. |
| Cap-158 | 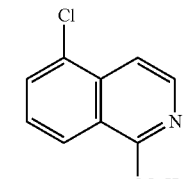<br>Prepared from 1,5-dichloroisoquinoline, which can be synthesized following the procedure in WO 2003/099274 | B | 5N NaOH | 0.69 min (Cond.-MS-W1); 90%; LCMS: Anal. Calc. for $[M + H]^+$ $C_{10}H_7ClNO_2$: 208.02; found: 208.01. |

-continued

| Cap # | Cap | Method | Hydrolysis | $R_f$ (LC-Cond.); % homogeneity index; MS data |
|---|---|---|---|---|
| Cap-159 | 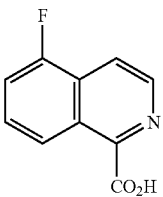<br>Prepared from 5-fluoro-1-chloroisoquinoline, which can be synthesized following the procedure in WO 2003/099274 | B | 5N NaOH | 0.41 min (Cond.-MS-W1); 90%; LCMS: Anal. Calc. for $[M + H]^+$ $C_{10}H_7FNO_2$: 192.05; found: 192.03. |
| Cap-160 | 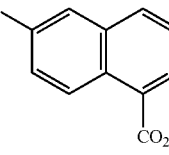<br>Prepared from 6-fluoro-1-chloroisoquinoline, which can be synthesized following the procedure in WO 2003/099274 | B | 5N NaOH | 0.30 min (Cond.-MS-W1); 90%; LCMS: Anal. Calc. for $[M + H]^+$ $C_{10}H_7FNO_2$: 192.05; found: 192.03. |
| Cap-161 | 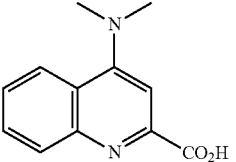<br>Prepared from 4-bromoquinoline-2-carboxylic acid and dimethylamine (DMSO, 100° C.) | — | — | 0.70 min (Cond. D1); 95%; LCMS: Anal. Calc. for $[M + H]^+$ $C_{12}H_{13}N_2O_2$: 217.10; found: 217.06. |
| Cap-162 | 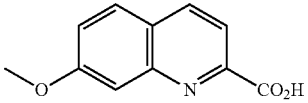<br>Prepared from m-anisidine following the procedure described in J. Hetero. Chem. 1993, 17 and Heterocycles, 2003, 60, 953. | — | — | 0.65 min (Cond.-M3); 95%; LCMS: Anal. Calc. for $[M + H]^+$ $C_{11}H_{10}NO_3$: 204.07; found: 203.94. |

Cap-163

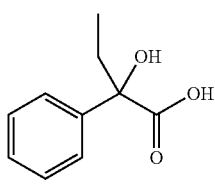

To a solution of 2-ketobutyric acid (1.0 g, 9.8 mmol) in diethylether (25 ml) was added phenylmagnesium bromide (22 ml, 1M in THF) dropwise. The reaction was stirred at ~25° C. under nitrogen for 17.5 h. The reaction was acidified with 1N HCl and the product was extracted with ethyl acetate (3×100 ml). The combined organic layer was washed with water followed by brine and dried over $MgSO_4$. After concentration in vacuo, a white solid was obtained. The solid was recrystallized from hexanes/ethyl acetate to afford Cap-163 as white needles (883.5 mg). $^1$H NMR (DMSO-$d_6$, δ=2.5 ppm, 500 MHz): 12.71 (br s, 1 H), 7.54-7.52 (m, 2H), 7.34-7.31 (m, 2H), 7.26-7.23 (m, 1H), 5.52-5.39 (br s, 1H), 2.11 (m, 1H), 1.88 (m, 1H), 0.79 (app t, J=7.4 Hz, 3H).

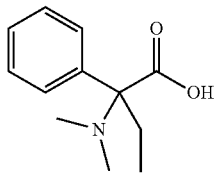

Cap-164

A mixture of 2-amino-2-phenylbutyric acid (1.5 g, 8.4 mmol), formaldehyde (14 mL, 37% in water), 1N HCl (10 mL) and 10% Pd/C (0.5 mg) in MeOH (40 mL) was exposed to $H_2$ at 50 psi in a Parr bottle for 42 h. The reaction was filtered over Celite and concentrated in vacuo, the residue was taken up in MeOH (36 mL) and the product was purified with a reverse phase HPLC (MeOH/$H_2O$/TFA) to afford the TFA salt of Cap-164 as a white solid (1.7 g). $^1$H NMR (DMSO-$d_6$, $\delta$=2.5 ppm, 500 MHz) 7.54-7.47 (m, 5H), 2.63 (m, 1H), 2.55 (s, 6H), 2.31 (m, 1H), 0.95 (app t, J=7.3 Hz, 3H).

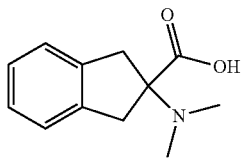

Cap-165

To a mixture of 2-amino-2-indanecarboxylic acid (258.6 mg, 1.46 mmol) and formic acid (0.6 ml, 15.9 mmol) in 1,2-dichloroethane (7 ml) was added formaldehyde (0.6 ml, 37% in water). The mixture was stirred at ~25° C. for 15 min then heated at 70° C. for 8 h. The volatile component was removed in vacuo, and the residue was dissolved in DMF (14 mL) and purified by a reverse phase HPLC (MeOH/$H_2O$/TFA) to afford the TFA salt of Cap-165 as a viscous oil (120.2 mg). $^1$H NMR (DMSO-$d_6$, $\delta$=2.5 ppm, 500 MHz): 7.29-7.21 (m, 4 H), 3.61 (d, J=17.4 Hz, 2H), 3.50 (d, J=17.4 Hz, 2H), 2.75 (s, 6H). LC/MS: Anal. Calcd. for [M+H]$^+$ $C_{12}H_{16}NO_2$: 206.12; found: 206.07.

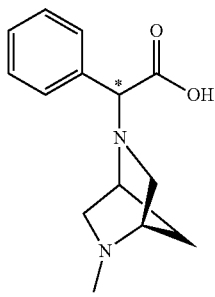

Cap-166a and 166b

Cap-166a: Diastereomer-1
Cap-166b: Diastereomer-2

Caps-166a and -166b were prepared from (1S,4S)-(+)-2-methyl-2,5-diazabicyclo[2.2.1]heptane (2HBr) according to the method described for the synthesis of Cap-7a and Cap-7b, with the exception that the benzyl ester intermediate was separated using a semi-prep Chiralcel OJ column, 20×250 mm, 10 µm eluting with 85:15 heptane/ethanol mixture at 10 mL/min elution rate for 25 min. Cap-166b: $^1$H NMR (DMSO-$d_6$, $\delta$=2.5 ppm, 500 MHz): 7.45 (d, J=7.3 Hz, 2H), 7.27-7.19 (m, 3H), 4.09 (s, 1H), 3.34 (app br s, 1H), 3.16 (app br s, 1H), 2.83 (d, J=10.1 Hz, 1H), 2.71 (m, 2H), 2.46 (m, 1H), 2.27 (s, 3H), 1.77 (d, J=9.8 Hz, 1H), 1.63 (d, J=9.8 Hz, 1H). LC/MS: Anal. Calcd. for [M+H]$^+$ $C_{14}H_{19}N_2O_2$: 247.14; found: 247.11.

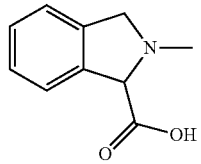

Cap-167

A solution of racemic Boa-1,3-dihydro-2H-isoindole carboxylic acid (1.0 g, 3.8 mmol) in 20% TFA/$CH_2Cl_2$ was stirred at ~25° C. for 4 h. All the volatile component was removed in vacuo. A mixture of the resultant crude material, formaldehyde (15 mL, 37% in water), 1N HCl (10 mL) and 10% Pd/C (10 mg) in MeOH was exposed to $H_2$ (40 PSI) in a Parr bottle for 23 h. The reaction mixture was filtered over Celite and concentrated in vacuo to afford Cap-167 as a yellow foam (873.5 mg). $^1$H NMR (DMSO-$d_6$, $\delta$=2.5 ppm, 500 MHz) 7.59-7.38 (m, 4H), 5.59 (s, 1H), 4.84 (d, J=14 Hz, 1H), 4.50 (d, J=14.1 Hz, 1H), 3.07 (s, 3H). LC/MS: Anal. Calcd. for [M+H]$^+$ $C_{10}H_{12}NO_2$: 178.09; found: 178.65.

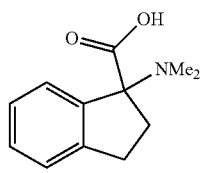

Cap-168

Racemic Cap-168 was prepared from racemic Boc-aminoindane-1-carboxylic acid according to the procedure described for the preparation of Cap-167. The crude material was employed as such.

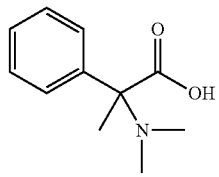

Cap-169

A mixture of 2-amino-2-phenylpropanoic acid hydrochloride (5.0 g, 2.5 mmol), formaldehyde (15 ml, 37% in water), 1N HCl (15 ml), and 10% Pd/C (1.32 g) in MeOH (60 mL) was placed in a Parr bottle and shaken under hydrogen (55 PSI) for 4 days. The reaction mixture was filtered through diatomaceous earth (Celite®) and concentrated in vacuo. The residue was taken up in MeOH and purified by reverse phase prep-HPLC (MeOH/water/TFA) to afford the TFA salt of Cap-169 as a viscous semi-solid (2.1 g). $^1$H NMR (CDCl$_3$, $\delta$=7.26 ppm, 500 MHz): 7.58-7.52 (m, 2 H), 7.39-7.33 (m, 3H), 2.86 (br s, 3H), 2.47 (br s, 3H), 1.93 (s, 3H). LC/MS: Anal. Calcd. for [M+H]$^+$ $C_{11}H_{16}NO_2$: 194.12; found: 194.12.

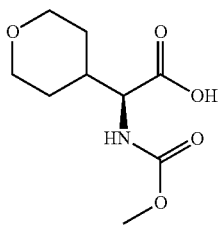

Cap-170

To (S)-2-amino-2-(tetrahydro-2H-pyran-4-yl)acetic acid (505 mg; 3.18 mmol; obtained from Astatech) in water (15 ml) was added sodium carbonate (673 mg; 6.35 mmol), and the resultant mixture was cooled to 0° C. and then methyl chloroformate (0.26 ml; 3.33 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford Cap-170 a colorless residue. $^1$H NMR (500 MHz, DMSO-$d_6$) δ ppm 12.65 (1 H, br s), 7.44 (1 H, d, J=8.24 Hz), 3.77-3.95 (3 H, m), 3.54 (3 H, s), 3.11-3.26 (2 H, m), 1.82-1.95 (1 H, m), 1.41-1.55 (2 H, m), 1.21-1.39 (2 H, m); LC/MS: Anal. Calcd. for [M+H]$^+$ $C_9H_{16}NO_5$: 218.1; found 218.1.

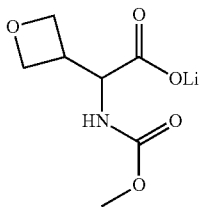

Cap-171

A solution of methyl 2-(benzyloxycarbonylamino)-2-(oxetan-3-ylidene)acetate (200 mg, 0.721 mmol; Il Farmaco (2001), 56, 609-613) in ethyl acetate (7 ml) and CH$_2$Cl$_2$ (4.00 ml) was degassed by bubbling nitrogen for 10 min. Dimethyl dicarbonate (0.116 ml, 1.082 mmol) and Pd/C (20 mg, 0.019 mmol) were then added, the reaction mixture was fitted with a hydrogen balloon and allowed to stir at ambient temperature overnight at which time TLC (95:5 CH$_2$Cl$_2$/MeOH: visualized with stain made from 1 g Ce(NH$_4$)$_2$SO$_4$, 6 g ammonium molybdate, 6 ml sulfuric acid, and 100 ml water) indicated complete conversion. The reaction was filtered through celite and concentrated. The residue was purified via Biotage® (load with dichloromethane on 25 samplet; elute on 25S column with dichloromethane for 3CV then 0 to 5% MeOH/dichloromethane over 250 ml then hold at 5% MeOH/dichloromethane for 250 ml; 9 ml fractions). Collected fractions containing desired material and concentrated to 120 mg (81%) of methyl 2-(methoxycarbonylamino)-2-(oxetan-3-yl)acetate as a colorless oil. $^1$H NMR (500 MHz, CHLOROFORM-D) δ ppm 3.29-3.40 (m, J=6.71 Hz, 1 H) 3.70 (s, 3 H) 3.74 (s, 3 H) 4.55 (t, J=6.41 Hz, 1H) 4.58-4.68 (m, 2 H) 4.67-4.78 (m, 2 H) 5.31 (br s, 1 H). LC/MS: Anal. Calcd. for [M+H]$^+$ $C_8H_{14}NO_5$: 204.2; found 204.0.

To methyl 2-(methoxycarbonylamino)-2-(oxetan-3-yl)acetate (50 mg, 0.246 mmol) in THF (2 mL) and water (0.5 mL) was added lithium hydroxide monohydrate (10.33 mg, 0.246 mmol). The resultant solution was allowed to stir overnite at ambient temperature. TLC (1:1 EA/Hex; Hanessian stain [1 g Ce(NH$_4$)$_2$SO$_4$, 6 g ammonium molybdate, 6 ml sulfuric acid, and 100 ml water]) indicated ~10% starting material remaining. Added an additional 3 mg LiOH and allowed to stir overnight at which time TLC showed no starting material remaining. Concentrated in vacuo and placed on high vac overnite providing 55 mg lithium 2-(methoxycarbonylamino)-2-(oxetan-3-yl)acetate as a colorless solid. $^1$H NMR (500 MHz, MeOD) δ ppm 3.39-3.47 (m, 1 H) 3.67 (s, 3 H) 4.28 (d, J=7.93 Hz, 1 H) 4.64 (t, J=6.26 Hz, 1 H) 4.68 (t, J=7.02 Hz, 1 H) 4.73 (d, J=7.63 Hz, 2 H).

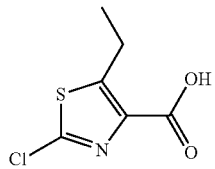

Cap-172

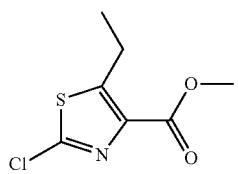

Cap-172, step a

The following diazotization step was adapted from Barton, A.; Breukelman, S. P.; Kaye, P. T.; Meakins, G. D.; Morgan, D. J. *J. C. S. Perkin Trans I* 1982, 159-164: A solution of NaNO$_2$ (166 mg, 2.4 mmol) in water (0.6 mL) was added slowly to a stirred, cold (0° C.) solution of methyl 2-amino-5-ethyl-1,3-thiazole-4-carboxylate (186 mg, 1.0 mmol), CuSO$_4$·5H$_2$O (330 mg, 1.32 mmol), NaCl (260 mg, 4.45 mmol) and H$_2$SO$_4$ (5.5 mL) in water (7.5 mL). The mixture was stirred at 0° C. for 45 min and allowed to warm up to room temperature where it stirred further for 1 h before CuCl (118 mg) was added. This mixture was stirred further at room temperature for 16 h before it was diluted with brine and extracted with ether twice. The organic layers were combined, dried over MgSO$_4$ and concentrated to give methyl 2-chloro-5-ethylthiazole-4-carboxylate (i.e. Cap-172, step a) (175 mg, 85%) as an orange oil (80% pure) which was used directly in the next reaction. R$_t$=1.99 min (Cond.-MD1); LC/MS: Anal. Calcd. for [M+H]$^+$ $C_7H_9ClNO_2S$: 206.01; found: 206.05.

Cap-172

To a solution of methyl 2-chloro-5-ethylthiazole-4-carboxylate (175 mg) in THF/H$_2$O/MeOH (20 mL/3 mL/12 mL) was added LiOH (305 mg, 12.76 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-172 (60 mg, 74%) as a red solid which was used without further purification. $^1$H NMR (300 MHz, DMSO-$d_6$) δ ppm 13.03-13.42 (1H, m), 3.16 (2 H, q, J=7.4 Hz), 1.23 (3 H, t, J=7.5 Hz). R$_t$=1.78 min (Cond.-MD1); LC/MS: Anal. Calcd. for [M+H]$^+$ $C_6H_7ClNO_2S$: 191.99; found: 191.99.

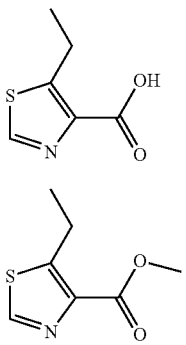

Cap-173

Cap-173, step a

The following diazotization step was adapted from Barton, A.; Breukelman, S. P.; Kaye, P. T.; Meakins, G. D.; Morgan, D. J. *J. C. S. Perkin Trans I* 1982, 159-164: A solution of NaNO$_2$ (150 mg, 2.17 mmol) in water (1.0 mL) was added dropwise to a stirred, cold (0° C.) solution of methyl 2-amino-5-ethyl-1,3-triazole-4-carboxylate (186 mg, 1.0 mmol) in 50% H$_3$PO$_2$ (3.2 mL). The mixture was stirred at 0° C. for 1 h and allowed to warm up to room temperature where it stirred further for 2 h. After recooling to 0° C., the mixture was treated slowly with a solution of NaOH (85 mg) in water (10 mL). The mixture was then diluted with saturated NaHCO$_3$ solution and extracted twice with ether. The organic layers were combined, dried over MgSO$_4$ and concentrated to give methyl 5-ethylthiazole-4-carboxylate (i.e. Cap-173, step a) (134 mg, 78%) as an orange oil (85% pure) which was used directly in the next reaction. R$_f$=1.58 min (Cond.-MD1); LC/MS: Anal. Calcd. for [M+H]$^+$ C$_7$H$_{10}$NO$_2$S: 172.05; found: 172.05.

Cap-173

To a solution of methyl 5-ethylthiazole-4-carboxylate (134 mg) in THF/H$_2$O/MeOH (18 mL/2.7 mL/11 mL) was added LiOH (281 mg, 11.74 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-173 (90 mg, 73%) as an orange solid which was used without further purification. $^1$H NMR (300 MHz, DMSO-d$_6$) δ ppm 12.74-13.04 (1 H, m), 3.20 (2 H, q, J=7.3 Hz), 1.25 (3 H, t, J=7.5 Hz). R$_f$=1.27 min (Cond.-MD1); LC/MS: Anal. Calcd. for [M+H]$^+$ C$_6$H$_8$NO$_2$S: 158.03; found: 158.04.

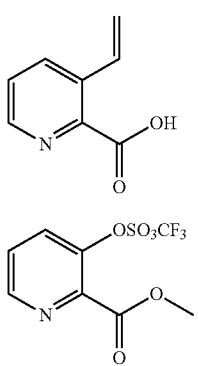

Cap-174

Cap-174, step a

Triflic anhydride (5.0 g, 18.0 mmol) was added dropwise to a cold (0° C.) solution of methyl 3-hydroxypicolinate (2.5 g, 16.3 mmol) and TEA (2.5 mL, 18.0 mmol) in CH$_2$Cl$_2$ (80 mL). The mixture was stirred at 0° C. for 1 h before it was allowed to warm up to room temperature where it stirred for an additional 1 h. The mixture was then quenched with saturated NaHCO$_3$ solution (40 mL) and the organic layer was separated, washed with brine, dried over MgSO$_4$ and concentrated to give methyl 3-(trifluoromethylsulfonyloxy)picolinate (i.e. Cap-174, step a) (3.38 g, 73%) as a dark brown oil (>95% pure) which was used directly without further purification. $^1$H NMR (300 MHz, CDCl$_3$) δ ppm 8.72-8.79 (1 H, m), 7.71 (1 H, d, J=1.5 Hz), 7.58-7.65 (1 H, m), 4.04 (3 H, s). R$_f$=1.93 min (Cond.-MD1); LC/MS: Anal. Calcd. for [M+H]$^+$C$_8$H$_7$F$_3$NO$_5$S: 286.00; found: 286.08.

Cap-174

To a solution of methyl 3-(trifluoromethylsulfonyloxy)picolinate (570 mg, 2.0 mmol) in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. overnight before a saturated solution of KF (20 mL) was added to the reaction mixture at room temperature. This mixture was stirred for 4 h before it was filtered through diatomaceous earth (Celite®) and the pad was washed with ethyl acetate. The aqueous phase of the filtrate was then separated and concentrated down in vacuo. The residue was treated with 4N HCl in dioxanes (5 mL) and the resulting mixture was extracted with methanol, filtered and evaporated to afford Cap-174 (260 mg) as a green solid which was slightly contaminated with inorganic salts but was used without further purification. $^1$H NMR (300 MHz, DMSO-d$_6$) δ ppm 8.21 (1 H, d, J=3.7 Hz), 7.81-7.90 (1 H, m), 7.09 (1 H, dd, J=7.7, 4.8 Hz), 6.98 (1 H, dd, J=17.9, 11.3 Hz), 5.74 (1 H, dd, J=17.9, 1.5 Hz), 5.20 (1 H, d, J=11.0 Hz). R$_f$=0.39 min (Cond.-MD1); LC/MS: Anal. Calcd. for [M+H]$^+$ C$_8$H$_8$NO$_2$: 150.06; found: 150.07.

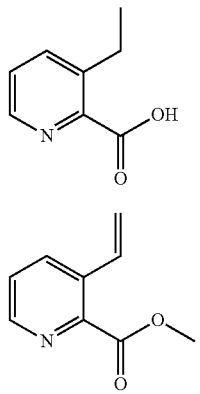

Cap-175

Cap-175, step a

To a solution of methyl 3-(trifluoromethylsulfonyloxy)picolinate (i.e. Cap 173, step a) (570 mg, 2.0 mmol), an intermediate in the preparation of Cap-174, in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. for 4 h before the solvent was removed in vacuo. The residue was taken up in acetonitrile (50 mL) and hexanes (50 mL) and the resulting mixture was washed twice with hexanes. The acetonitrile layer was then separated, filtered through Celite, and evaporated. Purification of the residue by flash chromatography on a Horizon instrument (gradient elution with 25% ethyl acetate in hexanes to 65% ethyl acetate in hexanes) afforded methyl 3-vinylpicolinate (i.e. Cap-175, step a) (130 mg, 40%) as a yellow oil. $^1$H NMR (300 MHz, CDCl$_3$) δ ppm 8.60 (1 H, dd, J=4.6, 1.7 Hz), 7.94 (1 H, d, J=7.7 Hz), 7.33-7.51 (2 H, m), 5.72 (1 H, d, J=17.2 Hz), 5.47 (1 H, d, J=11.0 Hz), 3.99 (3 H, s). R$_t$=1.29 min (Cond.-MD1); LC/MS: Anal. Calcd. for [M+H]$^+$ C$_9$H$_{10}$NO$_2$: 164.07; found: 164.06.

Cap-175, step b

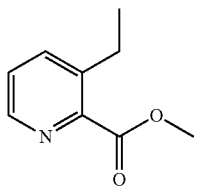

Palladium on carbon (10%, 25 mg) was added to a solution of methyl 3-vinylpicolinate (120 mg, 0.74 mmol) in ethanol (10 mL). The suspension was stirred at room temperature under an atmosphere of hydrogen for 1 h before it was filtered through Celite and the pad of diatomaceous earth (Celite®) was washed with methanol. The filtrate was concentrated down to dryness to yield methyl 3-ethylpicolinate (i.e. Cap-175, step b) which was taken directly into the next reaction. R$_t$=1.15 min (Cond.-MD 1); LC/MS: Anal. Calcd. for [M+H]$^+$ C$_9$H$_{12}$NO$_2$: 166.09; found: 166.09.

Cap-175

To a solution of methyl 3-ethylpicolinate in THF/H$_2$O/MeOH (5 mL/0.75 mL/3 mL) was added LiOH (35 mg, 1.47 mmol). The mixture was stirred at room temperature for 2 d before additional LiOH (80 mg) was added. After an additional 24 h at room temperature, the mixture was filtered and the solvent was removed in vacuo. The residue was then treated with 4N HCl in dioxanes (5 mL) and the resulting suspension was concentrated down to dryness to yield Cap-175 as a yellow solid which was used without further purification. $^1$H NMR (300 MHz, DMSO-d$_6$) δ ppm 8.47 (1 H, dd, J=4.8, 1.5 Hz), 7.82-7.89 (1 H, m), 7.53 (1 H, dd, J=7.7, 4.8 Hz), 2.82 (2 H, q, J=7.3 Hz), 1.17 (3 H, t, J=7.5 Hz). R$_t$=0.36 min (Cond.-MD1); LC/MS: Anal. Calcd. for [M+H]$^+$ C$_8$H$_{10}$NO$_2$: 152.07; found: 152.10.

Cap-176

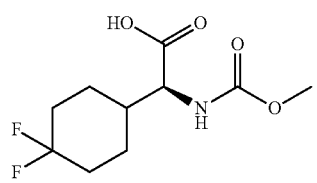

Cap-176, step a

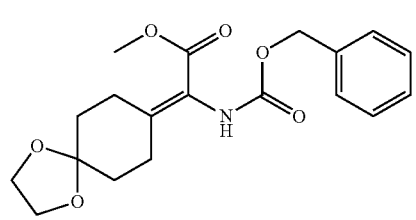

A solution of 1,4-dioxaspiro[4.5]decan-8-one (15 g, 96 mmol) in EtOAc (150 mL) was added to a solution of methyl 2-(benzyloxycarbonylamino)-2-(dimethoxyphosphoryl)acetate (21.21 g, 64.0 mmol) in 1,1,3,3-tetramethylguanidine (10.45 mL, 83 mmol) and EtOAc (150 mL). The resulting solution was the stirred at ambient temperature for 72 h and then it was diluted with EtOAc (25 mL). The organic layer was washed with 1N HCl (75 mL), H$_2$O (100 mL) and brine (100 mL), dried (MgSO$_4$), filtered and concentrated. The residue was purified via Biotage (5% to 25% EtOAc/Hexanes; 300 g column). The combined fractions containing the product were then concentrated under vacuum and the residue was re-crystallized from hexanes/EtOAc to give white crystals that corresponded to methyl 2-(benzyloxycarbonylamino)-2-(1,4-dioxaspiro[4.5]decan-8-ylidene)acetate (6.2 g) $^1$H NMR (400 MHz, CDCl$_3$-d) δ ppm 7.30-7.44 (5 H, m), 6.02 (1 H, br. s.), 5.15 (2 H, s), 3.97 (4 H, s), 3.76 (3 H, br. s.), 2.84-2.92 (2 H, m), 2.47 (2 H, t, J=6.40 Hz), 1.74-1.83 (4 H, m). LC (Cond. OL1): R$_t$=2.89 min. LC/MS: Anal. Calcd. For [M+Na]$^+$ C$_{19}$H$_{23}$NNaO$_6$: 745.21; found: 745.47.

Cap 176, step b

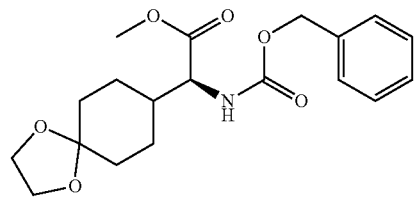

Ester Cap 176, step b was prepared from alkene Cap 176, step a according to the method of Burk, M. J.; Gross, M. F. and Martinez J. P. (*J. Am. Chem. Soc.*, 1995, 117, 9375-9376 and references therein): A 500 mL high-pressure bottle was charged with alkene Cap 176, step a (3.5 g, 9.68 mmol) in degassed MeOH (200 mL) under a blanket of N$_2$. The solution was then charged with (−)-1,2-Bis((2S,5S)-2,5-dimethylphospholano)ethane(cyclooctadiene)rhodium (1) tetrafluoroborate (0.108 g, 0.194 mmol) and the resulting mixture was flushed with N$_2$ (3×) and charged with H$_2$ (3×). The solution was shaken vigorously under 70 psi of H$_2$ at ambient temperature for 72 h. The solvent was removed under reduced pressure and the remaining residue was taken up in EtOAc. The brownish solution was then filtered through a plug of Silica Gel and eluted with EtOAc. The solvent was concentrated under vacuum to afford a clear oil corresponding to ester Cap 176, step b (3.4 g). $^1$H NMR (500 MHz, CDCl$_3$-d) δ ppm 7.28-7.43 (5 H, m), 5.32 (1 H, d, J=9.16 Hz), 5.06-5.16 (2 H, m), 4.37 (1 H, dd, J=9.00, 5.04 Hz), 3.92 (4 H, t, J=3.05 Hz), 3.75 (3 H, s), 1.64-1.92 (4 H, m), 1.37-1.60 (5 H, m). LC (Cond. OL1): R$_t$=1.95 min. LC/MS: Anal. Calcd. For [M+H]$^+$ C$_{19}$H$_{26}$NO$_6$: 364.18; found: 364.27.

Cap 176, step c

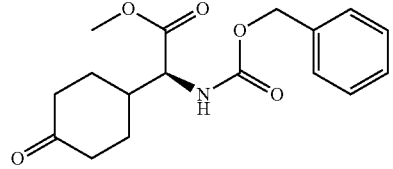

Ester Cap 176, step b (4.78 g, 13.15 mmol) was dissolved in THF (15 mL) followed by sequential addition of water (10 mL), glacial acetic acid (26.4 mL, 460 mmol) and dichloroacetic acid (5.44 mL, 65.8 mmol). The resulting mixture was stirred for 72 h at ambient temperature, and the reaction was quenched by slow addition of solid Na$_2$CO$_3$ with vigorous stirring until the release of gas was no longer visible. Crude product was extracted into 10% ethyl acetate-dichloromethane and the organic layers were combined, dried (MgSO$_4$) filtered and concentrated. The resulting residue was purified via Biotage (0 to 30% EtOAc/Hex; 25 g column) to afford ketone Cap 176, step c (3.86 g) as a clear oil. $^1$H NMR (400 MHz, CDCl$_3$-d) δ ppm 7.28-7.41 (5 H, m), 5.55 (1 H, d, J=8.28 Hz), 5.09 (2 H, s), 4.46 (1 H, dd, J=8.16, 5.14 Hz), 3.74 (3 H, s), 2.18-2.46 (5 H, m), 1.96-2.06 (1 H, m), 1.90 (1 H, ddd, J=12.99, 5.96, 2.89 Hz), 1.44-1.68 (2 H, m, J=12.36, 12.36, 12.36, 12.36, 4.77 Hz). LC (Cond. OL1): R$_t$=1.66 min. LC/MS: Anal. Calcd. For [M+Na]$^+$ C$_{17}$H$_{21}$NNaO$_5$: 342.13; found: 342.10.

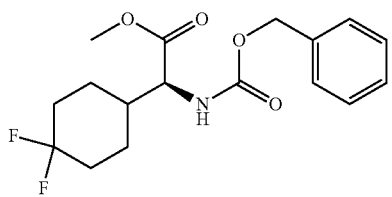

Cap 176, step d

Deoxo-Fluor® (3.13 mL, 16.97 mmol) was added to a solution of ketone Cap 176, step c (2.71 g, 8.49 mmol) in CH$_2$Cl$_2$ (50 mL) followed by addition of a catalytic amount of EtOH (0.149 mL, 2.55 mmol). The resulting yellowish solution was stirred at rt overnight. The reaction was quenched by addition of sat. aq. NaHCO$_3$ (25 mL) and the mixture was extracted with EtOAc (3×75 mL)). The combined organic layers were dried (MgSO$_4$), filtered and dried to give a yellowish oil. The residue was purified via Biotage chromatography (2% to 15% EtOAc/Hex; 90 g column) and a white solid corresponding to the difluoro amino acid dilforide Cap 176, step d (1.5 g) was recovered. $^1$H NMR (400 MHz, CDCl$_3$-d) δ ppm 7.29-7.46 (5 H, m), 5.34 (1 H, d, J=8.28 Hz), 5.12 (2 H, s), 4.41 (1 H, dd, J=8.66, 4.89 Hz), 3.77 (3 H, s), 2.06-2.20 (2 H, m), 1.83-1.98 (1 H, m), 1.60-1.81 (4 H, m), 1.38-1.55 (2 H, m). $^{19}$F NMR (376 MHz, CDCl$_3$-d) δ ppm −92.15 (1 F, d, J=237.55 Hz), −102.44 (1 F, d, J=235.82 Hz). LC (Cond. OL1): R$_t$=1.66 min. LC/MS: Anal. Calcd. For [2M+Na]$^+$ C$_{34}$H$_{42}$F$_4$N$_2$NaO$_8$: 705.28; found: 705.18.

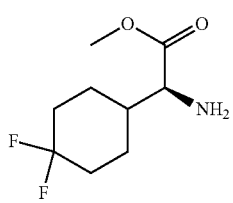

Cap 176, step e

Difluoride Cap 176, step d (4 g, 11.72 mmol) was dissolved in MeOH (120 mL) and charged with Pd/C (1.247 g, 1.172 mmol). The suspension was flushed with N$_2$ (3×) and the reaction mixture was placed under 1 atm of H$_2$ (balloon). The mixture was stirred at ambient temperature for 48 h. The suspension was then filtered though a plug of Celite and concentrated under vacuum to give an oil that corresponded to amino acid Cap 176, step e (2.04 g) and that was used without further purification. $^1$H NMR (400 MHz, DMSO-d$_6$) δ ppm 3.62 (3 H, s), 3.20 (1 H, d, J=5.77 Hz), 1.91-2.09 (2 H, m), 1.50-1.88 (7 H, m), 1.20-1.45 (2 H, m). $^{19}$F NMR (376 MHz, DMSO-d$_6$) δ ppm −89.39 (1 F, d, J=232.35 Hz), −100.07 (1 F, d, J=232.35 Hz). $^{13}$C NMR (101 MHz, DMSO-d$_6$) δ ppm 175.51 (1 C, s), 124.10 (1 C, t, J=241.21, 238.90 Hz), 57.74 (1 C, s), 51.39 (1 C, s), 39.23 (1 C, br. s.), 32.02-33.83 (2 C, m), 25.36 (1 C, d, J=10.02 Hz), 23.74 (1 C, d, J=9.25 Hz). LC (Cond. OL2): R$_t$=0.95 min. LC/MS: Anal. Calcd. For [2M+H]$^+$ C$_{18}$H$_{31}$F$_4$N$_2$O$_2$: 415.22; found: 415.40.

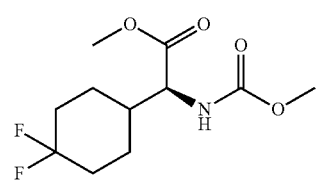

Cap 176, step f

Methyl chloroformate (1.495 mL, 19.30 mmol) was added to a solution of amino acid Cap 176, step e (2 g, 9.65 mmol) and DIEA (6.74 mL, 38.6 mmol) in CH$_2$Cl$_2$ (100 mL). The resulting solution was stirred at rt for 3 h and volatiles were removed under reduced pressure. The residue was purified via Biotage (0% to 20% EtOAc/Hex; 90 g column). A clear oil that solidified upon standing under vacuum and corresponding to carbamate Cap-176, step f (2.22 g) was recovered. $^1$H NMR (500 MHz, CDCl$_3$-d) δ ppm 5.27 (1 H, d, J=8.55 Hz), 4.39 (1 H, dd, J=8.85, 4.88 Hz), 3.77 (3 H, s), 3.70 (3 H, s), 2.07-2.20 (2 H, m), 1.84-1.96 (1 H, m), 1.64-1.82 (4 H, m), 1.39-1.51 (2 H, m). $^{19}$F NMR (471 MHz, CDCl$_3$-d) δ ppm −92.55 (1 F, d, J=237.13 Hz), −102.93 (1 F, d, J=237.12 Hz). $^{13}$C NMR (126 MHz, CDCl$_3$-d) δ ppm 171.97 (1 C, s), 156.69 (1 C, s), 119.77-125.59 (1 C, m), 57.24 (1 C, br. s.), 52.48 (1 C, br. s.), 52.43 (1 C, s), 39.15 (1 C, s), 32.50-33.48 (2 C, m), 25.30 (1 C, d, J=9.60 Hz), 24.03 (1 C, d, J=9.60 Hz). LC (Cond. OL1): R$_t$=1.49 min. LC/MS: Anal. Calcd. For [M+Na]$^+$ C$_{11}$H$_{17}$F$_2$NNaO$_4$: 288.10; found: 288.03.

Cap-176

A solution of LiOH (0.379 g, 15.83 mmol) in Water (25 mL) was added to a solution of carbamate Cap-176, step f (2.1 g, 7.92 mmol) in THF (75 mL) and the resulting mixture was stirred at ambient temperature for 4 h. THF was removed under vacuum and the remaining aqueous phase was acidified with 1N HCl solution (2 mL) and then extracted with EtOAc (2×50 mL). The combined organic layers were dried (MgSO$_4$), filtered and concentrated to give a white foam corresponding to Cap-176 (1.92 g). $^1$H NMR (400 MHz, DMSO-d$_6$) δ ppm 12.73 (1 H, s), 7.50 (1 H, d, J=8.78 Hz), 3.97 (1 H, dd, J=8.53, 6.02 Hz), 3.54 (3 H, s), 1.92-2.08 (2 H, m), 1.57-1.90 (5 H, m), 1.34-1.48 (1 H, m), 1.27 (1 H, qd, J=12.72, 3.26 Hz). $^{19}$F NMR (376 MHz, DMSO-d$_6$) δ ppm −89.62 (1 F, d, J=232.35 Hz), −99.93 (1 F, d, J=232.35 Hz). LC (Cond. OL2): R$_t$=0.76 min. LC/MS: Anal. Calcd. For [M−H]$^+$ C$_{10}$H$_{14}$F$_2$NO$_4$: 250.09; found: 250.10.

Biological Activity

An HCV Replicon assay was utilized in the present disclosure, and was prepared, conducted and validated as described in commonly owned PCT/US2006/022197 and in O'Boyle et. al. *Antimicrob Agents Chemother.* 2005 April; 49(4):1346-53. Assay methods incorporating luciferase reporters have also been used as described (Apath.com).

HCV-neo replicon cells and replicon cells containing mutations in the NS5A region were used to test the currently described family of compounds. The compounds were determined to have more than 10-fold less inhibitory activity on cells containing mutations than wild-type cells. Thus, the compounds of the present disclosure can be effective in inhibiting the function of the HCV NS5A protein and are understood to be as effective in combinations as previously described in application PCT/US2006/022197 and commonly owned WO/04014852. Further, the compounds of the present disclosure can be effective against the HCV 1b genotype. It should also be understood that the compounds of the present disclosure can inhibit multiple genotypes of HCV. Table 2 shows the $EC_{50}$ (Effective 50% inhibitory concentration) values of representative compounds of the present disclosure against the HCV 1b genotype. In one embodiment, compounds of the present disclosure are inhibitory versus 1a, 1b, 2a, 2b, 3a, 4a, and 5a genotypes. $EC_{50}$ values against HCV 1b are as follows A (10-350 nM); B (1-9.9 nM); C (0.1-0.99 nM); D (0.002-0.099 nM).

| Compound No. | 1b EC50 (nM) | Range | Name |
|---|---|---|---|
| OL-1 | | B | (1R)-2-((2S)-2-(4-(4-(4-(2-((2S)-1-((2R)-2-(dimethylamino)-2-phenylacetyl)-2-pyrrolidinyl)-1H-imidazol-5-yl)phenoxy)phenyl)-1H-imidazol-2-yl)-1-pyrrolidinyl)-N,N-dimethyl-2-oxo-1-phenylethanamine |
| OL-2 | 9.1 | B | (1R)-2-((2S)-2-(4-(4-(4-(2-((2S)-1-((2R)-2-hydroxy-2-phenylacetyl)-2-pyrrolidinyl)-1H-imidazol-5-yl)phenoxy)phenyl)-1H-imidazol-2-yl)-1-pyrrolidinyl)-2-oxo-1-phenylethanol |
| OL-3 | | B | dimethyl (oxybis(4,1-phenylene-1H-imidazole-4,2-diyl(2S)-2,1-pyrrolidinediyl((1R)-2-oxo-1-phenyl-2,1-ethanediyl)))biscarbamate |
| OL-4 | 0.07 | D | (1R)-2-((2S)-2-(4-(3-(4-(2-((2S)-1-((2R)-2-(dimethylamino)-2-phenylacetyl)-2-pyrrolidinyl)-1H-imidazol-4-yl)phenoxy)phenyl)-1H-imidazol-2-yl)-1-pyrrolidinyl)-N,N-dimethyl-2-oxo-1-phenylethanamine |
| OL-5 | 80 | A | (1R)-2-((2S)-2-(4-(3-(4-(2-((2S)-1-((2R)-2-hydroxy-2-phenylacetyl)-2-pyrrolidinyl)-1H-imidazol-4-yl)phenoxy)phenyl)-1H-imidazol-2-yl)-1-pyrrolidinyl)-2-oxo-1-phenylethanol |
| OL-6 | | D | methyl ((1R)-2-((2S)-2-(4-(3-(4-(2-((2S)-1-((2R)-2-((methoxycarbonyl)amino)-2-phenylacetyl)-2-pyrrolidinyl)-1H-imidazol-4-yl)phenoxy)phenyl)-1H-imidazol-2-yl)-1-pyrrolidinyl)-2-oxo-1-phenylethyl)carbamate |
| OL-7 | | D | (1R)-2-((2S)-2-(4-(4-((4-(2-((2S)-1-((2R)-2-(dimethylamino)-2-phenylacetyl)-2-pyrrolidinyl)-1H-imidazol-4-yl)benzyl)oxy)phenyl)-1H-imidazol-2-yl)-1-pyrrolidinyl)-N,N-dimethyl-2-oxo-1-phenylethanamine |
| OL-8 | | D | methyl ((1R)-2-((2S)-2-(4-(4-((4-(2-((2S)-1-((2R)-2-((methoxycarbonyl)amino)-2-phenylacetyl)-2-pyrrolidinyl)-1H-imidazol-4-yl)benzyl)oxy)phenyl)-1H-imidazol-2-yl)-1-pyrrolidinyl)-2-oxo-1-phenylethyl)carbamate |
| OL-9 | | D | (1R)-2-((2S)-2-(4-(4-(2-(4-(2-((2S)-1-((2R)-2-(dimethylamino)-2-phenylacetyl)-2-pyrrolidinyl)-1H-imidazol-5-yl)phenyl)ethyl)phenyl)-1H-imidazol-2-yl)-1-pyrrolidinyl)-N,N-dimethyl-2-oxo-1-phenylethanamine |
| OL-10 | | D | (1R,1'R)-2,2'-(1,2-ethanediylbis(4,1-phenylene-1H-imidazole-4,2-diyl(2S)-2,1-pyrrolidinediyl))bis(2-oxo-1-phenylethanol) |
| OL-11 | | D | dimethyl (1,2-ethanediylbis(4,1-phenylene-1H-imidazole-4,2-diyl(2S)-2,1-pyrrolidinediyl((1R)-2-oxo-1-phenyl-2,1-ethanediyl)))biscarbamate |
| OL-12 | | D | N',N'''-(1,2-ethanediylbis(4,1-phenylene-1H-imidazole-4,2-diyl(2S)-2,1-pyrrolidinediyl((1R)-2-oxo-1-phenyl-2,1-ethanediyl)))bis(1-ethylurea) |
| OL-13 | | D | 1-cyclopentyl-3-((1R)-2-((2S)-2-(4-(4-(2-(4-(2-((2S)-1-((2R)-2-((cyclopentylcarbamoyl)amino)-2-phenylacetyl)-2-pyrrolidinyl)-1H-imidazol-5-yl)phenyl)ethyl)phenyl)-1H-imidazol-2-yl)-1-pyrrolidinyl)-2-oxo-1-phenylethyl)urea |
| OL-14 | | C | (1R)-2-((2S)-2-(4-(4-(((4-(2-((2S)-1-((2R)-2-(dimethylamino)-2-phenylacetyl)-2-pyrrolidinyl)-1H-imidazol-5-yl)benzyl)oxy)methyl)phenyl)-1H-imidazol-2-yl)-1-pyrrolidinyl)-N,N-dimethyl-2-oxo-1-phenylethanamine |

-continued

| Compound No. | 1b EC50 (nM) | Range | Name |
|---|---|---|---|
| OL-15 | 1.1 | B | (1R)-2-((2S)-2-(4-(4-(((4-(2-((2S)-1-((2R)-2-hydroxy-2-phenylacetyl)-2-pyrrolidinyl)-1H-imidazol-5-yl)benzyl)oxy)methyl)phenyl)-1H-imidazol-2-yl)-1-pyrrolidinyl)-2-oxo-1-phenylethanol |
| OL-16 | | D | dimethyl (oxybis(methylene-4,1-phenylene-1H-imidazole-4,2-diyl(2S)-2,1-pyrrolidinediyl((1R)-2-oxo-1-phenyl-2,1-ethanediyl)))biscarbamate |
| OL-17 | | D | 1-methyl-3-((1R)-2-((2S)-2-(4-(4-(((4-(2-((2S)-1-((2R)-2-((methylcarbamoyl)amino)-2-phenylacetyl)-2-pyrrolidinyl)-1H-imidazol-5-yl)benzyl)oxy)methyl)phenyl)-1H-imidazol-2-yl)-1-pyrrolidinyl)-2-oxo-1-phenylethyl)urea |
| OL-18 | | D | 1-ethyl-3-((1R)-2-((2S)-2-(4-(4-(((4-(2-((2S)-1-((2R)-2-((ethylcarbamoyl)amino)-2-phenylacetyl)-2-pyrrolidinyl)-1H-imidazol-5-yl)benzyl)oxy)methyl)phenyl)-1H-imidazol-2-yl)-1-pyrrolidinyl)-2-oxo-1-phenylethyl)urea |
| OL-19 | | B | 1-cyclopentyl-3-((1R)-2-((2S)-2-(4-(4-(((4-(2-((2S)-1-((2R)-2-((cyclopentylcarbamoyl)amino)-2-phenylacetyl)-2-pyrrolidinyl)-1H-imidazol-5-yl)benzyl)oxy)methyl)phenyl)-1H-imidazol-2-yl)-1-pyrrolidinyl)-2-oxo-1-phenylethyl)urea |
| OL-20 | | C | (1R)-2-((2S)-2-(4-(3-(((4-(2-((2S)-1-((2R)-2-(dimethylamino)-2-phenylacetyl)-2-pyrrolidinyl)-1H-imidazol-4-yl)benzyl)oxy)methyl)phenyl)-1H-imidazol-2-yl)-1-pyrrolidinyl)-N,N-dimethyl-2-oxo-1-phenylethanamine |
| OL-21 | | C | (1R)-2-((2S)-2-(4-(3-(((4-(2-((2S)-1-((2R)-2-hydroxy-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethanol |
| OL-22 | | D | (methyl ((1R)-2-((2S)-2-(4-(3-(((4-(2-((2S)-1-((2R)-2-((methoxycarbonyl)amino)-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethyl)carbamate |
| OL-23 | | C | 1-methyl-3-((1R)-2-((2S)-2-(4-(3-(((4-(2-((2S)-1-((2R)-2-((methylcarbamoyl)amino)-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethyl)urea |
| OL-24 | | D | 1-ethyl-3-((1R)-2-((2S)-2-(4-(3-(((4-(2-((2S)-1-((2R)-2-((ethylcarbamoyl)amino)-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethyl)urea |
| OL-25 | | D | 1-cyclopentyl-3-((1R)-2-((2S)-2-(4-(3-(((4-(2-((2S)-1-((2R)-2-((cyclopentylcarbamoyl)amino)-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethyl)urea |
| D-1 | | D | dimethyl (1,1':4',1''-terphenyl-4,4''-diylbis(1H-imidazole-4,2-diyl(2S)-2,1-pyrrolidinediyl((1R)-2-oxo-1-phenyl-2,1-ethanediyl)))biscarbamate |
| D-2 | | C | (1R)-2-((2S)-2-(4-(4''-(2-((2S)-1-((2R)-2-(dimethylamino)-2-phenylacetyl)-2-pyrrolidinyl)-1H-imidazol-5-yl)-1,1':4',1''-terphenyl-4-yl)-1H-imidazol-2-yl)-1-pyrrolidinyl)-N,N-dimethyl-2-oxo-1-phenylethanamine |
| D-3 | 0.006 | D | methyl ((1S)-1-(((2S)-2-(4-(4-((2-((2S)-1-((2S)-2-((methoxycarbonyl)amino)-3-methylbutanoyl)-2-pyrrolidinyl)-4,5-dihydro-1H-naphtho[1,2-d]imidazol-7-yl)ethynyl)phenyl)-1H-imidazol-2-yl)-1-pyrrolidinyl)carbonyl)-2-methylpropyl)carbamate |

-continued

| Compound No. | 1b EC50 (nM) | Range | Name |
|---|---|---|---|
| D-4 | | D | methyl ((1R)-2-((2S)-2-(4-(4-((2-((2S)-1-((2R)-2-((methoxycarbonyl)amino)-2-phenylacetyl)-2-pyrrolidinyl)-4,5-dihydro-1H-naphtho[1,2-d]imidazol-7-yl)ethynyl)phenyl)-1H-imidazol-2-yl)-1-pyrrolidinyl)-2-oxo-1-phenylethyl)carbamate |
| D-5 | | D | methyl ((1R)-2-((2S)-2-(7-((4-(2-((2S)-1-((2R)-2-((methoxycarbonyl)amino)-2-phenylacetyl)-2-pyrrolidinyl)-1H-imidazol-4-yl)phenyl)ethynyl)-1H-naphtho[1,2-d]imidazol-2-yl)-1-pyrrolidinyl)-2-oxo-1-phenylethyl)carbamate |
| D-6 | | D | methyl ((1S)-1-(((2S)-2-(4-(4-((2-((2S)-1-((2S)-2-((methoxycarbonyl)amino)-3-methylbutanoyl)-2-pyrrolidinyl)-1H-naphtho[1,2-d]imidazol-7-yl)ethynyl)phenyl)-1H-imidazol-2-yl)-1-pyrrolidinyl)carbonyl)-2-methylpropyl)carbamate |
| D-7 | | D | methyl ((1S)-1-(((1R,3S,5R)-3-(4-((2-((1R,3S,5R)-2-((2S)-2-((methoxycarbonyl)amino)-3-methylbutanoyl)-2-azabicyclo[3.1.0]hex-3-yl)-1H-naphtho[1,2-d]imidazol-7-yl)ethynyl)phenyl)-1H-imidazol-2-yl)-2-azabicyclo[3.1.0]hex-2-yl)carbonyl)-2-methylpropyl)carbamate |
| D-8 | 0.005 | D | methyl ((1R)-2-((1R,3S,5R)-3-(7-((4-(2-((1R,3S,5R)-2-((2R)-2-((methoxycarbonyl)amino)-2-phenylacetyl)-2-azabicyclo[3.1.0]hex-3-yl)-1H-imidazol-4-yl)phenyl)ethynyl)-1H-naphtho[1,2-d]imidazol-2-yl)-2-azabicyclo[3.1.0]hex-2-yl)-2-oxo-1-phenylethyl)carbamate |
| D-9 | | D | methyl ((1S)-1-(((1R,3S,5R)-3-(7-((2-((1R,3S,5R)-2-((2S)-2-((methoxycarbonyl)amino)-3-methylbutanoyl)-2-azabicyclo[3.1.0]hex-3-yl)-4,5-dihydro-1H-naphtho[1,2-d]imidazol-7-yl)ethynyl)-4,5-dihydro-1H-naphtho[1,2-d]imidazol-2-yl)-2-azabicyclo[3.1.0]hex-2-yl)carbonyl)-2-methylpropyl)carbamate |
| D-10 | | D | methyl ((1S)-1-(((1R,3S,5R)-3-(7-((2-((3S)-2-((2S)-2-((methoxycarbonyl)amino)-3-methylbutanoyl)-2-azabicyclo[3.1.0]hex-3-yl)-1H-naphtho[1,2-d]imidazol-7-yl)ethynyl)-1H-naphtho[1,2-d]imidazol-2-yl)-2-azabicyclo[3.1.0]hex-2-yl)carbonyl)-2-methylpropyl)carbamate |
| D-11 | | D | methyl ((1S)-2-((1R,3S,5R)-3-(7-((2-((1R,3S,5R)-2-((2S)-2-((methoxycarbonyl)amino)-3-methylbutanoyl)-2-azabicyclo[3.1.0]hex-3-yl)-1H-naphtho[1,2-d]imidazol-7-yl)ethynyl)-1H-naphtho[1,2-d]imidazol-2-yl)-2-azabicyclo[3.1.0]hex-2-yl)-2-oxo-1-(tetrahydro-2H-pyran-4-yl)ethyl)carbamate |
| M1 | | D | methyl ((1S)-1-(((2S)-2-(4-(4-((4-(2-((2S)-1-((2S)-2-((methoxycarbonyl)amino)-3-methylbutanoyl)-2-pyrrolidinyl)-1H-imidazol-4-yl)phenyl)ethynyl)phenyl)-1H-imidazol-2-yl)-1-prrolidinyl)carbonyl)-2-methylpropyl)carbamate |
| M2 | 0.24 | C | dimethyl (1,2-ethynediylbis(4,1-phenylene-1H-imidazole-4,2-diyl(2S)-2,1-pyrrolidinediyl((1R)-2-oxo-1-phenyl-2,1-ethanediyl)))biscarbamate |
| M2.1 | | D | dimethyl (1,2-ethynediylbis(4,1-phenylene-1H-imidazole-4,2-diyl(2S)-2,1-pyrrolidinediyl((1S)-2-oxo-1-(tetrahydro-2H-pyran-4-yl)-2,1-ethanediyl)))biscarbamate |
| M3 | | D | methyl ((1S)-1-(((1R,3S,5R)-3-(4-(4-((4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)ethynyl)phenyl)-1H-imidazol-2-yl)-2-azabicyclo[3.1.0]hex-2-yl)carbonyl)-2-methylpropyl)carbamate |

-continued

| Compound No. | 1b EC50 (nM) | Range | Name |
|---|---|---|---|
| M4 | | D | dimethyl (1,2-ethynediylbis(4,1-phenylene-1H-imidazole-4,2-diyl(1R,3S,5R)-2-azabicyclo[3.1.0]hexane-3,2-diyl((2S)-1-oxo-1,2-butanediyl)))biscarbamate |
| M5 | | C | dimethyl (1,2-ethynediylbis(4,1-phenylene-1H-imidazole-4,2-diyl(1R,3S,5R)-2-azabicyclo[3.1.0]hexane-3,2-diyl((1S)-1-cyclobutyl-2-oxo-2,1-ethanediyl)))biscarbamate |
| M6 | 0.0033 | D | dimethyl (1,2-ethynediylbis(4,1-phenylene-1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate |
| M7 | | D | methyl ((1S)-1-(((1R,3S,5R)-3-(4-(4-((4-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)phenyl)ethynyl)phenyl)-1H-imidazol-2-yl)-2-azabicyclo[3.1.0]hex-2-yl)carbonyl)-2-methylpropyl)carbamate |
| M8 | | D | methyl ((1S)-1-(((1R,3S,5R)-3-(4-chloro-5-(4-((4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)ethynyl)phenyl)-1H-imidazol-2-yl)-2-azabicyclo[3.1.0]hex-2-yl)carbonyl)-2-methylpropyl)carbamate |
| M9 | | D | methyl ((1S)-1-(((1R,3S,5R)-3-(4-chloro-5-(4-((4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)ethynyl)phenyl)-1H-imidazol-2-yl)-2-azabicyclo[3.1.0]hex-2-yl)carbonyl)-2-methylpropyl)carbamate |
| M9.1 | | D | methyl ((1S)-2-((1R,3S,5R)-3-(4-((4-(4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)phenyl)ethynyl)phenyl)-1H-imidazol-2-yl)-2-azabicyclo[3.1.0]hex-2-yl)-2-oxo-1-(tetrahydro-2H-pyran-4-yl)ethyl)carbamate |
| M9.2 | | D | dimethyl (1,2-ethynediylbis(4,1-phenylene(4-chloro-1H-imidazole-5,2-diyl)(1R,3S,5R)-2-azabicyclo[3.1.0]hexane-3,2-diyl((1S)-2-oxo-1-(tetrahydro-2H-pyran-4-yl)-2,1-ethanediyl)))biscarbamate |
| M9.3 | | D | methyl ((1S)-1-(((1R,3S,5R)-3-(4-(4-((1S,2S)-2-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)cyclopropyl)phenyl)-1H-imidazol-2-yl)-2-azabicyclo[3.1.0]hex-2-yl)carbonyl)-2-methylpropyl)carbamate |
| M9.4 | | D | dimethyl ((1S,2S)-1,2-cyclopropanediylbis(4,1-phenylene-1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate |
| m9.5 | | D | methyl ((1S)-1-(((1R,3S,5R)-3-(4-(4-((1R,2R)-2-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)cyclopropyl)phenyl)-1H-imidazol-2-yl)-2-azabicyclo[3.1.0]hex-2-yl)carbonyl)-2-methylpropyl)carbamate |
| M9.6 | | D | dimethyl ((1R,2R)-1,2-cyclopropanediylbis(4,1-phenylene-1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate |

| Compound No. | 1b EC50 (nM) | Range | Name |
|---|---|---|---|
| M9.7 | | D | methyl ((1S)-1-(((2S,4S)-2-(4-(4-((1S,2S)-2-(4-(2-((2S,4S)-1-((2S)-2-((methoxycarbonyl)amino)-3-methylbutanoyl)-4-methyl-2-pyrrolidinyl)-1H-imidazol-4-yl)phenyl)cyclopropyl)phenyl)-1H-imidazol-2-yl)-4-methyl-1-pyrrolidinyl)carbonyl)-2-methylpropyl)carbamate |
| M9.8 | | D | dimethyl ((1S,2S)-1,2-cyclopropanediylbis(4,1-phenylene-1H-imidazole-4,2-diyl((2S,4S)-4-methyl-2,1-pyrrolidinediyl)((1S)-2-oxo-1-(tetrahydro-2H-pyran-4-yl)-2,1-ethanediyl)))biscarbamate |
| M10 | | D | methyl ((1S)-1-(((2S,5S)-2-(4-(4-((4-(2-((2S,5S)-1-((2S)-2-((methoxycarbonyl)amino)-3-methylbutanoyl)-5-methyl-2-pyrrolidinyl)-1H-imidazol-4-yl)phenyl)ethynyl)phenyl)-1H-imidazol-2-yl)-5-methyl-1-pyrrolidinyl)carbonyl)-2-methylpropyl)carbamate |
| M11 | | D | dimethyl (1,2-ethynediylbis(4,1-phenylene-1H-imidazole-4,2-diyl((2S,5S)-5-methyl-2,1-pyrrolidinediyl)((2S)-1-oxo-1,2-butanediyl)))biscarbamate |
| M12 | | D | dimethyl (1,2-ethynediylbis(4,1-phenylene-1H-imidazole-4,2-diyl((2S,5S)-5-methyl-2,1-pyrrolidinediyl)((1S)-2-oxo-1-(tetrahydro-2H-pyran-4-yl)-2,1-ethanediyl)))biscarbamate |
| M12.1 | | D | methyl ((1S)-1-(((2S,5S)-2-(4-(4-((4-(2-((2S,5S)-1-((2S)-2-((methoxycarbonyl)amino)-2-(tetrahydro-2H-pyran-4-yl)acetyl)-5-methyl-2-pyrrolidinyl)-1H-imidazol-4-yl)phenyl)ethynyl)phenyl)-1H-imidazol-2-yl)-5-methyl-1-pyrrolidinyl)carbonyl)-2-methylpropyl)carbamate |
| M12.2 | | D | methyl ((1S)-1-(((2S,4S)-2-(4-(4-((4-(2-((2S,4S)-1-((2S)-2-((methoxycarbonyl)amino)-3-methylbutanoyl)-4-methyl-2-pyrrolidinyl)-1H-imidazol-4-yl)phenyl)ethynyl)phenyl)-1H-imidazol-2-yl)-4-methyl-1-pyrrolidinyl)carbonyl)-2-methylpropyl)carbamate |
| M12.3 | 0.014 | D | dimethyl (1,2-ethynediylbis(4,1-phenylene-1H-imidazole-4,2-diyl((2S,4S)-4-methyl-2,1-pyrrolidinediyl)((1S)-2-oxo-1-(tetrahydro-2H-pyran-4-yl)-2,1-ethanediyl)))biscarbamate |
| M12.4 | | D | methyl ((1S)-1-(((2S,4S)-2-(4-((4-(4-chloro-2-((2S,4S)-1-((2S)-2-((methoxycarbonyl)amino)-3-methylbutanoyl)-4-methyl-2-pyrrolidinyl)-1H-imidazol-5-yl)phenyl)ethynyl)phenyl)-1H-imidazol-2-yl)-4-methyl-1-pyrrolidinyl)carbonyl)-2-methylpropyl)carbamate |
| M12.5 | | D | methyl ((1S)-1-(((2S,4S)-2-(4-chloro-5-(4-((4-(4-chloro-2-((2S,4S)-1-(2S)-2-((methoxycarbonyl)amino)-3-methylbutanoyl)-4-methyl-2-pyrrolidinyl)-1H-imidazol-5-yl)phenyl)ethynyl)phenyl)-1H-imidazol-2-yl)-4-methyl-1-pyrrolidinyl)carbonyl)-2-methylpropyl)carbamate |
| M12.6 | | D | methyl ((1S)-2-((2S,4S)-2-(4-(4-((4-(4-chloro-2-((2S,4S)-1-((2S)-2-((methoxycarbonyl)amino)-2-(tetrahydro-2H-pyran-4-yl)acetyl)-4-methyl-2-pyrrolidinyl)-1H-imidazol-5-yl)phenyl)ethynyl)phenyl)-1H-imidazol-2-yl)-4-methyl-1-pyrrolidinyl)-2-oxo-1-(tetrahydro-2H-pyran-4-yl)ethyl)carbamate |
| M12.7 | 0.061 | D | dimethyl (1,2-ethynediylbis(4,1-phenylene(4-chloro-1H-imidazole-5,2-diyl)((2S,4S)-4-methyl-2,1-pyrrolidinediyl)((1S)-2-oxo-1-(tetrahydro-2H-pyran-4-yl)-2,1-ethanediyl)))biscarbamate |

-continued

| Compound No. | 1b EC50 (nM) | Range | Name |
|---|---|---|---|
| M12.8 | | D | methyl ((1S)-2-((2S,4S)-2-(4-(4-((4-(2-((2S,4S)-1-((2S)-2-((methoxycarbonyl)amino)-3-methylbutanoyl)-4-methyl-2-pyrrolidinyl)-1H-imidazol-4-yl)phenyl)ethynyl)phenyl)-1H-imidazol-2-yl)-4-methyl-1-pyrrolidinyl)-2-oxo-1-(tetrahydro-2H-pyran-4-yl)ethyl)carbamate |
| M12.9 | | D | methyl ((1S)-1-(((1S,3S,5S)-3-(4-(4-((4-(2-((1S,3S,5S)-2-((2S)-2-((methoxycarbonyl)amino)-3-methylbutanoyl)-5-methyl-2-azabicyclo[3.1.0]hex-3-yl)-1H-imidazol-4-yl)phenyl)ethynyl)phenyl)-1H-imidazol-2-yl)-5-methyl-2-azabicyclo[3.1.0]hex-2-yl)carbonyl)-2-methylpropyl)carbamate |
| M13 | | D | methyl ((1S)-1-(((1R,3S,5R)-3-(4-(4-((E)-2-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)vinyl)phenyl)-1H-imidazol-2-yl)-2-azabicyclo[3.1.0]hex-2-yl)carbonyl)-2-methylpropyl)carbamate |
| M14 | 0.017 | D | dimethyl ((E)-1,2-ethenediylbis(4,1-phenylene-1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate |
| M15 | | D | methyl ((1S)-2-((1R,3S,5R)-3-(4-(4-((E)-2-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)vinyl)phenyl)-1H-imidazol-2-yl)-2-azabicyclo[3.1.0]hex-2-yl)-2-oxo-1-(tetrahydro-2H-pyran-4-yl)ethyl)carbamate |
| N1 | | D | methyl ((1S)-1-(((2S)-2-(4-(4-((4-(2-((2S)-4,4-difluoro-1-((2S)-2-((methoxycarbonyl)amino)-3-methylbutanoyl)-2-pyrrolidinyl)-1H-imidazol-4-yl)phenyl)ethynyl)phenyl)-1H-imidazol-2-yl)-4,4-difluoro-1-pyrrolidinyl)carbonyl)-2-methylpropyl)carbamate |
| N2 | | D | dimethyl (ethyne-1,2-diylbis(4,1-phenylene-1H-imidazole-5,2-diyl((2S)-4,4-difluoropyrrolidine-2,1-diyl)((1S)-2-oxo-1-(tetrahydro-2H-pyran-4-yl)ethane-2,1-diyl)))biscarbamate |
| N3 | 0.25 | A | methyl ((1R)-2-((2S)-2-(5-(4-((4-(2-((2S)-4,4-difluoro-1-((2S)-2-((methoxycarbonyl)amino)-2-(tetrahydro-2H-pyran-4-yl)acetyl)pyrrolidin-2-yl)-1H-imidazol-5-yl)phenyl)ethynyl)phenyl)-1H-imidazol-2-yl)-4,4-difluoropyrrolidin-1-yl)-2-oxo-1-(tetrahydro-2H-pyran-4-yl)ethyl)carbamate |
| N4 | 0.18 | A | dimethyl (ethyne-1,2-diylbis(4,1-phenylene-1H-imidazole-5,2-diyl((2S)-4,4-difluoropyrrolidine-2,1-diyl)((1R)-2-oxo-1-(tetrahydro-2H-pyran-4-yl)ethane-2,1-diyl)))biscarbamate |
| N5 | | D | methyl ((1S)-1-(((3S)-3-(4-(4-((4-(2-((3S)-4-((2S)-2-((methoxycarbonyl)amino)-3-methylbutanoyl)-3-morpholinyl)-1H-imidazol-4-yl)phenyl)ethynyl)phenyl)-1H-imidazol-2-yl)-4-morpholinyl)carbonyl)-2-methylpropyl)carbamate |
| N6 | | A | methyl ((1S)-1-(((2S)-2-(4-(4-((4-(2-((2S)-1-((2S)-2-((methoxycarbonyl)amino)-3-methylbutanoyl)-2-piperidinyl)-1H-imidazol-4-yl)phenyl)ethynyl)phenyl)-1H-imidazol-2-yl)-1-piperidinyl)carbonyl)-2-methylpropyl)carbamate |
| N7 | | D | methyl ((1S)-1-(((2S,4S)-4-hydroxy-2-(4-(4-((4-(2-((2S,4S)-4-hydroxy-1-((2S)-2-((methoxycarbonyl)amino)-3-methylbutanoyl)-2-pyrrolidinyl)-1H-imidazol-4-yl)phenyl)ethynyl)phenyl)-1H-imidazol-2-yl)-1-pyrrolidinyl)carbonyl)-2-methylpropyl)carbamate |

-continued

| Compound No. | 1b EC50 (nM) | Range | Name |
|---|---|---|---|
| N7.1 | | | methyl ((1S)-1-(((2S)-2-(4-(4-((4-(2-((2S)-1-((2S)-2-((methoxycarbonyl)amino)-3-methylbutanoyl)-4-methylene-2-pyrrolidinyl)-1H-imidazol-4-yl)phenyl)ethynyl)phenyl)-1H-imidazol-2-yl)-4-methylene-1-pyrrolidinyl)carbonyl)-2-methylpropyl)carbamate |
| N7.2 | | | methyl ((1S)-1-(((2S,4R)-4-hydroxy-2-(4-(4-((4-(2-((2S,4R)-4-hydroxy-1-((2S)-2-((methoxycarbonyl)amino)-3-methylbutanoyl)-2-pyrrolidinyl)-1H-imidazol-4-yl)phenyl)ethynyl)phenyl)-1H-imidazol-2-yl)-1-pyrrolidinyl)carbonyl)-2-methylpropyl)carbamate |
| N8 | | A | methyl((1S)-1-((((1S,3S,5S)-3-(4-(4-((4-(2-((1S,3S,5S)-2-((2S)-2-((methoxycarbonyl)amino)-3-methylbutanoyl)-2-azabicyclo[3.1.0]hex-3-yl)-1H-imidazol-4-yl)phenyl)ethynyl)phenyl)-1H-imidazol-2-yl)-2-azabicyclo[3.1.0]hex-2-yl)carbonyl)-2-methylpropyl)carbamate |
| N9 | | D | dimethyl (1,2-ethynediylbis(4,1-phenylene-1H-imidazole-4,2-diyl(1S,3S,5S)-2-azabicyclo[3.1.0]hexane-3,2-diyl((1S)-2-oxo-1-(tetrahydro-2H-pyran-4-yl)-2,1-ethanediyl)))biscarbamate |
| J1 | | D | methyl ((1S)-1-(((2S)-2-(4-(3-((3-(2-((2S)-1-((2S)-2-((methoxycarbonyl)amino)-3-methylbutanoyl)-2-pyrrolidinyl)-1H-imidazol-4-yl)phenyl)ethynyl)phenyl)-1H-imidazol-2-yl)-1-pyrrolidinyl)carbonyl)-2-methylpropyl)carbamate |
| J1.1 | 338.8 | A | methyl ((1S)-2-methyl-1-(((2S)-2-(4-(3-((3-(2-((2S)-2-pyrrolidinyl)-1H-imidazol-4-yl)phenyl)ethynyl)phenyl)-1H-imidazol-2-yl)-1-pyrrolidinyl)carbonyl)propyl)carbamate |
| J2 | 0.12 | C | dimethyl (1,2-ethynediylbis(3,1-phenylene-1H-imidazole-4,2-diyl(2S)-2,1-pyrrolidinediyl((1S)-2-oxo-1-(tetrahydro-2H-pyran-4-yl)-2,1-ethanediyl)))biscarbamate |
| J3 | | D | methyl ((1S)-1-(((1R,3S,5R)-3-(4-(3-((3-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)ethynyl)phenyl)-1H-imidazol-2-yl)-2-azabicyclo[3.1.0]hex-2-yl)carbonyl)-2-methylpropyl)carbamate |
| J4 | | D | dimethyl (1,2-ethynediylbis(3,1-phenylene-1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate |
| J5 | | D | methyl ((1S)-1-(((2S)-2-(4-(4'-((4-(2-((2S)-1-((2S)-2-((methoxycarbonyl)amino)-3-methylbutanoyl)-2-pyrrolidinyl)-1H-imidazol-4-yl)phenyl)ethynyl)-4-biphenylyl)-1H-imidazol-2-yl)-1-pyrrolidinyl)carbonyl)-2-methylpropyl)carbamate |

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A, It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (Id):

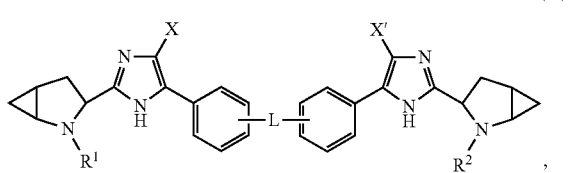

(Id)

or a pharmaceutically acceptable salt or a tautomer thereof, wherein

X is hydrogen or chloro (Cl);
X' is hydrogen or chloro (Cl);
L is selected from —O—, —CH$_2$CH$_2$—, —CH=CH—, —OCH$_2$—, —CH$_2$O—, —CH$_2$OCH$_2$—,

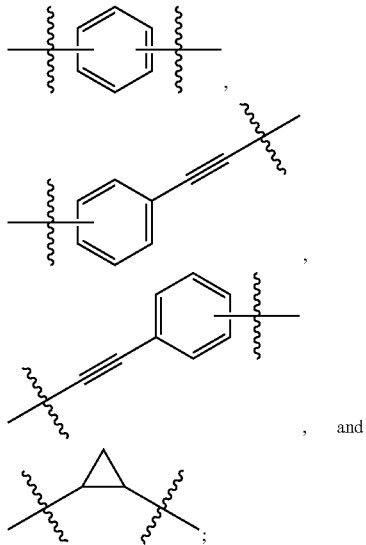

, and

;

$R^1$ is hydrogen or —C(O)R$^x$;
$R^2$ is hydrogen or —C(O)R$^y$;
R$^x$ and R$^y$ are independently selected from cycloalkyl, heteroaryl, heterocyclyl, alkoxy, and alkyl, said alkyl being substituted by one or more substituents independently selected from aryl, alkenyl, cycloalkyl, heterocyclyl, heteroaryl, —OR$^3$, —C(O)OR$^4$, —NR$^a$R$^b$, and —C(O)NR$^c$R$^d$,
wherein any said aryl and heteroaryl may optionally be substituted with one or more substituents independently selected from alkenyl, alkyl, haloalkyl, arylalkyl, heterocyclyl, heterocyclylalkyl, halogen, cyano, nitro, —C(O)OR$^4$, —OR$^5$, —NR$^a$R$^b$, (NR$^a$R$^b$)alkyl, and (MeO)(HO)P(O)O—, and
wherein any said cycloalkyl and heterocyclyl may optionally be fused onto an aromatic ring and may optionally be substituted with one or more substituents independently selected from alkyl, hydroxyl, halogen, aryl, —NR$^a$R$^b$, oxo, and —C(O)OR$^4$;
$R^3$ is hydrogen, alkyl, or arylalkyl;
$R^4$ is alkyl or arylalkyl;
$R^5$ is hydrogen, alkyl, or arylalkyl;
R$^a$ and R$^b$ are independently selected from hydrogen, alkyl, cycloalkyl, arylalkyl, heteroaryl, —C(O)R$^6$, —C(O)OR$^7$, —C(O)NR$^c$R$^d$, and (NR$^c$R$^d$)alkyl, or alternatively,
R$^a$ and R$^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;

$R^6$ is alkyl;
$R^7$ is alkyl, arylalkyl, cycloalkyl, or haloalkyl; and
R$^c$ and R$^d$ are independently selected from hydrogen, alkyl, arylalkyl, and cycloalkyl.

2. A composition comprising a compound of claim 1, or a pharmaceutically acceptable salt thereof, and a pharmaceutically acceptable carrier.

3. A method of treating an HCV infection in a patient, comprising administering to the patient a therapeutically effective amount of a compound of claim 1, or a pharmaceutically acceptable salt thereof.

4. A compound selected from
methyl((1S)-1-(((1R,3S,5R)-3-(4-(4-((4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)ethynyl) phenyl)-1H-imidazol-2-yl)-2-azabicyclo[3.1.0]hex-2-yl)carbonyl)-2-methylpropyl)carbamate;
dimethyl(1,2-ethynediylbis(4,1-phenylene-1H-imidazole-4,2-diyl(1R,3S,5R)-2-azabicyclo[3.1.0]hexane-3,2-diyl((2S)-1-oxo-1,2-butanediyl)))biscarbamate;
dimethyl(1,2-ethynediylbis(4,1-phenylene-1H-imidazole-4,2-diyl(1R,3S,5R)-2-azabicyclo[3.1.0]hexane-3,2-diyl((1S)-1-cyclobutyl-2-oxo-2,1-ethanediyl)))biscarbamate;
dimethyl(1,2-ethynediylbis(4,1-phenylene-1H-imidazole-4,2-diyl(1R,3S,5R)-2-azabicyclo[3.1.0]hexane-3,2-diyl(1S)-2-oxo-1-(tetrahydro-2H-pyran-4-yl)-2,1-ethanediyl)))biscarbamate;
methyl((1S)-1-(((1R,3S,5R)-3-(4-(4-((4-(2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-4-yl)phenyl)ethynyl)phenyl)-1H-imidazol-2-yl)-2-azabicyclo[3.1.0]hex-2-yl)carbonyl)-2-methylpropyl)carbamate;
methyl((1S)-1-(((1R,3S,5R)-3-(4-chloro-5-(4-((4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)ethynyl)phenyl)-1H-imidazol-2-yl)-2-azabicyclo[3.1.0]hex-2-yl)carbonyl)-2-methylpropyl)carbamate;
methyl((1S)-1-(((1R,3S,5R)-3-(4-chloro-5-(4-((4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)phenyl)ethynyl)phenyl)-1H-imidazol-2-yl)-2-azabicyclo[3.1.0]hex-2-yl)carbonyl)-2-methylpropyl)carbamate;
methyl((1S)-2-((1R,3S,5R)-3-(4-(4-((4-(4-chloro-2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-imidazol-5-yl)phenyl)ethynyl)phenyl)-1H-imidazol-2-yl)-2-azabicyclo[3.1.0]hex-2-yl)-2-oxo-1-(tetrahydro-2H-pyran-4-yl)ethyl)carbamate;
dimethyl(1,2-ethynediylbis(4,1-phenylene(4-chloro-1H-imidazole-5,2-diyl)(1R,3S,5R)-2-azabicyclo[3.1.0]hexane-3,2-diyl((1S)-2-oxo-1-(tetrahydro-2H-pyran-4-yl)-2, 1-ethanediyl)))biscarbamate;
methyl((1S)-1-(((1R,3S,5R)-3-(4-(4-((1S,2S)-2-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)cyclopropyl)phenyl)-1H-imidazol-2-yl)-2-azabicyclo[3.1.0]hex-2-yl)carbonyl)-2-methylpropyl)carbamate;
dimethyl((1S,2S)-1,2-cyclopropanediylbis(4,1-phenylene-1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate;

methyl((1S)-1-(((1R,3S,5R)-3-(4-(4-((1R,2R)-2-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)cyclopropyl)phenyl)-1H-imidazol-2-yl)-2-azabicyclo[3.1.0]hex-2-yl)carbonyl)-2-methylpropyl)carbamate;

dimethyl((1R,2R)-1,2-cyclopropanediylbis(4,1-phenylene-1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate;

methyl((1S)-1-(((1R,3S,5R)-3-(4-(4-((E)-2-(4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)vinyl)phenyl)-1H-imidazol-2-yl)-2-azabicyclo[3.1.0]hex-2-yl)carbonyl)-2-methylpropyl)carbamate;

dimethyl((E)-1,2-ethenediylbis(4,1-phenylene-1H-imidazole-4,2-diyl(1R,3S,5R)-2-azabicyclo [3.1.0]hexane-3,2-diyl((1S)-2-oxo-1-(tetrahydro-2H-pyran-4-yl)-2,1-ethanediyl))) biscarbamate;

methyl((1S)-2-((1R,3S,5R)-3-(4-(4((E)-2-(4-(2-((1R,3S,5R)-2-((2S)-2-((methoxycarbonyl) amino)-3-methylbutanoyl)-2-azabicyclo[3.1.0]hex-3-yl)-1H-imidazol-4-yl)phenyl)vinyl) phenyl)-1H-imidazol-2-yl)-2-azabicyclo[3.1.0]hex-2-yl)-2-oxo-1-(tetrahydro-2H-pyran-4-yl)ethyl)carbamate;

methyl((1S)-1-(((1S,3S,5S)-3-(4-(4-((4-(2-((1S,3S,5S)-2(2S)-2-((methoxycarbonyl)amino)-3-methylbutanoyl)-2-azabicyclo[3.1.0]hex-3-yl)-1H-imidazol-4-yl)phenyl)ethynyl)phenyl)-1H-imidazol-2-yl)-2-azabicyclo [3.1.0]hex-2-yl)carbonyl)-2-methylpropyl) carbamate;

dimethyl(1,2-ethynediylbis(4,1-phenylene-1H-imidazole-4,2-diyl(1S,3S,5S)-2-azabicyclo [3.1.0]hexane-3,2-diyl((1S)-2-oxo-1-(tetrahydro-2H-pyran-4-yl)-2,1-ethanediyl)))biscarbamate;

methyl((1S)-1-(1R,3S,5R)-3-(4-(3-((3-(2-((1R,3S,5R)-2(2S)-2-((methoxycarbonyl)amino)-3-methylbutanoyl)-2-azabicyclo [3.1.0]hex-3-yl)-1H-imidazol-4-yl)phenyl)ethynyl)phenyl)-1H-imidazol-2-yl)-2-azabicyclo [3.1.0]hex-2-yl)carbonyl)-2-methylpropyl) carbamate; and dimethyl(1,2-ethynediylbis(3,1-phenylene-1H-imidazole-4,2-diyl(1R,3S,5R)-2-azabicyclo [3.1.0]hexane-3,2-diyl((1S)-2-oxo-1-(tetrahydro-2H-pyran-4-yl)-2,1-ethanediyl)))biscarbamate;

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,796,466 B2 | Page 1 of 3 |
| APPLICATION NO. | : 12/729940 | |
| DATED | : August 5, 2014 | |
| INVENTOR(S) | : John A. Bender et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 370 days.

In the Specification:

Column 12, line 41, change "Imiqimod," to -- Imiquimod, --.

Column 13, line 34, change "Imiqimod," to -- Imiquimod, --.

In the Claims:

Claim 1:

Column 257, line 38, change "—$OR^3$,—$C(O)OR^4$,—$NR^aR^b$," to -- —$OR^3$, —$C(O)OR^4$, —$NR^aR^b$, --.

Claim 4:

Column 258, line 16, change "ethynyl) phenyl)-" to -- ethynyl)phenyl)- --.

Column 258, line 28, change "2-diyl(1S)-" to -- 2-diyl((1S)- --.

Column 258, lines 37 and 38, change "amino) -3-" to -- amino)-3- --.

Signed and Sealed this
Twenty-fifth Day of August, 2015

Michelle K. Lee
*Director of the United States Patent and Trademark Office*

In the Claims:

Claim 4 (continued):

Column 258, line 57, change "-2, 1-ethanediyl)))" to -- -2,1-ethanediyl))) --.

Column 259, line 12, change "-((methoxycarbonyl) amino)-" to -- -((methoxycarbonyl)amino)- --.

Column 259, line 14, change "vinyl) phenyl)-" to -- vinyl)phenyl)- --.

Column 259, line 18, change "-azabicyclo [3.1.0]" to -- -azabicyclo[3.1.0] --.

Column 259, line 20, change "ethanediyl))) biscarbamate;" to -- ethanediyl)))biscarbamate; --.

Column 259, line 21, change "-(4((E)-" to -- -(4-((E)- --.

Column 259, line 22, change "-((methoxycarbonyl) amino)-" to -- -((methoxycarbonyl)amino)- --.

Column 259, line 24, change "vinyl) phenyl)-" to -- vinyl)phenyl)- --.

Column 260, line 3, change "methyl((1 S)-1-(((1 S,3 S,5 S)-" to -- methyl((1S)-1-(((1S,3S,5S)- --.

Column 260, lines 3 and 4, change "-((1 S,3 S,5 S)-2(2S)-" to -- -((1S,3S,5S)-2-((2S)- --.

Column 260, lines 6 and 7, change "-azabicyclo [3.1.0]" to -- -azabicyclo[3.1.0] --.

Column 260, line 9, change "(4,1 -phenylene-" to -- (4,1-phenylene- --.

Column 260, line 10, change "(1 S ,3 S,5 S)-2-azabicyclo [3.1.0]" to -- (1S,3S,5S)-2-azabicyclo[3.1.0] --.

Column 260, lines 10 and 11, change "-3 ,2-diyl((1 S)-2-oxo-1 -(tetrahydro-" to -- 3,2-diyl((1S)-2-oxo-1-(tetrahydro- --.

Column 260, lines 11 and 12, change "-2,1 -ethanediyl)))" to -- -2,1-ethanediyl))) --.

Column 260, line 13, change "methyl((1 S)-1-(1R,3 S,5R)-" to -- methyl((1S)-1-(1R,3S,5R)- --.

Column 260, lines 13 and 14, change "-((1R,3 S,5R)-2(2S)-" to -- -((1R,3S,5R)-2-((2S)- --.

CERTIFICATE OF CORRECTION (continued)
U.S. Pat. No. 8,796,466 B2

In the Claims:

Claim 4 (continued):

Column 260, line 15, change "-azabicyclo [3.1.0]hex-3 -yl)-" to -- -azabicyclo[3.1.0]hex-3-yl)- --.

Column 260, line 16, change "-1 H-" to -- -1H- --.

Column 260, line 17, change "azabicyclo [3.1.0]" to -- azabicyclo[3.1.0] --.

Column 260, line 20, change "(1R,3 S,5R)-2-azabicyclo [3.1.0]" to -- (1R,3S,5R)-2-azabicyclo[3.1.0] --.

Column 260, line 21, change "-3 ,2-diyl((1 S)-2-oxo-1 -(tetrahydro-2H-" to -- -3,2-diyl((1S)-2-oxo-1-(tetrahydro-2H- --.

Column 260, line 22, change "-2,1 -ethanediyl)))" to -- -2,1-ethanediyl))) --.